United States Patent
Chintamanani et al.

(10) Patent No.: US 10,190,125 B2
(45) Date of Patent: *Jan. 29, 2019

(54) HAPLOID INDUCTION COMPOSITIONS AND METHODS FOR USE THEREFOR

(71) Applicant: Syngenta Participations AG, Basel (CH)

(72) Inventors: Satya Chintamanani, Slater, IA (US); Timothy Kelliher, Research Triangle Park, NC (US); Brent Delzer, Janesville, WI (US); Michael L. Nuccio, Durham, NC (US); Robert Arthur Dietrich, Research Triangle Park, NC (US); Suresh Babu Kadaru, Hydrabad (IN); Todd Lee Warner, Stanton, MN (US); William Paul Bullock, Slater, IA (US)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/586,649

(22) Filed: May 4, 2017

(65) Prior Publication Data

US 2017/0240912 A1    Aug. 24, 2017

Related U.S. Application Data

(62) Division of application No. 14/212,504, filed on Mar. 14, 2014, now Pat. No. 9,677,082.

(60) Provisional application No. 61/852,428, filed on Mar. 15, 2013.

(51) Int. Cl.
| | | |
|---|---|---|
| *C12N 15/82* | (2006.01) | |
| *C12Q 1/6895* | (2018.01) | |
| *A01H 1/04* | (2006.01) | |
| *A01H 1/08* | (2006.01) | |
| *C12N 9/18* | (2006.01) | |
| *C12Q 1/686* | (2018.01) | |

(52) U.S. Cl.
CPC .......... *C12N 15/8216* (2013.01); *A01H 1/04* (2013.01); *A01H 1/08* (2013.01); *C12N 9/18* (2013.01); *C12N 15/8218* (2013.01); *C12N 15/8261* (2013.01); *C12N 15/8287* (2013.01); *C12Q 1/6895* (2013.01); *C12Q 1/686* (2013.01); *Y02A 40/146* (2018.01)

(58) Field of Classification Search
CPC .................................................. C12N 15/8216
See application file for complete search history.

(56) References Cited

U.S. PATENT DOCUMENTS

| | | | |
|---|---|---|---|
| 7,411,117 B2 | 8/2008 | Bohning | .................. A01H 5/10 435/412 |
| 9,677,082 B2 * | 6/2017 | Chintamanani | .... C12N 15/8218 |

FOREIGN PATENT DOCUMENTS

WO     201230893     3/2012

OTHER PUBLICATIONS

Kelliher et al., "Unresolved issues in pre-meiotic anther development", Frontiers in Plant Science, Plant Evolution and Development, published Jul. 21, 2014, vol. 5, Article 341, pp. 1-9.
Dong et al., Fine mapping of qhir1 influencing in vivo haploid induction in maize. Theor. Appl. Genet 126: 2013, pp. 1713-1720.
Thomas et al. 2001, The Plant Journal 25(4):417-425.
1993 Hereditas 118:273-280.
Colliver et al. Plant Molecular Biology 35:509-522.

* cited by examiner

*Primary Examiner* — Li Zheng
(74) *Attorney, Agent, or Firm* — Christopher Leming

(57) ABSTRACT

Provided are isolated cDNAs comprising a nucleotide sequence having at least 90% identity to SEQ ID NO: 33, SEQ ID NO: 37, SEQ ID NO: 52 or SEQ ID NO: 53. Also provided are expression cassettes; vectors; transgenic plant cells; plants, plant parts, and seeds; isolated polypeptides; amplicons and informative fragments of the presently disclosed nucleic acids; compositions that include amplification primer pairs; methods for producing plants that exhibit HI; methods for identifying the presence or absence of an allele associated with HI in a plant; methods for introgressing Haploid-inducing nucleotide sequences into plants; and methods for selecting parental plants predicted to produce progeny generations with plants that exhibit Haploid Induction trait.

2 Claims, No Drawings

Specification includes a Sequence Listing.

SEQUENCE LISTING

<160> NUMBER OF SEQ ID NOS: 67

<210> SEQ ID NO 1
<211> LENGTH: 1302
<212> TYPE: DNA
<213> ORGANISM: Zea mays

<400> SEQUENCE: 1

```
cccgctacct gttcaccgcg cgccagcgaa acctccgcac gcccactgcc catctgttcc      60
ccgtgcgcca gcgaaacatc cgcacgcccg cggcccgcct gttccccgcg catcccgctg     120
cacgacttct gctaccgcaa cggccaccca cgcacgcccg cctgttcacc gcgcatcccg     180
ctgacctccc cttcacgctc gcacacgctc cgttccccca ccccaccgca atccccgacg     240
aactcattac cagtagaatc agttactaac tgcttttctt tttcttggat tagaatggct     300
ggggctatct ctcaccatgc gctagcattt tcacaatccc actggtgcag tgcgaagaac     360
tctagattcg gaagaggac gggcaatgct cgcctggttt atctaaaagg aagatgtggt     420
tcaggcagca gaaaactggg tttgatgtgg gcctcgagct cgcagtcttc tgtcatggag     480
ccgacgcacc taccatctga tggcaacagc agccacaccc caaaaaaatc aagtgaaagc     540
gctcttatat tgatttggca tggtgaatcc ctgtggaacg agaaaaatct atttcctggc     600
tgcatcgatg taccctgac accgaagggt gttgaggagg ccattgaggc aggtaaaagg     660
atatgcaata tcccaatcga tgtgatatat acttcatcac tgatttgtgc tcagatgacc     720
gcaatgcttg ccatgatgca gcatcgacgc aagaagatcc tagttatcac gcataatgag     780
agtgaacaag ctcacaggtg gagtcagata tacagtgagg agacaatgaa acagtccatt     840
cctgtcatca cagcttggca attgaatgaa cggatgtatg gtgagctaca aggccttaac     900
aagcaagaaa ctgtagatcg atttggcaaa gaacaagttc atgagtggcg ccgcagttat     960
gatattcctc cgccaaatgg agaaagtcta gagaagtgtg ctgagagagc tgttgcttat    1020
ttcaaagatc agattattcc acaacttgtg gctggaaaac atgtgatggt tgctgcacat    1080
gggaattcac ttcgttcaat tataatgcat ctggacaaat taacttctca gaaggtaata    1140
agccttgagc tgtctactgg cattcccatg ctttacatat tcaaagaggg aaagtttatt    1200
cgacgtggga ctccagtagg accttcggag gccagtgttt atgcttatac caggaccaaa    1260
cgatttgctg agcacattac atttcagaac aaattggcct ag                       1302
```

<210> SEQ ID NO 2
<211> LENGTH: 335
<212> TYPE: PRT
<213> ORGANISM: Zea mays

<400> SEQUENCE: 2

```
Met Ala Gly Ala Ile Ser His His Ala Leu Ala Phe Ser Gln Ser His
1               5                  10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Ser Leu Trp Asn Glu
                85                  90                  95
```

```
Lys Asn Leu Phe Pro Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
    130                 135                 140

Leu Ala Met Met Gln His Arg Arg Lys Ile Leu Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp Arg Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335

<210> SEQ ID NO 3
<211> LENGTH: 2992
<212> TYPE: DNA
<213> ORGANISM: Zea mays

<400> SEQUENCE: 3
ttcaaccacc aaaatcaatt aggaaaaggt gtaagcctat ttcccttttca ggaggcgtac      60 gtgagaggga gaggtgaaaa ggaacaacgc gtataccaga taaggtccca cagcctaagt     120
aggtagcctt ctgatatctc tactaactat taaggagaga gtgtagactg ccccgctcc      180 ctacccaacg ccccccgcta cctgttcacc gcgcgccagc gaaacctccg cacgcccact     240
gcccatctgt tccccgtgcg ccagcgaaac atccgcacgc ccgcggcccg cctgttcccc    300
gcgcatcccg ctgcacgact tctgctaccg caacggccac cccgcacgc ccgcctgttc     360 accgcgcatc ccgctgaccct cccttcacg ctcgcacacg ctccgttccc ccaccccacc    420
gcaatccccg acgctataag agcggtaacc aactccatct ccctggtgcc acgcattgtt    480
gagttcttaa ggtgcgtttc gttgaggact tgttcatttt tgttggtcat gtattccatt    540
ttactgctct accattttgt ggaataaagg gaggaatgtt tcactagaa gagttcatca     600 atcttatgtt ggtttcttgg atcagttttg ctctatggct aaatggcga attgagccta     660 tttcattata aagttagcga gcgaataatt gttcagcctc ttcctagaac tcattaccag    720
tagaatcagt tactaactgc ttttcttttt cttggattag aatggctggg gctatctctc    780
```

```
accatgcgct agcatttca caatcccact ggtgcagtgc gaagaactct agattcggaa      840
agaggacggg caatgctcgc ctggtttatc taaaaggaag atgtggttca ggcagcagaa      900
aactgggttt gatgtgggcc tcgagctcgc agtcttctgt catggagccg acgcacctac      960
catctgatgg caacagcagc cacaccccaa aaaaatcaag taattttaac gacctcctat     1020
ggtggttatt tgttttaat ttgagaaaac tatccatttg acacatttaa ctttgggctt     1080
ctcagaattt ggggcatata ataagatctg ctaatctgtt atctctatgt cgttgtaggt     1140
gaaagcgctc ttatattgat ttggcatggt gaatccctgt ggaacgagaa aaatctattt     1200
actggctgca tcgatgtacc cctgacaccg aagggtgttg aggaggccat tgaggcaggt     1260
aaaaggatat gcaatatccc aatcgatgtg atatatactt catcactgat tgtgctcag      1320
atgaccgcaa tgcttgccat gatgcagcat cgacgcaaga aggtttgtgt ctttccttg      1380
aaattccagt aatttcttct agcatttgta tgaacttgcc ggagaaatca tgctttgctg     1440
gtgatatatg tatttataga tcccagttat cacgcataat gagagtgaac aagctcacag     1500
gtggagtcag atatacagtg aggagacaat gaaacagtcc attcctgtca tcacagcttg     1560
gcaattgaat gaacggatgt aatactttct ccatactctt tgatttgcta attactccct     1620
ctgtctcaaa atagtattaa ttttagctct tgatttttat gtctatattc aaatagatga     1680
tgataaatct agattctaga cacaaatata aaacatatac atcaagtatt atatgaatct     1740
attaatttac taagaccaat tttaatttgg acagaggga gtatacgatt ataatagttg     1800
tttgactgtg cttctcttta aatatcccctt gacatttcta ggtatggtga gctacaaggc     1860
cttaacaagc aagaaactgt agatcgattt ggcaaagaac aagttcatga gtggcaccgc     1920
agttatgata ttcctccgcc aaatggagaa agtctagaga agtgtgctga gagagctgtt     1980
gcttatttca aagatcaggc acatctagca aggccacttt acactaattg aaagatacac     2040
tttttacttg ggttattggt cttgctgcag tattggtatg catgctaaag gttattcttg     2100
aatcgatgaa ttcctctact atgggatgca gaaatgcatg tgcttagttt tctttctatt     2160
gtgctagctc atatcaaatt tataacctga atttttatt tatgttcgac tctaaaaaac     2220
agttttttct agctcgattt gacctatagt aattttccg taatagatta ttccacaact     2280
tgtggctgga aaacatgtga tggttgctgc acatgggaat tcacttcgtt caattataat     2340
gcatctggac aaattaactt ctcagaaggt aattcactgt cgttttgtc tttccatcaa     2400
aaaggactcg gctaaacaga acatgtagca ttatgttaag tttgggagtg agcctttcgt     2460
cccttcaggt aataagcctt gagctgtcta ctggcattcc catgctttac atattcaaag     2520
agggaaagtt tattcgacgt gggactccag taggaccttc ggaggccagt gtttatgctt     2580
ataccagggt aagattcttt cccccacatg ttctaccata ggacgatact ccagtttaca     2640
aaccttatct gtacagacca aacgatttgc tgagcacatt acatttcaga acaaattggc     2700
ctagaagata aggggtgttt ggtttgagaa atcactctat tcaaaatgag atggtgtatc     2760
atgggtccat ttctcaaatt tggtgggatg accctattcc tcatattagt actaactagg     2820
tgagtgtccg tgcgttgcaa cgggaacata taataacatg ataacttata tacaaaatgt     2880
gtcttatatt gttataagaa aatgtttcat aatctatttg tgatcctggc catacataaa     2940
ttttgttatt ttaatttaac tgtttcacta ctacattgaa atcatcagta tc              2992
```

<210> SEQ ID NO 4
<211> LENGTH: 6916
<212> TYPE: DNA

<213> ORGANISM: Artificial Sequence
<220> FEATURE:
<223> OTHER INFORMATION: Synthetic

<400> SEQUENCE: 4

```
cctcgggacc cttgtcgcgt tgttcgttcc attgccgcat cacctccttt ctcatcgtgc    60
attacgaggt cttcaaaggg cttttggtca tcagccggga gcgcctccat cgccggcttg   120
atgatgttgg tagtggagat cttggtgtga tccttaaaac cggccattta tgggccgatt   180
tttagcagat ctagacacct attccccagc ggagtcgcca aaagtatgtt gacgcttttt   240
cggagcgcca atcactcaag aagaaccggc ggcggtgccc tctgcacagg ggcggacgct   300
ccgcgcgcag gggccggacg ctccgcggcc tggtgcgagg cggcggcgct ctctggttag   360
acgcggacgg tgcgcggcac agggccggac ggtgcgcgac ctagtgcagg agcacgggtt   420
ccctgcctga cggccggacg ctccgcgctc tagggccgga cggtgcgcgc gtgcgcaggg   480
gcggcggaag atcgccggcg cgcctggat ctcgctcccg ggaggagcc cgtcggggag   540
gagagatcct aggagttgtc taggctcggg ccggccgacc tagactcctc taatcgacgt   600
agagtcgagg agaggcagag aatttgggga ttggaatact aaactagggc taaactagaa   660
ctagactaga actactccta attgtgctga aaataaatgc gagatagaag ttgtattggt   720
tcgattgttg ggggtcaatc ggccgtagcc cttcatctat ataaagggga ggtctggatc   780
cgtttccaac tgatttccga gttaatcccg cggttttagg taacaaatcc cgcgagaaac   840
taggaaccct aactgactct gcgcacgcgc cgaccgtccg cgccaccacc gcggacggtc   900
ccgaccgcgg agcgtccggc ctccgggccg gagcgtccgc acggtcattt tgggttcgaa   960
cagagtccca acgaggttag taaatgtagt gatgaaatta agttttgtac gaagtttgta  1020
aatttaagga cctgttttac ataactattg gagaagagtt ttctctgaaa aattcttaaa  1080
tttatattta gggagttgtt tatataacta ttggcatttg agatgctcta aggaagcgaa  1140
ggaaataact tggcggcgat cctagtcgac aaccgttgaa ttcgtgagaa tcaatcattc  1200
tgtaggagta aaaaaataaa ataaaatatg catttcctcg ttcctatacg cttaaattag  1260
acgaccctgg actggaacca ggaactagga aggggcaccg atgtcatttg cgaagcaaca  1320
acaacatgcg tgaggacgac caagtcaaac gttgcgtcgc gttgcctcgc cggcgggccg  1380
gtcccaccaa gacgtggcgc catgcaagtg cgtcgtcgac cctcttctct ctctctcttg  1440
tagtcttgtt cctgttatct ctctcggctg tccgctgccc cgtgatctga gcgcgtttct  1500
ctcccgtcct ctcttctccc tctcccgcaa caaacacctg ctatccggtc tccctctccc  1560
ctgccatctc tctctagcgc attgctagcg cgagcgcaga aggcacacac gtagagcctt  1620
ggtgatacct cctcctcctc ctcctcctcc tcctgatctc ctctcctcct ccggcctccg  1680
tatacctata actaaaagat gatcatcgtg cgatgcaggc gaactcgtcg tccgaaaacc  1740
atggatccaa ctcattacca gtagaatcag ttactaactg cttttctttt tcttggatta  1800
gaatggctgg ggctatctct caccatgcgc tagcattttc acaatcccac tggtgcagtg  1860
cgaagaactc tagattcgga aagaggacgg gcaatgctcg cctggtttat ctaaaaggaa  1920
gatgtggttc aggcagcaga aaactgggtt tgatgtgggc ctcgtgctcg cagtcttctg  1980
tcatggagcc gacgcaccta ccatctgatg caacagcag ccacacccca aaaaaatcaa  2040
gtgaaagcgc tcttatattg atttggcatg gtgaatccct gtggaacgag aaaaatctat  2100
ttcctggctg catcgatgta ccctgacac cgaagggtgt tgaggaggcc attgaggcag  2160
gtaaaaggat atgcaatatc ccaatcgatg tgatatatac ttcatcactg atttgtgctc  2220
```

```
agatgaccgc aatgcttgcc atgatgcact cgagaaatct gaagaagaga catcagtagg    2280
aaaaccatga aacaactcac caagtgataa aactttgata aattcattca aaagtatcat    2340
gttctacgtg attcgcttgt atgccaaatt atctaaatat tagtaagaat taactactcg    2400
gacgatcatc agcaaatgaa aatgaaacag cacaccaatt gagactgatc agatcagaaa    2460
ccagaaaaac atctcaacat ggataaattc atcagcaata ctgtagcatt gatatatttg    2520
tgtttcttga aagaaagaca tcaaagaaac tttgcaatta tgtagtattg tttatttttc    2580
tgttacaaac ttaatcaact gacatgtaat gtgtctctat tgtcagttca agtattagac    2640
tatccattgt cacctttaa atgtaccttt actgtcagcg tacgagataa agttggccga     2700
ttgaattcta agctactata aaagcaactt tattatatag acatggcaaa caatcgttaa    2760
caaactgttt ttcttttga ttgattagga cttggaaaca cactgaacat gatcaaagtc     2820
acaaaagtca cttggttgcc tagtctgaca gcaagcgcag gtgtaaattc agaatgatag    2880
tgaaccaaaa ctcatctgct tccagtacca aattcgtcag aaggcagaac ggaggcataa    2940
gcacaagggg catgctcacc cgagtcgagt gcatcatggc aagcattgcg gtcatctgag    3000
cacaaatcag tgatgaagta tatatcacat cgattgggat attgcatatc cttttacctg    3060
cctcaatggc ctcctcaaca cccttcggtg tcaggggtac atcgatgcag ccaggaaata    3120 gattttctc gttccacagg gattcaccat gccaaatcaa tataagacg ctttcacttg       3180 atttttttgg ggtgtggctg ctgttgccat cagatggtag gtgcgtcggc tccatgacag    3240
aagactgcga gcacgaggcc cacatcaaac ccagttttct gctgcctgaa ccacatcttc    3300
cttttagata aaccaggcga gcattgcccg tcctcttcc gaatctagag ttcttcgcac      3360
tgcaccagtg ggattgtgaa aatgctagcg catggtgaga gatagcccca gccattctaa    3420
tccaagaaaa agaaaagcag ttagtaactg attctactgg taatgagttg gatctccatg    3480
ggagctctcg tcatcgtcct actatcaagc aacacgatcg accaccacct cgattatata    3540
tgcatcatta tagtatcgtt tattaatttc agacccaccc actgctaacc acatcgtcca    3600
cgagagatta tattcatccg tggactacgc tctcgatctt acaatttgaa acctttctat    3660
tttcctaatt actatgtatt ccaggttcat tttgattgtg accattcttc agttcttct     3720 gtaaggatcg gagcatatta tatactctat gtggctatgc caattatatt gttgggtata    3780
agaatgcatt ttgtttctgt aatacggaaa aatatatttt cttaagcaa caacaaggta     3840 aaaacttgcc tcgttgcata ttttctttat gtcaatctcc ttttgttcgt tgtatgatcc    3900
tctgtttgga aactgaatac tgatcgaaca actgatcagg agttaaaaca tattgtaaat    3960
atatataaaa acttgctgtg tacaactctt ctttattgta taagtttctt gaggtaaccg    4020
aaatagatag taaatcccaa tacaaataga ttcctccgtt actaactaat ctgaacataa    4080
atgctaataa aaaagtata aatttctatc tgcgtatgta ccttgacctt acctttattc     4140
tattaactcc tgattttcta ttcagatttt gaacggtctg ttacttcctt tctattctgt    4200
tctggtttcg tcgtcgtttg tttccgaacg gtctgctact tctgattttc tatttgttct    4260 tacgttggt tttgccgttc tagtttcttg cgttttcca tataaatata gaaacacaaa      4320
ataaatgtaa tgttgtagat acttgaacta tcgatctttt ccttttaaaaa atgatattgc   4380 taccactaat gtagttttaa ttaggaacaa aacttacaac caatgatcaa ctaatgaacc    4440
ggtctagaac agtctatatg gacatggtga gcaagcgtac gtaattccgg accgcgcggg    4500
cggccgcact agtcccgggc ccatcgatga tatcagatct ggttctatag tgtcacctaa    4560
```

```
atcgtatgtg tatgatacat aaggttatgt attaattgta gccgcgttct aacgacaata      4620
tgtccatatg gtgcactctc agtacaatct gctctgatgc cgcatagtta agccagcccc      4680
gacacccgcc aacacccgct gacgcgccct gacgggcttg tctgctcccg gcatccgctt      4740
acagacaagc tgtgaccgtc tccgggagct gcatgtgtca gaggttttca ccgtcatcac      4800
cgaaacgcgc gagacgaaag ggcctcgtga tacgcctatt tttataggtt aatgtcatga      4860
taataatggt tcttagacg tcaggtggca cttttcgggg aaatgtgcgc ggaaccccta       4920
tttgtttatt tttctaaata cattcaaata tgtatccgct catgagacaa taaccctgat      4980
aaatgcttca ataatattga aaaggaaga gtatgagtat tcaacatttc cgtgtcgccc       5040
ttattccctt ttttgcggca ttttgccttc ctgttttgc tcacccagaa acgctggtga       5100
aagtaaaaga tgctgaagat cagttgggtg cacgagtggg ttacatcgaa ctggatctca      5160
acagcggtaa gatccttgag agttttcgcc ccgaagaacg ttttccaatg atgagcactt      5220
ttaaagttct gctatgtggc gcggtattat cccgtattga cgccgggcaa gagcaactcg      5280
gtcgccgcat acactattct cagaatgact tggttgagta ctcaccagtc acagaaaagc      5340
atcttacgga tggcatgaca gtaagagaat tatgcagtgc tgccataacc atgagtgata      5400
acactgcggc caacttactt ctgacaacga tcggaggacc gaaggagcta accgcttttt      5460
tgcacaacat gggggatcat gtaactcgcc ttgatcgttg ggaaccggag ctgaatgaag      5520
ccataccaaa cgacgagcgt gacaccacga tgcctgtagc aatggcaaca acgttgcgca      5580
aactattaac tggcgaacta cttactctag cttcccggca acaattaata gactggatgg      5640
aggcggataa agttgcagga ccacttctgc gctcggccct tccggctggc tggtttattg      5700
ctgataaatc tggagccggt gagcgtgggt ctcgcggtat cattgcagca ctggggccag      5760
atggtaagcc ctcccgtatc gtagttatct acacgacggg gagtcaggca actatggatg      5820
aacgaaatag acagatcgct gagataggtg cctcactgat taagcattgg taactgtcag      5880
accaagttta ctcatatata ctttagattg atttaaaact tcatttttaa tttaaaagga      5940
tctaggtgaa gatcctttt gataatctca tgaccaaaat cccttaacgt gagttttcgt       6000
tccactgagc gtcagacccc gtagaaaaga tcaaaggatc ttcttgagat cctttttttc      6060
tgcgcgtaat ctgctgcttg caaacaaaaa aaccaccgct accagcggtg gtttgtttgc      6120
cggatcaaga gctaccaact ctttttccga aggtaactgg cttcagcaga gcgcagatac      6180
caaatactgt tcttctagtg tagccgtagt taggccacca cttcaagaac tctgtagcac      6240
cgcctacata cctcgctctg ctaatcctgt taccagtggc tgctgccagt ggcgataagt      6300
cgtgtcttac cgggttggac tcaagacgat agttaccgga taaggcgcag cggtcgggct      6360 gaacggggg ttcgtgcaca cagcccagct tggagcgaac gacctacacc gaactgagat      6420
acctacagcg tgagctatga gaaagcgcca cgcttcccga agggagaaag gcggacaggt      6480
atccggtaag cggcagggtc ggaacaggag agcgcacgag ggagcttcca gggggaaacg      6540
cctggtatct ttatagtcct gtcgggtttc gccacctctg acttgagcgt cgatttttgt      6600
gatgctcgtc agggggggcgg agcctatgga aaaacgccag caacgcggcc ttttacggt      6660 tcctggcctt ttgctggcct tttgctcaca tgttctttcc tgcgttatcc cctgattctg      6720
tggataaccg tattaccgcc tttgagtgag ctgataccgc tcgccgcagc cgaacgaccg      6780
agcgcagcga gtcagtgagc gaggaagcgg aagagcgccc aatacgcaaa ccgcctctcc      6840
ccgcgcgttg gccgattcat taatgcaggt taacctggct tatcgaaatt aatacgactc      6900
actataggga gaccgg                                                     6916
```

<210> SEQ ID NO 5
<211> LENGTH: 335
<212> TYPE: PRT
<213> ORGANISM: Zea mays

<400> SEQUENCE: 5

| Met | Ala | Gly | Ala | Ile | Ser | His | His | Ala | Leu | Ala | Phe | Ser | Gln | Ser | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Thr Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
    130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp His Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335
```

<210> SEQ ID NO 6
<211> LENGTH: 335
<212> TYPE: PRT
<213> ORGANISM: Zea mays

<400> SEQUENCE: 6

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Gln Ser Ser Val Met Glu Pro Thr
50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Ser Leu Trp Asn Glu
                85                  90                  95

Lys Asn Leu Phe Pro Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
        130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Thr Val Asp
        195                 200                 205

Arg Phe Gly Lys Glu Gln Val His Glu Trp His Arg Ser Tyr Asp Ile
210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
275                 280                 285

Gly Ile Pro Met Leu Tyr Ile Phe Lys Glu Gly Lys Phe Ile Arg Arg
        290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
            325                 330                 335

<210> SEQ ID NO 7
<211> LENGTH: 335
<212> TYPE: PRT
<213> ORGANISM: Zea mays

<400> SEQUENCE: 7

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu

```
                35                  40                  45
Gly Leu Met Trp Ala Ser Ser Gln Ser Ser Val Met Glu Pro Thr
 50                  55                  60

His Leu Pro Ser Asp Gly Asn Ser Ser His Thr Pro Lys Lys Ser Ser
 65                  70                  75                  80

Glu Ser Ala Leu Ile Leu Ile Trp His Gly Ser Leu Trp Asn Glu
                 85                  90                  95

Lys Asn Leu Phe Thr Gly Cys Ile Asp Val Pro Leu Thr Pro Lys Gly
                100                 105                 110

Val Glu Glu Ala Ile Glu Ala Gly Lys Arg Ile Cys Asn Ile Pro Ile
                115                 120                 125

Asp Val Ile Tyr Thr Ser Ser Leu Ile Cys Ala Gln Met Thr Ser Met
                130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
                180                 185                 190

Arg Met Tyr Gly Glu Leu Gln Gly Leu Asn Lys Gln Glu Thr Val Asp
                195                 200                 205

Arg Phe Gly Lys Glu Gln Val His Glu Trp His Arg Ser Tyr Asp Ile
                210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
                260                 265                 270

Leu Asp Lys Leu Thr Ser Gln Lys Val Ile Ser Leu Glu Leu Ser Thr
                275                 280                 285

Gly Ile Pro Met Leu Tyr Ile Phe Lys Glu Gly Lys Phe Ile Arg Arg
                290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335

<210> SEQ ID NO 8
<211> LENGTH: 335
<212> TYPE: PRT
<213> ORGANISM: Zea mays

<400> SEQUENCE: 8

Met Ala Gly Ala Ile Ser His His Ala Leu Ala Phe Ser Gln Ser His
 1               5                  10                  15

Trp Cys Ser Ala Lys Asn Ser Arg Phe Gly Lys Arg Thr Gly Asn Ala
                20                  25                  30

Arg Leu Val Tyr Leu Lys Gly Arg Cys Gly Ser Gly Ser Arg Lys Leu
                35                  40                  45

Gly Leu Met Trp Ala Ser Ser Gln Ser Ser Val Met Glu Pro Thr
 50                  55                  60

His Leu Pro Ser Asp Gly Asn Ser Ser His Thr Pro Lys Lys Ser Ser
 65                  70                  75                  80
```

Glu Ser Ala Leu Ile Leu Ile Trp His Gly Glu Ser Leu Trp Asn Glu
            85                  90                  95

Lys Asn Leu Phe Thr Gly Cys Ile Asp Val Pro Leu Thr Pro Lys Gly
        100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ser Met
    130                 135                 140

Leu Ala Met Met Gln His Arg Arg Lys Lys Ile Pro Val Ile Thr His
145                 150                 155                 160

Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp Arg Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335

<210> SEQ ID NO 9
<211> LENGTH: 4921
<212> TYPE: DNA
<213> ORGANISM: Zea mays

<400> SEQUENCE: 9
attgctataa gtataataat atctaagaga tggaagaaga ctggccggcc gggtagtgac      60
aataatgaat gaccaacggc agaaaagttg gtgcgaagat gttttaggtg aatgcaagtc     120
acaaaaggaa aaggctggca tctcgaatag aactcctata ccacggatca agaaacaatt     180
aaaaccatac ataattgtcg gagtaatatg ctaatcctag taattttagt cacatcattg     240
gaggtccttc gttccattca attttttttc tttcttcatg aacatttgtt caagatttat     300
ctcccacatg tttcaaagca tgcattattt attattattg gcaaatttca tgatctttca     360
aaagatatct cttgggcctg gcatggatat gctctatctc tagtaagtaa ttggctctgc     420
aataatgagt tggatattgc cacgaagaac cacgccttgc ttggaagaaa cttgatgaat     480
gccaaatctt gctctttttc aacatgttga tttaggaaat tatttggcaa ccaaacataa     540
tgtgactaga attagcacac ttctaatgac aaaaatataa tcacatttct gcgcgcacaa     600
aatatttgct tgccaaaatg caatcatgtt ttgatgtaca gttcgataga cattgaaaaa     660
gaatgcattt aggaaccttt tagtaccact ttgatcaatt tctgccatct acacgtcaaa     720

```
ctagataaaa agaataatgg cagccacatc ctacagaaaa aaaaagacat atcaagaatt      780
caacttaatt tcagaatata caagatttca tagtgacctt taacattgat ttttcgactc      840
acatcttata agcgggtgaa gcagtatata aagaattcc acaaaaaaat ctacaacagc       900
cataagcatt aattacacat aaacgctcac caccctataa aacacccaga ccttcacatt     960
tcttcttcag acctccaaca agcagcagat agatagagaa atgaagagat agattagagt     1020
taccatcata tccccaacaa tggcatagcc aacaagttgg atccttcgga ccctgtagct    1080
cctggtccat gaattgccaa gagaacacct tttagtttct ttgagcaacc tcgatctcgc    1140 catgggttc cgctgtggcc gtgcctcctc ttcgctgctg tgtgaagagg acgtggccgg      1200
catgtttgga tgcaatgggc acgacgacga agaggtgggg cttctggtgt tggggatgga    1260
cacgactttt gctgcgctgc catcacagag cgacgaggtc gtagcatccc tgatggagaa    1320
ggagaaggag cagctgcata gcgttgcgac gggggattac ctccagaggc tgagcagtgg    1380
aggactggag tcatcttgta ggattgccgc cattgattgg ataaaaaagg tttctgcttc    1440
tccatccata ctatatagta tgtatatgat ttctcgcgca tcgatcctag ttagaatctc    1500
atgtttctgt gttttgcagc aaaatgcaat ttatttgact ccaagtttga cttaaacttc    1560
agtttgttca aaaaaaaaa gtttgccctt gcttgaccaa aacctcgttt tgcatatata     1620
gataaatata tagttactga aatgtgtact acttgtctct tacatgtgta ttaattgcag    1680
gcccaggctt atcacgactt tggaccgttg tctgcttatc ttgctgttaa ctaccttgat    1740
agggtcctct ccacaaatca agtcccagtg agttctacaa atgtacccaa cttgtttatt    1800
cttttttcta catgtccaat cagcatgtgg ttgtcagagg tctttgcctc tccctctcta    1860 gaaaaccttta tggcatgttt ggttcagcgg cggaccagga actaaagaca gcctatgcga   1920
gattataagt gtcaataact atagctaatt tcatataaaa aaatacatgc atatttggat    1980
ttgagatgca ctttcgtccg atcagtagat aaggtcattt ggtttaggat catgagttga    2040
gttaggactt agcactattg gaatcgagct ctttgtcaat tgtctgaagc actcggcaaa    2100
gctgggaaaa cactcgacga cgtctttgcc gagtgtagca ctcggcaaag agagctcggc    2160
gaacagtata tcgacacggc ttctttgccg agtatttttt atcgggcact cgacaaagac    2220
tttgccgagt gtcactcggt actcggcaaa gaaaagtcgc cgtcaaggcg accggaaacg    2280
gagacagcgc ctttgccgag tgttctaggt gacactcggc aaagagatta cctttgtcga    2340
gtgtccgcca gtctacactc gccaaggggg ctaccagcgg acccctttgt cagtttcttt   2400
gccgagtgcg ctagaaggca ctcggcaaag cttgcttctt tgtcgagtgc caaggccaca   2460
gcactcggca aataagcttt accggtgccc aggaatggca ctcggcaaaa tgttctttat    2520
cgagtgtcag gcgataggac actcggcaaa gtagcttctt tgccgaatgc caaagcctag   2580
cgttcggcat agataacagc cgtcagctat agacggctgc tgacggttct ttgcctagca    2640
ccgaattgtg tcgagtgttt ggcactcgac aaagtagtct ttgccactac tttgccgagt    2700
gtctttctgt gccgagagtc ctattatcgg caaacgcgat cgttatcgag agtgaaactt    2760
tgtcgagtgt ggcactcggc aaagaagtgt cgagtgcccg ataaaaaaca cttggcaaag    2820
agccaaattc cgatagcgta gcattcgtgc agccgtacgt tagaattgga cagacgaggg    2880
atgtgactgt gctcggctgt tccagctata tcctgcaacc aaacacaacc ttacattttg    2940
atggggcaca atctttatgt gagtttcttg gtgtaggctg atgctgacca ccagccctgg    3000
atgccacagc tgctgtccgt tgcttgccta accattgcag ccaagatgga ggagaccgtg    3060
```

```
gttcctcgcc gtctggacat ccatcagaat caggtggaca aaattggata tatagtacag    3120
tttcacgttt gagttcacca aatctttatc tttattatat atatatatat gtcacaggtt    3180
ctcagcgaga agtacagatt cgatttagat gctattcaga ggatggagat ttacattcta    3240
gactctctga attggaggat gcaagctgtg acgccattct cttacatcaa ctatttcgtg    3300
gacaagttca ctgatgggaa gccgctaagt tgcggattca tttctcggtg caccgagatc    3360
atacttggca gtcttgaagg tacatcagat tacttcatgc atgagcgagc gaatcggact    3420
tacccgcctt ttccattcga taagcaattg ttactatgtg attggaacat gcatctaaat    3480
agatgtctgt gtgcatttga tttgcagcaa cgaagctcct acagttcagg ccttctgaga    3540
tggcagcagc agtggttctg tcagcagctg ctgagtctca agtcattgcc ttcagcggcg    3600
ctcttttagc ttctaatatc cttgtcaata aggtgtagat cctctctctc tatgaaggtt    3660 tagtatttt tttaatgtac gtatttacat ttctaggaaa atgtaaggag atgccatgaa    3720
gcattgcaag aagtgggatt agtgaagaag aaaacagact acagtgcgag tccatctcgc    3780
gtgctagatg cctcatgctt cagcttcaag actgacgata accagacagc cggttcatcc    3840
caatcccaag caaacaacaa tggcaactac aaccaggctt actctccagc tagcaagagg    3900
acaaggctag acatctagac tcaatcagga aaaattgcat gagatcatag acgtacacat    3960
atacacacaa gttttctta gataaaggat acataaagtt aaatttgatt ctggctacat     4020
ttctgagtac gtgcttctca actcagaaga gttcataggg aacattatac atgcatgcat    4080
gctaacaggc aaaagaaggc tgaattatta agagcaatcc tatttatttc ctcctttgtt    4140
cctttgttaa cttttctttt cttcttgtct actttaaatc atggcattag caaagacatt    4200
tgcgtgtatg ggacaggtga tgcaatgata caacataaaa gaaggctagg cattgttttc    4260
aacataagca gaggtaatct cgtttcagga aaaaaatgag cgccaggaac tttgatatct    4320
gatcaaggga gaagcaaagt tagttgttgt gggaatctgt ggctgagttc ttggttctcg    4380
atttcttgtt tgtttgtttg tctgtgatga atattttca gatttattca atgaactgac     4440
catgttatgc tatagagcaa gtacaacaat aggttctaag caggataaat gatgaggtac    4500
aggagagaga agatgagaga gaggataagc gagctataaa cttacaacca tctaagactt    4560
agatataaga ataaaaaaac tttgagagag acaaatgagt tatgtattag tagtgaacgg    4620
ttaactatta tgtagatgga ctaagagata ggacgcaaat agccaatagt cagctatatt    4680
attagcctcg ctcttattca gcacccgggc aatttatcg tccaaatttg ttagcatgca     4740
tgctacttct tatagaatga atattagata tgcattaggc ttcacatcct attcaaaata    4800
aggtgctaga ggccttaaaa tttaagtgtt ttagatgagt tccatggatg aatcttagtt    4860
gcgccataca tataattaat ttaaaacaca caaaaaaaac actagccata tacttactat    4920
g                                                                    4921
```

<210> SEQ ID NO 10
<211> LENGTH: 1071
<212> TYPE: DNA
<213> ORGANISM: Zea mays

<400> SEQUENCE: 10

```
atgaagagat agattagagt taccatcata tccccaacaa tggcatagcc aacaagttgg      60
atccttcgga ccctgtagct cctggtccat gaattgccaa gagaacacct tttagtttct     120
ttgagcaacc tcgatctcgc catggggttc cgctgtggcc gtgcctcctc ttcgctgctg     180
tgtgaagagg acgtggccgg catgtttgga tgcaatgggc acgacgacga agaggtgggg     240
```

```
cttctggtgt tggggatgga cacgactttt gctgcgctgc catcacagag cgacgaggtc    300
gtagcatccc tgatggagaa ggagaaggag cagctgcata gcgttgcgac gggggattac    360
ctccagaggc tgagcagtgg aggactggag tcatcttgta ggattgccgc cattgattgg    420
ataaaaaagg cccaggctta tcacgacttt ggaccgttgt ctgcttatct tgctgttaac    480
taccttgata gggtcctctc cacaaatcaa gtcccagtga gttctacaaa taagtacaga    540
ttcgatttag atgctattca gaggatggag atttacattc tagactctct gaattggagg    600
atgcaagctg tgacgccatt ctcttacatc aactatttcg tggacaagtt cactgatggg    660
aagccgctaa gttgcggatt catttctcgg tgcaccgaga tcatacttgg cagtcttgaa    720
gcaacgaagc tcctacagtt caggccttct gagatggcag cagcagtggt tctgtcagca    780
gctgctgagt ctcaagtcat tgccttcagc ggcgctcttt tagcttctaa tatccttgtc    840
aataaggaaa atgtaaggag atgccatgaa gcattgcaag aagtgggatt agtgaagaag    900
aaaacagact acagtgcgag tccatctcgc gtgctagatg cctcatgctt cagcttcaag    960
actgacgata accagacagc cggttcatcc caatcccaag caaacaacaa tggcaactac   1020
aaccaggctt actctccagc tagcaagagg acaaggctag acatctagac t            1071
```

<210> SEQ ID NO 11
<211> LENGTH: 5918
<212> TYPE: DNA
<213> ORGANISM: Zea mays

<400> SEQUENCE: 11

```
ttggtagtgg aattagctag ctaacaaata actatctaac tattaactaa tttaccaaaa     60
atagctaata gttgaactat taactaaagt gtttggatgt ctcaactaat tttagctact    120
aactattagc tctagtgcat tcaaacaccc cttaagtgaa tgtcatggta tgggctgaca    180
tttcgagagg tggagagtgt catggtatgg gctgccatgt gggccgagag tccgagaccg    240
ggctaaatga gctgggctga ataggactga ctgcaggtag aaaggcaagc gcaacatttg    300
gcaccgttag ctctccacta aacttgtcag atgcaataat ttatgttttt attaatggca    360
aagccctcct gccagccagt gccttccttc cgggtcaacc actggtacag tcacatcacg    420
aattcccact ggcagtacga taacctcact gagcggtagg gcctcccgtc ccagaatcct    480
gcaggaccca tcgatcatgg ccccacgggt cctgctcctg cgtgggttcc aattccaagt    540
cgcccaccgt gacgcccatc gagtcaaccg aacccaagcc gtgtggcgac tggcgaggcg    600
agtgccccag ttcctaactc cggtgggcgc gctcccaccg ccgcgcggct caaaacccgc    660
cctcagcctc ccgcgctcca gtccacacgg gagcgggtgg tgtcgtctga agcggcgcga    720
tcaaggagtc ttcgggcgct ccggtgagct atctagatct caacatcctc tcccctctgt    780
agtctgtagt tgtactctcc cgcccgatgg ttcagttaag ttatatcctc tccccttatt    840
tttactcggt cgataccatt tcgttgtgga ttgggcgccc ccgcaggttg aaatgctgcc    900
catcatgctg cggccctgta ctatgaggat ggttctagtt ttgcgtctgg caatttgggg    960
cgtacatgct tttggctgcg tactgttact gatcggagaa aatgtttgta acgtatgatt   1020 cgttttttcag gacgtaacgt gctggcggtt gcttatctcc ggatgtatat ataagcggaa   1080
atgttctcct tgttctatgg cctgtggaag tatgtgttcg ccaaggacga gttccgtgtt   1140
ctgattcttg tgttgacag agctggcaag acggtagctg ctagctccca gccttcatat   1200
atatatttcc ctttctgaac tagaaattga tgatacttac ctgtacacga tgtttctgga   1260
```

```
accgttgcca tagactttgc tggagaagtt gaaatcgata tatctcaagg gggaaggact      1320
tccgcctgac cgtgtcgttc aacagttgg gctcaacatt ggccgcatcg aagacgcaaa       1380
ggcaaaactt gttttctggg atctaggtgg tcaggtaaga acgtttacgt acgtagtaaa      1440
gtgagccttc tgttgccgtg gcaccaccct acgatcgttg atatttgagt cttgtcagtt      1500
tggtgctata tcagggtttc taatgcctgg gaaatacatg tcataaattc aaattactag      1560
gatgtggttg ctttagttat taacctagca tcttttttgcg ttccagcaga atatatataa     1620
tctagttata tggaatgctc aatagaattt tcagaaagca aagatatgct ctgttggcta      1680
acattcacag tactcaatag aattgtttac tagtagaaca gcatcagctt ctctgctatg      1740
ttataagaat tagtgtaaaa ctaacttcag tatcactgct tgctagtatg ataattaagc      1800
ttccatgcca agttcagtat ttcttacaca cttgcctgct tggcaggtta gcctacgaac      1860
aatctgggag aaatactatg aagaggccca tgccataatg tacgttattg acgctgccac      1920
agcatcgtca tttgaagatt ccaaatctgc tctgggtaag gttcttattt gtgttaatta      1980
taaactactc cctccattcc aaattataag acattttggc ctttttttcta gataaataaa     2040 ttttgctatg gacttaaata ttatttatat atatatatat atatatataa aatgtcctgg      2100
tacatagtta aaacattata tcttaaaaag ctaaacatt gtcttataac ttggaacaag       2160
ggagtactgg tttgtttcta ttgctagatc ttccgagaag atgcattgcc tctctggtaa      2220
atgggatgag aactcattct agctagagaa cctaacctaa atttcttact tcagagaagg      2280
ttattcgcca tgaacatctg agaggagcac cactcttgat agttgcaaac aaacaggtga      2340
agggtttact tccactttct atattttgta ccacagtaca taattatgat tgaaagattc      2400
agtgcttaca ataagttgc catcgtagta aaataaagat tttgttttg tcatgtgccc        2460 atgctgtgag gcatacaaat ctaaattcct acgttgcaaa gcgcctatgc gccattgcga      2520
ggttgaatac cagatgtagt ttggccaatt gtgatgtaca gatgtgccac attgacaatt      2580
gacacgcagt ttaaggaga gtcagactac tagttttttc attgcccaac atatacccttt     2640 ggccacttat tgaaaatgtg agagatcatt tgagtttgaa cagtaagttt tgtgagatat      2700
cattttattt agtaatcatg cacacatgtc tagaattgtg aaatgcacaa taaagacgca      2760
aactcccacg agcatgcagg tacacccgat tgaggattct cagcgaatgt tccagtttcg      2820
agaatcaaac aacatataac aatgatgaat ttttaaatc aattaaaact tcctgaaaag       2880
atcacatgga aaccaatgac tacatgcact gtctgtttct gttaagctgg gtacacatta      2940
ttctatcaaa ttgtttatta tttacctctt gttctcatgt ttggagggtg cttctggatt     3000
tcttttggca ggatttacct ggagccattg atgaggaaga attggctaaa tttctgcata     3060
aagaactgga tgagaggcca tatacatttc aggctgtatc tgcatatgat gggtgagcgc     3120
agaaactcaa ctggttcctg aggaaatttg actcgccatg aaaaaaatg acaattttac      3180 tcaaagatac aaaaaattca cacattcgtc tgttatattg tttcctgggt gcatgaaact     3240
caactggttc gtgaggaaat ttgactcgcc atgaaaaaaa tgacaatttt actcaaagat     3300
acaaaaaatt cacacattcg tctgttatat tgtttcctgg gtgcatgata ttctaaagat     3360
ctgttatatt gtttaaatgt gacaccggct cttgcagcag ggggatcaaa tctggcatag     3420
actggctggt ggaacaaatg gaaaaaagca aacgtaccga gacactgcag gctcgtgctg     3480
gcgtagctgg acaaatttag aatggggtga atttgttaaa gaacaaagca ttggatagga     3540
cggcttcctt cgtatcgcgt aagcagccat ttgctgcatt ccgggattat cgttccaggt     3600
cgcccagagt gctgcaagaa atgtttggct ggttgctcct gtggtggtgg tgattggtga     3660
```

```
ggcgattcgt tggtattat tgaggttgca ttcatatgta cctaaaggtc gcaagcatac      3720
atgtctatat gatgcttttc aattttcgta gcaaactagt agcttcaata cagaggatca      3780
aagagagccg tgttctttaa cttgtttgtg ataaaaaaaa aggaagaaag gaaagcgaag      3840
aaggaattat tggtgcatct gaaagtcttt attgcatatg tctaaaccat tttaaccgat      3900
gctggatgag cttttcttcg caccgatgtt acatctagtc tatcatatgt atcctcgttt      3960
catactcgca ccgatgttac atctagtcta tcatatgtat cctcgtttca tactcgatcc      4020
ttttttatgg ccaaactcca acacaacata tacatttctg tagcgcatac gtattgaaca      4080 tgtcttttt agactaacat tctgcaccga acaatatagc agatcgaatt gtcatcctat       4140
aaagattatt tttaactttt gtggtatcct attgtcatat ttattgaggt tgcattcata      4200
tgtacctaaa ggtcgcaagc atacatgtct atatgatgct tttcaatttt cgtagcaaac      4260
tagtagcttc aatacagagg atcaaagaga gccgtgttct ttaacttgtt tgtgataaaa      4320
aaaaaggaag aaaggaaagc gaagaaggaa ttattggtgc atctgaaagt ctttattgca      4380
tatgtctaaa ccatttttaac cgatgctgga tgagcttttc ttcgcaccga tgttacatct     4440
agtctatcat atgtatcctc gtttcatact cgcaccgatg ttacatctag tctatcatat      4500
gtatcctcgt ttcatactcg atcctttttt atggccaaac tccaacacaa catatacatt      4560
tctgtagcgc atacgtattg aacatgtctt ttttagacta acattctgca ccgaacaata      4620
tagcagatcg aattgtcatc ctataaagat tcttttttaac ttttgtggta tcctattgtc     4680
atatagaaca tcaaatgttt ggcgccacct catcctttga ctaataccctt tatcactatc     4740 tctacgtagc ctttcgtagc atagatccta aatatctatg catagatcct aaatatctat      4800
gcatagatcc taaatatcta aagatgtcct ttcagaacac tacttgattt ttcaaactaa      4860
catgtctttc ctcatatgta gtagcataga ttctaaatat ctaaagatgt ccttccggac      4920
actacttgat ttttcaaact aacatgtctt tcctcatatg tagtagtgtt gaaatcacat      4980
cttttatatt caatttgagt tctactgatc gagtccaaaa tcgtccaaaa cctttaaact      5040
ctagaatctc ccacgacaac tctagttttc catttactcg tgcttagctt tcatcaacta      5100
acactacatc cataaaaaca tatgttaaga gatccctttg tgatcttatc catagactca      5160 aagctaatt ttttatgtag tcatattcta atcggaaagt cacatgtgtc tccatcattt       5220
attcaaacat attcataaca ttgttgttgg aactttgctt cctcaaaaaa tagggataaa      5280
aaaaacagta aaaggaattg gcccttcagg ctagggctgc tgatatcccc actaagctgg      5340
gccaatcggc caagaaactt tgcttcattc agggcatggt atggacaacc cactgcgggt      5400
tgccaaacaa aggagttagt aagaaaccac aaaatgctta gtctgagctt gaagagttc       5460 tacttggtga gtaaaacagt taatcttaac tactgcttgg ctaagataag atgttagtca      5520
aaagaattct gtagatgtgc aatctcaaac caatctgcct ttgcatcatt tagaaaactg      5580
ctttaaaatt cgaaatattt tgcttaccat agctcatagc acagaagaat attatagaac      5640
aaaccaaggc aagtgacttt ctgaaacaca gttttcaaga acaggttcag attaaactag      5700
ataacaggat gccagcgttg gtaataagtg tactccccaa gagaagtcgc tgttttgttc      5760
tatctcaatg aaaaataacg acacgaaaat gaactatggc cgtctgcatt aatatggata      5820
ctcagcaaaa atggacatga gtaactcaaa atcgtcaatt gcttgctatg ttaggcaccc      5880
aagtcaatga tttctattcc atgctatcac aaagatta                              5918
```

<210> SEQ ID NO 12

<211> LENGTH: 1288
<212> TYPE: DNA
<213> ORGANISM: Zea mays

<400> SEQUENCE: 12

| | | | | | |
|---|---|---|---|---|---|
| ttccaagtcg | cccaccgtga | cgcccatcga | gtcaaccgaa | cccaagccgt | gtggcgactg | 60 |
| gcgaggcgag | tgccccagtt | cctaactccg | gtgggcgcgc | tcccaccgcc | gcgcggctca | 120 |
| aaacccgccc | tcagcctccc | gcgctccagt | ccacacggga | gcgggtggtg | tcgtctgaag | 180 |
| cggcgcgatc | aaggagtctt | cgggcgctcc | ggacgtaacg | tgctggcggt | tgcttatctc | 240 |
| cggatgtata | tataagcgga | aatgttctcc | ttgttctatg | gcctgtggaa | gtatgtgttc | 300 |
| gccaaggacg | agttccgtgt | tctgattctt | ggtgttgaca | gagctggcaa | gacgactttg | 360 |
| ctggagaagt | tgaaatcgat | atatctcaag | ggggaaggac | ttccgcctga | ccgtgtcgtt | 420 |
| ccaacagttg | ggctcaacat | tggccgcatc | gaagacgcaa | aggcaaaact | tgttttctgg | 480 |
| gatctaggtg | gtcaggttag | cctacgaaca | atctgggaga | aatactatga | agaggcccat | 540 |
| gccataatgt | acgttattga | cgctgccaca | gcatcgtcat | ttgaagattc | caaatctgct | 600 |
| ctggagaagg | ttattcgcca | tgaacatctg | agaggagcac | cactcttgat | agttgcaaac | 660 |
| aaacaggatt | tacctggagc | cattgatgag | gaagaattgg | ctaaatttct | gcataaagaa | 720 |
| ctggatgaga | ggccatatac | atttcaggct | gtatctgcat | atgatggcag | ggggatcaaa | 780 |
| tctggcatag | actggctggt | ggaacaaatg | gaaaaaagca | aacgtaccga | gacactgcag | 840 |
| gctcgtgctg | gcgtagctgg | acaaatttag | aatggggtga | atttgttaaa | gaacaaagca | 900 |
| ttggatagga | cggcttcctt | cgtatcgcgt | aagcagccat | ttgctgcatt | ccgggattat | 960 |
| cgttccaggt | cgcccagagt | gctgcaagaa | atgtttggct | ggttgctcct | gtggtggtgg | 1020 |
| tgattggtga | ggcgattcgt | ttggtattat | tgaggttgca | ttcatatgta | cctaaaggtc | 1080 |
| gcaagcatac | atgtctatat | gatgcttttc | aattttcgta | gcaaactagt | agcttcaata | 1140 |
| cagaggatca | aagagagccg | tgttctttaa | cttgtttgtg | ataaaaaaaa | aggaagaaag | 1200 |
| gaaagcgaag | aaggaattat | tggtgcatct | gaaagtcttt | attgcatatg | tctaaaccat | 1260 |
| tttaaccgat | gctggatgag | cttttctt | | | | 1288 |

<210> SEQ ID NO 13
<211> LENGTH: 979
<212> TYPE: DNA
<213> ORGANISM: Zea mays

<400> SEQUENCE: 13

| | | | | | |
|---|---|---|---|---|---|
| aatcgagtca | accgaaccca | agccgtgtgg | cgactggcga | ggcgagtgcc | ccagttccta | 60 |
| actccggtgg | gcgcgctccc | accgccgcgc | ggctcaaaac | ccgccctcag | cctcccgcgc | 120 |
| tccagtccac | acgggagcgg | gtggtgtcgt | ctgaagcggc | gcgatcaagg | agtcttcggg | 180 |
| cgctccggac | gtaacgtgct | ggcggttgct | tatcaccgga | tatatatata | taagcggaaa | 240 |
| tgttctcctt | gttctatggc | ctgtggaagt | atgtgttcgc | caaggacgag | ttccgtgttc | 300 |
| tgattcttgg | tgttgacaga | gctggcaaga | cgactttgct | ggagaagttg | aaatcgatat | 360 |
| atctcaaggg | ggaaggactt | ccgcctgacc | gtgtcgttcc | aacagttggg | ctcaacattg | 420 |
| gccgcatcga | agacgcaaag | gcaaaacttg | ttttctggga | tctaggtggt | caggttagcc | 480 |
| tacgaacaat | ctgggagaaa | tactatgaag | aggcccatgc | cataatgtac | gttattgacg | 540 |
| ctgccacagc | atcgtcattt | gaagattcca | aatctgctct | ggagaaggtt | attcgccatg | 600 |
| aacatctgag | aggagcacca | ctcttgatag | ttgcaaacaa | acaggattta | cctggagcca | 660 |

```
ttgatgagga agaattggct aaatttctgc ataaagaact ggatgagagg ccatatacat      720
ttcaggctgt atctgcatat gatgggtgag cgcagaaact caactggttc ctgaggaaat      780
ttgactcgcc atgaaaaaaa atgacaattt tactcaaaga tacaaaaaat tcacacattc      840
gtctgttata ttgtttcctg ggtgcatgaa actcaactgg ttcgtgagga aatttgactc      900
gccatgaaaa aaatgacaat tttactcaaa gatacaaaaa attcacacat tcgtcaaaaa      960
aaaaaaaaaa aaaaaaaaa                                                  979

<210> SEQ ID NO 14
<211> LENGTH: 1305
<212> TYPE: DNA
<213> ORGANISM: Zea mays

<400> SEQUENCE: 14
aaccgaaccc aagccgtgtg gcgactggcg aggcgagtgc cccagttcct aactccggtg       60
ggcgcgctcc caccgtcgcg cggctcaaaa cccgccctca gcctcccgcg ctccagtcca      120
cacgggagcg ggtggtgtcg tctgaagcgg cgcgatcaag gagtcttcgg gcgctccgga      180
cgtaacgtgc tggcggttgc ttatcaccgg atatatatat ataagcggaa atgttctcct      240
tgttctatgg cctgtggaag tatgtgttcg ccaaggacga gttccgtgtt ctgattcttg      300
gtgttgacag agctggcaag acgactttgc tggagaagtt gaaatcgata tatctcaagg      360
gggaaggact tccgcctgac cgtgtcgttc aacagttggg gctcaacatt ggccgcatcg      420
aagacgcaaa ggcaaaactt gttttctggg atctaggtgg tcaggttagc ctacgaacaa      480
tctgggagaa atactatgaa gaggcccatg ccataatgta cgttattgac gctgccacag      540
catcgtcatt tgaagattcc aaatctgctc tggagaaggt tattcgccat gaacatctga      600
gaggagcacc actcttgata gttgcaaaca aacaggattt acctggagcc attgatgagg      660
aagaattggc taaatttctg cataaagaac tggatgagag gccatataca tttcaggctg      720
tatctgcata tgatgggagg gggatcaaat ctggcataga ctggctggtg aacaaatgg       780 aaaaaagcaa acgtaccgag acactgcagg ctcgtgctgg cgtagctgga caaatttaga      840
atggtaagct tgcagctgcg accggatgaa tttgttaaaa gaacaaagca ttggatagga      900
cggcttcctt cgtatcgcgt aagcagccat ttgctggatt acagggatta tcgttccagg      960
ccgcccagag tgctgcaaga aatgtttggc tggttgctcc tgtggtggtg gtgattggtg     1020
aggcgattcg tttggtatta gaggttgcat tcatatgtac ctaaaggtca cgagcataca     1080
tgtctatatg atgcttttca attttcgtag caaactagta gcttcaacac agaggatcaa     1140
agagagccgt gttctttaac ttgtttgtga taaaaaaag gaagaaagga agcgaagaa       1200 ggaatcactg gtgcatctga aagtctttat tggatatgtc taaaccattt caactgatgc     1260
tggataagtt tttcttaaaa aaaaaaaata aaaaaaaaa aaaaa                      1305

<210> SEQ ID NO 15
<211> LENGTH: 3993
<212> TYPE: DNA
<213> ORGANISM: Zea mays
<220> FEATURE:
<221> NAME/KEY: misc_feature
<222> LOCATION: (2094)..(2094)
<223> OTHER INFORMATION: n is a, c, g, or t

<400> SEQUENCE: 15
tgaaaatata tattgaataa cttttaacgg cttttagtgg tttccatcaa acggttttta       60
```

```
gctttttaac atctcacagc ccacagtaac ttttccaca gctcacaacc tatagcagct   120
tttttcacag ccacatccca actaaaaaga ccctaagtga atgtcatggt atgggctgac   180
atttcgagag gtggacaaat ggagaatggc atgatatggg ctgccatgtg ggccgagggt   240
ctgagaccgg gctaaatgag ctgggctgaa gaggactgac tgtaggtaga aaggcaagcg   300
caacatttgg caccgttagc tctccactaa acttgtcaga tgcaataatt tatgtttttt   360
aaatggcaaa gccctcctgc cagccagtgc cttccttccg ggtcaaccac tggtaccgtc   420
acatcacgaa ttcccactgg cagtacgata acctcactga gcggtagggc ctcccgtccc   480
agaatcctgc aggacccatc gatcatggcc ccacgggtcc tgctcctgcg tgggttccaa   540
ttccaagtcg cccaccgtga cgcccatcga gtcaaccgaa cccaagccgt gtggcgactg   600
gcgaggcgag tgccccagtt cctaactccg gtgggcgcgc tcccaccgcc gcgcggctca   660
aaacccgccc tcagcctccc gcgctccagt ccacacggga gcgggtggtg tcgtctgaag   720
cggcgcgatc aaggagtctt cgggcgctcc ggtgagctat ctagatctca acatcctctc   780
ccctctgtag tctgtagttg tactctcccg cccgatggtt cagttaagtt atatcctctc   840
cccttatttt tactcggtcg ataccatttc gttgtggatt gggcgccccc gcaggttgaa   900
atgctgccca tcatgctgcg gccctgtact atgaggatgg ttctagtttt gcgtctggca   960
atttggggcg tacatgcttt tggctgcgta ctgttactga tcggagaaaa tgtttgtaac  1020
gtatgattcg tttttcagga cgtaacgtgc tggcggttgc ttatctccgg atgtatatat  1080
aagcggaaat gttctccttg ttctatggcc tgtggaagta tgtgttcgcc aaggacgagt  1140
tccgtgttct gattcttggt gttgacagag ctggcaagac ggtagctgct agctcccagc  1200
cttcatatat atatttccct ttctgaacta gaaattgatg atacttacct gtacacgatg  1260
tttctggaac cgttgccata gactttgctg agaagttga atcgatata tctcaagggg  1320 gaaggacttc cgcctgaccg tgtcgttcca acagttgggc tcaacattgg ccgcatcgaa  1380
gacgcaaagg caaaacttgt tttctgggat ctaggtggtc aggtaagaac gtttacgtac  1440
gtagtaaagt gagccttctg ttgccgtggc accaccctac gatcgttgat atttgagtct  1500
tgtcagtttg gtgctatatc agggtttcta atgcctggga aatacatgtc ataaattcaa  1560
attactagga tgtggttgct ttagttatta acctagcatc ttttttgcgtt ccagcagaat  1620 atatataatc tagttatatg gaatgctcaa tagaattttc agaaagcaaa gatatgctct  1680
gttggctaac attcacagta ctcaatagaa ttgtttacta gtagaacagc atcagcttct  1740
ctgctatgtt ataagaatta gtgtaaaact aacttcagta tcactgcttg ctagtatgat  1800
aattaagctt ccatgccaag ttcagtattt cttacacact tgcctgcttg gcaggttagc  1860
ctacgaacaa tctgggagaa atactatgaa gaggcccatg ccataatgta cgttattgac  1920
gctgccacag catcgtcatt tgaagattcc aaatctgctc tgggtaaggt tcttatttgt  1980
gttaattata aactactccc tccattccaa attataagac attttggcct tttttctaga  2040
taaataaatt ttgctatgga cttaaatatt atttatatat atantatata  2100
tatatatata tataaaatgt cctggtacat agttaaaaca ttatatctta aaaagctaaa  2160
acattgtctt ataacttgga acaagggagt actggtttgt ttctattgct agatcttccg  2220
agaagatgca ttgcctctct ggtaaatggg atgagaactc attctagcta gagaacctaa  2280
cctaaatttc ttacttcaga gaaggttatt cgccatgaac atctgagagg agcaccactc  2340
ttgatagttg caaacaaaca ggtgaagggt ttacttccac tttctatatt ttgtaccaca  2400
gtacataatt atgattgaaa gattcagtgc ttacaataaa gttgccatcg tagtaaaata  2460
```

```
aagattttgt ttttgtcatg tgcccatgct gtgaggcata caaatctaaa ttcctacgtt    2520
gcaaagcgcc tatgcgccat tgcgaggttg aataccagat gtagtttggc caattgtgat    2580
gtacagatgt gccacattga caattgacac gcagtttaaa ggagagtcag actactagtt    2640
ttttcattgc ccaacatata cctttggcca cttattgaaa atgtgagaga tcatttgagt    2700
ttgaacagta agttttgtga gatatcattt tatttagtaa tcatgcacac atgtctagaa    2760
ttgtgaaatg cacaataaag acgcaaactc ccacgagcat gcaggtacac ccgattgagg    2820
attctcagcg aatgttccag tttcgagaat caaacaacat ataacaatga tgaattttt     2880 aaatcaatta aaacttcctg aaaagatcac atggaaacca atgactacat gcactgtctg    2940
tttctgttaa gctgggtaca cattattcta tcaaattgtt tattatttac ctcttgttct    3000
catgtttgga gggtgcttct ggatttcttt tggcaggatt tacctggagc cattgatgag    3060
gaagaattgg ctaaatttct gcataaagaa ctggatgaga ggccatatac atttcaggct    3120
gtatctgcat atgatgggtg agcgcagaaa ctcaactggt tcctgaggaa atttgactcg    3180
ccatgaaaaa aaatgacaat tttactcaaa gatacaaaaa attcacacat tcgtctgtta    3240
tattgtttcc tgggtgcatg aaactcaact ggttcgtgag gaaatttgac tcgccatgaa    3300
aaaaatgaca atttttactca aagatacaaa aaattcacac attcgtctgt tatattgttt    3360
cctgggtgca tgatattcta aagatctgtt atattgttta aatgtgacac cggctcttgc    3420
agcaggggga tcaaatctgg catagactgg ctggtggaac aaatggaaaa aagcaaacgt    3480
accgagacac tgcaggctcg tgctggcgta gctggacaaa tttagaatgg ggtgaatttg    3540
ttaaagaaca aagcattgga taggacggct tccttcgtat cgcgtaagca gccatttgct    3600
gcattccggg attatcgttc caggtcgccc agagtgctgc aagaaatgtt tggctggttg    3660
ctcctgtggt ggtggtgatt ggtgaggcga ttcgtttggt attattgagg ttgcattcat    3720
atgtacctaa aggtcgcaag catacatgtc tatatgatgc ttttcaattt tcgtagcaaa    3780
ctagtagctt caatacagag gatcaaagag agccgtgttc tttaacttgt ttgtgataaa    3840
aaaaaaggaa gaaaggaaag cgaagaagga attattggtg catctgaaag tctttattgc    3900
atatgtctaa accattttaa ccgatgctgg atgagctttt cttcgcaccg atgttacatc    3960
tagtctatca tatgtatcct cgtttcatac tcg                                 3993

<210> SEQ ID NO 16
<211> LENGTH: 6492
<212> TYPE: DNA
<213> ORGANISM: Zea mays

<400> SEQUENCE: 16
cgaagaacaa ggaaagcact tgtccatcaa ttgcacttga gtagcaaagg tttcaggttg      60
tcggtgctga catctcttct actctgttaa gaccaggcta aggggtgtt tgaatgcact      120 agaactaata gttagttggc taaaaattgg tagtggaatt agctagctaa caataacta      180 tctaactatt aactaattta ccaaaaatag ctaatagttg aactattaac taaagtgttt     240
ggatgtctca actaatttta gctactaact attagctcta gtgcattcaa acaccccta      300 agtgaatgtc atggtatggg ctgacatttc gagaggtgga gagtgtcatg gtatgggctg     360
ccatgtgggc cgagagtccg agaccgggct aaatgagctg ggctgaatag gactgactgc     420
aggtagaaag gcaagcgcaa catttggcac cgttagctct ccactaaact tgtcagatgc     480
aataatttat gttttttatta atggcaaagc cctcctgcca gccagtgcct tccttccggg     540
```

```
tcaaccactg gtacagtcac atcacgaatt cccactggca gtacgataac ctcactgagc    600
ggtagggcct cccgtcccag aatcctgcag gacccaccga tcatagcccc acgggtcctg    660
ctcctgcgtg ggttccagtt ccaagtcgcc caccgtgacg cccatcgagt caaccgaacc    720
caagccgtgt ggcgactggc gaggcgagtg ccccagttcc taactccggt gggcgcgctc    780
ccaccgccgc gcggctcaaa acccgccctc agcctcccgc gctccagtcc acacgggagc    840
gggtggtgtc gtctgaagcg gcgcgatcaa ggagccttcg agcgctccgg tgagctatct    900
agatctcaac atcctctccc ctctgtagtc tgtagttgta ctctcccgcc cgatggttca    960
gttaagttat atcctctccc cttatttta ctcggtcgat accatttcgt tgtggattga    1020
aatgctgcgg ccctgtacta tgaggatggt tcctagtttt gcgtctggca atttggggcg    1080
tacatgcttt tggctgcgta ctgttactga tcggagaaaa tgtttgtaac gtatgattcg    1140
tttttcagga cgtaacgtgc tggcggttgc ttatcgccgg atatatatat ataagcggaa    1200
atgttctcct tgttctatgg cctgtggaag tatgtgttcg ccaaggacga gttccgtgtt    1260
ctgattcttg gtgttgacag agctggcaag acggtagctg ctagctccca gccttcatat    1320
atatatattt ccctttctga actagaaatt gatgaaactt acctgtacac aatgtttctg    1380
gaaccgttgc catagacttt gctggagaag ttgaaatcga tatatctcaa ggggaagga    1440
cttccgcctg accgtgtcgt tccaacagtt gggctcaaca ttggccgcat cgaagacgca    1500
aaggcaaaac ttgttttctg ggatctaggt ggtcaggtaa gaacgtttac gtacgtagta    1560
aagtgagcct tctgttgccg tggcaccacc ctacgatcgt tgatatttga gtcttgtcag    1620
tttggtgcta tatcagggtt tctaatgcct gggaaataca tgtcataaaa tcaaattact    1680
aggatgtggt tgctttagtt attaacctag catcttttg cgttccagca gaatatatat    1740
aatctagtta tatggaatgc tcaatagaat tttcagaaag caaagatatg ctctgttggc    1800
taacattcac agtactcaat agaattgggt ggctagtaga acagcatcag cttctctgct    1860
atgttataag aattagtgta aaactaactt cagtatcact gcttgctagt atgataatta    1920
agcttccatg ccaagttcag tatttcttac acacttgcct gcttggcagg ttagcctacg    1980
aacaatctgg gagaaatact atgaagaggc ccatgccata atgtacgtta ttgacgctgc    2040
cacagcatcg tcatttgaag attccaaatc tgctttgggt aaggttctta tttgtgtcaa    2100
ttataaacta cgccatccat tccaaattat aagacatttt ggccttttc tagataaata    2160
aattttgcta tggacttaaa tattaaaaat atatataatg tcctggtaca tagttaaaac    2220
aatatatcta gaaaagctaa aacatcgtct tataacttgg aacagaggga gtactggttt    2280
gtttctattg ctagatcttt ccagaagatg caatgcctct ctggtaaatg ggatgagaac    2340
tcattctaga gaacctaacc taaatttctt acttcagaga aggttattcg ccatgaacat    2400
ctgagaggag caccactctt gatagttgca acaaacagg tgaagggttt acttccactt    2460
tctatatttt gtaccacagt acataattat gattgaaaga tttagtgctt acaataaagt    2520
tgccatcgta gttaaaataa agattttgtt tttgtcatgt gcacatgctg tgaggcatac    2580
aaatataaat tcctacgttg caaagcgcct atgcgccatt gcgaggttga ataccagatg    2640
tagttttaa atcaattaaa acttcctgaa aagatcacat ggaaaccaat gactacatgc    2700
actgtctgtt tctgttaagc tgggtacaca ttattctatc aaattgttta ttatttacct    2760
ctagcttgtt ctcatgtttg gagggtgctt ctggatttct tttggcagga tttacctgga    2820
gccattgatg aggaagaatt ggctaaattt ctgcataaag aactggatga gaggacatat    2880
acatttcagg ctgtatctgc atatgatggg tgagcgcaga aactcaactg gttcctgagg    2940
```

```
aaatttgact cgccatgaaa aaaatgacaa ttttactcaa agatacaaaa aaattcacac    3000
attcgtctgt tatattgttt cctgggtgca tgatattcta aagatctgtt atattgttta    3060
aatgtgacac cggctcttgc aggaggggga tcaaatctgg catagactgg ctggtggaac    3120
aaatggaaaa aagcaaacgt accgagacac tgcaggctcg tgctggcgta gctggacaaa    3180
tttagaatgg ggtgaatttg ttaaagaaca aagcattgga taggaccgct tccttcgtat    3240
cgcgtaagca gccatttgct gcattccggg attatcgttc caggtcgccc agagtgctgc    3300
aagaaatgtt tggctggttg ctcctgtggt ggtggtgatt ggtgaggcga ttcgtttggt    3360
attattgagg ttgcattctt atgtacctaa aggtcgcaag catacatgtt tatatgatgc    3420
ttttcaattt tcgtagcaaa ctagtagctt caatacagag gatcaaagag agccgtgttc    3480
tttaacttgt ttgtgataaa aaaaggaag aaaggaaagc gaagaaggaa ttattggtgc    3540
atctgaaagt ctttattgat atgtctaaac catttcaacc gatgttggat gaggttttct    3600
tcgcaccggt gttacatcta gtctatcata tgtatcgtcg tttcatactc gatccttttt    3660
tatggccaaa ctccaacaca acatatgcat ttctgtagcg catatgtatt gaacatgtct    3720 ttttttagact aacattttgc accgaacaac atagcagatc gaattgtcat cctataaaac    3780 ttcttttttaa cttttgtggt atcctattgt catatagaat atcaaatgtt tggcgctacc    3840
tcatccattg actaatacct ttatcaatat ctctacgtag catagatcct aaatatctaa    3900
agatgtcctt catggacact acttgatttt tcaaactaac atgtctttcc taatatgtag    3960
tagcatagat cctaaatatc taaagatgtc cttcctggac actacttgat ttttcaaact    4020
aacatgtctt tcctcatatg tagtagtgtt gaaatcacat cttttatatt caatttgagt    4080
tctactgatc gagtccaaaa tcgtccaaaa cctttaaact ctagaatctc ccaccacaac    4140
tctagttttc tatttactcg tgcttagctt tcatcaacta acactacatc cataaaaaac    4200
atatgttaag agatatccct ttgtgatctt atccatagac tcagctaatt ttttatgtag    4260
tcatattcta atcgaaaagt cacatgtgtc tccatcattt attcaaacat attcataaca    4320
ttgttgttgg aactttgctt cctcaaaaaa cagggataaa aaacagtaaa aggaattggc    4380
ccttcaggct agagctgctg atatccccac taagctgggc caatcggcca agaaactttg    4440
cttcattcag ggcatgatat ggacaaccca ctgcggattg ccaaacaaag aagttagtaa    4500
gaaaccacaa aatgcttagt ctgagctttg aagagttcta cttggtgagt aaaacagtta    4560
atcttaacta ctgcttggct aagataagat gttagctaaa agaattctgt agatgtgcaa    4620
tctcaaacca atctgccttt gcatcattta gaaaactgct ttaaaattcg aaatattttg    4680
cttacaatag ctcatagcac agaagaatat tatagaacaa accaaggcaa gtgactttct    4740
gaaacacagt tttcaagaac aggttcagat taaactagat aacaggatgc cagcgttggt    4800
aataagtcta ctccccaaga gaagtcactg ttttgttctt tctcaatgaa aaataacgac    4860
acaaaaatga actatggccg tctgcattaa tatggatacg cagcaaaaat ggacatgagt    4920
aactcaaaat cgtcaagtgc ttgctatgtt aagcacccaa gtcaatgatt tatattccat    4980
gatatcgcaa agattatcta taacaagttc tgagtgtgtt tcaaacatta aatgatccat    5040
gaaaggtaag cacttgtatt tagcggacag tactagtctg ctgtgggatt aacccatttt    5100
ttatggttct cgatggcctt ttgcttcaag ataatatctg atccaattaa tagacaaaat    5160
cacaagtaat ctttgttaca tgtcatcatc gaatcctatc ttctgtagga gcaaacttaa    5220
acggtgacat atcaagcaac actatgagaa ttcatgtgta tctgataaag gatcattcac    5280
```

-continued

```
ttcacatgta gacatatatg actacaaaag tggtatgaat attgttaaca gaatcaatgg    5340
aaaatggaat atatctcatt aggtaacata tggaattgta agcaggctat aaaaaatcag    5400
aggtattaag tatcaattca gacagcagaa tgatgcaatg atcacaacca agtcaacaag    5460
ttatcataac taagattagt cctttttgtag ccaaagaagt ttaccgaact cagaaagcag    5520
aacataattc acttacttga tctcaacaac attttgtgtc accatgccag gaagaaacca    5580
gaagtggcat ggtaagcatt gccagtccaa ccagacctct gtgaagcatt atcccatcac    5640
tggaaacctc cacaaagcgt gtttgctaag gcaaatggca tgtatctcca tctaatgaac    5700
atacaaattt tgccctgcct gatgttaagt aactacaggt accaggtaga ctacaagtct    5760
acaactacaa cattacataa cagggatgga acaattacac tcaaatgaac acttgaacag    5820
caagagccag tctctgagac atctgcttcg gcctggctaa tcatagcccc agtaaaccat    5880
aacaacagtt aaatcatccg tccaagattg tccaccctca agaagtgcat gttgtgcaaa    5940
ttccccaata tatcctcaga tgcatcaaca tcgatatgaa agttgctgat atcttcaact    6000
ccgccagcac cgctaacatt aaccctacca gtgccatctg tagcatgtgc tgcctcattt    6060
atgttaattc tcctcacctc ctcggcccctt ccatctccag cgttctcatc cccagcccag    6120
ccttcctgcc cgagcatcga agaatcaatg ccactctcca caccaagaga acgtctcctg    6180
agccctaccc cgaccttctt gcgggccgtc gtcttcttga tcctacctct agaagagcca    6240
ccacgagcac tgtcattctg tggctgccta ccaccatggt ttccgtgact cctaccacca    6300
ccaccttggc cactgggagc cgtgttccaa ggaaacatct tgtagaatgg cttccagttg    6360
gcacccaggt cggccgcgtt gggaaatccg agggggaaga accccaggc gcagtggtac    6420 atttcagtgc ccggcacaac ggtgggtggg gtcgggagct cagaagccac gaatccgcgg    6480
cggcagcccg cg                                                        6492
```

<210> SEQ ID NO 17
<211> LENGTH: 10054
<212> TYPE: DNA
<213> ORGANISM: Zea mays

<400> SEQUENCE: 17

```
tttggatgtc tcaactaatt ttagctacta actattagct ctagtgcatt caaacacccc     60
ttaagtgaat gtcatggtat gggctgacat ttcgagaggt ggagagtgtc atggtatggg    120
ctgccatgtg ggccgagagt ccgagaccgg gctaaatgag ctgggctgaa taggactgac    180
tgcaggtaga aaggcaagcg caacatttgg caccgttagc tctccactaa acttgtcaga    240
tgcaataatt tatgttttta ttaatggcaa agccctcctg ccagccagtg ccttccttcc    300
gggtcaacca ctggtacagt cacatcacga attccactg gcagtacgat aacctcactg    360
agcggtaggg cctcccgtcc cagaatcctg caggacccac cgatcatagc cccacgggtc    420
ctgctcctgc gtgggttcca gttccaagtc gcccaccgtg acgccatcg agtcaaccga    480 acccaagccg tgtggcgact ggcgaggcga gtgcccccagt tcctaactcc ggtgggcgcg    540
ctcccaccgc cgcgcggctc aaaacccgcc ctcagcctcc cgcgctccag tccacacggg    600
agcgggtggt gtcgtctgaa gcggcgcgat caaggagcct tcgagcgctc cggtgagcta    660
tctagatctc aacatcctct cccctctgta gtctgtagtt gtactctccc gcccgatggt    720
tcagttaagt tatatcctct ccccttattt ttactcggtc gataccattt cgttgtggat    780
tgaaatgctg cggccctgta ctatgaggat ggttcctagt tttgcgtctg caatttggg    840 gcgtacatgc ttttggctgc gtactgttac tgatcggaga aaatgtttgt aacgtatgat    900
```

```
tcgttttca ggacgtaacg tgctggcggt tgcttatcgc cggatatata tatataagcg      960
gaaatgttct ccttgttcta tggcctgtgg aagtatgtgt tcgccaagga cgagttccgt     1020
gttctgattc ttggtgttga cagagctggc aagacggtag ctgctagctc ccagccttca     1080
tatatatata tttccctttc tgaactagaa attgatgaaa cttacctgta cacaatgttt     1140
ctggaaccgt tgccatagac tttgctggag aagttgaaat cgatatatct caaggggaa      1200 ggacttccgc ctgaccgtgt cgttccaaca gttgggctca acattggccg catcgaagac     1260
gcaaaggcaa aacttgtttt ctgggatcta ggtggtcagg taagaacgtt tacgtacgta     1320
gtaaagtgag ccttctgttg ccgtggcacc accctacgat cgttgatatt tgagtcttgt     1380
cagtttggtg ctatatcagg gtttctaatg cctgggaaat acatgtcata aaatcaaatt     1440
actaggatgt ggttgcttta gttattaacc tagcatcttt ttgcgttcca gcagaatata     1500
tataatctag ttatatggaa tgctcaatag aattttcaga aagcaaagat atgctctgtt     1560
ggctaacatt cacagtactc aatagaattg ggtggctagt agaacagcat cagcttctct     1620
gctatgttat aagaattagt gtaaaactaa cttcagtatc actgcttgct agtatgataa     1680
ttaagcttcc atgccaagtt cagtatttct tacacacttg cctgcttggc aggttagcct     1740
acgaacaatc tgggagaaat actatgaaga ggcccatgcc ataatgtacg ttattgacgc     1800
tgccacagca tcgtcatttg aagattccaa atctgctttg ggtaaggttc ttatttgtgt     1860
caattataaa ctacgccatc cattccaaat tataagacat tttggccttt ttctagataa     1920
ataaattttg ctatggactt aaatattaaa aatatatata atgtcctggt acatagttaa     1980
aacaatatat ctagaaaagc taaaacatcg tcttataact tggaacagag ggagtactgg     2040
tttgtttcta ttgctagatc tttccagaag atgcaatgcc tctctggtaa atgggatgag     2100
aactcattct agagaaccta acctaaattt cttacttcag agaaggttat tcgccatgaa     2160
catctgagag gagcaccact cttgatagtt gcaaacaaac aggtgaaggg tttacttcca     2220 cttttctatat tttgtaccac agtacataat tatgattgaa agatttagtg cttacaataa     2280
agttgccatc gtagttaaaa taagattttt gttttttgtca tgtgcacatg ctgtgaggca     2340
tacaaatata aattcctacg ttgcaaagcg cctatgcgcc attgcgaggt tgaataccag     2400
atgtagtttt taaatcaatt aaaacttcct gaaaagatca catggaaacc aatgactaca     2460
tgcactgtct gtttctgtta agctgggtac acattattct atcaaattgt ttattattta     2520
cctctagctt gttctcatgt ttggagggtg cttctggatt tcttttggca ggatttacct     2580
ggagccattg atgaggaaga attggctaaa tttctgcata aagaactgga tgagaggaca     2640
tatacatttc aggctgtatc tgcatatgat gggtgagcgc agaaactcaa ctggttcctg     2700
aggaaatttg actcgccatg aaaaaaatga caatttttact caaagataca aaaaaattca     2760
cacattcgtc tgttatattg tttcctgggt gcatgatatt ctaaagatct gttatattgt     2820
ttaaatgtga caccggctct tgcaggaggg ggatcaaatc tggcatagac tggctggtgg     2880
aacaaatgga aaaaagcaaa cgtaccgaga cactgcaggc tcgtgctggc gtagctggac     2940
aaatttagaa tggggtgaat tgttaaaga acaaagcatt ggataggacc gcttccttcg      3000
tatcgcgtaa gcagccattt gctgcattcc gggattatcg ttccaggtcg cccagagtgc     3060
tgcaagaaat gttttggctgg ttgctcctgt ggtggtggtg attggtgagg cgattcgttt     3120
ggtattattg aggttgcatt cttatgtacc taaaggtcgc aagcatacat gtttatatga     3180 tgctttttcaa ttttcgtagc aaactagtag cttcaataca gaggatcaaa gagagccgtg     3240
```

-continued

```
ttctttaact tgtttgtgat aaaaaaaagg aagaaaggaa agcgaagaag gaattattgg     3300
tgcatctgaa agtctttatt gatatgtcta aaccatttca accgatgttg gatgaggttt     3360
tcttcgcacc ggtgttacat ctagtctatc atatgtatcg tcgtttcata ctcgatcctt     3420
ttttatggcc aaactccaac acaacatatg catttctgta gcgcatatgt attgaacatg     3480 tctttttag actaacattt tgcaccgaac aacatagcag atcgaattgt catcctataa     3540
aacttctttt taacttttgt ggtatccat tgtcatatag aatatcaaat gtttggcgct     3600
acctcatcca ttgactaata cctttatcaa tatctctacg tagcatagat cctaaatatc     3660
taaagatgtc cttcatggac actacttgat ttttcaaact aacatgtctt tcctaatatg     3720
tagtagcata gatcctaaat atctaaagat gtccttcctg gacactactt gattttcaa     3780 actaacatgt ctttcctcat atgtagtagt gttgaaatca catcttttat attcaatttg     3840
agttctactg atcgagtcca aaatcgtcca aaacctttaa actctagaat ctcccaccac     3900
aactctagtt ttctatttac tcgtgcttag ctttcatcaa ctaacactac atccataaaa     3960
aacatatgtt aagagatatc cctttgtgat cttatccata gactcagcta atttttatg     4020 tagtcatatt ctaatcgaaa agtcacatgt gtctccatca tttattcaaa catattcata     4080
acattgttgt tggaactttg cttcctcaaa aaacagggat aaaaaacagt aaaggaatt     4140 ggcccttcag gctagagctg ctgatatccc cactaagctg ggccaatcgg ccaagaaact     4200
ttgcttcatt cagggcatga tatggacaac ccactgcgga ttgccaaaca agaagttag     4260 taagaaacca caaaatgctt agtctgagct ttgaagagtt ctacttggtg agtaaaacag     4320
ttaatcttaa ctactgcttg gctaagataa gatgttagct aaaagaattc tgtagatgtg     4380
caatctcaaa ccaatctgcc tttgcatcat ttagaaaact gctttaaaat tcgaaatatt     4440
ttgcttacaa tagctcatag cacagaagaa tattatagaa caaaccaagg caagtgactt     4500
tctgaaacac agttttcaag aacaggttca gattaaacta gataacagga tgccagcgtt     4560
ggtaataagt ctactcccca agagaagtca ctgttttgtt ctttctcaat gaaaataac     4620 gacacaaaaa tgaactatgg ccgtctgcat taatatggat acgcagcaaa atggacatg     4680 agtaactcaa aatcgtcaag tgcttgctat gttaagcacc caagtcaatg atttatattc     4740
catgatatcg caaagattat ctataacaag ttctgagtgt gtttcaaaca ttaaatgatc     4800
catgaaaggt aagcacttgt atttagcgga cagtactagt ctgctgtggg attaacccat     4860 ttttatggt tctcgatggc cttttgcttc aagataatat ctgatccaat taatagacaa     4920
aatcacaagt aatctttgtt acatgtcatc atcgaatcct atcttctgta ggagcaaact     4980
taaacggtga catatcaagc aacactatga gaattcatgt gtatctgata aaggatcatt     5040
cacttcacat gtagacatat atgactacaa aagtggtatg aatattgtta acagaatcaa     5100
tggaaaatgg aatatatctc attaggtaac atatggaatt gtaagcaggc tataaaaaat     5160
cagaggtatt aagtatcaat tcagacagca gaatgatgca atgatcacaa ccaagtcaac     5220
aagttatcat aactaagatt agtccttttg tagccaaaga agtttaccga actcagaaag     5280
cagaacataa ttcacttact tgatctcaac aacattttgt gtcaccatgc caggaagaaa     5340
ccagaagtgg catggtaagc attgccagtc caaccagacc tctgtgaagc attatcccat     5400
cactggaaac ctccacaaag cgtgtttgct aaggcaaatg gcatgtatct ccatctaatg     5460
aacatacaaa ttttgccctg cctgatgtta agtaactaca ggtaccaggt agactacaag     5520
tctacaacta caacattaca taacagggat ggaacaatta cactcaaatg aacacttgaa     5580
cagcaagagc cagtctctga gacatctgct tcggcctggc taatcatagc cccagtaaac     5640
```

```
cataacaaca gttaaatcat ccgtccaaga ttgtccaccc tcaagaagtg catgttgtgc    5700
aaattcccca atatatcctc agatgcatca acatcgatat gaaagttgct gatatcttca    5760
actccgccag caccgctaac attaacccta ccagtgccat ctgtagcatg tgctgcctca    5820
tttatgttaa ttctcctcac ctcctcggcc cttccatctc cagcgttctc atccccagcc    5880
cagccttcct gcccgagcat cgaagaatca atgccactct ccacaccaag agaacgtctc    5940
ctgagcccta ccccgacctt cttgcgggcc gtcgtcttct tgatcctacc tctagaagag    6000
ccaccacgag cactgtcatt ctgtggctgc ctaccaccat ggtttccgtg actcctacca    6060
ccaccacctt ggccactggg agccgtgttc aaggaaaca tcttgtagaa tggcttccag    6120
ttggcaccca ggtcggccgc gttgggaaat ccaggggga agaaccccca ggcgcagtgg    6180
tacatttcag tgcccggcac aacggtgggt ggggtcggga gctcagaagc cacgaatccg    6240
cggcggcagc ccgcgttggg gcacttgagg gcgcgcccga tcaggctgcg cgggtactgg    6300
tgcacgtagc agcagaaggg gcacgccgtc cagaactccg gggtgtccga ggcgggagcg    6360
gccgcggcgg gatactggga ggagtaaggg gtaccagtgg cgggatcggc gggcggcggg    6420
gggcggcgag agggatccga gaggaaggcg taggcgtcgt tgacgaggcg gagcgccatc    6480
tcggctcccg ggtgcgggtt gctggggccg aggaggagcg cgaggcggcg gaaggcgcgg    6540
gacacggcgg cctggtcggg gctgactccg ggcggcagct ggaggatggc gagcgggtcc    6600
ggctggcccg aggggcccat gaactgggaa gcgaggagga cgtcggcgac ggcgaggagc    6660
tcgtcaacgc cagcgaggag cgggttcgcc tccatcgacc gctccgcgaa gcgcttgcag    6720
ccgacgaggt cgcgcgccgc gaggagcttc tcggcgatct ccagccagcg ctccgcctgc    6780
gcggggccgt cgctggcgcc tccgccgccc ccgctcacgc tcccgccggt ggagaagtcc    6840
atggtttggg ggaggaaaag gtggatgctg tcggaggcag ctggtttggt tttggggagg    6900
gggaagatcc tgctgcccga ggggctcttg actggcgact gtctgtcagt ccgagagtat    6960
tttgttgggc agcacattta ttttaaggac aactgtgatt atacgttttc aacttcgtga    7020
attattgatt acgaaaatta aaaatgaggg gtaaaatcat aattgtaagg aagagaagg    7080 atatactcaa aattaatctg aaaataatat taaacttttt atggttaatt gtgattatag    7140
ccttctctca ctttacaatt gtgattttac cccttatttt tatttttaat cactaattct    7200
gatttttatt aacgttgata aggcggtgca acaacggct tgttttcaa aacagagggg    7260 taacaaagtt aaaaagaag ggataaaatc acaattaaaa tattagaaaa gggtataatc    7320
acaattatcc cttgatttta ttaggctctc tccaatcatt ctccatctca aatcccacat    7380
ttggactttc tattcatatt taaatatcct catcttcact attatttccc tattttacct    7440
cctctccaag catccctcta ttcagctctc cctttaccct ttaactaagc tatttgactt    7500
ttctacatca gtttttagag ttttaatat ttataatatc ataatacaca ttgtcactta    7560
accaaactta tagcagatta atttatagt taaaaacact aattagtgaa gagtagggtt    7620
ctatctttct cgttttacaa ggtgttttcc ttctctcacc ctacaagagg gaggagaggg    7680
acctgttgaa gctctctcga tgtacgaaat caccgaatac gtcgtgaagg ggaggggaaa    7740
ggatccgttg gagagcgtct tatagcctgt tagcttcgaa ttaaagtcag ttgtttagat    7800
tattgtagct gcaattcaca gagaccaaaa cactacagaa atagtaaaag ccgtttcgaa    7860
ttaaaaccaa gggaacgggc tattagtttt cccatatgca aacataccag accattgtag    7920
cgccccaccg cagagcaagt tttgcataca atcaatgtat aattggacta ccaaaaacca    7980
```

| | | | | |
|---|---|---|---|---|
| taaaaaattc | taaaaatata | taaatataat | ttattgttta | ctttattaga ttataaaatt | 8040 |
| ttaagtttaa | atttatacaa | tagtaaaaga | aaaaatatat | tcaattagat aaaaaaaatt | 8100 |
| ccctcaattc | cgtaaaataa | ggcctgcatt | ttaaaaaaaa | aagactcaat gttttaaaac | 8160 |
| ttttgactag | taattcagcc | aaaagcatat | attttagtat | atacatgtta tatacttgat | 8220 |
| ttgtattcaa | aaattacttt | aatttaatgc | tcgttatgtt | tttattgata gcatattttg | 8280 |
| aaataaacaa | atagtcaaag | tttcgctcca | aagactgtac | caaaaatata taccttgtta | 8340 |
| tataagatga | atgaattata | tattaacata | gcataaatca | atctaggatc ttaaatatga | 8400 |
| tatattgata | aagtaaataa | tatatatgta | taatttttta | aatattttg tgacttttga | 8460 |
| tagttggatt | gtatagaatg | tttggttgca | caatagtatt | ttcctcaagt gaaagatctt | 8520 |
| catcaatgtt | gtaatacagt | gacatgtcat | catcaagcct | ggttagatct atcctcaaaa | 8580 |
| tctactccat | aaatttaagg | gccaattccc | tgtatgccac | tagaaaatat actcattcct | 8640 |
| tgtatgccac | tgaccccaca | tgtcatagac | accaaaaaat | atacctatat gccactcagt | 8700 |
| ggcacacaag | gaatgagtat | aaaatttgat | ggcataccag | gaattttctc taaatttaat | 8760 |
| ttagagtttc | tagagtactt | ctcttttaac | ttcacctttt | ttagctacac ttgtttggtt | 8820 |
| gaaatataga | gccgcacagt | cccaaacaaa | ctctaaggat | gagttgatgt atccccaagt | 8880 |
| atatcttaca | aaaaatgata | taatgactct | atttatctta | tagggtattt gtgattatac | 8940 |
| cctctctggt | cttgaaattg | tgattttacc | catcgttttt | caacttttgtg atattttatc | 9000 |
| ccttcatttt | gaaaacgaag | agttgccata | cccttgtgcc | gttagatgca gttaacaatg | 9060 |
| ttaaatttga | tgcaaaagat | aaaaatacccc | aagcaattta | ttttgatttt accctcgtta | 9120 |
| tattatgtaa | tagtgatttc | acccctatta | gggttgtgcc | cataaagaat agaaaaggt | 9180 |
| agtttgaacc | tttcacccat | ttatttctc | atttttttat | ttttaatcac taattctgat | 9240 |
| tttcactaac | gatgttgaga | gtgaagggca | aatggtagct | tcgtatttaa aacggaggtg | 9300 |
| taaaattaga | aagttgaaaa | tgcagagtaa | aatcacaatt | gcaaggccaa cgaagggtat | 9360 |
| aatcacaatt | atctcttatc | ttactagtag | taattattag | attgtgagga ataaagtaat | 9420 |
| ggcagattat | ttcattctat | tttataaacc | aaacaaaact | tggaaaagta aaatatgat | 9480 |
| ggagtgtatg | tgggggtggt | tagggaggaa | aggcccaaaa | caagggtttt tcgaatctta | 9540 |
| cctaaataaa | aatcatggca | agctaaattg | ctaaaacaag | aatctaacgt gtttgtttgg | 9600 |
| cacttgcata | aagatggtat | cttttctatt | aattatatgt | ataaattctt agttactaat | 9660 |
| ggaattaatg | ttttatgaat | aatttggtgt | ctaaagatac | cttaaagat aaaaatcttc | 9720 |
| atgtagttct | ttcaaaaaaa | gagggtcatt | ctcacaatct | cacaaaaggt aattttatca | 9780 |
| aaaagaaatt | gaaatagtga | cacaacttgc | tcttttgagc | cacaaaccat ctgatacata | 9840 |
| ttttctttga | gtgcacttat | gctaggttac | tatagagaga | agtttatatt ttttttctc | 9900 |
| gaacacgcag | gaaaactgcg | catcattata | ttgaaagaga | gaaaggtccg aaatggacca | 9960 |
| aagtacaaag | ccaagcaggc | aaaaaataaa | aaggaaaaat | agtacagcct catgcactag | 10020 |
| gaatagccct | gatcctagca | aaagcagcca | gaag | | 10054 |

<210> SEQ ID NO 18
<211> LENGTH: 5714
<212> TYPE: DNA
<213> ORGANISM: Zea mays

<400> SEQUENCE: 18

| | | | | | |
|---|---|---|---|---|---|
| atcacgcctc | gcccgagcct | agcctcgggc | aagggcagcc | gaccccgaag gggtttccgt | 60 |

```
ctcgcccgag ccccccttc aacggcggac acatctccgg cttgcccgag gccttgcctt      120
cgctgagaag caaccctgac tgaatcgccg caccgaccgg ccaagtcgca ggagcattta      180
acgcaaagga aaccaggccc tgccaaaggc accataggaa actccgctcc gcccaaccca      240
gggctcggac tcgggcaaag ccccggaaga cggcgaactc cgctccgccc gacccagggc      300
tcggactcgg gctaagcccc ggaagacggc gaactccgct ccgcccgacc cagggctcgg      360
actcgggcta agcccggaa gacggcgaac tccgctccgc cgaccaagg gctcggactc       420 gggctaagcc ccggaagacg gcgaactccg ctccgcccga ccaagggctc ggactcgggc      480
taagccccgg aagacggcga actccgctcc gcccgaccaa gggctcggac tcgggctaag      540
ccccggaaga cgacgaactc cgcctcgccc gacctagggg ctcggactcg gcctctgctg      600
acgaactctg cctcgcccga cccaggggct cggactcggc tctgctgac gaactccgcc       660 tcgcccgacc caggggctcg gactcggcct ctgctgacga actccgcctc gcccgacccg      720
ggggctcgga ctcggcctct gctgacgacc tccgcctcgc ccgacccagg ggctcggact      780
cggcttctgc tgacgacctc cgcctcgccc gacccagggg ctcggactcg gcctcggcca      840
tggaagacag actcgacccc ggcttcggag gagcctccac gtcgcccaac ctagggccca      900
ggccagccac gtcgacagga agcgccatca tcaccctacc cgagccgac tcgggtcgca       960 gagaacaaga cctgtgtccc atctggctgg ctccgccaga taggcaatga tggcgccccg     1020
ctagccccgt gacgacggcg gctctcagct ctcttacgga agcagggcga cgtcagcaag     1080
gacacaaccg ttccaacagc tgtccctccg ccaggctccg ttgctcctcc gacagccacg     1140
acatcacgcc agcagggtgc caagatctct ccggctgcca tattggcatg tacttagggc     1200
actagctctc ccccgctag acacgtagca ctccgctaca ccccattgta cgcctggatc      1260
ctctccttac gcctataaaa ggaaggacca gggccttctt agagaaggtt ggccgcgcgg     1320
ggacgaggac ggggacaggc actctcttgc ggccgctcgc ttccctcacc cgtgtggacg     1380
cttgtaaccc cctattgcaa gcgcacccga cctgggcgcg ggacgaacac gaaggccgcg     1440
ggattcccac ctctctctcg ccggactccg gcctcctcgc tcctttcccc cttcgcgctc     1500
gcccacgcgc tcgacccatc tgggctgggg cacgcagcac actcactcgt cggcttaggg     1560
accccccggt ctcgaaacgc cgacactact cttgaggaga ttattagatt atcataatct     1620
aggctttaga ttatataatc tgaacacata atctagttgt ttgtttatct aatgattat      1680 ttacgctaga ttatataatc tggagagatt ataatctgaa acaaacatgg ccttagtgat     1740
taaaaataaa aataaggggt aaaatcacaa ttgtaaagtg agagaaggct ataatcacaa     1800
ttaaccataa aaagtttaat attattttca ggttaatttt gagtatatcc ttctcttccc     1860
ttacagttat gattttaccc cttatttta attttgtaa tcataattc acaagttga         1920 aaacgtataa tcacagttgt ccttaaaatt aaatgtgctg cccaacaaa tactctcgga     1980 ctgacagaca gtcgccagtc aagagcccct cgggcagcag gatcttcccc ctccccaaaa     2040
ccaaaccagc tgcctccgac agcatccacc ttttcctccc ccaaaccatg gacttctcca     2100
ccggcgggag cgtgagcggg ggcggcgag cgccagcga cggccccgcg caggcggagc        2160
gctggctgga gatcgccgag aagctcctcg cggcgcgcga cctcgtcggc tgcaagcgct     2220
tcgcggagcg gtcggtggag gcgaacccgc tcctcgccgg cgttgacgaa ctcctcgccg     2280
tcgccgacgt cctcctcgct tcccagttca tgggcacctc gggccagccg gacccgctcg     2340
ccatcctcca gctgccgccc ggagtcagcc ccgaccaggc cgccgtgtcc cgcgccttcc     2400
```

```
gccgcctcgc gctcctcctc ggtcccagca acccgcaccc gggagccgag atggcgctcc      2460
gcctcgtcaa cgacgcctac gccttcctct cggatccctc tcgccgcccc cgccgcccg       2520
ccgatcccgc cactggtacc ccttactcct cccagtatcc cgccgcggcc gctcccgcct      2580
ccgacacccc ggagttctgg acggcgtgcc ccttctgctg ctacgtgcac cagtacccgc      2640
gcagcctgat cgggcgcgcc ctcaagtgcc ccaacgcggg ctgccgccgc ggattcgtgg      2700
cttctgagct cccgacccca cccacggttg tgccgggcac tgaaatgtac cactgcgcct      2760
gggggttctt cccctcgga tttcccaacg cggccgacct gggtgccaac tggaagccat       2820
tctacaagat gttcccttgg aacacggctc ccagtggcca aggtggtggt ggtaggagtc      2880
acggaaacca tggtggtagg cagccacaga atgacagtgc tcgtggtggc tcttctagag      2940
gtaggatcaa gaagacgacg gcccgcaaga aggtcggggt agggctcagg agacgttctc      3000
ttggtgtgga gagtggcatt gattcttcga tgctcgggca ggaaggctgg gctggggatg      3060
agaacgctgg agatgaagg gccgaggagg tgaggagaat taacataaat gaggcagcac      3120
atgctacaga tggcactggt agggttaatg ttagcggtgc tggcggagtt gaagatatcg      3180
gcaactttca tatcgatgtt gatgcatccg aggatatatt ggggaatttg cacaacatgc      3240
acttcttgag ggtggacaat cttggacgga tgatttaact gttgttatgg tttactgggg      3300
ctatgattag ccaggccgac tcttgctgtt caagtgttca tttgagtgta attgttccat      3360
ccctgttatg taatgttgta gttgtagact tgtagtctac ctggtacctg tagttactta      3420
acatcaggca gggaaaaatt tgtatgttca ttagatggag atacatgcca tttgccttag      3480
caaacacact ttgtggaggt ttccagtgat gggataatgc ttcgcagagg tgtggttgga      3540
ctggcaatgc ttaccatgcc acttctggtt tcttcctggc atggtgacac aaaatgttgt      3600
tgagatcaag taagtgaatt atgttctgct ttctgagttc ggtaaacttc tttggctaca      3660
aaaggactaa gcttagttat gctaacttgt tgatttggtt gtgatcattg catcattctg      3720
ctgtgtgaat tgatacttaa tacctctgat ttttttatagc ctgcttacaa ttacatatgt      3780
tacctaatga gatatattcc attttccatt gattctgtta acaatattca taccactttg      3840
gtcgtgataa attcatttga ctattgtata gaagtcatat atgtctacat gtgaagtgaa      3900
tgatccatta tcagatacac atgaattctc atagtgttgc ttgatatgtc accgtttaag      3960
tttgctccta cagaagatag gattcgatga ttacatgtaa caaagattag ttgtgatttt      4020
gtctattaat tggatgagat attatcttga agcaaaaggt catcgagaac cataaaaaat      4080
gggttaatcc cacagcagac tagtactgtc cgctaaatac aagtgcttac cttcctgga      4140
ccatttaatc tttgaaacac acgcagaact tgttatagat aatctttgtg atagcatgga      4200
atagaaatca ttgacttggg tgcctaacat agcaagcaat tgacgatttt gagttactca      4260
tgtccatttt tgctgagtat ccatattaat gcagacggcc atagttcatt ttcgtgtcgt      4320
tattttcat tgagatagaa caaaacagcg acttctcttg gggagtacac ttattaccaa       4380
cgctggcatc ctgttatcta gtttaatctg aacctgttct tgaaaactgt gtttcagaaa      4440
gtcacttgcc ttggtttgtt ctataatatt cttctgtgct atgagctatg gtaagcaaaa      4500
tatttcgaat tttaaagcag ttttctaaat gatgcaaagg cagattggtt tgagattgca      4560
catctacaga attcttttga ctaacatctt atcttagcca agcagtagtt aagattaact      4620
gttttactca ccaagtagaa ctcttcaaag ctcagactaa gcattttgtg gtttcttact      4680
aactcctttg tttggcaacc cgcagtgggt tgtcctacc atgccctgaa tgaagcaaag       4740
tttcttggcc gattggccca gcttagtggg gatatcagca gccctagcct gaagggccaa      4800
```

```
ttcctttac  tgtttttttt  atccctattt  tttgaggaag  caaagttcca  acaacaatgt    4860
tatgaatatg  tttgaataaa  tgatggagac  acatgtgact  ttccgattag  aatatgacta   4920
cataaaaaaa  ttagctttga  gtctatggat  aagatcacaa  agggatctct  taacatatgt   4980
ttttatggat  gtagtgttag  ttgatgaaag  ctaagcacga  gtaaatggaa  actagagttt   5040
gtcgtgggag  attctagagt  ttaaaggttt  tggacgattt  tggactcgat  cagtagaact   5100
caaattgaat  ataaaagatg  tgatttcaac  actactacat  atgaggaaag  acatgttagt   5160
ttgaaaaatc  aagtagtgtc  cggaaggaca  tctttagata  tttagaatct  atgctactac   5220
atatgaggaa  agacatgtta  gtttgaaaaa  tcaagtagtg  ttctgaaagg  acatcttag    5280 atatttagga  tctatgcata  gatatttagg  atctatgcat  agatatttag  gatctatgct   5340
acgaaaggct  acgtagagat  agtgataaag  gtattagtca  aaggatgagg  tggcgccaaa   5400
catttgatgt  tctatatgac  aataggatac  cacaaaagtt  aaaaagaatc  tttataggat   5460
gacaattcga  tctgctatat  tgttcggtgc  agaatgttag  tctaaaaaag  acatgttcaa   5520
tacgtatgcg  ctacagaaat  gtatatgttg  tgttggagtt  tggccataaa  aaaggatcga   5580
gtatgaaacg  aggatacata  tgatagacta  atgtaaacat  cggtgcgagt  atgaaacgag   5640
gatacatatg  atagactaga  tgtaacatcg  gtgcgaagaa  aagctcatcc  agcatcggtt   5700
aaaatggttt  agac                                                         5714

<210> SEQ ID NO 19
<211> LENGTH: 577
<212> TYPE: DNA
<213> ORGANISM: Zea mays

<400> SEQUENCE: 19
actcgatcct  tcctcttcct  caaccgtgcg  ggcgatcgat  cgcaccgccc  cctcgcccga     60
ccccatgcct  tccacgtcgc  ggtcggggta  gggctcagga  gacgttctct  tggtgtggag    120
agtggcattg  attcttcgat  gctcgggcag  gaaggctggg  ctggggatga  aacgctggaa    180
gatggaaggg  ccgaggaggt  gaggagaatt  aacataaatg  aggcagcaca  tgctacagat    240
ggcactggta  gggttaatgt  tagcggtgct  ggcggagttg  aagatatcgg  caactttcat    300
atcgatgttg  atgcatccga  ggatatattg  gggaatttgc  acaacatgca  cttcttgagg    360
gtggacaatc  ttggacggat  gatttaactg  ttgttatggt  ttactggggc  tatgattagc    420
caggccgact  cttgctgttc  aagtgttcat  ttgagtgtaa  ttgttccatc  cctgttatgt    480
aatgttgtag  ttgtagactt  gtagtctacc  tggtacctgt  agttacttaa  catcaggcag    540
ggaaaaattt  gtatgttcat  taaaaaaaaa  aaaaaaa                                577

<210> SEQ ID NO 20
<211> LENGTH: 4090
<212> TYPE: DNA
<213> ORGANISM: Zea mays

<400> SEQUENCE: 20
cacactcact  cgtcggctta  gggaccccccc  ggtctcgaaa  cgccgacact  actcttgagg    60
agattattag  attatcataa  tctaggcttt  agattatata  atctgaacac  ataatctagt   120
tgtttgttta  tctaatggat  tatttacgct  agattatata  atctggagag  attataatct   180
gaaacaaaca  tggccttagt  gattaaaaat  aaaaataagg  ggtaaaatca  caattgtaaa   240
gtgagagaag  gctataatca  caattaacca  taaaaagtta  atattatttt  caggttaatt   300
```

```
ttgagtatat ccttctcttc ccttacagtt atgattttac cccttatttt taattttttgt    360
aatcaataat tcacaaagtt gaaaacgtat aatcacagtt gtccttaaaa ttaaatgtgc    420
tgcccaacaa aatactctcg gactgacaga cagtcgccag tcaagagccc ctcgggcagc    480
aggatcttcc ccctccccaa aaccaaacca gctgcctccg acagcatcca ccttttcctc    540
ccccaaacca tggacttctc caccggcggg agcgtgagcg gggcggcgg aggcgccagc    600
gacggccccg cgcaggcgga gcgctggctg gagatcgccg agaagctcct cgcggcgcgc    660
gacctcgtcg gctgcaagcg cttcgcggag cggtcggtgg aggcgaaccc gctcctcgcc    720
ggcgttgacg aactcctcgc cgtcgccgac gtcctcctcg cttcccagtt catgggcacc    780
tcgggccagc cggacccgct cgccatcctc cagctgccgc ccggagtcag ccccgaccag    840
gccgccgtgt cccgcgcctt ccgccgcctc gcgctcctcc tcggtcccag caacccgcac    900
ccgggagccg agatggcgct ccgcctcgtc aacgacgcct acgccttcct ctcggatccc    960
tctcgccgcc ccccgccgcc cgccgatccc gccactggta cccccttactc ctcccagtat  1020
cccgccgcgg ccgctcccgc ctccgacacc ccggagttct ggacggcgtg cccccttctgc  1080
tgctacgtgc accagtaccc gcgcagcctg atcgggcgcg ccctcaagtg ccccaacgcg  1140
ggctgccgcc gcggattcgt ggcttctgag ctcccgaccc cacccacggt tgtgccgggc  1200
actgaaatgt accactgcgc ctggggggttc ttccccctcg gatttcccaa cgcggccgac  1260
ctgggtgcca actggaagcc attctacaag atgttccctt ggaacacggc tcccagtggc  1320
caaggtggtg gtggtaggag tcacggaaac catggtggta ggcagccaca gaatgacagt  1380
gctcgtggtg gctcttctag aggtaggatc aagaagacga cggcccgcaa aaggtcggg   1440
gtagggctca ggagacgttc tcttggtgtg gagagtggca ttgattcttc gatgctcggg  1500
caggaaggct gggctgggga tgagaacgct ggagatggaa gggccgagga ggtgaggaga  1560
attaacataa atgaggcagc acatgctaca gatggcactg gtagggttaa tgttagcggt  1620
gctggcggag ttgaagatat cggcaacttt catatcgatg ttgatgcatc cgaggatata  1680
ttggggaatt tgcacaacat gcacttcttg agggtggaca atcttggacg gatgatttaa  1740
ctgttgttat ggtttactgg ggctatgatt agccaggccg actcttgctg ttcaagtgtt  1800
catttgagtg taattgttcc atccctgtta tgtaatgttg tagttgtaga cttgtagtct  1860
acctggtacc tgtagttact taacatcagg caggaaaaa tttgtatgtt cattagatgg   1920
agatacatgc catttgcctt agcaaacaca ctttgtggag gtttccagtg atgggataat  1980
gcttcgcaga ggtgtggttg gactggcaat gcttaccatg ccacttctgg tttcttcctg  2040
gcatggtgac acaaaatgtt gttgagatca agtaagtgaa ttatgttctg ctttctgagt  2100
tcggtaaact tctttggcta caaaaggact aagcttagtt atgctaactt gttgatttgg  2160
ttgtgatcat tgcatcattc tgctgtgtga attgatactt aatacctctg atttttata    2220
gcctgcttac aattacatat gttacctaat gagatatatt ccattttcca ttgattctgt  2280
taacaatatt cataccactt tggtcgtgat aaattcattt gactattgta tagaagtcat  2340
atatgtctac atgtgaagtg aatgatccat tatcagatac acatgaattc tcatagtgtt  2400
gcttgatatg tcaccgttta agtttgctcc tacagaagat aggattcgat gattacatgt  2460
aacaaagatt agttgtgatt ttgtctatta attggatgag atattatctt gaagcaaaag  2520
gtcatcgaga accataaaaa atgggttaat cccacagcag actagtactg tccgctaaat  2580
acaagtgctt acctttcctg gaccatttaa tctttgaaac acacgcagaa cttgttatag  2640
ataatctttg tgatagcatg gaatagaaat cattgacttg ggtgcctaac atagcaagca  2700
```

```
attgacgatt ttgagttact catgtccatt tttgctgagt atccatatta atgcagacgg    2760
ccatagttca ttttcgtgtc gttattttc attgagatag aacaaaacag cgacttctct    2820
tggggagtac acttattacc aacgctggca tcctgttatc tagtttaatc tgaacctgtt    2880
cttgaaaact gtgtttcaga aagtcacttg ccttggtttg ttctataata ttcttctgtg    2940
ctatgagcta tggtaagcaa aatatttcga atttaaagc agttttctaa atgatgcaaa     3000
ggcagattgg tttgagattg cacatctaca gaattctttt gactaacatc ttatcttagc    3060
caagcagtag ttaagattaa ctgttttact caccaagtag aactcttcaa agctcagact    3120
aagcattttg tggtttctta ctaactcctt tgtttggcaa cccgcagtgg gttgtccata    3180
ccatgccctg aatgaagcaa agtttcttgg ccgattggcc cagcttagtg gggatatcag    3240
cagccctagc ctgaagggcc aattccttt actgtttttt ttatccctat ttttgagga     3300 agcaaagttc caacaacaat gttatgaata tgtttgaata aatgatggag acacatgtga    3360 cttccgatt agaatatgac tacataaaaa aattagcttt gagtctatgg ataagatcac     3420
aaagggatct cttaacatat gttttatgg atgtagtgtt agttgatgaa agctaagcac     3480
gagtaaatgg aaaactagag ttgtcgtggg agattctaga gtttaaaggt tttggacgat    3540
tttggactcg atcagtagaa ctcaaattga atataaaga tgtgatttca acactactac     3600
atatgaggaa agacatgtta gtttgaaaaa tcaagtagtg tccggaagga catctttaga    3660
tatttagaat ctatgctact acatatgagg aaagacatgt tagtttgaaa aatcaagtag    3720
tgttctgaaa ggacatcttt agatatttag gatctatgca tagatattta ggatctatgc    3780
atagatattt aggatctatg ctacgaaagg ctacgtagag atagtgataa aggtattagt    3840
caaaggatga ggtggcgcca aacatttgat gttctatatg acaataggat accacaaaag    3900
ttaaaaagaa tctttatagg atgacaattc gatctgctat attgttcggt gcagaatgtt    3960
agtctaaaaa agacatgttc aatacgtatg cgctacagaa atgtatatgt tgtgttggag    4020
tttggccata aaaaaggatc gagtatgaaa cgaggataca tatgatagac tagatgtaac    4080
atcggtgcga                                                           4090
```

<210> SEQ ID NO 21
<211> LENGTH: 10452
<212> TYPE: DNA
<213> ORGANISM: Zea mays

<400> SEQUENCE: 21

```
tgcggataga cttcagagga aaggactacc gcacccggtg gtttgtccat tatgtgatca      60
agagcaggaa actatcttgc acctcttgtg ctcttgcagt ttcgctagac aattttggca     120
tgttatattt tcagctttga ggatgggcca tcttacgcct actagagagg cgggctcttt     180
tgtggattgg tgggaaaagg tgcataggag agtccccaaa catatcagaa aaaggttttc     240
atagtctcat tatcctaggg gcctggtgtt tatggctaca tcgcaataag gcggttttg     300 atggtgtcaa ccccttcattg agcaccattc agaggctttt catggatgag gtggaatgct    360
ggtatatggc tggtgcaaag cagctcgaga gtctcggact tctggctgct tttgctagga    420
tcagggctat tcctagtgca tgaggctgta ctattttcc ttttattt ttgcctgctt        480 ggctttgtac tttggtccat ttcggacctt tctctctttc aatataatga tgcgcagttt    540
tcctgcgtgt tcgagaaaaa aaatataaa cttctctcta tagtaaccta gcataagtgc     600
actcaaagaa aatatgtatc agatggtttg tggctcaaaa gagcaagttg tgtcactatt    660
```

```
tcaatttctt tttgataaaa ttacctttg tgagattgtg agaatgaccc tcttttttg    720
aaagaactac atgaagattt ttatctttaa aggtatcttt agacaccaaa ttattcataa    780
aacattaatt ccattagtaa ctaagaattt atacatataa ttaatagaaa agataccatc    840
tttatgcaag tgccaaacaa acacgttaga ttcttgtttt agcaatttag cttgccatga    900
ttttatttta ggtaagattc gaaaacccctt tgttttgggc ctttcctccc taaccacccc    960
cacatacact ccatcatatt tttacttttc caagttttgt ttggtttata aaatagaatg   1020
aaataatctg ccattacttt attcctcaca atctaataat tactactagt aagataagag   1080
ataattgtga ttatacccctt cgttggcctt gcaattgtga ttttactctg cattttcaac   1140
tttctaattt tacacctccg ttttaaatac gaagctacca tttgcccttc actctcaaca   1200
tcgttagtga aaatcagaat tagtgattaa aaataaaaaa atgagaaaat aaatgggtga   1260
aaggttcaaa ctacctttttt ctattcttta tgggcacaac cctaataggg gtgaaatcac   1320
tattacataa tataacgagg gtaaaatcaa aataaattgc ttgggtattt ttatcttttg   1380
catcaaattt aacattgtta actgcatcta acggcacaag ggtatggcaa ctcttcgttt   1440
tcaaatgaa gggataaaat atcacaaagt tgaaaacga tgggtaaaat cacaatttca   1500
agaccagaga gggtataatc acaaataccc tataagataa atagagtcat tatatcattt   1560
tttgtaagat atacttgggg atacatcaac tcatccttag agtttgtttg ggactgtgcg   1620
gctctatatt tcaaccaaac aagtgtagct aaaaaaggtg aagttaaaag agaagtactc   1680
tagaaactct aaattaaatt tagagaaaat tcctggtatg ccatcaaatt ttatactcat   1740
tccttgtgtg ccactgagtg gcatataggt atatttttg tgtctatga catgtggggt   1800
cagtggcata caaggaatga gtatattttc tagtggcata cagggaattg gcccttaaat   1860
ttatggagta gattttgagg atagatctaa ccaggcttga tgatgacatg tcactgtatt   1920
acaacattga tgaagatctt tcacttgagg aaaatactat tgtgcaacca acattctat   1980
acaatccaac tatcaaaagt cacaaaaata tttaaaaaat tatacatata tattatttac   2040
tttatcaata tatcatattt aagatcctag attgatttat gctatgttaa tatataattc   2100
attcatctta tataacaagg tatatattt tggtacagtc tttggagcga aactttgact   2160
atttgtttat ttcaaaatat gctatcaata aaaacataac gagcattaaa ttaaagtaat   2220
ttttgaatac aaatcaagta tataacatgt atatactaaa atatatgctt ttggctgaat   2280
tactagtcaa aagttttaaa acattgagtc ttttttttt aaaatgcagg ccttatttta   2340
cggaattgag ggaatttttt ttatctaatt gaatatattt tttctttttac tattgtataa   2400
atttaaactt aaaattttat aatctaataa agtaaacaat aaattatatt tatatatttt   2460
tagaattttt tatggttttt ggtagtccaa ttatacattg attgtatgca aaacttgctc   2520
tgcggtgggg cgctacaatg gtctggtatg tttgcatatg ggaaaactaa tagcccgttc   2580
ccttggttttt aattcgaaac ggcttttact attttctgtag tgttttggtc tctgtgaatt   2640
gcagctacaa taatctaaac aactgacttt aattcgaagc taacaggcta aagacgctc   2700
tccaacggat ccttttcccct ccccttcacg acgtattcgg tgatttcgta catcgagaga   2760
gcttcaacag gtccctctcc tccctcttgt agggtgagag aaggaaaaca ccttgtaaaa   2820
cgagaaagat agaaccctac tcttcactaa ttagtgtttt taactataaa attaatctgc   2880
tataagtttg gttaagtgac aatgtgtatt atgatattat aaatattaaa aactctaaaa   2940
actgatgtag aaaagtcaaa tagccttagtt aaagggtaaa gggagagctg aatagaggga   3000
tgcttggaga ggaggtaaaa tagggaaata atagtgaaga tgaggatatt taaatatgaa   3060
```

```
tagaaagtcc aaatgtggga tttgagatgg agaatgattg gagagagcct aataaaatca   3120
agggataatt gtgattatac ccttttctaa tattttaatt gtgattttat cccttctttt   3180
ttaactttgt taccccctctg ttttgaaaac aaagccgttg tttgcaccgc cttatcaacg   3240
ttaataaaaa tcagaattag tgattaaaaa taaaaataag gggtaaaatc acaattgtaa   3300
agtgagagaa ggctataatc acaattaacc ataaaaagtt taatattatt ttcagattaa   3360
ttttgagtat atccttctct tcccttacaa ttatgatttt accctcatt tttaattttc    3420
gtaatcaata attcacgaag ttgaaaacgt ataatcacag ttgtccttaa aataaatgtg   3480
ctgcccaaca aaatactctc ggactgacag acagtcgcca gtcaagagcc cctcgggcag   3540
caggatcttc cccctcccca aaaccaaacc agctgcctcc gacagcatcc accttttcct   3600
ccccaaacc atggacttct ccaccggcgg gagcgtgagc ggggcggcg gaggcgccag     3660
cgacggcccc gcgcaggcgg agcgctggct ggagatcgcc gagaagctcc tcgcggcgcg   3720
cgacctcgtc ggctgcaagc gcttcgcgga gcggtcgatg gaggcgaacc cgctcctcgc   3780
tggcgttgac gagctcctcg ccgtcgccga cgtcctcctc gcttcccagt tcatgggccc   3840
ctcgggccag ccggacccgc tcgccatcct ccagctgccg cccggagtca gccccgacca   3900
ggccgccgtg tcccgcgcct tccgccgcct cgcgctcctc ctcggcccca gcaacccgca   3960
cccgggagcc gagatggcgc tccgcctcgt caacgacgcc tacgccttcc tctcggatcc   4020
ctctcgccgc ccccgccgc ccgccgatcc cgccactggt acccccttact cctcccagta    4080
tcccgccgcg gccgctcccg cctcggacac cccggagttc tggacggcgt gccccttctg   4140
ctgctacgtg caccagtacc cgcgcagcct gatcgggcgc gccctcaagt gccccaacgc   4200
gggctgccgc cgcggattcg tggcttctga gctcccgacc ccacccaccg ttgtgccggg   4260
cactgaaatg taccactgcg cctgggggtt cttcccctc ggatttccca acgcggccga    4320
cctgggtgcc aactggaagc cattctacaa gatgtttcct tggaacacgg ctcccagtgg   4380
ccaaggtggt ggtggtagga gtcacggaaa ccatggtggt aggcagccac agaatgacag   4440
tgctcgtggt ggctcttcta gaggtaggat caagaagacg acggcccgca agaaggtcgg   4500
ggtagggctc aggagacgtt ctcttggtgt ggagagtggc attgattctt cgatgctcgg   4560
gcaggaaggc tgggctgggg atgagaacgc tggagatgga agggccgagg aggtgaggag   4620
aattaacata aatgaggcag cacatgctac agatggcact ggtagggtta atgttagcgg   4680
tgctggcgga gttgaagata tcagcaactt tcatatcgat gttgatgcat ctgaggatat   4740
attggggaat ttgcacaaca tgcacttctt gagggtggaa aatcttggac ggatgattta   4800
actgttgtta tggtttactg gggctatgat tagccaggcc gaagcagatg tctcagagac   4860
tggctcttgc tgttcaagtg ttcatttgag tgtaattgtt ccatccctgt tatgtaatgt   4920
tgtagttgta gacttgtagt ctacctggta cctgtagtta cttaacatca ggcagggcaa   4980
aatttgtatg ttcattagat ggagatacat gccatttgcc ttagcaaaca cgctttgtgg   5040
aggtttccag tgatgggata atgcttcaca gaggtctggt tggactggca atgcttacca   5100
tgccacttct ggtttcttcc tggcatggtg acacaaaatg ttgttgagat caagtaagtg   5160
aattatgttc tgctttctga gttcggtaaa cttctttggc tacaaaagga ctaatcttag   5220
ttatgataac ttgttgactt ggttgtgatc attgcatcat tctgctgtct gaattgatac   5280
ttaataccctc tgatttttta tagcctgctt acaattccat atgttaccta atgagatata   5340
ttccattttc cattgattct gttaacaata ttcataccac ttttgtagtc atatatgtct   5400
```

```
acatgtgaag tgaatgatcc tttatcagat acacatgaat tctcatagtg ttgcttgata    5460
tgtcaccgtt taagtttgct cctacagaag ataggattcg atgatgacat gtaacaaaga    5520
ttacttgtga ttttgtctat taattggatc agatattatc ttgaagcaaa aggccatcga    5580
gaaccataaa aaatgggtta atcccacagc agactagtac tgtccgctaa atacaagtgc    5640
ttacctttca tggatcattt aatgtttgaa acacactcag aacttgttat agataatctt    5700
tgcgatatca tggaatataa atcattgact gggtgctta acatagcaag cacttgacga    5760
ttttgagtta ctcatgtcca ttttttgctgc gtatccatat taatgcagac ggccatagtt    5820
cattttgtg tcgttatttt tcattgagaa agaacaaaac agtgacttct cttggggagt    5880
agacttatta ccaacgctgg catcctgtta tctagtttaa tctgaacctg ttcttgaaaa    5940
ctgtgtttca gaaagtcact tgccttggtt tgttctataa tattcttctg tgctatgagc    6000
tattgtaagc aaaatatttc gaatttaaaa gcagttttct aaatgatgca aaggcagatt    6060
ggtttgagat tgcacatcta cagaattctt ttagctaaca tcttatctta gccaagcagt    6120
agttaagatt aactgtttta ctcaccaagt agaactcttc aaagctcaga ctaagcattt    6180
tgtggtttct tactaacttc tttgtttggc aatccgcagt gggttgtcca tatcatgccc    6240
tgaatgaagc aaagtttctt ggccgattgg cccagcttag tggggatatc agcagctcta    6300
gcctgaaggg ccaattcctt ttactgtttt ttatccctgt tttttgagga agcaaagttc    6360
caacaacaat gttatgaata tgtttgaata aatgatggag acacatgtga cttttcgatt    6420
agaatatgac tacataaaaa attagctgag tctatggata agatcacaaa gggatatctc    6480
ttaacatatg ttttttatgg atgtagtgtt agttgatgaa agctaagcac gagtaaaatag    6540
aaaactagag ttgtggtggg agattctaga gtttaaaggt tttggacgat tttggactcg    6600
atcagtagaa ctcaaattga atataaaaga tgtgatttca acactactac atatgaggaa    6660
agacatgtta gtttgaaaaa tcaagtagtg tccaggaagg acatctttag atatttagga    6720
tctatgctac tacatattag gaaagacatg ttagtttgaa aaatcaagta gtgtccatga    6780
aggacatctt tagatattta ggatctatgc tacgtagaga tattgataaa ggtattagtc    6840
aatggatgag gtagcgccaa acatttgata ttctatatga cataggata ccacaaaagt    6900
taaaagaag ttttatagga tgacaattcg atctgctatg ttgttcggtg caaaatgtta    6960
gtctaaaaaa gacatgttca atacatatgc gctacagaaa tgcatatgtt gtgttggagt    7020
ttggccataa aaaaggatcg agtatgaaac gacgatacat atgatagact agatgtaaca    7080
ccggtgcgaa gaaaacctca tccaacatcg gttgaaatgg tttagacata tcaataaaga    7140
ctttcagatg caccaataat tccttcttcg ctttcctttc ttcctttttt ttatcacaaa    7200
caagttaaag aacacggctc tctttgatcc tctgtattga agctactagt ttgctacgaa    7260
aattgaaaag catcatataa acatgtatgc ttgcgacctt taggtacata agaatgcaac    7320
ctcaataata ccaaacgaat cgcctcacca atcaccacca ccacaggagc aaccagccaa    7380
acatttcttg cagcactctg ggcgacctgg aacgataatc ccggaatgca gcaaatggct    7440
gcttacgcga tacgaaggaa gcggtcctat ccaatgcttt gttctttaac aaattcaccc    7500
cattctaaat ttgtccagct acgccagcac gagcctgcag tgtctcggta cgtttgcttt    7560
tttccatttg ttccaccagc cagtctatgc cagatttgat cccctcctg caagagccgg    7620
tgtcacattt aaacaatata acagatcttt agaatatcat gcacccagga aacaatataa    7680
cagacgaatg tgtgaatttt tttgtatctt tgagtaaaat tgtcattttt ttcatggcga    7740
gtcaaatttc ctcaggaacc agttgagttt ctgcgctcac ccatcatatg cagatacagc    7800
```

```
ctgaaatgta tatgtcctct catccagttc tttatgcaga aatttagcca attcttcctc    7860
atcaatggct ccaggtaaat cctgccaaaa gaaatccaga agcaccctcc aaacatgaga    7920
acaagctaga ggtaaataat aaacaatttg atagaataat gtgtacccag cttaacagaa    7980
acagacagtg catgtagtca ttggtttcca tgtgatcttt tcaggaagtt ttaattgatt    8040
taaaaactac atctggtatt caacctcgca atggcgcata ggcgctttgc aacgtaggaa    8100
tttatatttg tatgcctcac agcatgtgca catgacaaaa acaaaatctt tattttaact    8160
acgatggcaa ctttattgta agcactaaat ctttcaatca taattatgta ctgtggtaca    8220
aaatatagaa agtggaagta aacccttcac ctgtttgttt gcaactatca agagtggtgc    8280
tcctctcaga tgttcatggc gaataacctt ctctgaagta agaaatttag gttaggttct    8340
ctagaatgag ttctcatccc atttaccaga gaggcattgc atcttctgga agatctagc     8400 aatagaaaca aaccagtact ccctctgttc caagttataa gacgatgttt tagcttttct    8460
agatatattg ttttaactat gtaccaggac attatatata tttttaatat ttaagtccat    8520
agcaaaattt atttatctag aaaaaggcca aaatgtctta taatttggaa tggatggcgt    8580
agtttataat tgacacaaat aagaacctta cccaaagcag atttggaatc ttcaaatgac    8640
gatgctgtgg cagcgtcaat aacgtacatt atggcatggg cctcttcata gtatttctcc    8700
cagattgttc gtaggctaac ctgccaagca ggcaagtgtg taagaaatac tgaacttggc    8760
atggaagctt aattatcata ctagcaagca gtgatactga agttagtttt acactaattc    8820
ttataacata gcagagaagc tgatgctgtt ctactagcca cccaattcta ttgagtactg    8880
tgaatgttag ccaacagagc atatctttgc tttctgaaaa ttctattgag cattccatat    8940
aactagatta tatatattct gctggaacgc aaaaagatgc taggttaata actaaagcaa    9000
ccacatccta gtaatttgat tttatgacat gtatttccca ggcattagaa accctgatat    9060
agcaccaaac tgacaagact caaatatcaa cgatcgtagg gtggtgccac ggcaacagaa    9120
ggctcacttt actacgtacg taaacgttct tacctgacca cctagatccc agaaaacaag    9180
ttttgccttt gcgtcttcga tgcggccaat gttgagccca actgttggaa cgacacggtc    9240
aggcggaagt ccttccccct tgagatatat cgatttcaac ttctccagca aagtctatgg    9300
caacggttcc agaaacattg tgtacaggta agtttcatca atttctagtt cagaaaggga    9360
aatatatata tatgaaggct gggagctagc agctaccgtc ttgccagctc tgtcaacacc    9420
aagaatcaga acacggaact cgtccttggc gaacacatac ttccacaggc catagaacaa    9480
ggagaacatt tccgcttata tatatatatc cggcgataag caaccgccag cacgttacgt    9540
cctgaaaaac gaatcatacg ttacaaacat tttctccgat cagtaacagt acgcagccaa    9600
aagcatgtac gccccaaatt gccagacgca aaactaggaa ccatcctcat agtacagggc    9660
cgcagcattt caatccacaa cgaaatggta tcgaccgagt aaaaataagg ggagaggata    9720
taacttaact gaaccatcgg gcgggagagt acaactacag actacagagg ggagaggatg    9780
ttgagatcta gatagctcac cggagcgctc gaaggctcct tgatcgcgcc gcttcagacg    9840
acaccacccg ctcccgtgtg gactggagcg cgggaggctg agggcgggtt ttgagccgcg    9900
cggcggtggg agcgcgccca ccggagttag gaactggggc actcgcctcg ccagtcgcca    9960
cacggcttgg gttcggttga ctcgatgggc gtcacggtgg gcgacttgga actggaaccc   10020
acgcaggagc aggacccgtg gggctatgat cggtgggtcc tgcaggattc tgggacggga   10080
ggccctaccg ctcagtgagg ttatcgtact gccagtggga attcgtgatg tgactgtacc   10140
```

| | |
|---|---:|
| agtggttgac ccggaaggaa ggcactggct ggcaggaggg ctttgccatt aataaaaaca | 10200 |
| taaattattg catctgacaa gtttagtgga gagctaacgg tgccaaatgt tgcgcttgcc | 10260 |
| tttctacctg cagtcagtcc tattcagccc agctcattta gcccggtctc ggactctcgg | 10320 |
| cccacatggc agcccatacc atgacactct ccacctctcg aaatgtcagc ccataccatg | 10380 |
| acattcactt aagggtgtt tgaatgcact agagctaata gttagtagct aaaattagtt | 10440 |
| gagacatcca aa | 10452 |

<210> SEQ ID NO 22
<211> LENGTH: 6816
<212> TYPE: DNA
<213> ORGANISM: Zea mays

<400> SEQUENCE: 22

| | |
|---|---:|
| tgtcccgcgc ctcccgccgc ctcgcgctcc tcctcggccc cagcaacccg cacccgggag | 60 |
| ccgagatggc gctccgcctc gtcaacgacg cctacgcctt cctctcggat ccctctcgcc | 120 |
| gccccccgcc gccgccgat cccgccactg gtacccctta ctcctcccag tatcccgccg | 180 |
| cggccgctcc cgcctcggac acccggagt tctggacggc gtgccccttc tgctgctacg | 240 |
| tgcaccagta cccgcgcagc ctgatcgggc gcgcccctcaa gtgccccaac gcgggctgcc | 300 |
| gccgcggatt cgtggcttct gcgacgcggg ctgccgccgc ggattcgtgg cttctgagct | 360 |
| cccgacccca cccaccgttg tgccgggcac tgaaatgtac cactgcgcct gggggttctt | 420 |
| cccctcgga tttcccaacg cggccgacct gggtgccaac tggaagccat tctacaagat | 480 |
| gtttccttgg aacacggctc ccagtggcca aggtggtggt ggtaggagtc acggaaacca | 540 |
| tggtggtagg cagccacaga atgacagtgc tcgtggtggc tcttctagag gtaggatcaa | 600 |
| gaagacgacg gcccgcaaga aggtcggggt agggctcagg agacgttctc ttggtgtgga | 660 |
| gagtggcatt gattcttcga tgctcgggca ggaaggctgg gctggggatg agaacgctgg | 720 |
| agatggaagg gccgaggagg tgaggagaat taacataaat gaggcagcac atgctacaga | 780 |
| tggcactggt agggttaatg ttagcggtgc tggcggagtt gaagatatca gcaactttca | 840 |
| tatcgatgtt gatgcatctg aggatatatt ggggaatttg cacaacatgc acttcttgag | 900 |
| ggtggacaat cttggacgga tgatttaact gttgttatgg tttactgggg ctatgattag | 960 |
| ccaggccgaa gcagatgtct cagagactgg ctcttgctgt tcaagtgttc atttgagtgt | 1020 |
| aattgttcca tccctgttat gtaatgttgt agttgtagac ttgtagtcta cctggtacct | 1080 |
| gtagttactt aacatcaggc agggcaaaat ttgtatgttc attagatgga gatacatgcc | 1140 |
| atttgcctta gcaaacacgc tttgtggagg tttccagtga tgggataatg cttcacagag | 1200 |
| gtctggttgg actggcaatg cttaccatgc cacttctggt ttcttcctgg catggtgaca | 1260 |
| caaaatgttg ttgagatcaa gtaagtgaat tatgttctgc tttctgagtt cggtaaactt | 1320 |
| ctttggctac aaaaggacta atcttagtta tgataacttg ttgacttggt tgtgatcatt | 1380 |
| gcatcattct gctgtctgaa ttgatactta ataccctga ttttttatag cctgcttaca | 1440 |
| attccatatg ttacctaatg agatatattc cattttccat tgattctgtt aacaatattc | 1500 |
| ataccacttt tgtagtcata tatgtctaca tgtgaagtga atgatccttt atcagataca | 1560 |
| catgaattct catagtgttg cttgatatgt caccgtttaa gtttgctcct acagaagata | 1620 |
| ggattcgatg atgacatgta acaaagatta cttgtgattt tgtctattaa ttggatcaga | 1680 |
| tattatcttg aagcaaaagg ccatcgagaa ccataaaaaa tgggttaatc ccacagcaga | 1740 |
| ctagtactgt ccgctaaata caagtgctta cctttcatgg atcatttaat gtttgaaaca | 1800 |

```
cactcagaac ttgttataga taatctttgc gatatcatgg aatataaatc attgacttgg    1860
gtgcttaaca tagcaagcac ttgacgattt tgagttactc atgtccattt ttgctgcgta    1920
tccatattaa tgcagacggc catagttcat ttttgtgtcg ttattttca ttgagaaaga     1980 acaaaacagt gacttctctt ggggagtaga cttattacca acgctggcat cctgttatct    2040
agtttaatct gaacctgttc ttgaaaactg tgtttcagaa agtcacttgc cttggtttgt    2100
tctataatat tcttctgtgc tatgagctat tgtaagcaaa atatttcgaa ttttaaagca    2160
gttttctaaa tgatgcaaag gcagattggt ttgagattgc acatctacag aattctttta    2220
gctaacatct tatcttagcc aagcagtagt taagattaac tgttttactc accaagtaga    2280
actcttcaaa gctcagacta agcattttgt ggtttcttac taacttcttt gtttggcaat    2340
ccgcagtggg ttgtccatat catgccctga atgaagcaaa gtttcttggc cgattggccc    2400
agcttagtgg ggatatcagc agctctagcc tgaagggcca attccttta ctgttttta     2460 tccctgtttt ttgaggaagc aaagttccaa caacaatgtt atgaatatgt ttgaataaat    2520
gatggagaca catgtgactt ttcgattaga atatgactac ataaaaatt agctgagtct     2580 atggataaga tcacaaaggg atatctctta acatatgttt tttatggatg tagtgttagt    2640
tgatgaaagc taagcacgag taaatagaaa actagagttg tggtgggaga ttctagagtt    2700 taaggtttt ggacgatttt ggactcgatc agtagaactc aaattgaata taaaagatgt      2760
gatttcaaca ctactacata tgaggaaaga catgttagtt tgaaaaatca agtagtgtcc    2820
aggaaggaca tctttagata tttaggatct atgctactac atattaggaa agacatgtta    2880
gtttgaaaaa tcaagtagtg tccatgaagg acatctttag atatttagga tctatgctac    2940
gtagagatat tgataaaggt attagtcaat ggatgaggta gcgccaaaca tttgatattc    3000
tatatgacaa taggatacca caaagttaa aaagaagttt tataggatga caattcgatc      3060
tgctatgttg ttcggtgcaa aatgttagtc taaaaaagac atgttcaata catatgcgct    3120
acagaaatgc atatgttgtg ttggagtttg gccataaaaa aggatcgagt atgaaacgac    3180
gatacatatg atagactaga tgtaacaccg gtgcgaagaa aacctcatcc aacatcggtt    3240
gaaatggttt agacatatca ataaagactt tcagatgcac caataattcc ttcttcgctt    3300
tcctttcttc ctttttttta tcacaaacaa gttaaagaac acggctctct ttgatcctct    3360
gtattgaagc tactagtttg ctacgaaaat tgaaagcat catataaaca tgtatgcttg     3420
cgacctttag gtacataaga atgcaacctc aataatacca aacgaatcgc ctcaccaatc    3480
accaccacca caggagcaac cagccaaaca tttcttgcag cactctgggc gacctggaac    3540
gataatcccg gaatgcagca aatggctgct tacgcgatac gaaggaagcg gtcctatcca    3600
atgctttgtt ctttaacaaa ttcaccccat tctaaatttg tccagctacg ccagcacgag    3660
cctgcagtgt ctcggtacgt ttgctttttt ccatttgttc caccagccag tctatgccag    3720
atttgatccc cctcctgcaa gagccggtgt cacatttaaa caatataaca gatctttaga    3780
atatcatgca cccaggaaac aatataacag acgaatgtgt gaattttttt gtatctttga    3840
gtaaaattgt cattttttc atggcgagtc aaatttcctc aggaaccagt tgagtttctg     3900
cgctcaccca tcatatgcag atacagcctg aaatgtatat gtcctctcat ccagttcttt    3960
atgcagaaat ttagccaatt cttcctcatc aatggctcca ggtaaatcct gccaaaagaa    4020
atccagaagc accctccaaa catgagaaca agctagaggt aaataataaa caatttgata    4080
gaataatgtg tacccagctt aacagaaaca gacagtgcat gtagtcattg gtttccatgt    4140
```

```
gatcttttca ggaagtttta attgatttaa aaactacatc tggtattcaa cctcgcaatg    4200
gcgcataggc gctttgcaac gtaggaattt atatttgtat gcctcacagc atgtgcacat    4260
gacaaaaaca aaatctttat tttaactacg atggcaactt tattgtaagc actaaatctt    4320
tcaatcataa ttatgtactg tggtacaaaa tatagaaagt ggaagtaaac ccttcacctg    4380
tttgtttgca actatcaaga gtggtgctcc tctcagatgt tcatggcgaa taaccttctc    4440
tgaagtaaga aatttaggtt aggttctcta gaatgagttc tcatcccatt taccagagag    4500
gcattgcatc ttctggaaag atctagcaat agaaacaaac cagtactccc tctgttccaa    4560
gttataagac gatgttttag cttttctaga tatattgttt taactatgta ccaggacatt    4620
atatatattt ttaatattta agtccatagc aaaatttatt tatctagaaa aaggccaaaa    4680
tgtcttataa tttggaatgg atggcgtagt ttataattga cacaaataag aaccttaccc    4740
aaagcagatt tggaatcttc aaatgacgat gctgtggcag cgtcaataac gtacattatg    4800
gcatgggcct cttcatagta tttctcccag attgttcgta ggctaacctg ccaagcaggc    4860
aagtgtgtaa gaaatactga acttggcatg gaagcttaat tatcatacta gcaagcagtg    4920
atactgaagt tagttttaca ctaattctta taacatagca gagaagctga tgctgttcta    4980
ctagccaccc aattctattg agtactgtga atgttagcca acagagcata tctttgcttt    5040
ctgaaaattc tattgagcat tccatataac tagattatat atattctgct ggaacgcaaa    5100
aagatgctag gttaataact aaagcaacca catcctagta atttgatttt atgacatgta    5160
tttcccaggc attagaaacc ctgatatagc accaaactga caagactcaa atatcaacga    5220
tcgtagggtg gtgccacggc aacagaaggc tcactttact acgtacgtaa acgttcttac    5280
ctgaccacct agatcccaga aaacaagttt tgcctttgcg tcttcgatgc ggccaatgtt    5340
gagcccaact gttggaacga cacggtcagg cggaagtcct tcccccttga gatatatcga    5400
tttcaacttc tccagcaaag tctatggcaa cggttccaga acattgtgt acaggtaagt    5460 ttcatcaatt tctagttcag aaagggaaat atatatatat gaaggctggg agctagcagc    5520
taccgtcttg ccagctctgt caacaccaag aatcagaaca cggaactcgt ccttggcgaa    5580
cacatacttc cacaggccat agaacaagga gaacatttcc gcttatatat atatatccgg    5640
cgataagcaa ccgccagcac gttacgtcct gaaaaacgaa tcatacgtta caaacatttt    5700
ctccgatcag taacagtacg cagccaaaag catgtacgcc ccaaattgcc agacgcaaaa    5760
ctaggaacca tcctcatagt acagggccgc agcatttcaa tccacaacga aatggtatcg    5820
accgagtaaa aataagggga gaggatataa cttaactgaa ccatcgggcg ggagagtaca    5880
actacagact acagagggga gaggatgttg agatctagat agctcaccgg agcgctcgaa    5940
ggctccttga tcgcgccgct tcagacgaca ccacccgctc ccgtgtggac tggagcgcgg    6000
gaggctgagg gcgggttttg agccgcgcgg cggtgggagc gcgccaccg gagttaggaa    6060 ctggggcact cgcctcgcca gtcgccacac ggcttgggtt cggttgactc gatgggcgtc    6120
acggtgggcg acttggaact ggaacccacg caggagcagg acccgtgggg ctatgatcgg    6180
tgggtcctgc aggattctgg gacgggaggc cctaccgctc agtgaggtta tcgtactgcc    6240
agtgggaatt cgtgatgtga ctgtaccagt ggttgacccg gaaggaaggc actggctggc    6300
aggagggctt tgccattaat aaaaacataa attattgcat ctgacaagtt tagtggagag    6360
ctaacggtgc caaatgttgc gcttgccttt ctacctgcag tcagtcctat tcagcccagc    6420
tcatttagcc cggtctcgga ctctcggccc acatggcagc ccataccatg acactctcca    6480
cctctcgaaa tgtcagccca taccatgaca ttcacttaag gggtgtttga atgcactaga    6540
```

```
gctaatagtt agtagctaaa attagttgag acatccaaac actttagtta atagttcaac    6600
tattagctat ttttggtaaa ttagttaata gttagatagt tatttgttag ctagctaatt    6660
ccactaccaa tttttagcca actaactatt agttctagtg cattcaaaca ccccttagc     6720 ctggtcttaa cagagtagaa gagatgtcag caccgacaac ctgaaacctt tgctactcaa    6780
gtgcaattga tggacaagtg ctttccttgt tcttcg                              6816
```

<210> SEQ ID NO 23
<211> LENGTH: 3904
<212> TYPE: DNA
<213> ORGANISM: Zea mays

<400> SEQUENCE: 23

```
tgcggataga cttcagagga aaggactacc gcacccggtg gtttgtccat tatgtgatca      60
agagcaggaa actatcttgc acctcttgtg ctcttgcagt ttcgctagac aattttggca     120
tgttatattt tcagctttga ggatgggcca tcttacgcct actagagagg cgggctcttt     180
tgtggattgg tgggaaaagg tgcataggag agtccccaaa catatcagaa aaaggttttc     240
atagtctcat tatcctaggg gcctggtgtt tatggctaca tcgcaataag gcggttttg      300 atggtgtcaa cccttcattg agcaccattc agaggctttt catggatgag gtggaatgct     360
ggtatatggc tggtgcaaag cagctcgaga gtctcggact tctggctgct tttgctagga     420
tcagggctat tcctagtgca tgaggctgta ctatttttcc tttttatttt ttgcctgctt     480
ggctttgtac tttggtccat ttcggacctt tctctctttc aatataatga tgcgcagttt     540
tcctgcgtgt tcgagaaaaa aaatataaa cttctctcta tagtaaccta gcataagtgc      600
actcaaagaa aatatgtatc agatggtttg tggctcaaaa gagcaagttg tgtcactatt     660
tcaatttctt tttgataaaa ttaccttttg tgagattgtg agaatgaccc tctttttttg     720
aaagaactac atgaagattt ttatctttaa aggtatcttt agacaccaaa ttattcataa     780
aacattaatt ccattagtaa ctaagaattt atacatataa ttaatagaaa agataccatc     840
tttatgcaag tgccaaacaa acacgttaga ttccttgtttt agcaatttag cttgccatga    900
tttttattta ggtaagattc gaaaacccctt tgttttgggc ctttcctccc taaccacccc    960
cacatacact ccatcatatt tttacttttc caagttttgt ttggtttata aaatagaatg    1020
aaataatctg ccattacttt attcctcaca atctaataat tactactagt aagataagag    1080
ataattgtga ttatacccctt cgttggcctt gcaattgtga ttttactctg cattttcaac    1140
tttctaattt tacacctccg ttttaaatac gaagctacca tttgccccttc actctcaaca   1200 tcgttagtga aaatcagaat tagtgattaa aaataaaaaa atgagaaaat aaatgggtga    1260
aaggttcaaa ctaccttttt ctattctttta tgggcacaac cctaataggg gtgaaatcac    1320
tattacataa tataacgagg gtaaaatcaa aataaattgc ttgggtattt ttatcttttg    1380
catcaaattt aacattgtta actgcatcta acggcacaag ggtatggcaa ctcttcgttt    1440
tcaaaatgaa gggataaaat atcacaaagt tgaaaaacga tgggtaaaat cacaattttca   1500 agaccagaga gggtataatc acaaataccc tataagataa atagagtcat tatatcatttt   1560 tttgtaagat atacttgggg atacatcaac tcatccttag agtttgtttg ggactgtgcg    1620
gctctatatt tcaaccaaac aagtgtagct aaaaaaggtg aagttaaaag agaagtactc    1680
tagaaactct aaattaaatt tagagaaaat tcctggtatg ccatcaaatt ttatactcat    1740
tccttgtgtg ccactgagtg gcatataggt atatttttttg gtgtctatga catgtgggt    1800
```

-continued

| | | | |
|---|---|---|---|
| cagtggcata caaggaatga gtatattttc tagtggcata cagggaattg ccccttaaat | 1860 |
| ttatggagta gattttgagg atagatctaa ccaggcttga tgatgacatg tcactgtatt | 1920 |
| acaacattga tgaagatctt tcacttgagg aaaatactat tgtgcaacca acattctat | 1980 |
| acaatccaac tatcaaaagt cacaaaaata tttaaaaaat tatacatata tattatttac | 2040 |
| tttatcaata tatcatattt aagatcctag attgatttat gctatgttaa tatataattc | 2100 |
| attcatctta tataacaagg tatatatttt tggtacagtc tttggagcga aacttttgact | 2160 |
| atttgtttat ttcaaaatat gctatcaata aaaacataac gagcattaaa ttaaagtaat | 2220 |
| ttttgaatac aaatcaagta tataacatgt atatactaaa atatatgctt ttggctgaat | 2280 |
| tactagtcaa aagttttaaa acattgagtc tttttttttt aaaatgcagg ccttatttta | 2340 |
| cggaattgag ggaattttt ttatctaatt gaatatattt tttcttttac tattgtataa | 2400 |
| atttaaactt aaaattttat aatctaataa agtaaacaat aaattatatt tatatatttt | 2460 |
| tagaattttt tatggttttt ggtagtccaa ttatacattg attgtatgca aaacttgctc | 2520 |
| tgcggtgggg cgctacaatg gtctggtatg tttgcatatg ggaaaactaa tagcccgttc | 2580 |
| ccttggtttt aattcgaaac ggcttttact atttctgtag tgttttggtc tctgtgaatt | 2640 |
| gcagctacaa taatctaaac aactgacttt aattcgaagc taacaggcta taagacgctc | 2700 |
| tccaacggat cctttcccct ccccttcacg acgtattcgg tgatttcgta catcgagaga | 2760 |
| gcttcaacag gtccctctcc tccctcttgt agggtgagag aaggaaaaca ccttgtaaaa | 2820 |
| cgagaaagat agaaccctac tcttcactaa ttagtgtttt taactataaa attaatctgc | 2880 |
| tataagtttg gttaagtgac aatgtgtatt atgatattat aaatattaaa aactctaaaa | 2940 |
| actgatgtag aaaagtcaaa tagcttagtt aaagggtaaa gggagagctg aatagaggga | 3000 |
| tgcttggaga ggaggtaaaa tagggaaata atagtgaaga tgaggatatt taaatatgaa | 3060 |
| tagaaagtcc aaatgtggga tttgagatgg agaatgattg gagagagcct aataaaatca | 3120 |
| agggataatt gtgattatac cctttctaa tattttaatt gtgattttat cccttctttt | 3180 |
| ttaactttgt taccctctg ttttgaaaac aaagccgttg tttgcaccgc cttatcaacg | 3240 |
| ttaataaaaa tcagaattag tgattaaaaa taaaaataag gggtaaaatc acaattgtaa | 3300 |
| agtgagagaa ggctataatc acaattaacc ataaaaagtt taatattatt ttcagattaa | 3360 |
| ttttgagtat atccttctct tcccttacaa ttatgatttt accctcatt tttaattttc | 3420 |
| gtaatcaata attcacgaag ttgaaaacgt ataatcacag ttgtccttaa aataaatgtg | 3480 |
| ctgcccaaca aaatactctc ggactgacag acagtcgcca gtcaagagcc ctcgggcag | 3540 |
| caggatcttc cccctcccca aaaccaaacc agctgcctcc gacagcatcc acctttcct | 3600 |
| ccccaaacc atggacttct ccaccggcgg gagcgtgagc gggggcggcg gaggcgccag | 3660 |
| cgacggcccc gcgcaggcgg agcgctggct ggagatcgcc gagaagctcc tcgcggcgcg | 3720 |
| cgacctcgtc ggctgcaagc gcttcgcgga gcggtcgatg gaggcgaacc cgctcctcgc | 3780 |
| tggcgttgac gagctcctcg ccgtcgccga cgtcctcctc gcttcccagt tcatgggccc | 3840 |
| ctcgggccag ccggacccgc tcgccatcct ccagctgccg cccggagtca gccccgacca | 3900 |
| ggcc | 3904 |

<210> SEQ ID NO 24
<211> LENGTH: 1191
<212> TYPE: DNA
<213> ORGANISM: Zea mays

<400> SEQUENCE: 24

```
atggacttct ccaccggcgg gagcgtgagc gggggcggcg gaggcgccag cgacggcccc    60
gcgcaggcgg agcgctggct ggagatcgcc gagaagctcc tcgcggcgcg cgacctcgtc   120
ggctgcaagc gcttcgcgga gcggtcgatg gaggcgaacc cgctcctcgc tggcgttgac   180
gagctcctcg ccgtcgccga cgtcctcctc gcttcccagt tcatgggccc ctcgggccag   240
ccggacccgc tcgccatcct ccagctgccg cccggagtca gccccgacca ggccgccgtg   300
tcccgcgcct tccgccgcct cgcgctcctc ctcggcccca gcaacccgca cccgggagcc   360
gagatggcgc tccgcctcgt caacgacgcc tacgccttcc tctcggatcc ctctcgccgc   420
cccccgccgc ccgccgatcc cgccactggt acccccttact cctcccagta tcccgccgcg   480
gccgctcccg cctcggacac cccggagttc tggacggcgt gccccttctg ctgctacgtg   540
caccagtacc cgcgcagcct gatcgggcgc gccctcaagt gccccaacgc gggctgccgc   600
cgcggattcg tggcttctga gctcccgacc ccacccaccg ttgtgccggg cactgaaatg   660
taccactgcg cctgggggtt cttcccctc ggatttccca acgcggccga cctgggtgcc   720
aactggaagc cattctacaa gatgtttcct ggaacacgg ctcccagtgg ccaaggtggt   780
ggtggtagga gtcacggaaa ccatggtggt aggcagccac agaatgacag tgctcgtggt   840
ggctcttcta gaggtaggat caagaagacg acggcccgca agaaggtcgg ggtagggctc   900
aggagacgtt ctcttggtgt ggagagtggc attgattctt cgatgctcgg gcaggaaggc   960
tgggctgggg atgagaacgc tggagatgga agggccgagg aggtgaggag aattaacata  1020
aatgaggcag cacatgctac agatggcact ggtagggtta atgttagcgg tgctggcgga  1080
gttgaagata tcagcaactt tcatatcgat gttgatgcat ctgaggatat attggggaat  1140
ttgcacaaca tgcacttctt gagggtggac aatcttggac ggatgattta a           1191
```

<210> SEQ ID NO 25  
<211> LENGTH: 5776  
<212> TYPE: DNA  
<213> ORGANISM: Zea mays

<400> SEQUENCE: 25

```
acctagaggg ggtaaataga tgatcctgca aaattagctt taaacaacac aaacttggtt    60
tgtaaaatat gttagtgaga actaaaacca agttaggtta cgaagagagg agaaaagaga   120
actcttcact tgattgctcc tttaaaataa gtattaaagt tagtagcaat attataaata   180
aatatgagaa ttaaatagat aataatcgca ataagcagaa tggtccctct caggccaacc   240
gttccatccg tatccatttc tatcacatca tctctcacgt ctgcatgaac atgtgcacat   300
ggtatttcct tctcaaattt aacccgcgat atgaaaaaca tcgttatcaa tctttcacat   360
ctcaaaataa ctctacataa attttagtat ttgttttatt tagttcaatg agaaaaagat   420
ttgattatat acattgtagt acacctcacg ttctgcttgg acacctctat atatcttcct   480
ctaggcccta tactccctgg cccaattaaa caacacggca tcatgcagta ccaaaagaca   540
aaaacaattt ctagtagtcg agtgcctcct ctctctcctc gataccacat aatatgatat   600
atcacatggc agacggtaga taaagtaggc ggactttgct gggcatagaa aaaaaaaagg   660
atcggcgcca attccatgg caccgatctt ctgtcacgta gacgcagat cagcgtgaaa    720 gagtgagatc tcgacgccat cttatattgg cgcgcgagac atgcaaactc ggtactaata   780 ataatgcgc cggagtaaag gttcatttt tgaattgaaa cttaaaaaga cgtatttgta    840
ataatcttac aaaaaaatat caaatataaa aaaagtcag cgaaacaacg cttcacctat   900
```

```
tttaaaacgg gcctcggcgc tcgccctctt ggccacagcg cgcctcacag cgacacccac    960
aagaccacgc ccccggtcgt gcatcatcat catcgctcgc gtcttcgagt tcgaggacat   1020
ggagaggccg cgttgctact ctccgcttgc cctgcacctc ctcctctgcc tcttctcgct   1080
ccgcgcctgt tccgccgcgt ccatcacagc cggcaccccc gacgagtcgg agctgtgggg   1140
gtacgtcgag gtccggccaa gtacgtaaca acccctccct atctcgttgc gcttcagagc   1200
ctctcctcgt cgaaggcgag gtgtcgccgt tgacgacgct tgccgccctt gtcgcagagg   1260
cgcacctgtt ctggtggtac tacaagagcc cgcagaagac gtcgacgccg tccaagccat   1320
ggcccacggt cctctggctg cagggcggcc cggtaggcag ctgctgcctc gttctctctt   1380
tccctcctca caccaccaca atttctcggc ttcggcacag gagggcatga tccggcctct   1440
gtgcttcatt acgggagcac ggtctagcta cctgatgagc gagagcgagt gatcaaccat   1500
ggttgttttg tccctctcgc agggcgcgtc cggggtcggg ctcggcaact tcctggagat   1560
ggggccgctg gacgtggacc tgaagccgcg caactcgacg tggctccaca aggccgacct   1620
catctttgtg gtcagaccag agagcgatag ctgatgcctg atggcggctc tcttctcctc   1680
tcttctgccc cccgctcttc tacaccttc gctgtcgtga tgtcctcgct gaccgacttc   1740
ttccatggcc gggcgcgcgc gcgcaggaca acccggtcgg cacagggtac agctacgtgg   1800
aggacgacag cctgttcgtg accagcgact ggcagcaggc cgcggacatg acgacggtgg   1860
tcagggcgct ggcgaaggag gtgcccaccc tggcgagcag cccgctgttc ctggtcgccg   1920
agtcctacgg cggcaagtac gccgccacgc tcggcgcgtc cattgccagg gccgtccgcg   1980
ctggcgagct caacgtcacg ctcggaggtt cgtaaggtta cttccgttcc atctccgggc   2040
tccgactcga tgaaccaaat cgacgttggg ggagcagagc agctgactcg atgaaattct   2100
cgttccctcc tgctgcaggt gtggcggttg gagatagctg gatctcgccg gaggatttca   2160
cggtgaggtt gaccattcct agtttcgtta gtgcagaaat aaaccacgga cacattacag   2220
agctaatagt tacctgctaa aattagctaa atacatttag tctagctaat aatttaacta   2280 ttagctatt tagtaaacta gcgtatagcc tgtactaata tattatctag ccaaacaata   2340
atttatattg tttgtttacc ctttaactta tttaagtttg attatataat ctagaggata   2400
tccaaaccta taaaactaat agctagaagc taaaactagc tatctcaacc tagctaaaac   2460
cagctaataa gtgattggcg attaaattgc tccgaaccat ttctacctat tagcttatta   2520
gaaaaaggga cgtggatagc ttatcagaat aatctagggt attagcttta gatttagaac   2580
atcctcagct aataatagtt agccagtaac aattagttgt agaggtttgg cttcatctag   2640
actaatgcta ctaaccgaga ctaaattaga ccagtgattt tagtcttgtt ttccatctga   2700
tcgggactaa aagatgaaga cttgttctgt actagtgttc tcttggataa atcacaaatg   2760
atgaatacgc atgtgataat taaagtgagg cctgagtgct gctgcagctt tcctacacac   2820
cgctgcttct gagcgtgtcg aggctggacg acaacgccgg cgacgaagca aacaagtaag   2880
gcagcaacaa cacgcacact gcaccaccac catttgcatg cataaatttc tcttgacgct   2940
tagcgcaccc ccatcacata tatgggcatg cgaatttgag ttcaggaagg cggagacggt   3000
gaaggagcaa atcgtggcgg ggcagtgggc cgcctcgcag aagtcatggg gcagcctgct   3060
agatttcatc gacacaaaga gcggcaacgt cgtaagacta gtttacttat cttcgttctt   3120
atattcaaac ttcactcttc gaacaatata atctacagtg caatctcttt tttttggcag   3180
gacgtttaca atttcatgct cgactccggc atggacccgg tggcactgcc cgtgggttct   3240
tcatcactga tgagcagctt gcaggcgatg aagtactcga cgtacggcca ggactcccag   3300
```

```
cctggctcca acaccattga cggcatcatg aatggggtca tcaagcaaaa gctcaagata    3360
atccccaaga acttcacgta tgtcagtcca tagcagtgct catatcgcat cacaagtcac    3420
agccggtttc ctgctgctaa tataatgctg cctgtgacgc tggctgcgct tccaaattaa    3480
acgtctacag gtgggggag caatccgact cggtctacaa cgcgctggtc aacgatttca    3540
tgaaaccgaa gatcgatgag gtaaacggat cgagcagatc aatgaaaagc gccctcgatc    3600
agtttctgaa atttatccct ctttgttttc ttattcagat tgatgagctg ctgtcttatg    3660
gcattaatgt gacggtgtac aatggccagg tcagtaacag tctgcaactt cttcttacga    3720
tccccagcag ctcaaaacta ctcggagctc gtcatcggtt tttactgcat gcatgcgttc    3780
tgttagttcg attagtatta cactgcctgg catcctatct gctataaagc cgtccactct    3840
ttgtaattaa aaaaaaaaca cagatcatga aaactagaag acagaccagg ataaggtcat    3900
tggatagtgg cttagtgaat gattggcatt gactataata atattcgaag ttgagattat    3960
tagcatttac taataagact gcattttttt cattactgaa cttgatatat acatgacttt    4020
tcctctatct gaagctcgac gtaatctgct cgaccaacgg agcagaagca tgggttcaga    4080
agctcaagta agtttttttt tgcgacctat tcccttccct ccccttctct ggcaggattt    4140
caacgatgca tctggattgc tcgttttcag atgggatggt ctgaggacct tcctgagcct    4200
gccaaggcag cccctctact gtggcgccag caagggtacc aaggcctttg tcaggtccca    4260
caagaacctg catttctact ggatacttgg agcagggcac tatgtaagtc ccaagtctga    4320
accccaactg tgccgtctca tctgagatct gcttcccatg tctgtgagag tgtgaggttc    4380
ttaggtttgg atgaaccaaa taaaaccttg tttgttttct cgtgggatca tctctctgat    4440
tgcattgcag gtgcctgcag accagccctg catcgcgcta agcatgatca gcagcataac    4500
ccagtcgcca gcaagctagt tcactgactc tatgtggtgt atgccaagaa caaggaggc    4560
gttgaagcag gtagcgcaag gtcccggagg accattcggc gttcttgaag tgcggtatag    4620
gttggatacc tgaaagacga tgcagttgac aaggacattt ttttttacaga aaaagatccg    4680
ataaaaacat atatgatcta cgtattacaa aatattgtaa agaggccgga acttgttttt    4740
ttaataatag aaatgtatct ggcttcatcc tggtccaaat aacgtgccaa ataacgtgaa    4800
aaatacattg ccgcattctc tagcttgcgg aatgcctgca acatcggctc ctgctcctca    4860
gacattgtat ttgggcccaa gatccaagcc aatgcattcg actgaaaatg acatacaaga    4920
gattttggtc agcaaagttg tcaaattttg acagcttcgt ttcttgttag ctagatagat    4980
taacagatca cagacgtcat gtccataaaa aatggatctt tgtagggtat taatcattga    5040
aacagttttg gatattcagc ggcggagagg tcttcgtcag ggagaccctc tcttccctat    5100
gttgtttgtg ctgatcatgg acgtgcttag cagtctttc aggactgctg aatgtagggg    5160
attgctgcac agtttggaaa gggcaagagt ccataacagg cttttctatct atgttgatga    5220
tgtggtcctt tttgttaaac ccattgagga agatctgaaa tgtgttagat tgattctgaa    5280
ttgttttggg tcggcctccg gattggttac caatatgaat aagagttatg ctattcctat    5340
cagatgtgag gagcatgtgg ttcaagaggg ctgcaatatg ctgaggtgca gtgtggcctc    5400
atttccttgt tcttacttgg gtctgccaat ctcagacagg aagctgaagc gagatgatct    5460
taagttgtgg atagataaaa ttgcagacag actccctaac tggaaggctc gtttattgaa    5520
cctagccggg aggacaacat tagtgcggtt tgtcttatcg gtcatcccaa tttatcttct    5580
tattgccatt aaaattccca aatgggttat taaatcaatt gacaagattc gaagagagtt    5640
```

```
tctttggaaa gggtgaaagg aggtgaatgg tggaagttgt attgttccct gggaaactgt    5700
gacaaggcca taagtttagg gggtcttggt gttcctaatt tgcaattgaa gagttgggca    5760
ctgcaggcta agtggc                                                    5776

<210> SEQ ID NO 26
<211> LENGTH: 1653
<212> TYPE: DNA
<213> ORGANISM: Zea mays

<400> SEQUENCE: 26
gtcttcgagt tcgaggacat ggagaggccg cgttgctact ctccgcttgc cctgcacctc      60
ctcctctgcc tcttctcgct ccgcgcctgt tccgccgcgt ccatcacagc cggcaccccc     120
gacgagtcgg agctgtgggg gtacgtcgag gtccggccaa aggcgcacct gttctggtgg     180
tactacaaga gcccgcagaa gacgtcgacg ccgtccaagc catggcccac ggtcctctgg     240
ctgcagggcg gccgggcgc gtccggggtc gggctcggca acttcctgga gatggggccg     300
ctggacgtga acctgaagcc gcgcaactcg acgtggctcc acaaggccga cctcatcttt     360
gtggacaacc cggtcggcac agggtacagc tacgtggagg acgacagcct gttcgtgacc     420
agcgactgga gcaggccgc ggacatgacg acggtggtca gggcgctggc gaaggaggtg     480
cccaccctgg cgagcagccc gctgttcctg gtcgccgagt cctacggcgg caagtacgcc     540
gccacgctcg gcgcgtccat tgccaggcc gtccgcgctg gcgagctcaa cgtcacgctc     600
ggaggtgtgg cggttggaga tagctggatc tcgccggagg atttcacgct ttcctacaca     660
ccgctgcttc tgagcgtgtc gaggctggac gacaacgccg gcgacgaagc aaacaagaag     720
gcggagacgg tgaaggagca aatcgtggcg gggcagtggg ccgcctcgca gaagtcatgg     780
ggcagcctgc tagatttcat cgacacaaag agcggcaacg tcgacgttta caatttcatg     840
ctcgactccg gcatggaccc ggtggcactg cccgtgggtt cttcatcact gatgagcagc     900
ttgcaggcga tgaagtactc gacgtacggc caggactccc agcctggctc caacaccatt     960
gacggcatca tgaatggggt catcaagcaa aagctcaaga taatccccaa gaacttcacg    1020 tgggggagc aatccgactc ggtctacaac gcgctggtca acgatttcat gaaaccgaag    1080
atcgatgaga ttgatgagct gctgtcttat ggcattaatg tgacggtgta caatggccag    1140
ctcgacgtaa tctgctcgac caacggagca gaagcatggg ttcagaagct caaatgggat    1200
ggtctgagga ccttcctgag cctgccaagg cagcccctct actgtggcgc cagcaagggt    1260
accaaggcct ttgtcaggtc ccacaagaac ctgcatttct actggatact ggagcaggg    1320 cactatgtgc ctgcagacca gccctgcatc gcgctaagca tgatcagcag cataacccag    1380
tcgccagcaa gctagttcac tgactctatg tggtgtatgc caagaacaaa ggaggcgttg    1440
aagcaggtag cgcaaggtcc cggaggacca ttcggcgttc ttgaagtgcg gtataggttg    1500
gatacctgaa agacgatgca gttgacaagg acatttttttt tacagaaaaa gatccgataa    1560
aaacatatat gatctacgta ttacaaaata ttgtaaagag gccggaactt gtttttttaa    1620
taatagaaat gtatctggct tcatcctggt cca                                1653

<210> SEQ ID NO 27
<211> LENGTH: 1800
<212> TYPE: DNA
<213> ORGANISM: Zea mays

<400> SEQUENCE: 27
acgtgggaga ccacgccccc ggtcgtgcat catcatcatc gctcgcgtct acgagttcga      60
```

```
ggacatggag aggccgcgtt gctactctcc gcttgccctg cacctcctcc tctgcctctt     120
ctcgctccgc gcctgttccg ccgcgtccat cacagccggc accccgacg agtcggagct      180 gtggggtac gtcgaggtcc ggccaaaggc gcacctgttc tggtggtact acaagagccc      240
gcagaagacg tcgacgccgt ccaagccatg cccacggtc tctggctgc agggcggccc      300 gggcgcgtcc ggggtcgggc tcggcaactt cctggagatg gggccgctgg acgtggacct    360
gaagccgcgc aactcgacgt ggctccacaa ggccgacctc atctttgtgg acaacccggt    420
cggcacaggg tacagctacg tggaggacga cagcctgttc gtgaccagcg actggcagca    480
ggccgcggac atgacgacgg tggtcagggc gctggcgaag gaggtgccca ccctggcgag    540
cagcccgctg ttcctggtcg ccgagtccta cggcggcaag tacgccgcca cgctcggcgc    600
gtccattgcc agggccgtcc gcgctggcga gctcaacgtc acgctcggag gtgtggcggt    660
tggagatagc tggatctcgc cggaggattt cacgctttcc tacacaccgc tgcttctgag    720
cgtgtcgagg ctggacgaca acgccggcga cgaagcaaac aagaaggcgg agacggtgaa    780
ggagcaaatc gtggcggggc agtgggccgc ctcgcagaag tcatggggca gcctgctaga    840
tttcatcgac acaaagagcg gcaacgtcga aggacaaatt caggctgagc agtgggccgc    900
ctcgcagaag tcaaacggca ccctgcgaac aatataatcg acacagcaag agcggcaacg    960
tggcaggacg tttacaattt catgctcgac tccggcatgg acccggtggc actgccgtg   1020 ggttcttcat cactgatgag cagcttgcag gcgatgaagt actcgacgta cggccaggac   1080
tcccagcctg gctccaacac cattgacggc atcatgaatg gggtcatcaa gcaaaagctc   1140
aagataatcc ccaagaactt cacgtggggg gagcaatccg actcggtcta caacgcgctg   1200
gtcaacgatt tcatgaaacc gaagatcgat gagattgatg agctgctgtc ttatggcatt   1260
aatgtgacgg tgtacaatgg ccagctcgac gtaatctgct cgaccaacgg agcagaagca   1320
tgggttcaga agctcaaatg ggatggtctg aggaccttcc tgagcctgcc aaggcagccc   1380
ctctactgtg gcgccagcaa gggtaccaag gcctttgtca ggtcccacaa gaacctgcat   1440
ttctactgga tacttggagc agggcactat gtgcctgcag accagccctg catcgcgcta   1500
agcatgatca gcagcataac ccagtcgcca gcaagctagt tcactgactc tatgtggtgt   1560
atgccaagaa caaggaggc gttgaagcag gtagcgcaag gtcccggagg accattcggc    1620
gttcttgaag tgcggtatag gttggatacc tgaaagacga tgcagttgac aaggacattt   1680 tttttttacag aaaaagatcc gataaaaaca tatatgatct acgtattaca aaatattgta   1740
aagaggccgg aacttgtttt tttaataata gaaatgtatc tggcttcatc ctggtccaaa   1800

<210> SEQ ID NO 28
<211> LENGTH: 1150
<212> TYPE: DNA
<213> ORGANISM: Zea mays

<400> SEQUENCE: 28
tcacaaatga tgaatacgca tgtgataatt aaagtgaggc ctgagtgctg ctgcagcttt     60
cctacacacc gctgcttctg agcgtgtcga ggctggacga caacgccggc gacgaagcaa    120
acaagaaggc ggagacggtg aaggagcaaa tcgtggcggg gcagtgggcc gcctcgcaga    180
agtcatgggg cagcctgcta gatttcatcg acacaaagag cggcaacgtc gtaagactag    240
tttacttatc ttcgttctta tattcaaact tcactcttcg aacaatataa tctacagtgc    300
aatctctttt ttttggcagg acgtttacaa tttcatgctc gactccggca tggacccggt    360
```

```
ggcactgccc gtgggttctt catcactgat gagcagcttg caggcgatga agtactcgac      420
gtacggccag gactcccagc ctggctccaa caccattgac ggcaccatga atggggtcat      480
caagcaaaag ctcaagataa tccccaagaa cttcacgtgg ggggagcaat ccgactcggt      540
ctacaacgcg ctggtcaacg atttcatgaa accgaagatc gatgagattg atgagctgct      600
gtcttatggc attaatgtga cggtgtacaa tggccagctc gacgtaatct gctcgaccaa      660
cggagcagaa gcatgggttc agaagctcaa atgggatggt ctgaggacct tcctgagcct      720
gccaaggcag cccctctact gtggcgccag caagggtacc aaggcctttg tcaggtccca      780
caagaacctg catttctact ggatacttgg agcagggcac tatgtgcctg cagaccagcc      840
ctgcatcgcg ctaagcatga tcagcagcat aacccagtcg ccagcaagct agttcactga      900
ctctatgtgg tgtatgccaa gaacaaagga ggcgttgaag caggtagcgc aaggtcccgg      960
aggaccattc ggcgttcttg aagtgcggta taggttggat acctgaaaga cgatgcagtt     1020
gacaaggaca ttttttttac agaaaaagat ccgataaaaa catatatgat ctacgtatta     1080
caaaatattg taaagaggcc ggaacttgtt ttttaataa tagaaatgta tctggcttca      1140
tcctggtcca                                                            1150
```

```
<210> SEQ ID NO 29
<211> LENGTH: 4215
<212> TYPE: DNA
<213> ORGANISM: Zea mays

<400> SEQUENCE: 29
```

```
aaggacatat ttgtaataat ctttccaaaa aagtgtcaaa atacaaaaaa aaaagtcagc       60
gaaacaacgc ttcacctatt ttaaaacggg tctcggcgct cgccctcttg gccacaggcc      120
cacagcgcgc ctcacagcga cacccaccac gccccggtc gtgcatcatc atcatcactc       180
gcgtcttcga gttcgaggac atggacaggc gcgttgcta ctccccgctt gccctgcacc       240
tcctcctctg cctcgtctcg ctccgcgcct gttccgccgc gtccatcact gccggcaccc      300
ccgacgagtc ggagctgtgg gggtacgtcg aggtccggcc aagtacgtaa caccccctcc      360
ctagctcgtt gcgcttcaga gcctctcttc gtcgaaggcg aggtgtcgcc gttgacgacg      420 cttt gccgcc ttgtcgcaga ggcgcacctg ttctggtggt actacaagag cccgcagagg      480
acgtcgacgc cgtccaagcc atggcccacg gtcctctggc tgcagggcgg cccggtaggc      540
agctgctgcc tcgttctctc tttccctcct cacaccacca caatttctcg gcttcggcac      600
aggaggacat gatccggcct ctgtgcttca ttacgggagc acgtctagc tacctgatga       660 gcaagagcga gtaatcaacc atggttgtct tgtccctctc gcagggcgcg tccggggtcg      720
ggctcggcaa cttcctggag atggggccgc tggacgtgga cctgaagccg cgcaactcga      780
cgtggctcca caaggccgac ctcatctttg tggtcagacc agagagcgat agctgatggc      840
ggctctcttc tccgatcctc tcttctgccc cccgctcttc ttctacacct ttcgctgtcg      900
tgatgtcctc actgaccgac ttcttccatg gccgggcgcg cgcgcaggac aacccggtcg      960
gcacagggta cagctacgtg gaggacgaca gcctgttcgt gaccagcgac tggcagcagg     1020
ccgcggacat gacgacggtg gtcagggcgc tggcgaagga ggtgcccacc ctggcgagca     1080
gcccgctgtt cctggtcgcc gagtcctacg gcggcaagta cgccgccacg ctcggcgcgt     1140
ccatcgccag ggccgtccgc gctggcgagc tcaacgtcac gctcggaggt tcgtaaggtt     1200
gcttccgttc catctccggg ctccgactcg atgaaccaaa tcgacgttgg gggagcagag     1260
cagagcagag cagctgactc gatgaaattc tcgttccctc ctgctgcagg tgtggcggtt     1320
```

```
ggagatagct ggatctcgcc ggaggatttc acggtgaggt tgaccgttct tagtttcgtt    1380
agtgcagaaa taaactgcgg ctacgttgca gagctaatag ttagctgata aaattagcta    1440
aaaacattta aatagtctag ctaataattt aactattagc tattttagta aactagcgtg    1500
tagcatgtac taatatatta tctaaaagcc aaataataat ctatattgtt tgtttaccct    1560
ttaacttatt taagtttaat tatataatct agaggatatc caaacttata aaattaatag    1620
ctagaagcta aaactagcta tcccaaccta gctaaaacca gctaataagt gattgacgat    1680
taaattgctt cgaaccattt ctacctatta gcttattaga aaaagggacg tggatagctt    1740
atcagaataa tctagggtat tagctttaga tttagaacat cctcaactaa taatagttcc    1800
agtaacaatt agttctagag gtttggcttg atctagacta atgctactaa ccgagactaa    1860
attagaccag tgatttagt cttgtttggt agcttcaatc gagactaatg cttccatctg     1920
atcgggacta aaagatgaag acttgttctg tactagtgtt ctcttggata aatcacaaat    1980
gatgaatatg catgtgataa ttaaagtgag gcctgaatgc tgctgcagct ttcctacaca    2040
ccgctgcttc tgagcgtgtc gaggctggac gacaacgccg gcgacgaagc aaacaagtaa    2100
ggggtgtttt ggtttctagg gactaatgtt tagtcccttc attttattcc ttttagtgt     2160 ataaattgat aaacatagaa attaaaataa agttttagtt tctatatttg gtaattttgg    2220
accaaaaatg gaataaaatc tagggactaa acattagtcc ctagaaacca aacaccctct    2280
aaggcagcaa caacacgcac actgcaccac caccatttgc atgcataaat ttctcttgac    2340
gcttagcgca cccccatcac atatatgggc atgcgaattt gagttcagga aggcggagac    2400
ggtgaaggag caaatcgtgg cggggcagtg ggccgcctcg cagaagtcat ggagcagcct    2460
gctagatttc atcgacacaa agagcggcaa cgtcgtaagg ctagtttact tatcttcatt    2520
cttatattta aacttcactc ttcgaacaat ataatctaca gtgcaatctc ttttttttgg    2580
caggacgttt acaatttcat gctcgactcc ggcatggacc cggtggcact gctgcccgtg    2640
ggttcttcat cactgatgag cagcttgcag gcgatgaaga agtactcgac gtacggccag    2700
gactcccagc ctggctccaa caccattgac ggcatcatga atgggtcat caagcaaaag      2760 ctcaagataa tccccaagaa cttcacgtat gtcagtccat agcagtgctc atatcgcatc    2820
acaagtcaca gccggtttcc tgctgctaat gtaatgctgc ctgtgacgct ggctgcgctt    2880
ccaaattaaa cgtctacagg tggggcagc aatccgactc ggtctacaac gcgctggtca      2940
acgatttcat gaaaccgagg atcgatgagg taaactggtc gagcagataa atgaaaagcg    3000
ccctcgatca gtttctgaaa ttaatccctc ttcattttct cattcagatt gatgagctgc    3060
tgtcttatgg cattaatgtg acggtgtaca atggccaggt cagtaacagt ctgcaacttc    3120
aattcttacg atcccagca gctcaaaact actcggaaaa aaatttgctg cagcccggct      3180
gcaaaacagt atgtttacag cccctcacaa aaggaggat agatctctac tcttttttt      3240 ctcgaatata caggagacct gcatatctgt tagttcgatt agtattacac tgccatccta    3300
tctgctataa agccgtccac tctttgtaat taaaaaaaac acagatcatg aaaactagaa    3360
gacagaccag gataaggtca ttggatagtg gcttagtgaa tgattggcat tgactaataa    3420
tattcgaagt tgagattgag attattagca tttactaata agactgcatt ttttcatta    3480 ctgaacttga tatatacatg acttttcctc tatctgaagc tcgacgtaat ctgctcgacc    3540
aacggagcag aagcatgggt tcagaagctc aagtaagttt ttttttggc aacctattcc     3600 ctcccattct ctggcaggat ttcaacgatg catctggatt gctcgttttc agatgggatg    3660
```

| | |
|---|---|
| gtctgaggac cttcctgagc ctgccaaggc agccctctca ctgtggcgcc agcaagggca | 3720 |
| ccaaggcctt tgtcaggtcc cacaagaacc tgcatttcta ctggattctt ggagcagggc | 3780 |
| actatgtaag tcccaagtct gaaccctaac tgtgccgtct catctgagat ctgcttccca | 3840 |
| tgtctgtgag agtgggaggt tcttaggttt ggatgaacca aaaccttatt tgttttctcg | 3900 |
| tgggatcatc tctctgattg cattgcaggt gcctgcagac cagccctgca tcgcgctaag | 3960 |
| catgatcagc agcataaccc agtcgccagc aagctagttg actgactcta tgtggtgtat | 4020 |
| gccaaaaaca aaggaggcgt tgaagcaggt agcgcaaggt cccggaggac cattcggcgt | 4080 |
| tcttgaagtg cggtataggt tggatacctg aaaaaataca taagattata ttataaaaag | 4140 |
| gaagaatata cactaaatgg tagtataatt aattataaaa tgtttgtagt cctttctctg | 4200 |
| cgaagaaaat ctttt | 4215 |

<210> SEQ ID NO 30
<211> LENGTH: 5108
<212> TYPE: DNA
<213> ORGANISM: Zea mays

<400> SEQUENCE: 30

| | |
|---|---|
| tataatccga ctacatttaa tacccggaac ggaggttcaa acattcgatg ggacagggac | 60 |
| taaattttag cggggtgtaa ccaaacaccc ccttagtagc aatattacaa gtgaatatga | 120 |
| gaacttaaga agacaataat cgcaataaga agaatggtcc ctctccggcc aaccgttcca | 180 |
| tccatatcca tttctatcac atcatctctc acgtctccat gaacatgtgc acatggtatt | 240 |
| tccttctcaa atttttaccc gcgatatgaa aaacatcgtt atcaatcttt cacatctcaa | 300 |
| aataactcta ctataaattt ttagtatttg ttatatttag ttcaatgaga aaggatttg | 360 |
| attatataca ttgtagtaca cgtcatgttc tgcttggaca cctctgtata tctccctcta | 420 |
| ggctctatac tccctgcccc aattaaacaa cacggcatca tgccaaaaac aatttctagt | 480 |
| agtcgagtgc ctactctctc tcctcgttct ctctccccag tggcatcgaa ggaaaagtat | 540 |
| atatgattgt acccatgatg tgatatacca tatgacagac ggtagataaa gcaggcggac | 600 |
| tttgatgggc atagaaaaca gggtcggcgc caattaccat ggcgccgatc tcatgtcaca | 660 |
| tagacgccac atcagcgtga gagagtgaga tctcgacagt cgacgccatc tatattgccg | 720 |
| cgcgagacgt gcaaactcgg tactaataat aatggcgccg ggtaaaggtc tattttttta | 780 |
| attgaaactt aaaaggacat atttgtaata atctttccaa aaaagtgtca aaatacaaaa | 840 |
| aaaaagtca gcgaaacaac gcttcaccta ttttaaaacg ggtctcggcg ctcgccctct | 900 |
| tggccacagg cccacagcgc gcctcacagc gacacccacc acgcccccgg tcgtgcatca | 960 |
| tcatcatcac tcgcgtcttc gagttcgagg acatggacag gccgcgttgc tactccccgc | 1020 |
| ttgccctgca cctcctcctc tgcctcgtct cgctccgcgc ctgttccgcc gcgtccatca | 1080 |
| ctgccggcac ccccgacgag tcggagctgt ggggtacgt cgaggtccgg ccaagtacgt | 1140 |
| aacaccccct ccctagctcg ttgcgcttca gagcctctct tcgtcgaagg cgaggtgtcg | 1200 |
| ccgttgacga cgctttgccg ccttgtcgca gaggcgcacc tgttctggtg gtactacaag | 1260 |
| agcccgcaga ggacgtcgac gccgtccaag ccatggccca cggtcctctg ctgcagggc | 1320 |
| ggcccggtag gcagctgctg cctcgttctc tctttccctc ctcacaccac cacaatttct | 1380 |
| cggcttcggc acaggaggac atgatccggc ctctgtgctt cattacggga gcacggtcta | 1440 |
| gctacctgat gagcaagagc gagtaatcaa ccatggttgt cttgtccctc tcgcagggcg | 1500 |
| cgtccggggt cgggctcggc aacttcctgg agatggggcc gctggacgtg gacctgaagc | 1560 |

```
cgcgcaactc gacgtggctc cacaaggccg acctcatctt tgtggtcaga ccagagagcg   1620
atagctgatg gcggctctct tctccgatcc tctcttctgc cccccgctct tcttctacac   1680
ctttcgctgt cgtgatgtcc tcactgaccg acttcttcca tggccgggcg cgcgcgcagg   1740
acaacccggt cggcacaggg tacagctacg tggaggacga cagcctgttc gtgaccagcg   1800
actggcagca ggccgcggac atgacgacgg tggtcagggc gctggcgaag gaggtgccca   1860
ccctggcgag cagcccgctg ttcctggtcg ccgagtccta cggcggcaag tacgccgcca   1920
cgctcggcgc gtccatcgcc agggccgtcc gcgctggcga gctcaacgtc acgctcggag   1980
gttcgtaagg ttgcttccgt tccatctccg ggctccgact cgatgaacca aatcgacgtt   2040
gggggagcag agcagagcag agcagctgac tcgatgaaat tctcgttccc tcctgctgca   2100
ggtgtggcgg ttggagatag ctggatctcg ccggaggatt tcacggtgag gttgaccgtt   2160
cttagtttcg ttagtgcaga ataaactgc ggctacgttg cagagctaat agttagctga    2220
taaaattagc taaaaacatt taaatagtct agctaataat ttaactatta gctattttag   2280
taaactagcg tgtagcatgt actaatatat tatctaaaag ccaaataata atctatattg   2340 tttgttacc ctttaactta tttaagttta attatataat ctagaggata tccaaactta    2400
taaaattaat agctagaagc taaaactagc tatcccaacc tagctaaaac cagctaataa   2460
gtgattgacg attaaattgc ttcgaaccat ttctacctat tagcttatta gaaaaaggga   2520
cgtggatagc ttatcagaat aatctagggt attagcttta gatttagaac atcctcaact   2580
aataatagtt ccagtaacaa ttagttctag aggtttggct tgatctagac taatgctact   2640
aaccgagact aaattagacc agtgatttta gtcttgtttg gtagcttcaa tcgagactaa   2700
tgcttccatc tgatcgggac taaaagatga agacttgttc tgtactagtg ttctcttgga   2760
taaatcacaa atgatgaata tgcatgtgat aattaaagtg aggcctgaat gctgctgcag   2820 cttttcctaca caccgctgct tctgagcgtg tcgaggctgg acgacaacgc cggcgacgaa   2880
gcaaacaagt aaggggggtgt ttggtttcta gggactaatg tttagtccct tcattttatt   2940 ccttttagt gtataaattg ataaacatag aaattaaaat aaagttttag tttctatatt    3000
tggtaatttt ggaccaaaaa tggaataaaa tctagggact aaacattagt ccctagaaac   3060
caaacaccct ctaaggcagc aacaacacgc acactgcacc accaccattt gcatgcataa   3120
atttctcttg acgcttagcg cacccccatc acatatatgg gcatgcgaat ttgagttcag   3180
gaaggcggag acgtgaagg agcaaatcgt ggcggggcag tgggccgcct cgcagaagtc    3240
atggagcagc ctgctagatt tcatcgacac aaagagcggc aacgtcgtaa ggctagttta   3300
cttatcttca ttcttatatt taaacttcac tcttcgaaca atataatcta cagtgcaatc   3360 tcttttttt ggcaggacgt ttacaatttc atgctcgact ccggcatgga cccggtggca    3420
ctgctgcccg tgggttcttc atcactgatg agcagcttgc aggcgatgaa gaagtactcg   3480
acgtacggcc aggactccca gcctggctcc aacaccattg acggcatcat gaatgggggtc   3540 atcaagcaaa agctcaagat aatccccaag aacttcacgt atgtcagtcc atagcagtgc   3600
tcatatcgca tcacaagtca cagccggttt cctgctgcta atgtaatgct gcctgtgacg   3660
ctggctgcgc ttccaaatta aacgtctaca ggtgggggca gcaatccgac tcggtctaca   3720
acgcgctggt caacgatttc atgaaaccga ggatcgatga ggtaaactgg tcgagcagat   3780
aaatgaaaag cgccctcgat cagtttctga aattaatccc tcttcatttt ctcattcaga   3840
ttgatgagct gctgtcttat ggcattaatg tgacggtgta caatggccag gtcagtaaca   3900
```

```
gtctgcaact tcaattctta cgatccccag cagctcaaaa ctactcggaa aaaatttgc    3960 tgcagcccgg ctgcaaaaca gtatgtttac agcccctcac aaaaaggagg atagatctct    4020 actcttttt  ttctcgaata tacaggagac ctgcatatct gttagttcga ttagtattac    4080
actgccatcc tatctgctat aaagccgtcc actctttgta attaaaaaaa acacagatca    4140
tgaaaactag aagacagacc aggataaggt cattggatag tggcttagtg aatgattggc    4200
attgactaat aatattcgaa gttgagattg agattattag catttactaa taagactgca    4260 ttttttcat  tactgaactt gatatataca tgacttttcc tctatctgaa gctcgacgta    4320
atctgctcga ccaacggagc agaagcatgg gttcagaagc tcaagtaagt ttttttttg    4380 gcaacctatt ccctcccatt ctctggcagg atttcaacga tgcatctgga ttgctcgttt    4440
tcagatggga tggtctgagg accttcctga gcctgccaag gcagcccctc tactgtggcg    4500
ccagcaaggg caccaaggcc tttgtcaggt cccacaagaa cctgcatttc tactggattc    4560
ttggagcagg gcactatgta agtcccaagt ctgaaccta actgtgccgt ctcatctgag    4620
atctgcttcc catgtctgtg agagtgggag gttcttaggt ttggatgaac caaaaccta    4680 tttgtttct  cgtgggatca tctctctgat tgcattgcag gtgcctgcag accagccctg    4740
catcgcgcta agcatgatca gcagcataac ccagtcgcca gcaagctagt tgactgactc    4800
tatgtggtgt atgccaaaaa caaggaggc gttgaagcag gtagcgcaag gtcccggagg    4860
accattcggc gttcttgaag tgcggtatag gttggatacc tgaaaaaata cataagatta    4920
tattataaaa aggaagaata tacactaaat ggtagtataa ttaattataa aatgtttgta    4980
gtccttttct tgcgaagaaa atcttttaaa tggcatttgt gtgaagcaca atgtttagag    5040
tcctaaaaat gcaattgtct ctgttgggga cttgctctca aatgctatga atcaagagca    5100
agacaaca                                                              5108
```

<210> SEQ ID NO 31
<211> LENGTH: 1659
<212> TYPE: DNA
<213> ORGANISM: Zea mays

<400> SEQUENCE: 31

```
gtcttcgagt tcgaggacat ggacaggccg cgttgctact ctccgcttgc cctgcacctc      60
ctcctctgcc tcttctcgct ccgcgccgt tccgccgcgt ccatcacagc cggcacccc      120 gacgagtcgg agctgtgggg gtacgtcgag gtccggccaa aggcgcacct gttctggtgg    180
tactacaaga gcccgcagaa gacgtcgacg ccgtccaagc catggcccac ggtcctctgg    240
ctgcagggcg gcccgggcgc gtccggggtc gggctcggca acttcctgga gatggggccg    300
ctggacgtgg acctgaagcc gcgcaactcg acgtggctcc acaaggccga cctcatcttt    360
gtggacaacc cggtcggcac agggtacagc tacgtggagg acgacagcct gttcgtgacc    420
agcgactggc agcaggccgc ggacatgacg acggtggtca gggcgctggc gaaggaggtg    480
cccaccctgg cgagcagccc gctgttcctg gtcgccgagt cctacggcgg caagtacgcc    540
gccacgctcg gcgcgtccat tgccagggcc gtccgcgctg gcgagctcaa cgtcacgctc    600
ggaggtgtgg cggttggaga tagctggatc tcgccggagg atttcacgct tcctacaca    660 ccgctgcttc tgagcgtgtc gaggctggac gacaacgccg gcgacgaagc aaacaagaag    720
gcggagacgg tgaaggagca aatcgtggcg gggcagtggg gcgcctcgca gaagtcatgg    780
ggcagcctgc tagatttcat cgacacaaag agcggcaacg tcgacgttta caatttcatg    840
ctcgactccg gcatggaccc ggtggcactg ctgcccgtgg gttcttcatc actgatgagc    900
```

| | |
|---|---|
| agcttgcagg cgatgaagaa gtactcgacg tacggccagg actcccagcc tggctccaac | 960 |
| accattgacg gcatcatgaa tggggtcatc aagcaaaagc tcaagataat ccccaagaac | 1020 |
| ttcacgtggg gggagcaatc cgactcggtc tacaacgcgc tggtcaacga tttcatgaaa | 1080 |
| ccgaagatcg atgagattga tgagctgctg tcttatggca ttaatgtgac ggtgtacaat | 1140 |
| ggccagctcg acgtaatctg ctcgaccaac ggagcagaag catgggttca gaagctcaaa | 1200 |
| tgggatggtc tgaggaccct cctgagcctg ccaaggcagc cctctactg tggcgccagc | 1260 |
| aagggtacca aggcctttgt caggtcccac aagaacctgc atttctactg gatacttgga | 1320 |
| gcagggcact atgtgcctgc agaccagccc tgcatcgcgc taagcatgat cagcagcata | 1380 |
| acccagtcgc cagcaagcta gttcactgac tctatgtggt gtatgccaag aacaaaggag | 1440 |
| gcgttgaagc aggtagcgca aggtcccgga ggaccattcg gcgttcttga agtgcggtat | 1500 |
| aggttggata cctgaaagac gatgcagttg acaaggacat tttttttaca gaaaaagatc | 1560 |
| cgataaaaac atatatgatc tacgtattac aaaatattgt aaagaggccg gaacttgttt | 1620 |
| ttttaataat agaaatgtat ctggcttcat cctggtcca | 1659 |

<210> SEQ ID NO 32
<211> LENGTH: 1795
<212> TYPE: DNA
<213> ORGANISM: Zea mays

<400> SEQUENCE: 32

| | |
|---|---|
| agttcatcac taatcacact tattgtgccc tcgacgagta tctatagcta gctcattaat | 60 |
| cgattcgggg gtgtgttgtc gaaggcggca atggcgagct actcgtcgcg gcgtccatgc | 120 |
| aatacctgta gcacgaaggc gatggccggg agcgtggtcg gcgagcccgt cgtgctgggg | 180 |
| cagagggtga cggtgctgac ggtggacggc ggcggcgtcc ggggtctcat cccgggaacc | 240 |
| atcctcgcct tcctggaggc caggctgcag gagctggacg gaccggaggc gaggctggcg | 300 |
| gactacttcg actacatcgc cggaaccagc accggcggtc tcatcaccgc catgctcacc | 360 |
| gcgcccggca aggacaagcg gcctctctac gctgccaagg acatcaacca cttttacatg | 420 |
| cagaactgcc cgcgcatctt tcctcagaag tgagtccgat gctgccgcca ttgttcttgc | 480 |
| atccatccag catcgtacgt acgtcctcta tacatctgcg gatcatcatg tgcgcatgtt | 540 |
| tgtggcatga atgcatgcat gtgagcagga gcaggcttgc ggccgccatg tccgcgctga | 600 |
| ggaagccaaa gtacaacggc aagtgcatgc gcagcctgat taggagcatc ctcggcgaga | 660 |
| cgagggtaag cgagacgctg accaacgtca tcatccctgc cttcgacatc aggctgctgc | 720 |
| agcctatcat cttctctacc tacgacgtac gtacgtcgtc acgaatgatt catctgtacg | 780 |
| tcgtcgcatg cgaatggctg cctacgtacg ccgtgcgcta acatactcag ctcttccta | 840 |
| tctgctgcgc caatttgcag gccaagagca cgcctctgaa gaacgctctg ctctcggacg | 900 |
| tgtgcattgg cacgtccgcc gcgccgacct acctcccggc gcactacttc cagactgaag | 960 |
| acgccaacgg caaggagcgc gaatacaacc tcatcgacgg cggtgtggcg ccaacaacc | 1020 |
| cggtaactga ctagctaact ggaaaacgga cgcacagact ccatgtccat ggcggcccac | 1080 |
| aaggtcgatg ctaattgttg cttatgtatg tcgcccgatt gcacatgcgt agacgatggt | 1140 |
| tgcgatgacg cagatcacca aaaagatgct tgccagcaag gacaaggccg aggagctgta | 1200 |
| cccagtgaag ccgtcgaact gccgcaggtt cctggtgctg tccatcggga cggggtcgac | 1260 |
| gtccgagcag ggcctctaca cggcgcggca gtgctcccgg tggggtatct gccggtggct | 1320 |

```
ccgcaacaac ggcatggccc ccatcatcga catcttcatg gcggccagct cggacctggt      1380
ggacatccac gtcgccgcga tgttccagtc gctccacagc gacggcgact acctgcgcat      1440
ccaggacaac tcgctccgtg gcgccgcggc caccgtggac gcggcgacgc ggagaacat       1500 gcggacgctc gtcgggatcg gggagcggat gctggcacag agggtgtcca gggtcaacgt      1560
ggagacaggg aggtacgaac cggtgactgg cgaaggaagc aatgccgatg ccctcggtgg      1620
gctcgctagg cagctctccg aggagaggag aacaaggctc gcgcgccgcg tctctgccat      1680
caacccaaga ggctctagat gtgcgtcgta cgatatctaa gacaagtggc tttactgtca      1740
gtcacatgct tgtaaataag tagactttat tttaataaaa cataaaaata tatat           1795
```

<210> SEQ ID NO 33
<211> LENGTH: 1452
<212> TYPE: DNA
<213> ORGANISM: Zea mays

<400> SEQUENCE: 33

```
agttcatcac taatcacact tattgtgccc tcgacgagta tctatagcta gctcattaat        60
cgattcgggg gtgtgttgtc gaaggcggca atggcgagct actcgtcgcg gcgtccatgc       120
aatacctgta gcacgaaggc gatggccggg agcgtggtcg gcgagcccgt cgtgctgggg       180
cagagggtga cggtgctgac ggtggacggc ggcggcgtcc ggggtctcat cccgggaacc       240
atcctcgcct tcctggaggc caggctgcag gagctggacg gaccggaggc gaggctggcg       300
gactacttcg actacatcgc cggaaccagc accggcggtc tcatcaccgc catgctcacc       360
gcgcccggca aggacaagcg gcctctctac gctgccaagg acatcaacca cttttacatg       420
cagaactgcc gcgcatcttt cctcagaag agcaggcttg cggccgccat gtccgcgctg        480
aggaagccaa agtacaacgg caagtgcatg cgcagcctga ttaggagcat cctcggcgag       540
acgagggtaa gcgagacgct gaccaacgtc atcatccctg ccttcgacat caggctgctg       600
cagcctatca tcttctctac ctacgacgcc aagagcacgc ctctgaagaa cgctctgctc       660
tcggacgtgt gcattggcac gtccgccgcg ccgacctacc tcccggcgca ctacttccag       720
actgaagacg ccaacggcaa ggagcgcgaa tacaacctca tcgacggcgg tgtggcggcc       780
aacaacccga cgatggttgc gatgacgcag atcaccaaaa agatgcttgc cagcaaggac       840
aaggccgagg agctgtaccc agtgaagccg tcgaactgcc gcaggttcct ggtgctgtcc       900
atcgggacgg ggtcgacgtc cgagcagggc ctctacacgg cgcggcagtg ctcccggtgg       960
ggtatctgcc ggtggctccg caacaacggc atggcccccca tcatcgacat cttcatggcg     1020
gccagctcgg acctggtgga catccacgtc gccgcgatgt tccagtcgct ccacagcgac     1080
ggcgactacc tgcgcatcca ggacaactcg ctccgtggcg ccgcggccac cgtggacgcg     1140
gcgacgccgg agaacatgcg gacgctcgtc gggatcgggg agcggatgct ggcacagagg     1200
gtgtccaggg tcaacgtgga gacagggagg tacgaaccgg tgactggcga aggaagcaat     1260
gccgatgccc tcggtgggct cgctaggcag ctctccgagg agaggagaac aaggctcgcg     1320
cgccgcgtct ctgccatcaa cccaagaggc tctagatgtg cgtcgtacga tatctaagac     1380
aagtggcttt actgtcagtc acatgcttgt aaataagtag actttatttt aataaaacat     1440
aaaaatatat at                                                         1452
```

<210> SEQ ID NO 34
<211> LENGTH: 4564
<212> TYPE: DNA
<213> ORGANISM: Zea mays

<400> SEQUENCE: 34

```
aaggaaaggt cacacatcct agctagcttc actggttcta gctccttcca attttgcaaa    60
aaagtcacaa aggataagcc attttccaa atgatttgtg aaatgcctat gctaaaaagc    120
ctacttttcc gaaaaaccag agctagagcc attttgaca agtcagaacc ctaccaaata    180
gtccctcagt ttaagcaaag tgaggccata ctgaagctaa attatgccaa attgggccta    240
catctccata ttttcaacca aatgctttag ggtttcttgt aatcgacatg atttgtttct    300
tcataaatag tatatggacc gctccaaaat actccatccg tttcaattta tatttcgttt    360
gatcttttta ccctaaattt gatcgactcg tcttattaaa aaaagttcat aactattaat    420
aatctttact gtgatatcat ttagcatata atatacttta attgtggctt tgatttttt    480
ccgcaaaaat taaatgaaac gacccaatca aacttgataa aaaagtaaaa ctaattataa    540
atttggacag aaggagtagg agggtgtttg aatacactag agttaatagt tagttgcctt    600
aaaatttgct agtacaatta gctagctaac aaatatttag gtaactatta gctaatttgc    660
taaaaacagc taatagttaa actattagct agactgtttg gatgtattca gctaatttta    720
gcagctaact attagctata gtataatatt caaacacctc ctaattaaaa tggacaaata    780
tctcttccct tggtcccttg cgttagattt ccatatctcc ttatttagta taaaaagaat    840
catcaaaaag tggacaaccc ctagtggaac accattttag tagtggttgc atgaaacctt    900
tcgcgcatca gttactatgt gtcactctaa aaatggggca gcatgtacgc agtgcctata    960
tttatacaag gcatctatcg ttgcctcctc agttcatcac taatcacact tattgttccc   1020
tcgacgagta tctagctagc tcattaatcg atcaatcggg gtgtgcggtc gaaggcggca   1080
atggcgagct actcgtcgcg gcgtccatgc aatacctgta gcacgaaggc gatggccggg   1140
agcgtggtcg gcgagcccgt cgtgctgggg cagagggtga cggtgctgac ggtggacggc   1200
ggcggcgtcc ggggtctcat cccgggaacc atcctcgcct tcctcgaggc caggctgcag   1260
gagctggacg gaccggaggc gaggctggcg gactacttcg actacatcgc cggaaccagc   1320
accggcggtc tcatcaccgc catgctcacc gcgcccggca aggacaagcg gcctctctac   1380
gctgccaagg acatcaacca cttttacatg gagaactgcc gcgcatctt ccctcagaag   1440
tgagtccgat gctgccgcca ttgttcttgc atccatgcat ccagcatcgt acgtcctcta   1500
tacatctgcg gatgatcatt tgcgcatgtt tgtggcatgc atgcatgtga tgtgagcagg   1560
agcaggcttg cggccgccat gtccgcgctg aggaagccaa agtacaacgg caagtgcatg   1620
cgcagcctga ttaggagcat cctcggcgag acgagggtaa gcgagacgct gaccaacgtc   1680
atcatccctg ccttcgacat caggctgctg cagcctatca tcttctctac ctacgacgta   1740
cgtacgtcgt cacgaatgat tcatctgtac gtcgtcgcat gcgaatggct gcctacgtac   1800
gccgtgcgct aacatactca gctctttcct atctgctgcg ccaatttgca ggccaagagc   1860
acgcctctga agaacgctct gctctcggac gtgtgcattg gcacgtccgc cgcgccgacc   1920
tacctcccgg cgcactactt ccagactgaa gacgccaacg gcaaggagcg cgaatacaac   1980
ctcatcgacg gcgtgtggc ggccaacaac ccggtaactg actagctaac tggaaaacgg   2040
acgcacagac tccatgtcca tggcggccca caaggtcgat gctaattgtt gcttatgtat   2100
gtcgcccgat tgcacatgcg tagacgatgg ttgcgatgac gcagatcacc aaaaagatgc   2160
ttgccagcaa ggacaaggcc gaggagctgt acccagtgaa gccgtcgaac tgccgcaggt   2220
tcctggtgct gtccatcggg acggggtcga cgtccgagca gggcctctac acggcgcggc   2280
```

```
agtgctcccg gtggggtatc tgccggtggc tccgcaacaa cggcatggcc cccatcatcg    2340
acatcttcat ggcggccagc tcggacctgg tggacatcca cgtcgccgcg atgttccagt    2400
cgctccacag cgacggcgac tacctgcgca tccaggacaa ctcgctccgt ggcgccgcgg    2460
ccaccgtgga cgcggcgacg ccggagaaca tgccgacgct cgtcgggatc ggggagcgga    2520
tgctggcaca gagggtgtcc agggtcaacg tggagacagg gaggtacgaa ccggtgactg    2580
gcgaaggaag caatgccgat gccctcggtg ggctcgctag gcagctctcc gaggagagga    2640
gaacaaggct cgcgcgccgc gtgtctgcca tcaacccaag aggctctaga tgtgcgtcgt    2700
acgatatcta agacaagtgg ctttactgtc agtcacatgc ttgtaaataa gtagacttta    2760
ttttaataaa acataaaaat atatatatgt tcttgaatat aaaattgata accaaaattc    2820
gaaccatcac ttatacataa ttttacttta tttttttataa aacgtgaacg ggaaggacta    2880
ccatgaatga ctatagaacc aatcatacta gtataaaata tatgatgaca ctacgagaga    2940
gacaaacttt gtctggcgct aaatattttg ccgagtgtga attcacgggc actaggcaaa    3000
gatcttcttt gccgagtgtt acgctgggca aagtaagaca ctaggtaaat cagtcatttg    3060
ccgagtgtcc gccactaggc aaagcaaaac actggcaaat caaaagttta cctagtgcca    3120
gacactaggc aaaaaaaaac gctcggcaaa tcggaagttt ccctagtgcc agacactaga    3180
caaagaaaaa cacttgataa actagcgtcg tcagctaaca ccatccacca accgttaacg    3240
ttgccgagta tctgacttcg acactcggca agaaggtct ctttgcctag tgtcggtctg    3300
gaacactagg caaagaggca ctttacctag tgtcgtattt tgacactcag taaaataatt    3360
ttttttcttt ctgcttccaa actttttatg atgtgttcct atagcaccta gaactacatg    3420
tcaagttttg gtaaaatttt tgaagttttt gctatattta cttaatttat tttatttaat    3480
tgaatttctt ttgataattc aaatttgaac tcggcaaggt aagaagcgag ggtagcctgg    3540
aaacacactt tgcctagtgt tacactcggt acaggagcct ccctgccta gtgctgcact    3600 cgacaaaaga ttcgcctttg cctagcgctg cactcggcac aggagtcgcc tttgcctagt    3660
gctgcactag gcaaagcctc cgttaccgtg ccttccatcg tcatggaaac ttttcttcgc    3720
cgagtgacgt gtggcactag gcaaagtttt tgccgagtgc ccgagaaatg gcactcggca    3780
aggactcttt gtcgatccct tcgttgccga cttctttttg ccgagtgcaa cactaggcaa    3840
accatttgcc gagtgtaaaa gaggctttgc ctagtgtctg tggcactagg caaagaagac    3900
gagtcctgta gtgaacctag taggccagtg cgggaccatt ccaaaaaata cctataaaaa    3960
taaatttaat attaaattaa acatatggtc cacgtaccaa gatattaaac tcaaaagaac    4020
aattattaca atttatctta gctaaaaggc cgagaaaagt atatgttaaa aaggagtgtg    4080
atcccatttt tatagctcgc tcggtcgatc gcccgtccac ttttaggtaa cgaggtggta    4140
ccatgtagga gtgttgcgtt gcgtgcgact tcctatcatg ttgggcttag gtggcttctc    4200
acgacccaat gataggcgag aagtgtggaa gatgaacaaa cctacttgtt tcgtgcacga    4260
cgcatgtgtt tgaacaacga gttagattag aaaaaaaata taatgacttt ttttttgcaa    4320
aagtgaggat aatgaaaacc agaaaaactg gtgcttcata agagtagaga tttgatggta    4380
aatatagtag taatgcaatg gctatactac acgcgagagt ccaatggcaa gccggtgtgt    4440
tggggcgaag gcgaagacgc taccccttcgc tccaggcctt tgtcaactcg ctgcaccaac    4500
agaggcaaga tgaccggcgc ggcccaccct tcgtcctctt cactgcaaga cgaaggccta    4560
cgac                                                                4564
```

<210> SEQ ID NO 35
<211> LENGTH: 2089
<212> TYPE: DNA
<213> ORGANISM: Zea mays

<400> SEQUENCE: 35

```
caccggcggt ctcatcaccg ccatgctcac cgcgcccggc aaggacaagc ggcctctcta      60
cgctgccaag gacatcaact acttttacat ggagaactgc ccgcgcatct tccctcagaa     120
gtgagtccga tgctgccgcc attgttctcg catccatcca gcatcgtacg tcctctatac     180
atctgcggat gatcatttgc gcatgtttgt ggcatgcatg tgagcaggag caggcttgcg     240
gccgccatgt ccgcgctgag gaagccaaag tacaacggca agtgcatgcg cagcctgatt     300
aggagcatcc tcggcgagac gagggtaagc gagacgctga ccaacgtcat catccctgcc     360
ttcgacatca ggctgctgca gcctatcatc ttctctacct acgacgtacg tacgtcgtca     420
cgaatgattc atctgtacgt cgtcgcatgc gaatggctgc ctacgccgtg cgctaacata     480
ctcagctctt tccgatctgc tgcgccaatt gcaggccaa gagcacgcct ctgaagaacg     540
cgctgctctc ggacgtgtgc attggcacgt ccgccgcgcc gacctacctc ccggcgcact     600
acttccagac tgaagacgcc aacggcaagg agcgcgaata caactcatc gacgcggtg      660
tggcggccaa caacccggta actgactagc taactgcaaa acgaacgcac agactccatg     720
tccatggcgg cccacaaggt cgatgctaat tgttgcttat gtatgtcgcc cgattgcaca     780
tgcgtagacg atggttgcga tgacgcagat caccaaaaag atgcttgcca gcaaggacaa     840
ggccgaggag ctgtacccag tgaacccgtc gaactgccgc aggttcctgg tgctgtccat     900
cgggacgggg tcgacgtccg agcagggcct ctacacggcg cggcagtgct cccggtgggg     960
catctgccgg tggctccgca caacggcat ggcccccatc atcgacatct tcatggcggc    1020
cagctcggac ctggtggaca tccacgtcgc cgcgatgttc cagtcgctcc acagcgacgg    1080
cgactaccta cgcatccagg acaactcgct ccgtggcgcc gcggcaaccg tggacgcggc    1140
gacgccggag aacatgcgga cgctcgtcgg gatcggggag cggatgctgg cacagcgggt    1200
gtccagggtc aacgtggaga cagggagcga ggtacgaacc ggtgaccgga gaaggaagca    1260
atgccgatgc cctcggtggg ctcgctaggc agctctccga ggagaggaga acaaggctcg    1320
cgcgccgcgt ctctgccatc aaccccagaa gctctagatg tgcgccctac gatatctaag    1380
acaagtggct ttactgtcaa tcacatgctt gtaaataagt agactttatt ttaataaaat    1440
ataaatatat atatattctg ataaccaaga ttcgaaccct cacttataca caattttatc    1500
ttatttttta taaatgaga atggaaagga ctaccgtgaa cgactataga accaatcata    1560
ctagtttaaa atgctcgtaa gctatgacga acctagtagg ccggtgctgg accattccaa    1620
aaaacctata aaaataaatt taatattaaa ttaaacatat ggtctatata tcagatatta    1680
aactcaaaag aataattatt ataatttatc ttagctaaaa ggttgagaaa ggtatgcgtt    1740
aaaaaagagt tttaacccat ttttatagct tatttgatcg cccgtccact tttagggagc    1800
gaggtggtac tatgcagaag tgttgcgctg tgtgcgactt actatcatgt tgggtttagg    1860
tggattctca cgacccaatg atagacgaga agtgtgggag atgaacaaac ctacgcattt    1920
cgcgtacgac acatgtgttt gaacaacgag ttagattgga aaaatataa tgacctttt    1980
tgcaaaaatg actacaatga aaaccaggaa aaccggtgct tcataggagt agagatttga    2040
cggtaaattg ttacgatcta ctggtatttg ctgcgaggat gtattcgct                2089
```

<210> SEQ ID NO 36

<211> LENGTH: 3557
<212> TYPE: DNA
<213> ORGANISM: Zea mays

<400> SEQUENCE: 36

```
tgacgtttgg taaaacgact tcttccgaaa acacccaaa aacccaagat attttatact      60
acgaaggaaa ggtcacacat cctagttagc ttcactggtt ctagctcctt ccaatttgc     120
aaaaaagtca caaggataa gccatttttt caaatgattt gtgaaatgcc tacgctaaaa     180
agtctacttt tccaaaaaaa ctagagctag agccgttttt ggcaagtcag aaccctacca    240
aatagtccct cagtttaagc aaagtgaggc tatactgaag ctaaattatg ccaaattggg    300
cctacatctc catattttca accaaatgct ttagggtttc ttgtaatcga catgatttgt    360
ttcttcataa atagtatatg gaccgctcca aaatactcca tccgtttcaa tttatattac    420
gtttgatctt tttaccctaa atttgatcga ctcgtcttat taaaaaagtt cataactatt    480
aataatcttt actgtgatat catttagcat ataatatact ttaagtgtag ctttgatttt    540
tttttgcaa aaattaaatg aaacgaccca atcaaacttg ataaaaagt aaaactaatt      600
ataaatttgg acataaggag taggagggtg tttgaataca ctagagttaa tagttagttg    660
tcttaaaatt tgctagtaca attagctagc taacaaatat ttaggtaact attagctaat    720
ttgctaaaaa cagctaatag ttgaactatt agttgaacta ttagctagac tgtttggatg    780
tattcaacta attttagcag ctaactatta gttatagtat aatattcaaa cacctcctaa    840
ttaaaatgga caaatatcta ttcccttggt cccttgcgtt agattttcca tatatcctca    900
tttagtataa aaagaatcat caaaaagtgg acaaccccta gtggaacacc attttagtag    960
tggttgcatg aaacctttcg cgcatcagtt actatgtgtc actctaaaaa tggggcagca   1020
tgtacgcagt gcctatattt atacaaggca tctatcgttg cctcctcagt tcatcactaa   1080
tcacacttat tgtgccctcg acgagtatct agctagctca ttaatcgatc aatcggggtg   1140
tgcggtcgaa ggcggcaatg gcgagctact cgtcgcggcg tccatgcaat acctgtagca   1200
cgaaggcgat ggccgggagc gtggtcggcg agcccgtcgt gctgggcag agggtgacgg    1260
tgctgacggt ggacggcggc ggcgtccggg gtctcatccc gggaaccatc ctcgccttcc   1320
tggaggccag gctgcaggag ctggacggac cggaggcgag gctggcggac tacttcgact   1380
acatcgccgg aaccagcacc ggcggtctca tcaccgccat gctcaccgcg cccggcaagg   1440
acaagcggcc tctctacgct gccaaggaca tcaactactt ttacatggag aactgcccgc   1500
gcatcttccc tcagaagtga gtccgatgct gccgccattg ttctcgcatc catccagcat   1560
cgtacgtcct ctatacatct gcggatgatc atttgcgcat gtttgtggca tgcatgtgag   1620
caggagcagg cttgcggccg ccatgtccgc gctgaggaag ccaaagtaca acggcaagtg   1680
catgcgcagc ctgattagga gcatcctcgg cgagacgagg gtaagcgaga cgctgaccaa   1740
cgtcatcatc cctgccttcg acatcaggct gctgcagcct atcatcttct ctacctacga   1800
cgtacgtacg tcgtcacgaa tgattcatct gtacgtcgtc gcatgcgaat ggctgcctac   1860
gccgtgcgct aacatactca gctctttccg atctgctgcg ccaatttgca ggccaagagc   1920
acgcctctga agaacgcgct gctctcggac gtgtgcattg gcacgtccgc cgcgccgacc   1980
tacctcccgg cgcactactt ccagactgaa gacgccaacg gcaaggagcg cgaatacaac   2040
ctcatcgacg gcggtgtggc ggccaacaac ccggtaactg actagctaac tgcaaaacga   2100
acgcacagac tccatgtcca tggcggccca caaggtcgat gctaattgtt gcttatgtat   2160
gtcgcccgat tgcacatgcg tagacgatgg ttgcgatgac gcagatcacc aaaaagatgc   2220
```

```
ttgccagcaa ggacaaggcc gaggagctgt acccagtgaa cccgtcgaac tgccgcaggt      2280
tcctggtgct gtccatcggg acggggtcga cgtccgagca gggcctctac acggcgcggc      2340
agtgctcccg gtggggcatc tgccggtggc tccgcaacaa cggcatggcc cccatcatcg      2400
acatcttcat ggcggccagc tcggacctgg tggacatcca cgtcgccgcg atgttccagt      2460
cgctccacag cgacggcgac tacctacgca tccaggacaa ctcgctccgt ggcgccgcgg      2520
caaccgtgga cgcggcgacg ccggagaaca tgccgacgct cgtcgggatc ggggagcgga      2580
tgctggcaca gcgggtgtcc agggtcaacg tggagacagg gagcgaggta cgaaccggtg      2640
accggagaag gaagcaatgc cgatgccctc ggtgggctcg ctaggcagct ctccgaggag      2700
aggagaacaa ggctcgcgcg ccgcgtctct gccatcaacc ccagaagctc tagatgtgcg      2760
ccctacgata tctaagacaa gtggctttac tgtcaatcac atgcttgtaa ataagtagac      2820
tttattttaa taaatataa atatatatat attctgataa ccaagattcg aaccctcact       2880
tatacacaat tttatcttat tttttataaa atgagaatgg aaaggactac cgtgaacgac      2940
tatagaacca atcatactag tttaaaatgc tcgtaagcta tgacgaacct agtaggccgg      3000
tgctggacca ttccaaaaaa cctataaaaa taaatttaat attaaattaa acatatggtc      3060
tatatatcag atattaaact caaaagaata attattataa tttatcttag ctaaaaggtt      3120
gagaaaggta tgcgttaaaa aagagtttta acccattttt atagcttatt tgatcgcccg      3180
tccactttta gggagcgagg tggtactatg cagaagtgtt gcgctgtgtg cgacttacta      3240
tcatgttggg tttaggtgga ttctcacgac ccaatgatag acgagaagtg tgggagatga      3300
acaaacctac gcatttcgcg tacgacacat gtgtttgaac aacgagttag attggaaaaa      3360
atataatgac cttttttgca aaaatgacta caatgaaaac caggaaaacc ggtgcttcat      3420
aggagtagag atttgacggt aaattgttac gatctactgg tatttgctgc gaggatgtat      3480
tcgcttggtg aaaacagaat tacagagtag cagtagcagg gaagacagta gcgagaggag      3540
aagaagaaac ttgagga                                                     3557
```

<210> SEQ ID NO 37
<211> LENGTH: 1382
<212> TYPE: DNA
<213> ORGANISM: Zea mays

<400> SEQUENCE: 37

```
agttcatcac taatcacact tattgtgccc tcgacgagta tctagctagc tcattaatcg       60
atcaatcggg gtgtgcggtc gaaggcggca atggcgagct actcgtcgcg gcgtccatgc      120
aatacctgta gcacgaaggc gatggccggg agcgtggtcg gcgagcccgt cgtgctgggg      180
cagagggtga cggtgctgac ggtggacggc ggcggcgtcc ggggtctcat cccgggaacc      240
atcctcgcct tcctggaggc caggctgcag gagctggacg gaccggaggc gaggctggcg      300
gactacttcg actacatcgc cggaaccagc accggcggtc tcatcaccgc catgctcacc      360
gcgcccggca aggacaagcg gcctctctac gctgccaagg acatcaacta cttttacatg      420
gagaactgcc cgcgcatctt ccctcagaag agcaggcttg cggccgccat gtccgcgctg      480
aggaagccaa agtacaacgg caagtgcatg cgcagcctga ttaggagcat cctcggcgag      540
acgagggcca agagcacgcc tctgaagaac gcgctgctct cggacgtgtg cattggcacg      600
tccgccgcgc cgacctacct cccggcgcac tacttccaga ctgaagacgc caacggcaag      660
gagcgcgaat acaacctcat cgacggcggt gtggcggcca acaacccgac gatggttgcg      720
```

| | |
|---|---|
| atgacgcaga tcaccaaaaa gatgcttgcc agcaaggaca aggccgagga gctgtaccca | 780 |
| gtgaacccgt cgaactgccg caggttcctg gtgctgtcca tcgggacggg gtcgacgtcc | 840 |
| gagcagggcc tctacacggc gcggcagtgc tcccggtggg gcatctgccg gtggctccgc | 900 |
| aacaacggca tggcccccat catcgacatc ttcatggcgg ccagctcgga cctggtggac | 960 |
| atccacgtcg ccgcgatgtt ccagtcgctc cacagcgacg gcgactacct acgcatccag | 1020 |
| gacaactcgc tccgtggcgc cgcggcaacc gtggacgcgg cgacgccgga gaacatgcgg | 1080 |
| acgctcgtcg ggatcgggga gcggatgctg gcacagcggg tgtccagggt caacgtggag | 1140 |
| acagggagcg aggtacgaac cggtgaccgg agaaggaagc aatgccgatg ccctcggtgg | 1200 |
| gctcgctagg cagctctccg aggagaggag aacaaggctc gcgcgccgcg tctctgccat | 1260 |
| caacccaga agctctagat gtgcgcccta cgatatctaa gacaagtggc tttactgtca | 1320 |
| atcacatgct tgtaaataag tagactttat tttaataaaa tataaatata tatatattct | 1380 |
| ga | 1382 |

<210> SEQ ID NO 38
<211> LENGTH: 10843
<212> TYPE: DNA
<213> ORGANISM: Zea mays

<400> SEQUENCE: 38

| | |
|---|---|
| cgcacacact gtctttctct gcctttcttt ccctagcgcc gcgccggcgc cgccattcga | 60 |
| tcaggccgct tcgccggcga cagcatattc caggtatgcc gtcccttctg ctccttctgc | 120 |
| gagaattcaa acacccgaa ctccccaaat ctagtatttg tattcggatc tgaccatttt | 180 |
| tcactgggcc cgcccctgat tcgcaggtcg gttggttttg gcacttcgga ccggcggcca | 240 |
| tggcttccga cggcatcggc cccagaggta taactgtttc atctcttctt tgtgttcaaa | 300 |
| cagacagacg tcaaaccgcc gagaggaggt acaaatatag attttgggct atgagcacgc | 360 |
| cattgcgctt ccagcgatct gacatattgg gaattcttgt tttttttttg ggtaccttgc | 420 |
| aaggccgaaa tttgacgctt ttctgtttaa ttctagtgcc tgtctgcatc cattagggca | 480 |
| tcctagctgc tccatgctcg tgatctcgtc cgtttgcttg attgaatcca ttgttttcca | 540 |
| aagttcattg ctactgcgaa atacgtttat atgattacca caatttgtgt ttttgccttt | 600 |
| tcgggttgca cagagggtac tgccatcatt gttgttttag cgccatttgg aacaagtgat | 660 |
| tcactggtac tagtacagta tgtgcttttc atgtgtgttt ggtttgtacc atcagatgga | 720 |
| attttgagcg cggtttacaa attagtacta tagatatact gtgaggtgca cactagatgg | 780 |
| ttctgctttg ttctacagtc agtaactttt tcttccttgc tcacagatgt atgtgttgtt | 840 |
| gggggttgcac gcacccccaat gggcggtttc cttggtgcct tgtctccctt gcctgctacg | 900 |
| aaacttggct ctatagtaat tcaaggtgag atccgaatct tctctgcatt tacatccgag | 960 |
| ctctgaacat ggtcatggct gggggctgtt agctgctctg gaaagagcaa acgtggatcc | 1020 |
| agccctcgtg caggaggtct actttggaaa cgtcttgagt gctaatttgg ggcaagctcc | 1080 |
| tgcaaggcaa gctgctctgg gtgccgggat accaaactct gttgtttgca ccactgttaa | 1140 |
| caaagtctgt gcatctggca tgaaaggttt gaatcgaatt tatctgtctg tccttgtgta | 1200 |
| ctctgctcag agttcacaga agtgagagat tacctgacca tgctcttgtt ttcctttcct | 1260 |
| atatgcagct actatgtttg cagcacagtc aattcaattg ggtatcaatg atattgttgt | 1320 |
| ggctggtggc atggaaagca tgtccaatgc cccaaagtac attgctgaag ctaggtatgc | 1380 |
| aattattact tggtggatat attcaatatc gagctgcata aaccaaatga tagtcttaag | 1440 |

```
ttatttggta gatacatgca tgcttactta tcttcattgc attttctaaa tttgtttgta    1500
agaaatgttg attcaccagc agcgaggcta ttaacgaagt ggccagtttt gttgtgaaag    1560
tatattctgt tcatgtttaa agtgcatttc aactgcttat aagcttgcta attacaattg    1620
caggaagggg tctcgttttg gtcatgacac acttgttgat gccatgctta aggatgggct    1680
ttgggatgta tacaatgatt gtgccatggg aatgtgtgcc gagctttgtg ctgacaacca    1740
tgccctcaca agagaagacc aggtctctta atacagatag cagtaaatgc tgtttgttat    1800
aatattccca tattttcaa gatataagtt gtgctataca acatgtcaat gctggcaatt     1860
cttttgagac tgccctggaa tcttcgtgct ttatcttggt catcatcata aatggtctag    1920
agactctaga ccagcatctg cattccttgt ctgatgaact agtaacttgg atcctttcta    1980
gcaatgattt tctgttatgt tgtgacatga ttgatagggt gggcttttat gcatgctctg    2040
ggtctgtgaa ctgaccattc atctgcttcc agagatgaaa gtagatgtgc cacacaaaaa    2100
tgagcactct tttgtattcc tgttagagct atacaagtat aatctcttaa aagctgctca    2160
tcagtacatg acactagtac cttgatgatt ttactgtatc tgtttatgta attttttct     2220 taataaattt gatatagtat aattaaaatt gagttgcctt ttaattttca cttatatgtt    2280
gcaatttatt tttgtctata ttgcaataaa tatatttcca atttctggta tatttaattt    2340
tacttattct tgaataggat gcatttgcta tccaaagcaa cgagcgtgga attgctgctc    2400
gtgacagtgg tgcttttgca tgggagatta ttccggtaat tttctccctc attgatgata    2460
ctagacatgc ttttcttggt tttctgatgg tcagtgttgt cacccaggtt caagttcctg    2520
ttggtagagg aaaaccccca acattaattg agagagatga aagcctggat aaggtatttt    2580
ttctgacgtg acaaaatatt tttaacaaaa taaagcttgt agttgatcaa aggcaaaaag    2640 actgcaggc actttgattt attgttcttg cttcctccaa atgcaacgtt ccttgcataa     2700
tgagctttgc tagcagttat ttgtaagatc aatgcatgac agtttttattt atgtcttgtg   2760 ctattccttt tgtgtcttag tttgacccag taaaactaaa gaaacttcgc ccaagtttca    2820
aggagaatgg tggtacagtt acagctggaa atgcttctag tataaggtag ctgcttgaaa    2880
tatttctgag gccttttgtc ctacaaagtc tttctgagac cttgttttc ggccatatgt     2940 tgtttagctg acagatatga aggacaacct atttcattgt tgacagttaa attatattat    3000
tgtattatgc atgcattttt aactgatata ttatgcttgc atttttgtcaa cttcattgtt   3060 tctctatttg ttttagact gcttgggtat gctctactcc gttaaataga tggtaatttt     3120
ttctttagat ttggtaccca attggtgtga atgatttatc acaatatcac ataagaaagt    3180
aaaaacattt taaatgcctt attatgccca ttcaaacaac aaaagttgcc ctacctttta    3240
aatttcttca tggttgccct agaccttgtt tgtctcactt tgtactgtgt ctattttag     3300 ctgacaagta ctgtccggtg tactgcctac tatggcttgt gtagccttct gcaaccagtc    3360
atctaatttg ttttatatgg atcagtgatg gagctgctgc attagtttta gtgagtgggc    3420
agaaggctca agagcttggc cttcaagtcc ttgcaaggat caaaggttat gctgatgcag    3480
ctcaagtaag ccacagaaac aattgttagc tctcctaaga gtagaatgcg cttattctaa    3540
tttacactgt gatctaaata ttttaggata taggaagtta tttttatctg aacgattttt    3600
atgttactat tttagatatc gaaatttatc aactattgga acttgtgatc tggaatatta    3660
ttttgtaatg tggatgctgt ttatacaggc tccggagctt tttacaacca ctccagcact    3720
tgcaatacca aaggctatcg caaatgctgg attagagtca tcccgtgttg atttctatga    3780
```

```
gattaatgaa gccttttcgg tatgcattga gtttctttta ctcacatttt ttgtaagcct    3840
tttgttatgc attgagagtt tattttactt attactttt ttgtaataat gtctttttta    3900
cttgtcaata taggctgttg cgcttgcaaa tcaaaaactt cttggaattc cttcagtaag    3960
tgtcacctgt attaaactgc cattcttgt ggattttaga agttaaacaa tcactttcag    4020
aaagtacata ttgtctcttt tttgttattt gctatgcagc agcaacgtgt aattgcatta    4080
taacagtatt atctgtacta acagcatatg tgtttgcagg aaaagattaa tgttcatgga    4140
ggagctgtat ccttaggaca tcctctcggg tgcagtggtg ctcgcatttt ggttaccctt    4200
attggtgtaa gttctatctt aagatgcttg ttttaccttt tgagttacaa tccctttgt    4260 ttaaaaaaaa tgtgcaatgt ttttctagta aaaaatga tggtctttga gtaaataatg    4320
aattctgaca tatgttacca tatcatcata gggttcgtga tgaacagtaa gcatcttcac    4380
tattgctact aggtctactt cctctatccc aaattataag acgtcttggg atgttggcat    4440
tgttagattt atagctttta ctacgtgtac tgagacataa tgtttatcgc aataaaaact    4500
acaaatctag aaaagtaaa aacatcttat aatttgaaac ataggagta tgttggatca    4560 agccacccca tccctgcacc aaacactacc ttaggccatg ttcggttaca agtggttcga    4620
gggggattga aggggattaa atcccttct agttaaaatt gaataggagg ggatttaatc    4680
cccctcaatc ccctccaatc ctctcgcaac cgaacaagcc cttagtgatt tccaatgtgc    4740
aaattatctg caaatagaat cttgtataaa gctgcaaatg tagagtttca cattgatatc    4800
ggctcatccc ttgtttcact tgttgctggt gatcaatagt ttcttttct cttcattttc    4860 tttaagcaaa acgttgggca caatatagtg ccatcatgtt gggacatcaa aatatattgt    4920
gcttgaccct cctaatcatt gtttcttgtt aacaggttct cagggcgaag agtggcaaga    4980
tcggagttgc tggtgtctgc aacggtggag gcggagcatc agctcttgtt ctggagctcg    5040
cataagaaat ctagaccttg taagactcaa acaccgaat atatctcaac tcaaattgat    5100
tcttttacta gctggcagta ggagctaacc agtataaggt gctattatca aactgtaata    5160
tggtcgcata ttcagctagg cctaattaag ttgtattttt tcctttaca actgttgtgc    5220 aatttgacta actgctgcac cttgatattg caggtagtta gcaaaagctc cctgaggtga    5280
tcttgtagtc ttattttccg ttgtagtagt cccatagaac atttcttaat ttaatttggc    5340
aataaagcaa aagctccctg aggagatatt gcttctgttg gttgcatagt agagtatcat    5400
gtaataagag ctacagaaat atttttgata tatttgtgag gatactacag aaatatttta    5460
tatatttgtg atgtgtcttg tacatttatc taggtcacat caactatcct gccgcccggg    5520
atctggaact ccgacagccc gatttcaaat agtttgaaag aacatcagca acacccaag    5580 gcaaatacaa agatcagaga agctggaggg ttagttacag gagcatcagg ttaccgagaa    5640
tgcaaccatg cacggcaaaa ggcgcctacc ccgcatcaaa atttctgcca gaaacaaaca    5700
agaaacgaaa gaatcacacg cacactatct acatccagaa acgtgatgtt atactagata    5760
gtcagcggca ttcaggaagc cctcgtactg ggtaccgttg agggcgctgt agacctcgtc    5820
ccagttctcg atctgctccg acagcggctt cgtgtgtatc ttcacgtgcc ggctcaccag    5880
cttcctcctc ggcactccga ggaaatccag gacatccaag agcttctgca gtgcagcagc    5940
gatggtaagc gacacaacca acggaaggga acagacaagg gaagggcatc agcgagaacg    6000
cactgttctg ttgcggacga cgtcctcgta gtagacgctc atgtgccggg tgttgtttag    6060
gttctcaaga gcgtcgcgag tgtactcgtc agctcgtttc agctgccata tcagtgacgt    6120
cgtgttgagc ctgggcctgt atcttgccag tatatgggcc tgtggagcga gaacgaacga    6180
```

```
cacgtcaaac acagagagag atcagatcag ctcagagact tgctgccata tccgtttctt    6240
agctagcatt actaacctca cgcttcgtgt ggacatgggc cttgtgcgtt ccgtttagtt    6300
gcttaagtaa cctgtcgtgg ttgttcgcta cctgtgatac caactggcgg agcaggttcc    6360
ttctgaaaag aaatatcgca gagactcctc ttcggttgaa gtagtcgact acgtccgcat    6420
ggtttgccac gaggccctga aaacatacac cccaaccccg ttcagaagaa atgctccttt    6480
gtttccactc tctagctaca atgcctgttt tgtttccagt ctctaaacct atgtttggcc    6540
aatattcatg gtttggttag gcaatctgtc taccaggaaa aagttcgtt ctcgcacaaa     6600 ttagatgaag ccctgaaaca acatgcttg acatgtagat tataatcagt ctactggaca     6660
cactacagaa tctatcaaat attactccat atgcatttgc agttctcatg catgttcgag    6720
agagagaaaa tttgtctaaa atgcaggatc tgacagcaag tcagaaaact aaactagcta    6780
ccgacagttc cataaggcct tgttcggtta ttcgcatccc acatggattg aagagattg     6840 gaaaatttta agaaggattt tgacttctta tggatttaaa ctcatccaat ctcgtccaat    6900
ccacatggat tggcactaaa acgagcaagc cctaaagtgg attcccaaaa aaaaatagtt    6960
acatggactt gaggaaagtt tggcgcaata tgcaataaca tttagcatct acagttgaga    7020
acatgtaggc cgtttaggag actacacata ctaataattg aaacatactg gaactaaatg    7080
gaaaaataaa tgaaaaagga tcatccaaat aaattatcta tactgcatgt tttagtccgc    7140
acctgattta gcatccactt gaagccaata gctgcagtgc actcattctt ggaagcgcta    7200
ctgttccagt ccaaattgta cactttatcc agggtatcta ttatagagga atgttactc     7260 ctcctttctt ttctagagaa aatttcacca ttggagctaa cattcatgtg gctgttaaga    7320
agtgtttcaa accagccact tccagatcgc tgcgatgata taattgcaaa ggaccggaca    7380
gcattgcact tgcattcctc cctagaaata aaaaattatg cattaggcat taaacaaacg    7440
agattgctca atcttaccac agtgcagatc tcacctgctg taaatatagg aagttatttt    7500
tatctggaac gattttatgt tactatttta gatatcgaaa tttatcaact attggaactt    7560
gtgatctgga atattatttt gtaatgtgga tgctgtttat acaggctccg gagcttttta    7620
caaccactcc agcacttgca ataccaaagg ctatcgcaaa tgctggatta gagtcatccc    7680
gtgttgattt ctatgagatt aatgaagcct tttcggtatg cattgagttt cttttactca    7740 catttttgt aagcctttg ttatgcattg agagtttatt ttacttatta cttttttgt       7800 aataatgtct tttttacttg tcaatatagg ctgttgcgct tgcaaatcaa aaacttcttg    7860
gaattccttc agtaagtgtc acctgtatta aactgccatt ctttgtggat tttagaagtt    7920
aaacaatcac tttcagaaag tacatattgt ctctttttg ttatttgcta tgcagcagca    7980
acgtgtaatt gcattataac agtattatct gtactaacag catatgtgtt tgcaggaaaa    8040
gattaatgtt catggaggag ctgtatcctt aggacatcct ctcgggtgca gtggtgctcg    8100
cattttggtt accctattg gtgtaagttc tatcttaaga tgcttgtttt accttttgag     8160
ttacaatccc ttttgtttaa aaaaaatgtg caatgttttt ctagtaaaaa aatagatggt    8220
ctttgagtaa ataatgaatt ctgacatatg ttaccatatc atcatagggt tcgtgatgaa    8280
cagtaagcat cttcactatt gctactaggt ctacttcctc tatcccaaat tataagacgt    8340
cttgggatgt tggcattgtt agatttatag cttttactac gtgtactgag acataatgtt    8400
tatcgcaata aaaactacaa atctagaaaa agtaaaaaca tctttataatt tgaaacatag   8460 ggagtatgtt ggatcaagcc accccatccc tgcaccaaac actaccttag gccatgttcg    8520
```

```
gttacaagtg gttcgagggg gattgaaggg gattaaatcc ccttctagtt aaaattgaat    8580
aggaggggat ttaatccccc tcaatcccct ccaatcctct cgcaaccgaa caagcccttta   8640
gtgatttcca atgtgcaaat tatctgcaaa tagaatcttg tataaagctg caaatgtaga   8700
gtttcacatt gatatcggct catcccttgt ttcacttgtt gctggtgatc aatagtttct   8760
ttttctcttc attttcttta agcaaaacgt tgggcacaat atagtgccat catgttggga   8820
catcaaaata tattgtgctt gaccctccta atcattgttt cttgttaaca ggttctcagg   8880
gcgaagagtg gcaagatcgg agttgctggt gtctgcaacg gtggaggcgg agcatcagct   8940
cttgttctgg agctcgcata agaaatctag accttgtaag actcaaaaca ccgaatatat   9000
ctcaactcaa attgattctt ttactagctg gcagtaggag ctaaccagta taaggtgcta   9060
ttatcaaact gtaatatggt cgcatattca gctaggccta attaagttgt attttttcct   9120
tttacaactg ttgtgcaatt tgactaactg ctgcaccttg atattgcagg tagttagcaa   9180
aagctccctg aggtgatctt gtagtcttat tttccgttgt agtagtccca tagaacattt   9240
cttaatttaa tttggcaata aagcaaaagc tccctgagga gatattgctt ctgttggttg   9300
catagtagag tatcatgtaa taagagctac agaaatattt ttgatatatt tgtgaggata   9360
ctacagaaat attttatata tttgtgatgt gtcttgtaca tttatctagg tcacatcaac   9420
tatcctgccg cccgggatct ggaactccga cagcccgatt tcaaatagtt tgaaagaaca   9480
tcagcaaaca cccaaggcaa atacaaagat cagagaacgr mmgtgagcat caggttaccg   9540
agaatgcaac catgcacggc aaaaggcgcc taccccgcat caaaatttct gccagaaaca   9600
aacaagaaac gaaagaatca cacgcacact atctacatcc agaaacgtga tgttatacta   9660
gatagtcagc ggcattcagg aagccctcgt actgggtacc gttgagggcg ctgtagacct   9720
cgtcccagtt ctcgatctgc tccgacagcg gcttcgtgtg tatcttcacg tgccggctca   9780
ccagcttcct cctcggcact ccgaggaaat ccaggacatc aagagcttc tgcagtgcag    9840
cagcgatggt aagcgacaca accaacggaa gggaacagac aagggaaggg catcagcgag   9900
aacgcactgt tctgttgcgg acgacgtcct cgtagtagac gctcatgtgc cgggtgttgt   9960
ttaggttctc aagagcgtcg cgagtgtact cgtcagctcg tttcagctgc catatcagtg  10020
acgtcgtgtt gagcctgggc ctgtatcttg ccagtatatg ggcctgtgga gcgagaacga  10080
acgacacgtc aaacacagag agagatcaga tcagctcaga gacttgctgc catatccgtt  10140
tcttagctag cattactaac ctcacgcttc gtgtggacat gggccttgtg cgttccgttt  10200
agttgcttaa gtaacctgtc gtggttgttc gctacctgtg ataccaactg gcggagcagg  10260
ttccttctga aaagaaatat cgcagagact cctcttcggt tgaagtagtc gactacgtcc  10320
gcatggtttg ccacgaggcc ctgaaaacat acaccccaac cccgttcaga agaaatgctc  10380
ctttgtttcc actctctagc tacaatgcct gttttgtttc cagtctctaa acctatgttt  10440
ggccaatatt catggtttgg ttaggcaatc tgtctaccag gaaaaaagtt cgttctcgca  10500
caaattagat gaagccctga acaaacatg cttgacatgt agattataat cagtctactg   10560
gacacactac agaatctatc aaatattact ccatatgcat ttgcagttct catgcatgtt  10620
cgagagagag aaaatttgtc taaaatgcag gatctgacag caagtcagaa aactaaacta  10680
gctaccgaca gttccataag gccttgttcg gttattcgca tcccacatgg attggaagag  10740
attggaaaat tttaagaagg attttgactt cttatggatt taaactcatc caatctcgtc  10800
caatccacat ggattggcac taaaacgagc aagccctaaa gtg                     10843
```

<210> SEQ ID NO 39
<211> LENGTH: 1704
<212> TYPE: DNA
<213> ORGANISM: Zea mays

<400> SEQUENCE: 39

| | | | | | |
|---|---|---|---|---|---|
| gtgttgcgtt | ccctacttgc | tcttttcttc | ctccgcttca | acctgtcccg | agcgcccccc | 60 |
| gcgcacacac | tgtctttctc | tgcctttctt | tccctagcgc | cgcgccggcg | ccgccattcg | 120 |
| atcaggccgc | ttcgccggcg | acagcatatt | ccaggtcggt | tggttttggc | acttcggacc | 180 |
| ggcggccatg | gcttccgacg | gcatcggccc | cagagatgta | tgtgttgttg | gggttgcacg | 240 |
| cacccccaatg | ggcggtttcc | ttggtgcctt | gtctcccttg | cctgctacga | aacttggctc | 300 |
| tatagtaatt | caaggtgaga | tccgaatctt | ctctgcattt | acatccgagc | tctgaacatg | 360 |
| gtcatggctg | ggggctgtta | gctgctctgg | aaagagcaaa | cgtggatcca | gccctcgtgc | 420 |
| aggaggtcta | ctttggaaac | gtcttgagtg | ctaatttggg | gcaagctcct | gcaaggcaag | 480 |
| ctgctctggg | tgccgggata | ccaaactctg | ttgtttgcac | cactgttaac | aaagtctgtg | 540 |
| catctggcat | gaaagctact | atgtttgcag | cacagtcaat | tcaattgggt | atcaatgata | 600 |
| ttgttgtggc | tggtggcatg | gaaagcatgt | ccaatgcccc | aaagtacatt | gctgaagcta | 660 |
| ggaagggggtc | tcgttttggt | catgacacac | ttgttgatgc | catgcttaag | gatgggcttt | 720 |
| gggatgtata | caatgattgt | gccatgggaa | tgtgtgccga | gctttgtgct | gacaaccatg | 780 |
| ccctcacaag | agaagaccag | gatgcatttg | ctatccaaag | caacgagcgt | ggaattgctg | 840 |
| ctcgtgacag | tggtgctttt | gcatgggaga | ttattccggt | tcaagttcct | gttggtagag | 900 |
| gaaaaccccc | aacattaatt | gagagagatg | aaagcctgga | taagtttgac | ccagtaaaac | 960 |
| taaagaaact | tcgcccaagt | ttcaaggaga | atggtggtac | agttacagct | ggaaatgctt | 1020 |
| ctagtataag | tgatggagct | gctgcattag | ttttagtgag | tgggcagaag | gctcaagagc | 1080 |
| ttggccttca | agtccttgca | aggatcaaag | gttatgctga | tgcagctcaa | gctccggagc | 1140 |
| tttttacaac | cactccagca | cttgcaatac | caaaggctat | cgcaaatgct | ggattagagt | 1200 |
| catcccgtgt | tgatttctat | gagattaatg | aagcctttc | ggctgttgcg | cttgcaaatc | 1260 |
| aaaaacttct | tggaattcct | tcagaaaaga | ttaatgttca | tggaggagct | gtatccttag | 1320 |
| gacatcctct | cgggtgcagt | ggtgctcgca | ttttggttac | ccttattggt | gttctcaggg | 1380 |
| cgaagagtgg | caagatcgga | gttgctggtg | tctgcaacgg | tggaggcgga | gcatcagctc | 1440 |
| ttgttctgga | gctcgcataa | gaaatctaga | ccttgtagtt | agcaaaagct | ccctgaggtg | 1500 |
| atcttgtagt | cttatttcc | gttgtagtag | tcccatagaa | catttcttaa | tttaatttgg | 1560 |
| caataaagca | aaagctccct | gaggagatat | tgcttctgtt | ggttgcatag | tagagtatca | 1620 |
| tgtaataaga | gctacagaaa | tattttgat | atatttgtga | ggatactaca | gaaatatttt | 1680 |
| atatatttgt | gatgtgtctt | gtac | | | | 1704 |

<210> SEQ ID NO 40
<211> LENGTH: 1637
<212> TYPE: DNA
<213> ORGANISM: Zea mays

<400> SEQUENCE: 40

| | | | | | |
|---|---|---|---|---|---|
| gtgttgcgtt | ccctacttgc | tcttttcttc | ctccgcttca | acctgtcccc | agcgcccccc | 60 |
| gcgcacacac | tgtctttctc | tgcctttctt | tccctagcgc | cgcgccggcg | ccgccattcg | 120 |
| atcaggccgc | ttcgccggcg | acagcatatt | ccaggtcggt | tggttttggc | acttcggacc | 180 |

```
ggcggccatg gcttccgacg gcatcggccc cagagatgta tgtgttgttg gggttgcacg        240
caccccaatg gcggtttcc ttggtgcctt gtctcccttg cctgctacga aacttggctc         300
tatagtaatt caagctgctc tggaaagagc aaacgtggat ccagccctcg tgcaggaggt        360
ctactttgga aacgtcttga gtgctaattt ggggcaagct cctgcaaggc aagctgctct        420
gggtgccggg ataccaaact ctgttgtttg caccactgtt aacaaagtct gtgcatctgg        480
catgaaagct actatgtttg cagcacagtc aattcaattg ggtatcaatg atattgttgt        540
ggctggtggc atggaaagca tgtccaatgc cccaaagtac attgctgaag ctaggaaggg        600
gtctcgtttt ggtcatgaca cacttgttga tgccatgctt aaggatgggc tttgggatgt        660
atacaatgat tgtgccatgg aatgtgtgc cgagctttgt gctgacaacc atgccctcac        720
aagagaagac caggatgcat tgctatcca agcaacgag cgtggaattg ctgctcgtga         780
cagtggtgct tttgcatggg agattattcc ggttcaagtt cctgttggta gaggaaaacc       840
cccaacatta attgagagag atgaaagcct ggataagttt gacccagtaa aactaaagaa       900
acttcgccca agtttcaagg agaatggtgg tacagttaca gctggaaatg cttctagtat       960
aagtgatgga gctgctgcat tagttttagt gagtgggcag aaggctcaag agcttggcct      1020
tcaagtcctt gcaaggatca aaggttatgc tgatgcagct caagctccgg agcttttac       1080 aaccactcca gcacttgcaa taccaaaggc tatcgcaaat gctggattag agtcatcccg      1140
tgttgatttc tatgagatta atgaagcctt ttcggctgtt gcgcttgcaa atcaaaaact      1200
tcttggaatt ccttcagaaa agattaatgt tcatggagga gctgtatcct taggacatcc      1260
tctcgggtgc agtggtgctc gcattttggt taccccttatt ggtgttctca gggcgaagag   1320
tggcaagatc ggagttgctg gtgtctgcaa cggtggaggc ggagcatcag ctcttgttct     1380
ggagctcgca taagaaatct agaccttgta gttagcaaaa gctccctgag gtgatcttgt    1440
agtcttattt ccgttgtag tagtcccata gaacatttct taatttaatt tggcaataaa      1500
gcaaaagctc cctgaggaga tattgcttct gttggttgca tagtagagta tcatgtaata     1560
agagctacag aaatattttt gatatatttg tgaggatact acagaaatat tttatatatt     1620
tgtgatgtgt cttgtac                                                    1637
```

<210> SEQ ID NO 41
<211> LENGTH: 1780
<212> TYPE: DNA
<213> ORGANISM: Zea mays

<400> SEQUENCE: 41

```
cagagcacca gctcaccgcc ccaccgattc aaaggcgctc ggatcctctg acgtcgacgt        60
tccctgccag ctcccggctg ccgccctcgc tccttccgcc atctgcgctg ctctgcggcg       120
ccagagccgg cgcccgcccg ctgccgccct cgacggaccg ggacacgggg ccccaccgtt      180
ctctttcctg cgctgcgctg cgcggcggct gtgctgctga tcagttaatg tgcctgtgag      240
gctgtgacag gcggcgtcga gcgagtccga ggcgggctaa ctaaacccgc cgtctctcga      300
ggcggcgccc gcggagggcc aggtggaggg ccgaggaagg tggaggcggt gaggcgatgg      360
ggggcgccaa gcggaggac aagcccgccg ccgccaccgc tgaagacgat tggtgttacc       420
agtttggaaa caagaatgcg tttgactcga aggccccgaa aaaatcacca cttgcattga      480
gagtggttgt ctttgccatg actgtgttat gtgggatatc tatttggtca atgtgtatga     540
agcagctagg gagtgatggc tggtcaagaa tagtgaagat cgaagttgtg gaacaaccat      600
gtaataagtc tacagttcct ccttctgagg ttcaatttgc gcattaccct caaccgacaa      660
```

```
cttacagcag ggaggaatgc aagtgcaatg ctgtccggtt ctttgcgatt atatcatcac    720
agcgatctgg aagtggctgg tttgaaaccc ttcttaacag ccacatgaat gttagctcca    780
acggtgaaat tttctctaga aaagaaagga gaagtaacat ttcctctata atagataccc    840
tggataaagt gtacaatttg gactggaaca gtagcgcttc caagaatgag tgcactgcag    900
ctattggctt caagtggatg ctaaatcagg gcctcgtggc aaaccatgcg gacgtagtcg    960
actacttcaa ccgaagagga gtctctgcga tatttctttt cagaaggaac ctgctccgcc   1020
agttggtatc acaggtagcg aacaaccacg acaggttact taagcaacta acggaacgc   1080 acaaggccca tgtccacacg aagcgtgagg cccatatact ggcaagatac aggcccaggc   1140
tcaacacgac gtcactgata tggcagctga acgagctga cgagtacact cgcgacgctc    1200
ttgagaacct aaacaacacc cggcacatga gcgtctacta cgaggacgtc gtccgcaaca   1260
gaacaaagct cttggatgtc ctggatttcc tcggagtgcc gaggaggaag ctggtgagcc   1320
ggcacgtgaa gatacacacg aagccgctgt cggagcagat cgagaactgg gacgaggtct   1380
acagcgccct caacggtacc cagtacgagg gcttcctgaa tgccgctgac tatctagtat   1440
aacatcacgt ttctggatgt agatagtgtg cgtgtgattc tttcgtttct tgtttgtttc   1500
tggcagaaat tttgatgcgg ggtaggcgcc ttttgccgtg catggttgca ttctcggtaa   1560
cctgatgctc ctgtaactaa ccctccagct tctctgatct ttgtatttgc cttgggtgtt   1620
tgctgatgtt ctttcaaact atttgaaatc gggctgtcgg agttccagat cccgggcggc   1680
aggatagttg atgtgaccta gataaatgta caagacacat cacaaatata taaaatattt   1740
ctgtagtatc ctcaaaaaaa aaaaaaaaaa aaaaaaaag                          1780

<210> SEQ ID NO 42
<211> LENGTH: 11900
<212> TYPE: DNA
<213> ORGANISM: Zea mays

<400> SEQUENCE: 42
aacgccatgg agaaatcaca catgagacac caattactca aggagtttac ttaattatat     60
tttacttaaa ttgagtatag gattcatcgt actaccaagg ggatccaaaa ataaggttgg    120
tgtttgccaa agctcaagcc tctatattca aaagctattt tttgaaaatc aaaaatctct    180
ttaaaattct atggttgact atggttaggt ttgagaaacc tagagtgttt ttgttgaaaa    240
gcagctgagc ttttcagctg aactaaactt cagctgagtt gagcttcttc agctgcagtt    300
gagcttttca gctgagctaa acttcagctg tgtcgagctt tctcaactcc agttgaactt    360
caacttcaac tgggggtccag tcaagttcaa ccggggtcca ggcaggttca accggggtcc    420
aaggcaagtt caaccggggt ccagagaggt tcaactgggg tccaggaaaa gttcaaccgg    480
ggtttagaga ggttcaacca gggatgggct gtacgcaacg cgtctaagaa ttgtacgtgt    540
gttctctcgt aaccagaagc agcctcacct cctttgtata tataaacgag cagagggagg    600
cgaacggata gtaacggtca ccatcagagc tatcattaca gccagccaga aacggacgcc    660
attagtgacg tccgttaata gctgacaagc attataactc gttcgttact atccataaca    720
taggaaacga ccaataacgt acaacagtaa tggacggtca tcactttagg caaaatgtgc    780
aaccgttagg aaggaatatt cggaccaagg tccgatctac cacggccacg gcccggcggc    840
gcgcgcgtgt ggcagtcctt catcattttc tcaacttctc actagatgca ccaaagatcc    900
gcctatttaa gttgattgaa ttgtcccttg tacttccggt atggtactaa agtactagta    960
```

```
caccgtagca ttaaagtggg cctttagcat tgactattat tgaatattaa tttgggttag    1020
gccctcatta attcaacagt agcttctagg cctaaccatc ccaccccca aactaagcat    1080 agatgaacta tgtttaggtt gctacaaaaa tattccaaaa ataattccc tccgtcctaa    1140 aatactaacc gttttagcat tttaatagat tcataaaaat atgtcagatc cacaagtcat    1200
acgaggcaac tgtctcgagc atgatggatg gagaaccaat atcccccttg taaaatgtct    1260
tcttcctcca cttccaatgc atgcaatcta tactcaatat cataatagaa aatcccctttt   1320 ccacctcctt agctaagata agcctaagtc attgacaatg gcatgataat tgtactccgc    1380
cctgaaacat gcaataccac ctctacagaa tagaccaaaa actccactcg tagggggaaat    1440 actgccccca cggtaagaag aagcttaatc ggagccctga tcgagaaagg tcacgaaaga    1500
tgtacccctc cccccatgca acatgagagt ccgcccccta taggccagat ctttactcgt    1560
gctttgagcc ctactagccc ttacacgagg atccgcccca taggtcagcc catctcatgt    1620
gcacacaact agggaaacta gtgagtgacc ttgttaacct cagcctaaaa ttcgctccca    1680
ccgggattca aacttaggac ctgaggagtg ctactcagac gacctaacca acttaactag    1740
ggaccctttc acacagaata gtccaaggca ctctgaggtg gaactttcct cattttgatg    1800
tactcatcga tggagtcagc aatgctacag tacgcaagca tgcttaggcc aattgtgcac    1860
ttctggtggg ggaggaaaca ctgcggttga atgcatcggt tcaaaaagtg aagtatggga    1920
agtgctcacc caatctctct aagatatgaa ggaagagact tctctagatg cggtaacttt    1980
gacaaaagta gagcagtggg tagacacaca ggtcgttgaa atggtcttgc attaaccggt    2040
cgtatgcaac tacatagtcg cagtcaatgt atctctgatg ttgccttggc cacctcatcg    2100
acctaggaga ctcggatcca agctctgacg cctgttgcat tatattttgt tgtaataact    2160
tgaataactc ttttcagtca tattgatgtc caagctgaac gaaaacatca caacaatgct    2220
tgatttgatt gaaacgagtg taagaggatt ataagggtg gtagagaaat ttgaagtgtg    2280
ggttgtgtga atgagatcaa acactcctct atttatagac caagttctag ttttttttatt    2340 tttgaaaaaa aatcaaaata aagcgaagca attagaacct gccacatggc aagaggcgat    2400
cgttatcgac atggccgcaa tagctgttca gtaccaacca gtcagtatcg accgacgcgg    2460
tcccaacacg gtcaatagta accctggcgg ccgatcagta gcctcgacaa ccacaagcga    2520
ggctattagt gctggcacca tgtcgggtga tactgaccat ttggttgtgc cacatgggtg    2580
ggcgggcagt agagccaagc gccggcactc gcctaacatg atctaaaaca atcgataaaa    2640
ctgacagatt ggttgcggtt catgactacc tagacctggt cgaccacaag tagaaaatga    2700
gtcgagccga gcttgactcg gctcgtccat ttcacgagct agagagttag gctcggctca    2760
gctcgaagtc ggctcgcgag ctacacccg atatatatta tttcattata tagtaaatta    2820
ttaatatata aacataaaat ataaaaatat tattcaccat tatgaattat cttatattta    2880
tcatcaaagg ctaagaaata agccgactat ctataaatta tctaatatct atcattattc    2940
tacatattga ttaatttggt acaactagct cgctcgcaga cgctccgaac ttgatctgac    3000
tcgtgagcct caagtttttt ttctagcctt aaccacatgc ccgcgaggat gattgttcga    3060
ggtgattagc aaaacgcaaac gatatcaatt gacattttttt attagtttca ttaggtttag    3120
agataaaatt atatcatgta tgtcactcgt ctagtatctt atttgttatc ataaatgttc    3180
taatcctttt tacgtcaccc gaatacaatt ttttactctt tcatgtcata gtaagggact    3240
aagacataca acatttttaca tttaacatttt ggccacgaca tgtaagagtg agatattgaa    3300
ttcgagtaac atacgaggta cgatgaataa ggtattacac aaaattacag tggcatatag    3360
```

```
tgaattgaat tgttctattt ttacttttt tttgcctaac ataaagccta ttttatttag      3420
tactttctct gattcagctt taatttttat gatttattaa ttttattata tatctatata      3480
ttgtatagat taaaaaataa aataaattat agatttagga aaaattacat tcgggtgatt      3540
tggctgttgg gtgttgcgtt ccctacttgc tcttttcttc ctccgcttca acctgtcccc      3600 agcgccccc gcgcacacac tgtctttctc tgcctttctt tccctagcgc cgcgccggcg       3660
ccgccattcg atcaggccgc ttcgccggcg acagcatatt ccaggtatgc cgtcccttct      3720
gctccttctg cgagaattca aacaccccga actccccaaa tctagtattt gtattcggat      3780
ctgaccattt ttcactgggc ccgcccctga ttcgcaggtc ggttggtttt ggcacttcgg      3840
accggcggcc atggcttccg acggcatcgg ccccagaggt ataactgttt catctcttct      3900
ttgtgttcaa acagacagac gtcaaaccgc cgagaggagg tacaaatata gattttgggc      3960
tatgagcacg ccattgcgct tccagcgatc tgacatattg ggaattcttg ttttttttt      4020 gggtaccttg caaggccgaa atttgacgct tttctgttta attctagtgc ctgtctgcat      4080
ccattagggc atcctagctg ctccatgctc gtgatctcgt ccgtttgctt gattgaatcc      4140
attgttttcc aaagttcatt gctactgcga aatacgttta tatgattacc acaatttgtg      4200
tttttgcctt ttcgggttgc acagagggta ctgccatcat tgttgtttta gcgccatttg      4260
gaacaagtga ttcactggta ctagtacagt atgtgctttt catgtgtgtt tggtttgtac      4320
catcagatgg aattttgagc gcggtttaca aattagtact atagatatac tgtgaggtgc      4380 acactgatg gttctgcttt gttctacagt cagtaacttt ttcttccttg ctcacagatg       4440
tatgtgttgt tggggttgca cgcaccccaa tgggcggttt ccttggtgcc ttgtctccct      4500
tgcctgctac gaaacttggc tctatagtaa ttcaaggtga gatccgaatc ttctctgcat      4560
ttacatccga gctctgaaca tggtcatggc tggggctgt tagctgctct ggaaagagca       4620
aacgtggatc cagccctcgt gcaggaggtc tactttggaa acgtcttgag tgctaatttg      4680
gggcaagctc ctgcaaggca agctgctctg ggtgccggga taccaaactc tgttgtttgc      4740
accactgtta acaaagtctg tgcatctggc atgaaaggtt tgaatcgaat ttatctgtct      4800
gtccttgtgt actctgctca gagttcacag aagtgagaga ttacctgacc atgctcttgt      4860
tttcctttcc tatatgcagc tactatgttt gcagcacagt caattcaatt gggtatcaat      4920
gatattgttg tggctggtgg catggaaagc atgtccaatg ccccaaagta cattgctgaa      4980
gctaggtatg caattattac ttggtggata tattcaatat cgagctgcat aaaccaaatg      5040
atagtcttaa gttatttggt agatacatgc atgcttactt atcttcattg catttctaa      5100 atttgtttgt aagaaatgtt gattcaccag cagcgaggct attaacgaag tggccagttt      5160
tgttgtgaaa gtatattctg ttcatgttta aagtgcattt caactgctta taagcttgct      5220
aattacaatt gcaggaaggg gtctcgtttt ggtcatgaca cacttgttga tgccatgctt      5280
aaggatgggc tttgggatgt atacaatgat tgtgccatgg gaatgtgtgc cgagctttgt      5340
gctgacaacc atgccctcac aagagaagac caggtctctt aatacagata gcagtaaatg      5400
ctgtttgtta taatattccc atattttca agatataagt tgtgctatac aacatgtcaa      5460
tgctggcaat tcttttgaga ctgccctgga atcttcgtgc tttatcttgg tcatcatcat      5520
aaatggtcta gagactctag accagcatct gcattccttg tctgatgaac tagtaacttg      5580
gatcctttct agcaatgatt ttctgttatg ttgtgacatg attgataggg tgggcttta      5640 tgcatgctct gggtctgtga actgaccatt catctgcttc cagagatgaa agtagatgtg      5700
```

```
ccacacaaaa atgagcactc ttttgtattc ctgttagagc tatacaagta taatctctta    5760
aaagctgctc atcagtacat gacactagta ccttgatgat tttactgtat ctgtttatgt    5820 aattttttc ttaataaatt tgatatagta taattaaaat tgagttgcct tttaattttc    5880
acttatatgt tgcaatttat ttttgtctat attgcaataa atatatttcc aatttctggt    5940
atatttaatt ttacttattc ttgaatagga tgcatttgct atccaaagca acgagcgtgg    6000
aattgctgct cgtgacagtg gtgcttttgc atgggagatt attccggtaa ttttctccct    6060
cattgatgat actagacatg cttttcttgg ttttctgatg gtcagtgttg tcacccaggt    6120
tcaagttcct gttggtagag gaaaacccccc aacattaatt gagagagatg aaagcctgga    6180 taaggtatt tttctgacgt gacaaaatat ttttaacaaa ataaagcttg tagttgatca    6240
aaggcaaaaa gactggcagg cactttgatt tattgttctt gcttcctcca aatgcaacgt    6300
tccttgcata atgagctttg ctagcagtta tttgtaagat caatgcatga cagttttatt    6360
tatgtcttgt gctattcctt ttgtgtctta gtttgaccca gtaaaactaa agaaacttcg    6420
cccaagtttc aaggagaatg gtggtacagt tacagctgga aatgcttcta gtataaggta    6480
gctgcttgaa atatttctga ggccttttgt cctacaaagt cttctgaga ccttgttttt    6540 cggccatatg ttgtttagct gacagatatg aaggacaacc tatttcattg ttgacagtta    6600
aattatatta ttgtattatg catgcatttt taactgatat attatgcttg cattttgtca    6660
acttcattgt ttctctattt gtttttagac tgcttgggta tgctctactc cgttaaatag    6720
atggtaattt tttctttaga tttggtaccc aattggtgtg aatgatttat cacaatatca    6780
cataagaaag taaaaacatt ttaaatgcct tattatgccc attcaaacaa caaaagttgc    6840 cctaccttt aaatttcttc atggttgccc tagaccttgt ttgtctcact ttgtactgtg    6900 tctatttta gctgacaagt actgtccggt gtactgccta ctatggcttg tgtagccttc    6960
tgcaaccagt catctaattt gttttatatg gatcagtgat ggagctgctg cattagtttt    7020
agtgagtggg cagaaggctc aagagcttgg ccttcaagtc cttgcaagga tcaaaggtta    7080
tgctgatgca gctcaagtaa gccacagaaa caattgttag ctctcctaag agtagaatgc    7140
gcttattcta atttacactg tgatctaaat attttaggat ataggaagtt attttttatct    7200 ggaacgattt tatgttacta ttttagatat cgaaatttat caactattgg aacttgtgat    7260
ctggaatatt attttgtaat gtggatgctg tttatacagg ctccggagct ttttacaacc    7320
actccagcac ttgcaatacc aaaggctatc gcaaatgctg gattagagtc atcccgtgtt    7380
gatttctatg agattaatga agccttttcg gtatgcattg agtttctttt actcacattt    7440
tttgtaagcc ttttgttatg cattgagagt ttattttact tattactttt tttgtaataa    7500
tgtctttttt acttgtcaat ataggctgtt gcgcttgcaa atcaaaaact tcttggaatt    7560
ccttcagtaa gtgtcacctg tattaaactg ccattctttg tggattttag aagttaaaca    7620
atcactttca gaaagtacat attgtctctt ttttgttatt tgctatgcag cagcaacgtg    7680
taattgcatt ataacagtat tatctgtact aacagcatat gtgtttgcag gaaaagatta    7740
atgttcatgg aggagctgta tccttaggac atcctctcgg gtgcagtggt gctcgcattt    7800
tggttaccct tattggtgta agttctatct taagatgctt gttttacctt ttgagttaca    7860 atccctttg tttaaaaaaa atgtgcaatg ttttttctagt aaaaaaatag atggtctttg    7920
agtaaataat gaattctgac atatgttacc atatcatcat agggttcgtg atgaacagta    7980
agcatcttca ctattgctac taggtctact tcctctatcc caaattataa gacgtcttgg    8040
gatgttggca ttgttagatt tatagctttt actacgtgta ctgagacata atgtttatcg    8100
```

```
caataaaaac tacaaatcta gaaaaagtaa aaacatctta taatttgaaa catagggagt    8160
atgttggatc aagccacccc atccctgcac caaacactac cttaggccat gttcggttac    8220
aagtggttcg aggggattg aagggatta atccccttc tagttaaaat tgaataggag    8280
gggatttaat ccccctcaat cccctccaat cctctcgcaa ccgaacaagc ccttagtgat    8340
ttccaatgtg caaattatct gcaaatagaa tcttgtataa agctgcaaat gtagagtttc    8400
acattgatat cggctcatcc cttgtttcac ttgttgctgg tgatcaatag tttcttttc    8460 tcttcatttt ctttaagcaa aacgttgggc acaatatagt gccatcatgt tgggacatca    8520
aaatatattg tgcttgaccc tcctaatcat tgtttcttgt taacaggttc tcagggcgaa    8580
gagtggcaag atcggagttg ctggtgtctg caacggtgga ggcggagcat cagctcttgt    8640
tctggagctc gcataagaaa tctagacctt gtaagactca aaacaccgaa tatatctcaa    8700
ctcaaattga ttcttttact agctggcagt aggagctaac cagtataagg tgctattatc    8760
aaactgtaat atggtcgcat attcagctag gcctaattaa gttgtatttt ttcctttac    8820 aactgttgtg caatttgact aactgctgca ccttgatatt gcaggtagtt agcaaaagct    8880 ccctgaggt atcttgtagt cttattttcc gttgtagtag tcccatagaa catttcttaa    8940
tttaatttgg caataaagca aaagctccct gaggagatat tgcttctgtt ggttgcatag    9000
tagagtatca tgtaataaga gctacagaaa tattttgat atatttgtga ggatactaca    9060
gaaatatttt atatatttgt gatgtgtctt gtacattat ctaggtcaca tcaactatcc    9120
tgccgcccgg gatctggaac tccgacagcc cgatttcaaa tagtttgaaa gaacatcagc    9180
aaacacccaa ggcaaataca aagatcagag aagctggagg gttagttaca ggagcatcag    9240
gttaccgaga atgcaaccat gcacggcaaa aggcgcctac cccgcatcaa aatttctgcc    9300
agaaacaaac aagaaacgaa agaatcacac gcacactatc tacatccaga aacgtgatgt    9360
tatactagat agtcagcggc attcaggaag ccctcgtact gggtaccgtt gagggcgctg    9420
tagacctcgt cccagttctc gatctgctcc gacagcggct tcgtgtgtat cttcacgtgc    9480
cggctcacca gcttcctcct cggcactccg aggaaatcca ggacatccaa gagcttctgc    9540
agtgcagcag cgatggtaag cgacacaacc aacggaaggg aacagacaaa gggcatcagc    9600
gagaacgcac tgttctgttg cggacgacat cctcgtagta gacgctcatg tgccgggtgt    9660
tgtttaggtt ctcaagagcg tcgcgagtgt actcgtcagc tcgtttcagc tgccatatca    9720
gtgacgtcgt gttgagcctg ggcctgtatc ttgccagtat atgggcctgt ggagcgagaa    9780
cgaacgacac gtcaaacaca gacagagatc agctcagctc agagacttgc tgtgagagtg    9840
agacattagc cgcgaacacg tttcttagct agcattacta acctcacgct tcgtgtggac    9900
atgggccttg tgcgttccgt ttagttgctt aagtaacctg tcgtgattgt tcgctacttg    9960
tgataccaac tggcggagca ggttccttct gaaaagaaat attgcagaga ctcctcttcg    10020
attgaagtag tcgactacgt ccgcatggtt tgccacgagg ccctgaaaac atacacccca    10080
accccaaccc cgttcagaag aaatgctcct ttgtttccac tctctagcta cagtgcctgt    10140
tttgtttcca gtctctaact ctatgtttgg ccaacattca tggtttggtt aggcaatctg    10200
tctaccagga aaaagtttg ttctcacaca aattagatga agccctgaaa caaacatgct    10260
tgacatgtag attataatca gtctactgga cacactacag aatctatcaa atattactcc    10320
atatgcattt gcagttctca tgcacgttcg agagaaaaaa attgtctaaa atgcaggatc    10380
tgacagcaag tcacaaaact aaactagcta tccgacagtc ccataaggtt attcgcatcc    10440
```

| | | | | |
|---|---|---|---|---|
| cacatagatt | ggaagggatt | ggaaaatttt | aagaaggatt | ttgacttctt acggatttaa | 10500 |
| acccgttcaa | tctcgtccaa | tccacatgga | ttggcactaa | gacgagcaag ccctaaagtg | 10560 |
| gattcccaaa | aaaaaatagt | tccatggact | tgaggaaagt | ttggagcaat atgcaatact | 10620 |
| ggaactaaat | ggaaaaataa | atgaaaaagg | gtcatccaaa | taaatctata ctgcatgttt | 10680 |
| tagtccgcac | ctgatttagc | atccacttga | agccaatagc | tgcagtgcac tcattcttgg | 10740 |
| aagcgctact | gttccagtcc | aaattgtaca | ctttatccag | ggtatctatt atagaggaaa | 10800 |
| tgttactcct | cctttctttt | ctagagaaaa | tttcaccatt | ggagctaaca ttcatgtggc | 10860 |
| tgttaagaag | agtttcaaac | cagccacttc | cagatcgctg | cgatgatata attgcaaagg | 10920 |
| accggacagc | attgcacttg | cattcctccc | tagaaattaa | aaattatgta ttaggcatta | 10980 |
| aacaaacgag | attgctcaat | cttaccacag | ttgcagatct | cacctgctgt aagttatcgg | 11040 |
| ttgaggatag | cgcacaaatt | gagcctccga | agaggagca | atggacttat tacatggttg | 11100 |
| tcccacaact | tcaatcttga | caactcttga | ccagccatca | ctccctagtt gcttcatgca | 11160 |
| cattgagcaa | atagatatcc | cgcataacat | agtcatagca | aagacaaccg ttctcaacgc | 11220 |
| gatcggtgat | tttttcgggg | gcttcaagtc | aaatgcatcc | tgcaaacaga tccgaccagt | 11280 |
| acaaaaccaa | tcagcaggtt | gcactgcgca | tacgcggttc | agtgccagta tatatacatt | 11340 |
| gcagcccttt | tttgaggtaa | gatctgttat | tttgtaacct | tctgctacag taaaaaaacc | 11400 |
| tttcagcaaa | caacacaaac | attaatgttc | aatgtgagct | gagaagcatc catttggcta | 11460 |
| catctatata | agcagaaata | aaaagaaata | aacaaataaa | acttcaaggt ctatctagtc | 11520 |
| ctcagggaag | ttaaaatgag | cacgtactat | tcaattcagc | tactagcctt tttaccaaca | 11580 |
| tggaagacac | ggcaagggat | gaaaaggccc | tttttgata | agttcaagta cattcccata | 11640 |
| tattctgtcg | cccagctgcc | ttaggggcg | tttggttgcc | ttctccagtg gtgcagctgc | 11700 |
| atctacacat | gcaaaagta | gtgtttgttt | ggttcgttgt | atcgcacgag acaggctagc | 11760 |
| acggaactta | aagcgccgcg | agccaggccc | ggcagaaacg | catcgcgcga ccgcacgcgc | 11820 |
| gcggccaggc | tccgctcagc | cagctctta | ctcgtgcacg | catatcgaga cacgttttta | 11880 |
| attggttttt | tcattatatc | | | | 11900 |

<210> SEQ ID NO 43
<211> LENGTH: 1411
<212> TYPE: DNA
<213> ORGANISM: Zea mays

<400> SEQUENCE: 43

| | | | | |
|---|---|---|---|---|
| gtgttgcgtt | ccctacttgc | tctttctc | ctccgcttca | acctgtcccc agcgcccccc | 60 |
| gcgcacacac | tgtctttctc | tgcctttctt | tccctagcgc | cgcgccggcg ccgccattcg | 120 |
| atcaggccgc | ttcgccggcg | acagcatatt | ccaggtcggt | tggttttggc acttcggacc | 180 |
| ggcggccatg | gcttccgacg | gcatcggccc | cagaggatgt | atgtgttgtt ggggttgcac | 240 |
| gcaccccaat | gggcggttc | cttggtgcct | tgtctcccct | gcctgctacg aaacttggct | 300 |
| ctatagtaat | tcaagctgct | ctggaaagag | caaacgtgga | tccagccctc gtgcaggagg | 360 |
| tctactttgg | aaacgtcttg | agtgctaatt | tggggcaagc | tcctgcaagg caagctgctc | 420 |
| tgggtgccgg | gataccaaac | tctgttgttt | gcaccactgt | taacaaagtc tgtgcatctg | 480 |
| gcatgaaagc | tactatgttt | gcagcacagt | caattcaatt | gggtatcaat gatattgttg | 540 |
| tggctggtgg | catggaaagc | atgtccaatg | ccccaaagta | cattgctgaa gctaggaagg | 600 |
| ggtctcgttt | tggtcatgac | acacttgttg | atgccatgct | taaggatggg ctttgggatg | 660 |

| | |
|---|---|
| tatacaatga ttgtgccatg ggaatgtgtg ccgagctttg tgctgacaac catgccctca | 720 |
| caagagaaga ccaggatgca tttgctatcc aaagcaacga gcgtggaatt gctgctcgtg | 780 |
| acagtggtgc ttttgcatgg gagattattc cggttcaagt tcctgttggt agaggaaaac | 840 |
| ccccaacatt aattgagaga gatgaaagcc tggataagtt tgacccagta aaactaaaga | 900 |
| aacttcgccc aagtttcaag gagaatggtg gtacagttac agctggaaat gcttctagta | 960 |
| taagtgatgg agctgctgca ttagttttag tgagtgggca gaaggctcaa gagcttggcc | 1020 |
| ttcaagtcct tgcaaggatc aaaggttatg ctgatgcagc tcaagctccg gagcttttta | 1080 |
| caaccactcc agcacttgca ataccaaagg ctatcgcaaa tgctggatta gagtcatccc | 1140 |
| gtgttgattt ctatgagatt aatgaagcct tttcggctgt tgcgcttgca aatcaaaaac | 1200 |
| ttcttggaat tccttcagaa aagattaatg ttcatggagg agctgtatcc ttaggacatc | 1260 |
| ctctcgggtg cagtggtgct cgcatttggg ttacccttat tggtgttctc agggcgaaga | 1320 |
| gtggcaagat cggagttgct ggtgtctgca acggtggagg cggagcatca gctcttgttc | 1380 |
| tggagctcgc ataagaaatc tagaccttgt a | 1411 |

<210> SEQ ID NO 44
<211> LENGTH: 5790
<212> TYPE: DNA
<213> ORGANISM: Zea mays

<400> SEQUENCE: 44

| | |
|---|---|
| gggggcagtc tatactgccc ccttaatagt tagtagagat ttggtacaac tcacgagcta | 60 |
| gctcgctcgc agacgctccg aacttgatct gactcgtgag cctcaagttt tttttctagc | 120 |
| cttaaccaca tgcccacgag gatgattgtt cgaggtgatt agcaaacgca aacgatatca | 180 |
| attgacattt tttattagtt tcattaggtt tagagataaa attatatcat gtatgtcact | 240 |
| catctagtat cttatttgtt atcataaatg ttctaatcct ttttacgtca cccgaataca | 300 |
| atttttact ctttcatgtc atcgttgatg acatagtaag ggactaagac atacaacatt | 360 |
| ttacatttaa catttggcca cgacatgtaa gagtgagata ttgaattcga gtaacatacg | 420 |
| aggtacgatg aataaggtat tacacaaaat tacagtggca tatagtgaat tgaattgttc | 480 |
| tatttttact ttttttttgc ctaacataaa gcctatttta tttagtactt tctctgattc | 540 |
| agctttaatt tttatgattt attaatttta ttatatatct atatattgta tagattaaaa | 600 |
| aataaaatag attatagatt taggaaaaat tacattcggg tgatttggct gttgggtgtt | 660 |
| gcgttcccta cttgctcttt tcttcctccg cttcaacctg tccccagcgc ccccgcgca | 720 |
| cacactgtct ttctctgcct ttcttttccct agcgccgcgc cggcgacgcc attcgatcag | 780 |
| gccgcttcgc cggcgacagc atattccagg tatgccgtcc cttctgctcc ttctgcgaga | 840 |
| attcaaacac cccgaactcc ccaaatctag tatttgtatt cggatctgac cattttttcac | 900 |
| tgggcccgcc cctgattcgc aggtcggttg gttttggcac ttcggaccgg cggccatggc | 960 |
| ttccgacggc atcggcccca gaggtattac tgtttcatct cttcttgtgt tcaaacagac | 1020 |
| agacgtcaag ccgccgagag gaggtacaaa tatagatttt gggtaatgag cacgccattg | 1080 |
| cgcttccagc gatctgacat attgggaatt cttgcttttt tttgggtacc ttgcaaggcc | 1140 |
| gaaatttgac gcttttctgt ttaattctag tgcctgtctg catccattag gcatcctag | 1200 |
| ctgctccatg ctcgtgatct cgtccgtttg cttgattgaa tccattgttt tccaaagttc | 1260 |
| attgctactg cgaaatacgt ttatatgatt accacaagtt gtgtttttc ctttttcgggt | 1320 |

```
tgcacagagg gtactgccat cattgttgtt atagcgccat ttggaacaag tgattcactg    1380
gtactagtac agtatgtgct tttcatgtgt gtttggtttg taccatcaga tggaattttg    1440
agcgcggttt acaaattagt actatagata tactgtgagg tgcacactag atggttctgc    1500
tttgttctac agtcagtaac ttttttcttcc ttgctcacag atgtatgtgt tgttggggtt    1560
gcacgcaccc caatgggcgg tttccttggt gccttgtctc ccttgcctgc tacgaaactt    1620
ggctctatag taattcaagg tgagatccga atcttctctg catttacatc cgagctctga    1680
acatggtcat ggctggggggc tgttagctgc tctggaaaga gcaaacgtgg atccagccct    1740
cgtgcaggag gtctactttg gaaacgtctt gagtgctaat ttggggcaag cgcctgcaag    1800
gcaagctgct ctgggtgccg ggataccaaa ctctgttgtt tgcaccactg ttaacaaagt    1860
ctgtgcatct ggcatgaaag gtttgaatcg aatttatctg tctgtccttg tgtactctgc    1920
tcagagttca cagaagtgag agattacctg accatgctct tgtttccctt tcctatatgc    1980
agctactatg tttgcagcac agtcaattca attgggtatc aatgatattg ttgtggctgg    2040
tggcatggaa agcatgtcca atgccccaaa gtacattgct gaagctaggt atgcaattat    2100
tacttggtgg atatattcaa tatcgagctg cataaaccaa atgatagtct aagttatttt    2160
ggtagataca tgcatgctta cttatcttca ttgcatttttc taaatttgtt tgtaagaaat    2220
gttgattcac cagcagcgag gctattaacg aagtggccag ttttgttgtg aaagtatatt    2280
ctgttcatgt ttaaagtgca tttcaactgc tttaatccaa taagcttgct acttacaatt    2340
gcaggaaggg gtctcgtttt ggtcatgaca cacttgttga tgccatgctt aaggatgggc    2400
tttgggatgt atacaatgat tgtgccatgg gaatgtgtgc cgagctttgt gctgacaatc    2460
atgccctcac aagagaagac caggtctctt aatacagata gcagtaaatg ctgtttgtta    2520
taatattccc atatttttca agatataagt tgtgctatac aacatgtcaa tgctggcaat    2580
tattttgaga gtgccctgga atcttcgtgc tttatcttgg ttatcatcat aaatggtcta    2640
gagactctag accagcatct gcattccttg tccgatgaac tagtaacttg gatccttcct    2700
ggcaatgatt ttctgttagg ttgtgacatg attgataggg tgggcttatg catgctctgg    2760
gtctgtgaac tgaccattca tttgcttcca gagatgaaag tagatgtgcc acacaaaaat    2820
gagcactctt ttgcattctt gttagagcta tacaagtata atctcttaaa agctgctcat    2880
cagtacatga cactagtacc ttgatgattt tactgtatct gtttatgtaa ttttttttctt    2940
aataaatttg atatagtata attaaaattg agttgccttt gaattttcac ttatatgttg    3000
caatgtattt ttgtctatat tgcaataaat atattcccaa tttctggtat atttacttat    3060
tcttgaatag gatgcatttg ctatccaaag caatgagcgt ggaattgctg ctcgtgacag    3120
tggtgctttt gcatgggaga ttattccggt aattttctcc ctcattgatg atactagaca    3180
tgcttttctt ggttttctga tggtcaatgt tgtcgcccag gttcaagttc ctgttggtag    3240
aggaaaaccc ccaacattaa ttgagagaga tgaaagcctg ataaggtttt ttttctgat    3300
ttgacaaaat atttttaaca aaataaagct tgtagttgat caaaggcaaa aagactggca    3360
ggcactttga tttattgttc ttgcttcctc caaatgcaac gttcctcgca taatgagctt    3420
tgctagcagt tatttgtaag atcaatgcat gacagtttta tttatgtctt gtgctattcc    3480
ttttgtgtct tagtttgacc cagtaaaact aaagaaactt cgcccaagtt tcaaggagaa    3540
tgatggtaca gttacagctg gaaatgcttc tagtataagg tagctgcttg aaatatttct    3600
gagaccttttt tgtcctacaa agtctttctg agaccttgtt tttcggccat atgttgttta    3660
gctgacagat atgaaggaca acctatttca ttgttgacag ttaaattata ttattgtatt    3720
```

```
atgcatgcat tttttaactga tatattatgc ttgcattttg tcaacttcat tgtttctcta    3780
tttgttttta gactgcttgg gtatgctcta ctctgtgaaa tagatggtaa ttttttcttt    3840
agaattggta cccaatcgat gtgaatgatt tatcacataa gaaagtaaaa acattttaaa    3900
tgccttatta tgcccattca aacaacaaaa gttgccctag accttgtctg tctcactttg    3960
tactgtgtct atttttagct gaccagtact gtccggtgta ctgcctacta tggcttgtct    4020
agccttctgc aaccagtcat atctaatttg ttttatatgg atcagtgatg gagctgctgc    4080
attagttttg gtgagtgggc agaaggctca agagcttggc cttcaagtcc ttgcaaggat    4140
caaaggttat gctgatgcag ctcaagtaag ccacagtaac aattgttagc tctcctaaga    4200
gtagaatgcg cttattctaa ttcacattgt gatctaaata ttttaggata taggaagtta    4260
tttttatctg gaacgatttt atgttactat tttagatatc gaaatttatc aactattgga    4320
acttgtgatc tggaatatta ttttgtaatg tggatgctgt ttatacaggc tccggagctt    4380
tttacaacca ctccagcact tgcaatacca aaggctatcg caaatgctgg attagagtca    4440
tcccatgttg atttctatga gattaatgaa gccttttcgg tatgcattgg gtttctttat    4500
ttgtaagcct tttgttatgc attgagagct tattttactt attactttt ttttgtaata    4560
atgtcttttt tacttatcaa tataggctgt tgcacttgca aatcaaaagc ttcttggaat    4620
tccttcagta agtgtcacct gtattaaact gccattcttt gtgcatttta gaagttaaaa    4680
catcactttc agaaagtaca tattggccct ttttttgttat ttgctatgca gcagcaacat    4740
gtaattgcat tataacagca ttatatgtac taacaacata tgtgtttgca ggaaaagatt    4800
aatgttcatg gaggagctgt atctttagga catcctctcg ggtgcagtgg tgctcgcatt    4860
ttggttaccc ttattggtgt aagttctatc ttaagatgct tgtttatct tttgagttac    4920
aatcccttt gttaaaaaa atgtgcaatg ttttttctagt aaaaaaatag atgatggtct    4980
ttgagtaatt gatgaattct gacatatgtt accgtatcat catagggttc gtgatgaaca    5040
gtaagcatct tcactattgc tactaagtct acttccttag tgttttccaa tgtgcaatgt    5100
ttttcttgta taaagctgca aatgtagagt ttcacttgtt gctggtgatc agtagtttct    5160
cttcatttt tttaagcaaa accttgagaa caatatggtg ccatcatgtt gggacatcaa    5220
atatatggtg cttgaccctc ctaatcattg tttcttgtta acaggttctc agggcgaaga    5280
gtggcaagat cggagttgct ggtgtctgca acggtggagg cggagcatca gctcttgttc    5340
tggagctcgc ataagaaatc tagaccttgt aaggctcaaa acaccgaata tatctcaact    5400
caaattgatt cttttactag ctggcaggag ctaaccagta taaggtgcta ttactgttgt    5460
gcaatttgac taactgctgc aactgatatt gcaggtattt agcaaaagtt ccctgaggtg    5520
atcttgtagt cttatttcc gttgtagtag tcccatagaa catttcttaa tttaatttgg    5580
caataaagcg aagtcgtgct tctgttggtt gcatagtaga gtatcatgta ataagagcaa    5640
tggggatgtt tcatagatat ttttgaggat gctacagaaa tattttatat actagtgagt    5700
gctcgtgcgt tgcaacggga atatataatt ctatgataac ttatatacaa aatgtgtgct    5760
acattgttat aagaaaatgt ttcataatct                                      5790
```

<210> SEQ ID NO 45
<211> LENGTH: 5881
<212> TYPE: DNA
<213> ORGANISM: Zea mays

<400> SEQUENCE: 45

```
gggcagtcta tactgccccc ttaatagtta gtagagattt ggtacaactc acgagctagc        60
tcgctcgcag acgctccgaa cttgatctga ctcgtgagcc tcaagttttt tttctagcct       120
taaccacatg cccacgagga tgattgttcg aggtgattag caaacgcaaa cgatatcaat       180 tgacatttt tattagtttc attaggttta gagataaaat tatatcatgt atgtcactca        240
tctagtatct tatttgttat cataaatgtt ctaatccttt ttacgtcacc cgaatacaat       300
tttttactct ttcatgtcat cgttgatgac atagtaaggg actaagacat acaacattt        360 acatttaaca tttggccacg acatgtaaga gtgagatatt gaattcgagt aacatacgag       420
gtacgatgaa taaggtatta cacaaaatta cagtggcata tagtgaattg aattgttcta      480
tttttacttt tttttttgcct aacataaagc ctatttttatt tagtactttc tctgattcag    540
ctttaatttt tatgatttat taattttatt atatatctat atattgtata gattaaaaaa      600
taaaatagat tatagattta ggaaaaatta cattcgggtg atttggctgt gggtgttgc       660 gttccctact tgctcttttc ttcctccgct caacctgtc cccagcgccc ccgcgcaca       720 cactgtcttt ctctgccttt cttctcccctag cgccgcgccg gcgacgccat tcgatcaggc   780
cgcttcgccg gcgacagcat attccaggta tgccgtccct tctgctcctt ctgcgagaat     840
tcaaacaccc cgaactcccc aaatctagta tttgtattcg gatctgacca ttttcactg      900 ggcccgcccc tgattcgcag gtcggttggt tttggcactt cggaccggcg gccatggctt    960
ccgacggcat cggccccaga ggtattactg tttcatctct tcttgtgttc aaacagacag    1020
acgtcaagcc gccgagagga ggtacaaata tagattttgg gtaatgagca cgccattgcg    1080
cttccagcga tctgacatat tgggaattct tgctttttt tgggtacctt gcaaggccga    1140 aattttgacgc ttttctgttt aattctagtg cctgtctgca tccattaggg catcctagct   1200
gctccatgct cgtgatctcg tccgtttgct tgattgaatc cattgttttc caaagttcat    1260
tgctactgcg aaatacgttt atatgattac acaagttgt gttttttcct tttcgggttg     1320
cacagagggt actgccatca ttgttgttat agcgccattt ggaacaagtg attcactggt    1380
actagtacag tatgtgcttt tcatgtgtgt ttggtttgta ccatcagatg gaatttgag     1440 cgcggtttac aaattagtac tatagatata ctgtgaggtg cacactagat ggttctgctt    1500
tgttctacag tcagtaactt tttcttcctt gctcacagat gtatgtgttg ttggggttgc    1560 acgcaccccca atgggcggtt tccttggtgc cttgtctccc ttgcctgcta cgaaacttgg   1620
ctctatagta attcaaggtg agatccgaat cttctctgca tttacatccg agctctgaac    1680
atggtcatgg ctggggctg ttagctgctc tggaaagagc aaacgtggat ccagccctcg    1740
tgcaggaggt ctactttgga aacgtcttga gtgctaattt ggggcaagcg cctgcaaggc    1800
aagctgctct gggtgccggg ataccaaact ctgttgtttg caccactgtt aacaaagtct   1860
gtgcatctgg catgaaaggt ttgaatcgaa tttatctgtc tgtccttgtg tactctgctc    1920
agagttcaca gaagtgagag attacctgac catgctcttg tttcccttc ctatatgcag    1980 ctactatgtt tgcagcacag tcaattcaat tgggtatcaa tgatattgtt gtggctggtg    2040
gcatggaaag catgtccaat gccccaaagt acattgctga agctaggtat gcaattatta    2100
cttggtggat atattcaata tcgagctgca taaaccaaat gatagtctta agttatttgg    2160
tagatacatg catgcttact tatcttcatt gcattttcta aatttgtttg taagaaatgt    2220
tgattcacca gcagcgaggc tattaacgaa gtggccagtt tgttgtgaa agtatattct    2280 gttcatgttt aaagtgcatt tcaactgctt taatccaata agcttgctac ttacaattgc    2340
aggaaggggt ctcgttttgg tcatgacaca cttgttgatg ccatgcttaa ggatgggctt    2400
```

```
tgggatgtat acaatgattg tgccatggga atgtgtgccg agctttgtgc tgacaatcat    2460
gccctcacaa gagaagacca ggtctcttaa tacagatagc agtaaatgct gtttgttata    2520
atattcccat atttttcaag atataagttg tgctatacaa catgtcaatg ctggcaatta    2580
ttttgagagt gccctggaat cttcgtgctt tatcttggtt atcatcataa atggtctaga    2640
gactctagac cagcatctgc attccttgtc cgatgaacta gtaacttgga tcctttctgg    2700
caatgatttt ctgttaggtt gtgacatgat tgatagggtg ggcttatgca tgctctgggt    2760
ctgtgaactg accattcatt tgcttccaga gatgaaagta gatgtgccac acaaaaatga    2820
gcactctttt gcattcttgt tagagctata caagtataat ctcttaaaag ctgctcatca    2880
gtacatgaca ctagtacctt gatgatttta ctgtatctgt ttatgtaatt tttttcttaa    2940
taaatttgat atagtataat taaaattgag ttgcctttga atttttcactt atatgttgca    3000 atgtattttt gtctatattg caataaatat attcccaatt tctggtatat ttacttattc    3060
ttgaatagga tgcatttgct atccaaagca atgagcgtgg aattgctgct cgtgacagtg    3120
gtgcttttgc atgggagatt attccggtaa ttttctccct cattgatgat actagacatg    3180
cttttcttgg ttttctgatg gtcaatgttg tcgcccaggt tcaagttcct gttggtagag    3240
gaaaaccccc aacattaatt gagagagatg aaagcctgga taaggttttt tttctgattt    3300
gacaaaatat ttttaacaaa ataaagcttg tagttgatca aaggcaaaaa gactggcagg    3360
cactttgatt tattgttctt gcttcctcca aatgcaacgt tcctcgcata atgagctttg    3420
ctagcagtta tttgtaagat caatgcatga cagtttttatt tatgtcttgt gctattcctt    3480
ttgtgtctta gtttgaccca gtaaaactaa agaaacttcg cccaagtttc aaggagaatg    3540
atggtacagt tacagctgga aatgcttcta gtataaggta gctgcttgaa atatttctga    3600 gaccttttg tcctacaaag tctttctgag accttgtttt tcggccatat gttgtttagc    3660
tgacagatat gaaggacaac ctatttcatt gttgacagtt aaattatatt attgtattat    3720
gcatgcattt ttaactgata tattatgctt gcattttgtc aacttcattg tttctctatt    3780 tgttttaga ctgcttgggt atgctctact ctgtgaaata gatggtaatt ttttctttag    3840
aattggtacc caatcgatgt gaatgattta tcacataaga aagtaaaaac attttaaatg    3900
ccttattatg cccattcaaa caacaaaagt tgccctagac cttgtctgtc tcactttgta    3960
ctgtgtctat tttagctga ccagtactgt ccggtgtact gcctactatg gcttgtctag    4020
ccttctgcaa ccagtcatat ctaatttgtt ttatatggat cagtgatgga gctgctgcat    4080
tagttttggt gagtgggcag aaggctcaag agcttggcct tcaagtcctt gcaaggatca    4140
aaggttatgc tgatgcagct caagtaagcc acagtaacaa ttgttagctc tcctaagagt    4200
agaatgcgct tattctaatt cacattgtga tctaaatatt ttaggatata ggaagttatt    4260
tttatctgga acgattttat gttactattt tagatatcga aatttatcaa ctattggaac    4320
ttgtgatctg gaatattatt ttgtaatgtg gatgctgttt atacaggctc cggagcttt    4380 tacaaccact ccagcacttg caataccaaa ggctatcgca aatgctggat tagagtcatc    4440
ccatgttgat ttctatgaga ttaatgaagc cttttcggta tgcattgggt ttcttatt    4500 gtaagccttt tgttatgcat tgagagctta ttttacttat tactttttt ttgtaataat    4560 gtcttttta cttatcaata taggctgttg cacttgcaaa tcaaaagctt cttggaattc    4620
cttcagtaag tgtcacctgt attaaactgc cattctttgt gcattttaga agttaaaaca    4680
tcactttcag aaagtacata ttggcccttt tttgttattt gctatgcagc agcaacatgt    4740
```

-continued

```
aattgcatta taacagcatt atatgtacta acaacatatg tgtttgcagg aaaagattaa    4800
tgttcatgga ggagctgtat ctttaggaca tcctctcggg tgcagtggtg ctcgcatttt    4860
ggttacccct attggtgtaa gttctatctt aagatgcttg ttttatcttt tgagttacaa    4920 tccctttgt ttaaaaaat gtgcaatgtt tttctagtaa aaaaatagat gatggtcttt       4980
gagtaattga tgaattctga catatgttac cgtatcatca tagggttcgt gatgaacagt    5040
aagcatcttc actattgcta ctaagtctac ttccttagtg ttttccaatg tgcaatgttt    5100
ttcttgtata aagctgcaaa tgtagagttt cacttgttgc tggtgatcag tagtttctct    5160 tcatttctt taagcaaaac cttgagaaca atatggtgcc atcatgttgg gacatcaaat     5220
atatggtgct tgaccctcct aatcattgtt tcttgttaac aggttctcag ggcgaagagt    5280
ggcaagatcg gagttgctgg tgtctgcaac ggtggaggcg gagcatcagc tcttgttctg    5340
gagctcgcat aagaaatcta gaccttgtaa ggctcaaaac accgaatata tctcaactca    5400
aattgattct tttactagct ggcaggagct aaccagtata aggtgctatt actgttgtgc    5460
aatttgacta actgctgcaa ctgatattgc aggtatttag caaaagttcc ctgaggtgat    5520
cttgtagtct tattttccgt tgtagtagtc ccatagaaca tttcttaatt taatttggca    5580
ataaagcgaa gtcgtgcttc tgttggttgc atagtagagt atcatgtaat aagagcaatg    5640
gggatgtttc atagatattt ttgaggatgc tacagaaata ttttatatac tagtgagtgc    5700
tcgtgcgttg caacgggaat atataattct atgataactt atatacaaaa tgtgtgctac    5760
attgttataa gaaatgtttt cataatctat acacaaagat gagatttctg caaagaatac    5820
catgccacat cactaaaata tgaatggctc acttatccct tataacagca gccttgtctt    5880
t                                                                      5881

<210> SEQ ID NO 46
<211> LENGTH: 1628
<212> TYPE: DNA
<213> ORGANISM: Zea mays

<400> SEQUENCE: 46
gtgttgcgtt ccctacttgc tcttttcttc ctccgcttca acctgtcccc agcgcccccc      60
gcgcacacac tgtctttctc tgcctttctt tccctagcgc cgcgccggcg acgccattcg     120
atcaggccgc ttcgccggcg acagcatatt ccaggtcggt tggttttggc acttcggacc     180
ggcggccatg gcttccgacg gcatcggccc cagagatgta tgtgttgttg gggttgcacg     240 cacccccaatg gcggtttcc ttggtgcctt gtctcccttg cctgctacga aacttggctc     300
tatagtaatt caagctgctc tggaaagagc aaacgtggat ccagccctcg tgcaggaggt     360
ctactttgga aacgtcttga gtgctaattt ggggcaagcg cctgcaaggc aagctgctct     420
gggtgccggg ataccaaact ctgttgtttg caccactgtt aacaaagtct gtgcatctgg     480
catgaaagct actatgtttg cagcacagtc aattcaattg ggtatcaatg atattgttgt    540
ggctggtggc atggaaagca tgtccaatgc cccaaagtac attgctgaag ctaggaaggg    600
gtctcgtttt ggtcatgaca cacttgttga tgccatgctt aaggatgggc tttgggatgt    660
atacaatgat tgtgccatgg gaatgtgtgc cgagctttgt gctgacaatc atgccctcac    720
aagagaagac caggatgcat tgctatcca aagcaatgag cgtggaattg ctgctcgtga      780
cagtggtgct tttgcatggg agattattcc ggttcaagtt cctgttggta gaggaaaacc    840
cccaacatta attgagagag atgaaagcct ggataagttt gacccagtaa aactaaagaa    900
acttcgccca gtttcaagg agaatgatgg tacagttaca gctggaaatg cttctagtat     960
```

```
aagtgatgga gctgctgcat tagttttggt gagtgggcag aaggctcaag agcttggcct    1020
tcaagtcctt gcaaggatca aaggttatgc tgatgcagct caagctccgg agcttttac     1080 aaccactcca gcacttgcaa taccaaaggc tatcgcaaat gctggattag agtcatccca    1140
tgttgatttc tatgagatta atgaagcctt ttcggctgtt gcacttgcaa atcaaaagct    1200
tcttggaatt ccttcagaaa agattaatgt tcatggagga gctgtatctt taggacatcc    1260
tctcgggtgc agtggtgctc gcattttggt taccttatt ggtgttctca gggcgaagag     1320
tggcaagatc ggagttgctg gtgtctgcaa cggtggaggc ggagcatcag ctcttgttct    1380
ggagctcgca taagaaatct agaccttgta tttagcaaaa gttccctgag gtgatcttgt    1440
agtcttattt tccgttgtag tagtcccata gaacatttct aatttaatt tggcaataaa     1500 gcgaagtcgt gcttctgttg gttgcatagt agagtatcat gtaataagag caatggggat    1560
gtttcataga tatttttgag gatgctacag aaatatttta tatactagtg agtgctcgtg    1620
cgttgcaa                                                             1628

<210> SEQ ID NO 47
<211> LENGTH: 1714
<212> TYPE: DNA
<213> ORGANISM: Zea mays

<400> SEQUENCE: 47
aagagcccct cgggcagcag gatcttcccc ctccccaaaa ccaaaccagc tgcctccgac     60
agcatccacc ttttcctccc ccaaaccatg gacttctcca ccggcgggag cgtgagcggg    120
ggcggcggag gcgccagcga cggccccgcg caggcggagc gctggctgga gatcgccgag    180
aagctcctcg cggcgcgcga cctcgtcggc tgcaagcgct tcgcggagcg gtcggtggag    240
gcgaacccgc tcctcgccgg cgttgacgaa ctcctcgccg tcgccgacgt cctcctcgct    300
tcccagttca tgggcaccctc gggccagccg gacccgctcg ccatcctcca gctgccgccc    360
ggagtcagcc ccgaccaggc cgccgtgtcc cgcgccttcc gccgcctcgc gctcctcctc    420
ggtcccagca acccgcaccc gggagccgag atggcgctcc gcctcgtcaa cgacgcctac    480
gccttcctct cggatccctc tcgccgcccc ccgccgcccg ccgatcccgc cactggtacc    540
ccttactcct cccagtatcc cgccgcggcc gctcccgcct ccgacaccc ggagttctgg      600 acggcgtgcc ccttctgctg ctacgtgcac cagtacccgc gcagcctgat cgggcgcgcc    660
ctcaagtgcc ccaacgcggg ctgccgccgc ggattcgtgg cttctgagct cccgaccca     720 cccacggttg tgccgggcac tgaaatgtac cactgcgcct ggggggttctt ccccctcgga    780 tttcccaacg cggccgacct gggtgccaac tggaagccat tctacaagat gttcccttgg    840
aacacggctc ccagtggcca aggtggtggt ggtaggagtc acggaaaacca tggtggtagg    900 cagccacaga atgacagtgc tcgtggtggc tcttctagag gtaggatcaa gaagacgacg    960
gcccgcaaga aggtcgggt agggctcagg agacgttctc ttggtgtgga gagtggcatt     1020
gattcttcga tgctcgggca ggaaggctgg gctggggatg agaacgctgg agatggaagg    1080
gccgaggagg tgaggagaat taacataaat gaggcagcac atgctacaga tggcactggt    1140
agggttaatg ttagcggtgc tggcggagtt gaagatatcg gcaactttca tatcgatgtt    1200
gatgcatccg aggatatatt ggggaatttg cacaacatgc acttcttgag ggtggacaat    1260
cttgacggga tgatttaact gttgttatgg tttactgggg ctatgattag ccaggccgac    1320
tcttgctgtt caagtgttca tttgagtgta attgttccat ccctgttatg taatgttgta    1380
```

| | |
|---|---|
| gttgtagact tgtagtctac ctggtacctg tagttactta acatcaggca gggaaaaatt | 1440 |
| tgtatgttca ttagatggag atacatgcca tttgccttag caaacacact ttgtggaggt | 1500 |
| ttccagtgat gggataatgc ttcgcagagg tgtggttgga ctggcaatgc ttaccatgcc | 1560 |
| acttctggtt tyttcctggc atggtgacac aaaatgttgt tgagatcaag taagtgaatt | 1620 |
| atgttctgct ttctgagttc ggtaaacttc tttggctaca aaaggactaa gcttagttat | 1680 |
| gctaacttgt tgatttggtt gtgatcattg catc | 1714 |

```
<210> SEQ ID NO 48
<211> LENGTH: 9828
<212> TYPE: DNA
<213> ORGANISM: Zea mays

<400> SEQUENCE: 48
```

| | |
|---|---|
| tggcctcagc atgtttgcaa aatgaatcag taaggaaaaa gaacacggct gcatcatcta | 60 |
| tatgatacct ccaagtgaac ataaaggaca acatcatcga ccaatttaat ataaatccaa | 120 |
| agcaaaccac atgaaaatca aactcgcagc aggtataaca tgaacaacac actgtaccaa | 180 |
| accctaactc atgaagcatg aaccagaaaa tagaacgatt gggggttgat ttcaccttgg | 240 |
| ggtcaaggtc gtagcaacgg agacggagca gacctagaag tataggaagc aaatcgacca | 300 |
| gagacgaagc gacgaagcag atgcccaacg ccacggagtc ctggcaccag gcggagctgg | 360 |
| acgcagccgc gacgcacagc cactcgccgc cggtctctca cgagggaggg aggggtggga | 420 |
| agaagaacga gcagcgagag gaggggaaaa ggagggtgca ccgtcgccat atatagccgc | 480 |
| aagaggattc accggagcgc tccttcccgc gcgcgcgaaa acctcaccat tcccgcgcga | 540 |
| gcccgcgcga gctcccgcca gccacctcgc ccgccgccac attccgccag tgcgccgcgc | 600 |
| gcagccgagc tccaggaaa cgaacccctag ccgcgtttcc tgggagccac ccaggaaaca | 660 |
| ggctgttttc agccaggctg cgaaacgggc caaccttgca aacaaggtta gttgtagccc | 720 |
| acgggcacaa tcgggctact gggccatcct ccgaaacacg cccttggtga tctctggtgg | 780 |
| cgaagcgata cgatacgatg gccggccgta gtacgtcccg tgggtggccg ctgacgtgac | 840 |
| gagaaacagt cggtcggcgg ccagccagta acgtgacact cgccatctgc ttccatcttt | 900 |
| tgtggttttt tcttctctag acttgactgc atgcagccaa gaaccagaaa ccggacgacc | 960 |
| gaccgacgac ggcgacgggt cgtcgtgcac cgccacacgg gggtcatacg atacgacacg | 1020 |
| acacgttccg ccgcgagatc gaggtcgatg agtccgaggc tctcggctcc caagtcccaa | 1080 |
| caagctgcac cggctcgacg aggacgacgt actgtacgaa cagaacaaca gccagaggcc | 1140 |
| ggccggccgg acgaccgacg gtcgccgtcg tgcaccgtgc acggtgcacc acgtctcatg | 1200 |
| ccgtctggcg tgtgggtgac gaatcactga aactgaaagg gtaggcagca cagcacatcc | 1260 |
| acacacatgt tctttgccta tcacacgctc tttgtaaaat tttagtacac tggtgacaat | 1320 |
| aggcggaccg agtccaacat caacaaaaaa atatatatat actggacgtt cgttagccgg | 1380 |
| gaccattttt cccccaaaag gaaccaacta cagcaggctg aaataaacgt tcctccctct | 1440 |
| atgccaaaat aaaattcgta ttagtaaatt agtggttcat ataacatttg atgtatgtgt | 1500 |
| tttgtatata tatacatgcc tatatttatt aacatttatt tgaatataga tataaaaaca | 1560 |
| cagagctaaa acgattacta ataaagttaa cttgacgctg cagtgttgtt ttttttata | 1620 |
| aactctgttc aagttagaga aatctgattt gtagcagctc ttgacttcaa cagagggatc | 1680 |
| agaataacta taaagctcca gtaaatagat tacagaatac agcttccctg tttcttttcaa | 1740 |
| caatacggca gtttagaatt ttttatgtaa caaagctaga gagtttgtgt tttatgtaac | 1800 |

```
taagccaaag tgtgggtaag tgatatacga taaagtagca tgacacacgg aagttccact   1860
catggaatgg ctttgttcgt ttacaccaat cccgctctag attagcatgg attggaatta   1920
aatccatgcc tcaatccatg ccccaaaata atccatgact acttaatttt ttttattcgg   1980
ttaaacccat catggaatat aacccaaagg tttgggaatt ttttaaacta tggaagacat   2040
ggattctatc catagcccat taggtatgga acaaatccat gagatattgc acaagtttac   2100
attagaattc atggatcaaa agaataacta gctttgaaag tcacatggat ttgttgatgg   2160
atttaatccc accatgggat taggtgtgag atatggattc acccaatcca tacccagatt   2220
aaatccatgg tgggattata tcccatataa ccgaacaaga ccttatgtgg aaatataact   2280
aaataggagg acaacaagct tacttctatt caagcacagc tctagcaagg gactatgaca   2340
atacagataa accaagatat agtaaggtag gacacaatag cattccaggg tgcaccacga   2400
gcgctatgct ttaacaaata gacctaacat catggagtac atagattagg gataaaaaca   2460
ggtacccgaa ctcttaaaac aaatctaata ttttaaaata gatatgtata aaatttaatc   2520
ataatctttc cttctgttat aagcacacta ttatatataa gaataaattt tacatagatt   2580
gttttataca ttatttactc tttacaacaa aaagatgaaa aaatgtttgt atccgtatcc   2640
gaatgctacc caaattttat atctatcatt ttaaaaaata tgataaattt gatgtttatt   2700
ttttataaat ctttacaagt tcaatgctaa aaacaagaat attaatttgt ctagcagatt   2760
ctatatcata tttattcact atcaaagaaa aaaataccaa aaaactggta tgcgaatagg   2820
tacccgtttt catccctaca taggatggac atggttgtca ccaccttcca actatcatta   2880
actatttaga ggcctaacca cattccggta cccggtagag taaacaccac tgaaaggccc   2940
tagtttgatt ttggtaaccg agtgacaacc taggtggact aatatatttt ctatgttgag   3000
atacacaggt gattagtcca caagtagact agtttgagat acttaaatca tgatggtgaa   3060
atgcttggat ttattgtaaa cctcaactag gtgtatgtga acatcacat ggtgtcttgt   3120 ggataggtgc aggcagtggc ggagccagga tttctgtaag tgtagggcca atataacact   3180
aacaaatatt tatatcagct agaaaatctt aaatcatgca aatgtataga taatgacaca   3240
tatgaccatg aacggattat acaaattctc tcattccttc agaacatatt tgggtcccta   3300
gcaatttttc ggctcaagag tagggcccaa gccctaatgg ccctatgcct gtctccgcca   3360
ctgggtgtag gatatcaaga gacatggttt gggtatgaag gactgattgt aaaagtgatt   3420
gacaagttag atactttgag gcgatggacc acatgtggca gagaagcttg agcaaggact   3480
tggcaccgat cgaccaagga aacaataaag accaaatgaa gttgcgataa ataaagtaat   3540
gaggccacaa tggtaacatg aagtggacca tatcattcaa agaagatcaa gccaattgtt   3600
tattcatgtt gatggtcaag tggcttgatg aagtatgatg gaggaacttc atgatatggt   3660
taatgatcaa aggtagcatg gttggctaca tctatggatg atcattgccc atcatgtgat   3720
gaggttggat gcttgtataa catcatcaac attaagatga aatggaatgt gcaagacaaa   3780
ggtattgtcc aagattgttc tgtagtgatt atgcaggtat gtcacgagat cgagagcata   3840
gtgattatgt aggtatttca cgagatcgat agcatatata gtgattatac gggatatgtc   3900
atgggatcga gagctaaagg ttagggcatg agagacatga ggatttatac atgtttggac   3960
tctcaatgtc agacaatact ttttgtcttg tgtgtgttgt tatatgttcg gaacgatcac   4020
agagttttcc cgtccctctt tttatattct aaggagggat agatgttaca cggtaagcat   4080
agagccgatt atcaagttca tgatggaatc aagtcaattg ccaagttgta cacaagtcca   4140
```

```
atttacggct tatctcatat tcagttgaga tctttaaaat ctatcctagt ttaatcattg    4200
attctttgga cttatggccg gacgcatagg tccttctgct tagcctcttc tttataaagc    4260
ttgatttagg tactcatgca tattattgac aatagcttca gactttgttt gacgataaaa    4320
aagactctct atatatgaga gcatccatac aaggttttga ccactttagg acgaaacttg    4380
aagatggaga gatatgagaa aatacaatgt cgtttccatc tctactcaca gccgtgagtc    4440
catacacgag ttgtttttat gttcaatttc cacggtcatg tccctgtatt taaatgataa    4500
aaaaactaaa attatattta aatataagat atgcacatatg gatgttggct ataaacctat    4560
attcacacac ctaactcatg gttctatagt cgtcgtgcat caccttctc attcccgttt     4620 atgcaaaaat aaagagaaaa tatgcatgat tggggatttg aactttagtt gtaggatcta    4680
agttcatacc ctcctatcca acagagcaca tatttttta tgtttcatta aaaacaaagt     4740
atactcatgt cttatataaa aaccgtttca acgaatgaac atctcattag tgatatttaa    4800
aaactatagc aatgcataag caactaacta ctcaaaaaaa tgcaacctga atacttcctt    4860
tgcttctcca cacatgaaat gaaagaaact gaaataagaa acgggcaaac ggcgctgcaa    4920
aagcgggaaa tccctttttcc ttgctgatag tgatacccgg tcaaaaccca ccgagacggc   4980
gagacgcggg gagcgggtac atacacactg acacacctca cgcgagccga gacgcccagc    5040
tcaccgcccc accgagtccc acagtctcag aggccacctc gagcccccc tgccccgcaa     5100 gccgcacccg ccgctccctc cgccatctgc gctgcgctgc tctgctctgc ggtgccaggc    5160
tgccagccag tgccggcgcg cgcccgctgc cgccccgacg ggcccaccgt tctcttctct    5220
ccgcgctgcg cgccggctgg gctgcaggtc agttaatgcg cccgtgacag gcggcgtcgg    5280
ggaggccaag ggcggtgccg ggttaatccc gccgtctctc gaggcggcgc ccgcggagga    5340
ccaggcggga gggggagacg tgaggcgcg gccatggggg gcgccaaggc ggaggacaaa     5400
cccgccgccg ccgctgcaga agattggtgc taccaatttg gaaacaaggt tcgatttctt    5460
caccatttgc actcctctgc aagactggga cacgttccg ggtttcgttc tgcctgggcg     5520
gcgacaaatc tcatggcaaa ttgcctttgt ggggctcatt ccctgggttc acactccaaa    5580
tccttccttg cgaccttctc tcagccgtcg cgctttccgt ggcaagcctt ttggaaccct    5640
gatctgaagt gtcactcaga tcaatgcagt cgcattgatt ctattcgttt cctgtttccg    5700
tttccccctt ttaacgtgtc tgctagttcc aagtcccgag cgttttccgt tctctgtttc    5760
agaattgaag cttgttaagt tctgtttttt ttacaatcct tcgttttgt cccagtcctt     5820 tctattcctg gagaagttag gaatctgttg ttctcctgtt ccatttctcc tttctattcc    5880
tggagaagtt aggaatctgt tgttctcctg ttccatttct cggtgcagta ttagttgcag    5940
aacaggaatc cacttgattt gtcagtttaa ttatgcttgt gtcacctcag atgtgtcata    6000
ttgattatga ctgcatttt gtcagctgta atatgcgtgt tggcttgcat ttgtttctct     6060
ctttattagt actaccagca ttttcggtca gtatttttg tcttccttgc tgaagaatga    6120
gaaggaaagc tgtcatactc ctcgtcggga tagcttcatt tattaaggca gctgggcgac    6180
agaatatatg ggaatgtact tgaacttcac aaaaaagggc cttttcatcc cttgccgtgt    6240
cttccatgtt ggtaaaaagg ctagtagctg aattgaatag tacgtgctca ttttaactac    6300
cctgaggact agatagatct tgaagtttta tttgtttatt tcttttttatt tctgcttata   6360 tagatgtagg atgtagccaa atggatgctt ctcagctcac attgaacatt aatgtttgtg    6420
ttgtttgctg aaaggttttt tactgtagca gaaggttaca aaataacaga tcttacctca    6480
aaaaagggct gcaatgtata tatactggca ctgaaccgcg tatgcgcagt gcaacctgct    6540
```

```
gattggtttt gtactggtcg gatctgtttg caggatgcat ttgacttgaa gcccccgaaa    6600
aaatcaccga tcgcgttgag aacggttgtc ttcgctatga ctatgttatg cgggatatct    6660
atttgctcaa tgtgcatgaa gcaactaggg agtgatggct ggtcaagagt tgtcaagatt    6720
gaagttgtgg aacaaccatg taataagtcc attgctcctc tttcggaggc tcaatttgtg    6780
cgctatcctc aaccgataac ttacagcagg tgagatctgc actgtggtaa gattgagcaa    6840
tctcgtttgt ttaatgccta atgcataatt ttttatttct agggaggaat gcaagtgcaa    6900
tgctgtccgg tcctttgcaa ttatatcatc gcagcgatct ggaagtggct ggtttgaaac    6960
acttcttaac agccacatga atgttagctc caatggtgaa attttctcta gaaaagaaag    7020
gaggagtaac atttcctcta taatagatac cctggataaa gtgtacaatt tggactggaa    7080
cagtagcgct tccaagaatg agtgcactgc agctattggc ttcaagtgga tgctaaatca    7140
ggtgcggact aaaacatgca gtatagataa tttatttgga tgatcctttt tcatttattt    7200
ttccatttag ttccagtatg tttcaattat tagtatgtgt agtctcctaa acggcctaca    7260
tgttctcaac tgtagatgct aaatgttatt gcatattgcg ccaaactttc ctcaagtcca    7320
tgtaactatt ttttttgggg aatccacttt agggcttgct cgttttagtg ccaatccatg    7380
tggattggac gagattggat gagtttaaat ccataagaag tcaaaatcct tcttaaaatt    7440
ttccaatctc ttccaatcca tgtgggatgc gaataaccga acaaggcctt atggaactgt    7500
cggtagctag tttagttttc tgacttgctg tcagatcctg catttttagac aaattttctc    7560 tctctcgaac atgcatgaga actgcaaatg catatggagt aatatttgat agattctgta    7620
gtgtgtccag tagactgatt ataatctaca tgtcaagcat gtttgtttca gggcttcatc    7680
taatttgtgc gagaacgaac tttttttcctg gtagacagat tgcctaacca aaccatgaat    7740
attggccaaa cataggttta gagactggaa acaaaacagg cattgtagct agagagtgga    7800
aacaaaggag catttcttct gaacggggtt gggggtgtatg ttttcagggc ctcgtggcaa    7860
accatgcgga cgtagtcgac tacttcaacc gaagaggagt ctctgcgata tttcttttca    7920
gaaggaacct gctccgccag ttggtatcac aggtagcgaa caaccacgac aggttactta    7980
agcaactaaa cggaacgcac aaggcccatg tccacacgaa gcgtgaggtt agtaatgcta    8040
gctaagaaac ggatatggca gcaagtctct gagctgatct gatctctctc tgtgtttgac    8100
gtgtcgttcg ttctcgctcc acaggcccat atactggcaa gatacaggcc caggctcaac    8160
acgacgtcac tgatatggca gctgaaacga gctgacgagt acactcgcga cgctcttgag    8220
aacctaaaca acacccggca catgagcgtc tactacgagg acgtcgtccg caacagaaca    8280
gtgcgttctc gctgatgccc ttcccttgtc tgttcccttc cgttggttgt gtcgcttacc    8340
atcgctgctg cactgcagaa gctcttggat gtcctggatt tcctcggagt gccgaggagg    8400
aagctggtga gccggcacgt gaagatacac acgaagccgc tgtcggagca gatcgagaac    8460
tgggacgagg tctacagcgc cctcaacggt acccagtacg agggcttcct gaatgccgct    8520
gactatctag tataacatca cgttctgga tgtagatagt gtgcgtgtga ttctttcgtt    8580
tcttgtttgt ttctggcaga aattttgatg cggggtaggc gccttttgcc gtgcatggtt    8640
gcattctcgg taacctgatg ctcctgtaac taaccctcca gcttctctga tctttgtatt    8700
tgccttgggt gtttgctgat gttcttttcaa actatttgaa atcgggctgt cggagttcca    8760
gatcccgggc ggcaggatag ttgatgtgac ctagataaat gtacaagaca catcacaaat    8820
atataaaata tttctgtagt atcctcacaa atatatcaaa aatatttctg tagctcttat    8880
```

```
tacatgatac tctactatgc aaccaacaga agcaatatct cctcagggag cttttgcttt     8940
attgccaaat taaattaaga aatgttctat gggactacta caacggaaaa taagactaca     9000
agatcacctc agggagcttt tgctaactac ctgcaatatc aaggtgcagc agttagtcaa     9060
attgcacaac agttgtaaaa ggaaaaaata caacttaatt aggcctagct gaatatgcga     9120
ccatattaca gtttgataat agcaccttat actggttagc tcctactgcc agctagtaaa     9180
agaatcaatt tgagttgaga tatattcggt gttttgagtc ttacaaggtc tagatttctt     9240
atgcgagctc cagaacaaga gctgatgctc cgcctccacc gttgcagaca ccagcaactc     9300
cgatcttgcc actcttcgcc ctgagaacct gttaacaaga acaatgatt aggagggtca      9360
agcacaatat attttgatgt cccaacatga tggcactata ttgtgcccaa cgttttgctt     9420
aaagaaaatg aagagaaaaa gaactattg atcaccagca acaagtgaaa caagggatga      9480
gccgatatca atgtgaaact ctacatttgc agctttatac aagattctat ttgcagataa     9540
tttgcacatt ggaaatcact aagggcttgt tcggttgcga gaggattgga ggggattgag     9600
ggggattaaa tccctcccta ttcaattta actagaaggg gatttaatcc ccttcaatcc      9660
ccctcgaacc acttgtaacc gaacatggcc taaggtagtg tttggtgcag gatggggtg      9720
gcttgatcca acatactccc tatgtttcaa attataagat gttttact tttctagatt       9780
tgtagttttt attgcgataa acattatgtc tcagtacacg tagtaaaa                  9828
```

<210> SEQ ID NO 49
<211> LENGTH: 11900
<212> TYPE: DNA
<213> ORGANISM: Zea mays

<400> SEQUENCE: 49

```
gatataatga aaaaaccaat taaaaacgtg tctcgatatg cgtgcacgag taaagagctg       60
gctgagcgga gcctggccgc gcgcgtgcgg tcgcgcgatg cgtttctgcc gggcctggct      120
cgcggcgctt taagttccgt gctagcctgt ctcgtgcgat acaacgaacc aaacaaacac      180
tacttttgc atgtgtagat gcagctgcac cactggagaa ggcaaccaaa cgcccctaa       240
ggcagctggg cgacagaata tatgggaatg tacttgaact tatcaaaaaa gggccttttc      300
atcccttgcc gtgtcttcca tgttggtaaa aaggctagta gctgaattga atagtacgtg      360
ctcattttaa cttccctgag gactagatag accttgaagt tttatttgtt tatttctttt      420
tatttctgct tatatagatg tagccaaatg gatgcttctc agctcacatt gaacattaat      480
gtttgtgttg tttgctgaaa ggttttttta ctgtagcaga aggttacaaa ataacagatc      540
ttacctcaaa aaagggctgc aatgtatata tactggcact gaaccgcgta tgcgcagtgc      600
aacctgctga ttggttttgt actggtcgga tctgtttgca gratgcattt gacttgaagc      660
ccccgaaaaa atcaccgatc gcgttgagaa cggttgtctt tgctatgact atgttatgcg      720
ggatatctat ttgctcaatg tgcatgaagc aactagggag tgatggctgg tcaagagttg      780
tcaagattga agttgtggaa caaccatgta ataagtccat tgctcctctt tcggaggctc      840
aatttgtgcg ctatcctcaa ccgataactt acagcaggtg agatctgcaa ctgtggtaag      900
attgagcaat ctcgtttgtt taatgcctaa tacataattt ttaatttcta gggaggaatg      960
caagtgcaat gctgtccggt cctttgcaat tatatcatcg cagcgatctg gaagtggctg     1020
gtttgaaach cttcttaaca gccacatgaa tgttagctcc aatggtgaaa ttttctctag     1080
aaagaaaagg aggagtaaca tttcctctat aatagatacc ctggataaag tgtacaattt     1140
ggactggaac agtagcgctt ccaagaatga gtgcactgca gctattggct tcaagtggat     1200
```

```
gctaaatcag gtgcggacta aaacatgcag tatagattta tttggatgac cctttttcat    1260 ttattttcc atttagttcc agtattgcat attgctccaa actttcctca agtccatgga    1320 actattttt tttgggaatc cactttaggg cttgctcgtc ttagtgccaa tccatgtgga    1380
ttggacgaga ttgaacgggt ttaaatccgt aagaagtcaa aatccttctt aaaattttcc    1440
aatcccttcc aatctatgtg ggatgcgaat aaccttatgg gactgtcgga tagctagttt    1500
agttttgtga cttgctgtca gatcctgcat tttagacaat ttttttctct cgaacgtgca    1560
tgagaactgc aaatgcatat ggagtaatat ttgatagatt ctgtagtgtg tccagtagac    1620
tgattataat ctacatgtca agcatgtttg tttcagggct tcatctaatt tgtgtgagaa    1680 caaactttt tcctggtaga cagattgcct aaccaaacca tgaatgttgg ccaaacatag    1740
agttagagac tggaaacaaa acaggcactg tagctagaga gtggaaacaa aggagcattt    1800
cttctgaacg gggttggggt tggggtgtat gttttcaggg cctcgtggca aaccatgcgg    1860
acgtagtcga ctacttcaac cgaagaggag tctctgcgat atttcttttc agaaggaacc    1920
tgctccgcca gttggtatca caggtagcga acaaccacga caggttactt aagcaactaa    1980
acggaacgca caaggcccat gtccacacga agcgtgaggt tagtaatgct agctaagaaa    2040
cgtgttcgcg gctaatgtct cactctcaca gcaagtctct gagctgagct gatctctgtc    2100
tgtgtttgac gtgtcgttcg ttctcgctcc acaggcccat atactggcaa gatacaggcc    2160
caggctcaac acgacgtcac tgatatggca gctgaaacga gctgacgagt acactcgcga    2220
cgctcttgag aacctaaaca acacccggca catgagcgtc tactacgagg acgtcgtccg    2280
caacagaaca gtgcgttctc gctgatgccc tttgtctgtt cccttccgtt ggttgtgtcg    2340
cttaccatcg ctgctgcact gcagaagctc ttggatgtcc tggatttcct cggagtgccg    2400
aggaggaagc tggtgagccg gcacgtgaag atacacacga agccgctgtc ggagcagatc    2460
gagaactggg acgaggtcta cagcgccctc aacggtaccc agtacgaggg cttcctgaat    2520
gccgctgact atctagtata acatcacgtt tctggatgta gatagtgtgc gtgtgattct    2580
ttcgtttctt gtttgtttct ggcagaaatt ttgatgcggg gtaggcgcct tttgccgtgc    2640
atggttgcat tctcggtaac ctgatgctcc tgtaactaac cctccagctt ctctgatctt    2700
tgtatttgcc ttgggtgttt gctgatgttc tttcaaacta tttgaaatcg gctgtcgga    2760 gttccagatc ccgggcggca ggatagttga tgtgacctag ataaatgtac aagacacatc    2820
acaaatatat aaaatatttc tgtagtatcc tcamaaatat atcaaaaata tttctgtagc    2880
tcttattaca tgatactcta ctatgcaacc aacagaagca atatctcctc agggagcttt    2940
tgctttattg ccaaattaaa ttaagaaatg ttctatggga ctactacaac ggaaaataag    3000
actacaagat cacctcaggg agcttttgct aactacctgc aatatcaagg tgcagcagtt    3060
agtcaaattg cacaacagtt gtaaaaggaa aaaatacaac ttaattaggc ctagctgaat    3120
atgcgaccat attacagttt gataatagca ccttatactg gttagctcct actgccagct    3180
agtaaaagaa tcaatttgag ttgagatata ttcggtgttt tgagtcttac aaggtctaga    3240
tttcttatgc gagctccaga acaagagctg atgctccgcc tccaccgttg cagacaccag    3300
caactccgat cttgccactc ttcgccctga gaacctgtta acaagaaaca atgattagga    3360
gggtcaagca caatatattt tgatgtccca acatgatggc actatattgt gcccaacgtt    3420
ttgcttaaag aaaatgaaga gaaaagaaa ctattgatca ccagcaacaa gtgaaacaag    3480
ggatgagccg atatcaatgt gaaactctac atttgcagct ttatacaaga ttctatttgc    3540
```

```
agataatttg cacattggaa atcactaagg gcttgttcgg ttgcgagagg attggagggg      3600
attgaggggg attaaatccc ctcctattca attttaacta gaaggggatt taatcccctt      3660
caatccccct cgaaccactt gtaaccgaac atggcctaag gtagtgtttg gtgcagggat      3720
ggggtggctt gatccaacat actccctatg tttcaaatta taagatgttt ttacttttc      3780 tagatttgta gtttttattg cgataaacat tatgtctcag tacacgtagt aaaagctata      3840
aatctaacaa tgccaacatc ccaagacgtc ttataatttg ggatagagga agtagaccta      3900
gtagcaatag tgaagatgct tactgttcat cacgaacccct atgatgatat ggtaacatat      3960
gtcagaattc attatttact caaagaccat ctattttttt actagaaaaa cattgcacat      4020 ttttttttaaa caaaagggat tgtaactcaa aaggtaaaac aagcatctta agatagaact      4080
tacaccaata agggtaacca aaatgcgagc accactgcac ccgagaggat gtcctaagga      4140
tacagctcct ccatgaacat taatctttc ctgcaaacac atatgctgtt agtacagata      4200
atactgttat aatgcaatta cacgttgctg ctgcatagca ataacaaaa aagagacaat      4260 atgtactttc tgaaagtgat tgtttaactt ctaaaatcca caaagaatgg cagtttaata      4320
caggtgacac ttactgaagg aattccaaga agttttgat ttgcaagcgc aacagcctat      4380
attgacaagt aaaaagaca ttattacaaa aaagtaata agtaaaataa actctcaatg      4440
cataacaaaa ggcttacaaa aaatgtgagt aaaagaaact caatgcatac cgaaaaggct      4500
tcattaatct catagaaatc aacacgggat gactctaatc cagcatttgc gatagccttt      4560
ggtattgcaa gtgctggagt ggttgtaaaa agctccggag cctgtataaa cagcatccac      4620
attacaaaat aatattccag atcacaagtt ccaatagttg ataaatttcg atatctaaaa      4680
tagtaacata aaatcgttcc agataaaaat aacttcctat atcctaaaat atttagatca      4740
cagtgtaaat tagaataagc gcattctact cttaggagag ctaacaattg tttctgtggc      4800
ttacttgagc tgcatcagca taacctttga tccttgcaag gacttgaagg ccaagctctt      4860
gagccttctg cccactcact aaaactaatg cagcagctcc atcactgatc catataaaac      4920
aaattagatg actggttgca gaaggctaca caagccatag taggcagtac accggacagt      4980
acttgtcagc taaaaataga cacagtacaa agtgagacaa acaaggtcta gggcaaccat      5040
gaagaaattt aaaaggtagg gcaacttttg ttgtttgaat gggcataata aggcatttaa      5100 aatgtttta ctttcttatg tgatattgtg ataaatcatt cacaccaatt gggtaccaaa      5160
tctaaagaaa aaattaccat ctatttaacg gagtagagca tacccaagca gtctaaaaac      5220
aaatagagaa acaatgaagt tgacaaaatg caagcataat atatcagtta aaaatgcatg      5280
cataatacaa taatataatt taactgtcaa caatgaaata ggttgtcctt catatctgtc      5340
agctaaacaa catatggccg aaaaacaagg tctcagaaag actttgtagg acaaaaggcc      5400
tcagaaatat ttcaagcagc taccttatac tagaagcatt tccagctgta actgtaccac      5460
cattctcctt gaaacttggg cgaagtttct ttagttttac tgggtcaaac taagacacaa      5520
aaggaatagc acaagacata aataaaactg tcatgcattg atcttacaaa taactgctag      5580
caaagctcat tatgcaagga acgttgcatt tggaggaagc aagaacaata aatcaaagtg      5640
cctgccagtc ttttttgcctt tgatcaacta caagctttat tttgttaaaa atattttgtc      5700
acgtcagaaa aaataccttta tccaggcttt catctctctc aattaatgtt gggggttttc      5760
ctctaccaac aggaacttga acctgggtga caacactgac catcagaaaa ccaagaaaag      5820
catgtctagt atcatcaatg agggagaaaa ttaccggaat aatctcccat gcaaaagcac      5880
cactgtcacg agcagcaatt ccacgctcgt tgctttggat agcaaatgca tcctattcaa      5940
```

```
gaataagtaa aattaaatat accagaaatt ggaaatatat ttattgcaat atagacaaaa    6000
ataaattgca acatataagt gaaaattaaa aggcaactca atttaatta tactatatca     6060 aatttattaa gaaaaaaatt acataaacag atacagtaaa atcatcaagg tactagtgtc    6120
atgtactgat gagcagcttt taagagatta tacttgtata gctctaacag gaatacaaaa    6180
gagtgctcat ttttgtgtgg cacatctact ttcatctctg gaagcagatg aatggtcagt    6240
tcacagaccc agagcatgca taaaagccca ccctatcaat catgtcacaa cataacagaa    6300
aatcattgct agaaaggatc caagttacta gttcatcaga caaggaatgc agatgctggt    6360
ctagagtctc tagaccattt atgatgatga ccaagataaa gcacgaagat tccagggcag    6420
tctcaaaaga attgccagca ttgacatgtt gtatagcaca acttatatct tgaaaaatat    6480
gggaatatta taacaaacag catttactgc tatctgtatt aagagacctg gtcttctctt    6540
gtgagggcat ggttgtcagc acaaagctcg gcacacattc ccatggcaca atcattgtat    6600
acatcccaaa gccatccttt aagcatggca tcaacaagtg tgtcatgacc aaaacgagac    6660
cccttcctgc aattgtaatt agcaagctta taagcagttg aaatgcactt taaacatgaa    6720
cagaatatac tttcacaaca aaactggcca cttcgttaat agcctcgctg ctggtgaatc    6780
aacatttctt acaaacaaat ttagaaaatg caatgaagat aagtaagcat gcatgtatct    6840
accaaataac ttaagactat catttggttt atgcagctcg atattgaata tatccaccaa    6900
gtaataattg catacctagc ttcagcaatg tactttgggg cattggacat gctttccatg    6960
ccaccagcca caacaatatc attgataccc aattgaattg actgtgctgc aaacatagta    7020
gctgcatata ggaaaggaaa acaagagcat ggtcaggtaa tctctcactt ctgtgaactc    7080
tgagcagagt acacaaggac agacagataa attcgattca aacctttcat gccagatgca    7140
cagactttgt taacagtggt gcaaacaaca gagtttggta tcccggcacc cagagcagct    7200
tgccttgcag gagcttgccc caaattagca ctcaagacgt ttccaaagta gacctcctgc    7260
acgagggctg gatccacgtt tgctctttcc agagcagcta acagccccca gccatgacca    7320
tgttcagagc tcggatgtaa atgcagagaa gattcggatc tcaccttgaa ttactataga    7380
gccaagtttc gtagcaggca agggagacaa ggcaccaagg aaaccgccca ttgggggtgcg   7440 tgcaaccccca acaacacata catctgtgag caaggaagaa aaagttactg actgtagaac  7500
aaagcagaac catctagtgt gcacctcaca gtatatctat agtactaatt tgtaaaccgc    7560
gctcaaaatt ccatctgatg gtacaaacca acacacatg aaaagcacat actgtactag    7620
taccagtgaa tcacttgttc caaatggcgc taaaacaaca atgatggcag tacccctctgt   7680 gcaacccgaa aaggcaaaaa cacaaattgt ggtaatcata taaacgtatt tcgcagtagc    7740
aatgaacttt ggaaaacaat ggattcaatc aagcaaacgg acgagatcac gagcatggag    7800
cagctaggat gccctaatgg atgcagacag gcactagaat taaacagaaa agcgtcaaat    7860
ttcggccttg caaggtaccc aaaaaaaaaa caagaattcc caatatgtca gatcgctgga    7920
agcgcaatgg cgtgctcata gcccaaaatc tatatttgta cctcctctcg gcggtttgac    7980
gtctgtctgt ttgaacacaa agaagagatg aaacagttat acctctgggg ccgatgccgt    8040
cggaagccat ggccgccggt ccgaagtgcc aaaaccaacc gacctgcgaa tcaggggcgg    8100
gcccagtgaa aaatggtcag atccgaatac aaatactaga tttggggagt tcggggtgtt    8160
tgaattctcg cagaaggagc agaagggacg gcatacctgg aatatgctgt cgccggcgaa    8220
gcggcctgat cgaatggcgg cgccggcgcg gcgctaggga aagaaaggca gagaaagaca    8280
```

| | |
|---|---|
| gtgtgtgcgc ggggggcgct ggggacaggt tgaagcggag gaagaaaaga gcaagtaggg | 8340 |
| aacgcaacac ccaacagcca aatcacccga atgtaatttt tcctaaatct ataatttatt | 8400 |
| ttatttttta atctatacaa tatatagata tataataaaa ttaataaatc ataaaaatta | 8460 |
| aagctgaatc agagaaagta ctaaataaaa taggctttat gttaggcaaa aaaaaagtaa | 8520 |
| aaatagaaca attcaattca ctatatgcca ctgtaatttt gtgtaatacc ttattcatcg | 8580 |
| tacctcgtat gttactcgaa ttcaatatct cactcttaca tgtcgtggcc aaatgttaaa | 8640 |
| tgtaaaatgt tgtatgtctt agtcccttac tatgacatga aagagtaaaa aattgtattc | 8700 |
| gggtgacgta aaaaggatta gaacatttat gataacaaat aagatactag acgagtgaca | 8760 |
| tacatgatat aattttatct ctaaacctaa tgaaactaat aaaaaatgtc aattgatatc | 8820 |
| gtttgcgttt gctaatcacc tcgaacaatc atcctcgcgg gcatgtggtt aaggctagaa | 8880 |
| aaaaaacttg aggctcacga gtcagatcaa gttcggagcg tctgcgagcg agctagttgt | 8940 |
| accaaattaa tcaatatgta gaataatgat agatattaga taatttatag atagtcggct | 9000 |
| tatttcttag cctttgatga taaatataag ataattcata atggtgaata atattttat | 9060 |
| attttatgtt tatatattaa taatttacta tataatgaaa taatatatat cggggtgtag | 9120 |
| ctcgcgagcc gacttcgagc tgagccgagc ctaactctct agctcgtgaa atggacgagc | 9180 |
| cgagtcaagc tcggctcgac tcattttcta cttgtggtcg accaggtcta ggtagtcatg | 9240 |
| aaccgcaacc aatctgtcag ttttatcgat tgttttagat catgttaggc gagtgccggc | 9300 |
| gcttggctct actgcccgcc cacccatgtg gcacaaccaa atggtcagta tcacccgaca | 9360 |
| tggtgccagc actaatagcc tcgcttgtgg ttgtcgaggc tactgatcgg ccgccagggt | 9420 |
| tactattgac cgtgttggga ccgcgtcggt cgatactgac tggttggtac tgaacagcta | 9480 |
| ttgcggccat gtcgataacg atcgcctctt gccatgtggc aggttctaat tgcttcgctt | 9540 |
| tattttgatt ttttttcaaa aataaaaaaa ctagaacttg gtctataaat agaggagtgt | 9600 |
| ttgatctcat tcacacaacc cacacttcaa atttctctac caccccttat aatcctctta | 9660 |
| cactcgtttc aatcaaatca agcattgttg tgatgttttc gttcagcttg acatcaata | 9720 |
| tgactgaaaa gagttattca agttattaca acaaaatata atgcaacagg cgtcagagct | 9780 |
| tggatccgag tctcctaggt cgatgaggtg gccaaggcaa catcagagat acattgactg | 9840 |
| cgactatgta gttgcatacg accggttaat gcaagaccat ttcaacgacc tgtgtgtcta | 9900 |
| cccactgctc tacttttgtc aaagttaccg catctagaga agtctcttcc ttcatatctt | 9960 |
| agagagattg ggtgagcact tcccatactt cactttttga accgatgcat tcaaccgcag | 10020 |
| tgtttcctcc cccaccagaa gtgcacaatt ggcctaagca tgcttgcgta ctgtagcatt | 10080 |
| gctgactcca tcgatgagta catcaaaatg aggaaagttc cacctcagag tgccttggac | 10140 |
| tattctgtgt gaaagggtcc ctagttaagt tggttaggtc gtctgagtag cactcctcag | 10200 |
| gtcctaagtt tgaatcccgg tgggagcgaa tttaggctg aggttaacaa ggtcactcac | 10260 |
| tagtttccct agttgtgtgc acatgagatg ggctgaccta tggggcggat cctcgtgtaa | 10320 |
| gggctagtag ggctcaaagc acgagtaaag atctggccta taggggcgg actctcatgt | 10380 |
| tgcatggggg gagggtaca tctttcgtga cctttctcga tcaggctcc gattaagctt | 10440 |
| cttcttaccg tgggggcagt atttccccta cgagtggagt ttttggtcta ttctgtagag | 10500 |
| gtggtattgc atgtttcagg gcggagtaca attatcatgc cattgtcaat gacttaggct | 10560 |
| tatcttagct aaggaggtgg aaaggggatt ttctattatg atattgagta tagattgcat | 10620 |
| gcattggaag tggaggaaga agacatttta caagggggat attggttctc catccatcat | 10680 |

```
gctcgagaca gttgcctcgt atgacttgtg gatctgacat attttatga atctattaaa    10740 atgctaaaac ggttagtatt ttaggacgga gggaattatt ttttggaata ttttgtagc    10800 aacctaaaca tagttcatct atgcttagtt tggggggtgg gatggttagg cctagaagct    10860
actgttgaat taatgagggc ctaacccaaa ttaatattca ataatagtca atgctaaagg    10920
cccactttaa tgctacggtg tactagtact ttagtaccat accggaagta caagggacaa    10980
ttcaatcaac ttaaataggc ggatctttgg tgcatctagt gagaagttga gaaaatgatg    11040
aaggactgcc acacgcgcgc gccgccgggc cgtggccgtg gtagatcgga ccttggtccg    11100
aatattcctt cctaacggtt gcacattttg cctaaagtga tgaccgtcca ttactgttgt    11160
acgttattgg tcgtttccta tgttatggat agtaacgaac gagttataat gcttgtcagc    11220
tattaacgga cgtcactaat ggcgtccgtt tctggctggc tgtaatgata gctctgatgg    11280
tgaccgttac tatccgttcg cctccctctg ctcgtttata tatacaaagg aggtgaggct    11340
gcttctggtt acgagagaac acacgtacaa ttcttagacg cgttgcgtac agcccatccc    11400
tggttgaacc tctctaaacc ccggttgaac ttttcctgga ccccagttga acctctctgg    11460
accccggttg aacttgcctt ggaccccggt tgaacctgcc tggaccccgg ttgaacttga    11520
ctggacccca gttgaagttg aagttcaact ggagttgaga aagctcgaca cagctgaagt    11580
ttagctcagc tgaaaagctc aactgcagct gaagaagctc aactcagctg aagtttagtt    11640
cagctgaaaa gctcagctgc ttttcaacaa aaacactcta ggtttctcaa acctaaccat    11700
agtcaaccat agaattttaa agagattttt gattttcaaa aaatagcttt tgaatataga    11760
ggcttgagct ttggcaaaca ccaaccttat ttttggatcc ccttggtagt acgatgaatc    11820
ctatactcaa tttaagtaaa atataattaa gtaaactcct tgagtaattg gtgtctcatg    11880
tgtgatttct ccatggcgtt                                                11900
```

<210> SEQ ID NO 50
<211> LENGTH: 3571
<212> TYPE: DNA
<213> ORGANISM: Zea mays
<220> FEATURE:
<221> NAME/KEY: misc_feature
<222> LOCATION: (1933)..(1933)
<223> OTHER INFORMATION: n is a, c, g, or t

<400> SEQUENCE: 50

```
ggaggggggag acggtgaggc gcggccatgg ggggcgccaa ggcggaggac aaaccggccg      60
ccgctgcaga agattggtgc taccaatttg gaaacaaggt tcgatttctt caccatttgc     120
actcctctgc aagactggga cacgtttccg ggtttcgttc tgcctgggcg gcgacaaatc     180
tcatggcaaa ttgcctttgg ggggctcatt ccctgggttc acactccaaa tccttccttg     240
cgaccttctc tcagccgtcg cgctttccgt ggcaagcctt ttggaaccct gatctgaagt     300
gtcactcaga tcaatgcagt cgcattgatt ctattcgttt cctgtttccg ttccccctt      360 ttaacgtgtc tgctagttcc aagtcccgag cgttttccgt tctctgtttc agaattgaag     420
cttgttaagt tctgtttttt tttacaatcc ttcgttttg tcccagtcct ttctattcct      480
ggagaagtta ggaatctgtt gttctcctgt tccatttctc ggtgcagtat tagttgcaga     540
acaggaatcc acttgatttg tcagtttaat tatgcttgtg tcacctcaga tgtgtcatat     600
tgatgatgac tgcatttttt tttcagctgt aaatatgcgtg ttggcttgca tttgtttctc    660
tctttattag tactaccagc attttcggtc agtatttttt gtcttccttg ctgaagaatg     720
```

```
agaaggaaag ctgtcatact cctcgtcggg atagcttcat ttattatggc agctgggcga    780
cagaatatat gggaatgtac ttgaacttca caaaaaaggg cctttcatc ccttgccgtg     840 tcttccatgt tggtaaaaag gctagtagct gaattgaata gtacgtgctc atttaacta     900 ccctgaggac tagatagatc ttgaagtttt atttgtttat ttcttttac ttctgcttat     960 atagatgtag ccaaatatat gcttcttcag ctcacgttga acattaatgt tgtgttgtt   1020 tgctgaaagg ttttttactg tagcagaagg ttacaaaata acagatctta cctcaaaaaa  1080
gggctgcaat gcatatatac tggcactgaa ccgcgtatgc gcagtgcaac ctgctgattg  1140
gttttgtact ggtcggatct gtttgcagga tgcatttgac ttgaagcccc cgaaaaaatc  1200
accgatcgcg ttgagaacgg ttgtctttgc tatgactatg ttatgcggga tatctatttg  1260
ctcaatgtgc atgaagcaac tagggagtga tggctggtca agagttgtca agattgaagt  1320
tgtggaacaa ccatgtaata agtccattgc tcctctttcg gaggctcaat tgtgcgcta   1380 tcctcaaccg ataacttaca gcaggtgaga tttgcactgt ggtaagattg agcaatctcg  1440
tttgtttaat gcctaatata taattttaa tttctaggga ggaatgcaag tgcaatgctg    1500
tccggtcctt tgcaattata tcatcgcagc gatctggaag tggctggttt gaaacacttc  1560
ttaacagcca catgaatgtt agctccaatg gtgaaatttt ctctagaaaa gaaggagga   1620 gtaacatttc ctctatagta gatacctgg ataaagtgta caatttggac tggaatagta    1680
gtgcttccaa gaatgagtgc actgcagcta ttggcttcaa gtggatgctg aatcaggtgc  1740
ggactaaaac atgcagtata gataatttat ttggatgatc ctttttcatt tattgttcca  1800
tttagttcca gtatgtttca attattacta tctgtagtct cctaaacggc ctacatgttc  1860
tcaactgtag atgctagatg ttattgcata ttgcgccaaa ctttcctcaa gaccatggaa  1920
cttttttttt ttntttttt ttttggaaac cactttaggg cttgttcgtt ttagtgccaa    1980
tccatatgga ttggatgggt ttaaatacat aagaagtcaa atccttctt aaaattttc     2040 aatctcttcc aatccatgtg ggtgggatgc gattccaatc catgtgggat gcgaataacc  2100
gaacaaggcc ttataggact gtcgaatagc tagtttagtt ttctgacttg ctgtcagatc  2160
ctgcatttta gacaatttct ctctctcgaa catgcatgag aactgcaaat gcatatggag  2220
taatatttga tagattctgt agtgtgtcca gtagactgat tataatctac atgtcaagca  2280
tgtttgtttc agggcttcat ctaatttgtg cgagaacaaa ctttttttcct ggtagacaga  2340 ttgcctaacc aaaccatgaa tattggccaa acagagagtt agagactgga aacaaaacag  2400
gcactctagc tagggagtgg aaacaaagga gcatttcttc tgaacggggt tggggttggg  2460
gtgtatgttt tcagggcctc gtggcaaacc atgcggacgt agtcgactac ttcaaccgaa  2520
gaggagtctc tgcaatattt cttttcagaa ggaacctgct ccgtcagttg gtatcacaag  2580
tagcgaacaa tcacgacagg ttacttaagc aactaaacgg aacgcacaag gcccatgtcc  2640
acacgaagcg tgaggttagt aatgctagct aagaaacgtg ttcgcggcta atgtctcact  2700
ctcacagcaa gtctctgagc tgagctgatc tctgtctgtg tttgacgtgt cgttcgttct  2760
cgctccacag gcccatatac tggcaagata caggcccagg ctcaacacga cgtcactgat  2820
atggcagctg aaacgagctg acgagtacac tcgcgacgct cttgagaacc taaacaacac  2880
ccggcacatg agcgtctact acgaggacgt cgtccgcaac agaacagtgc gttctcgctg  2940 atgcccttg tctgttccct tccgttggtt gtatcgctta ccatcgctgc tgcactgcag    3000
aagctcttgg atgtcctgga tttcctcgga gtgccgagga ggaagctggt gagccggcac  3060
gtgaagatac acacgaagcc gctgtcggag cagatcgaga actgggacga ggtctacagc  3120
```

```
gccctcaacg gtacccagta cgagggcttc ctgaatgccg ctgactatct agtataacat    3180
cacgtttctg gatgtagata gtgtgcgtgt gattctttcg tttcttgttt gtttctggca    3240
gaaattttga tgcggggtag gcgccttttg ccgtgcatgg ttgcattctc ggtaacctga    3300
tgctcctgta actaaccctc cagcttctct ggtctttgta tttgccttgg gtgtttgctg    3360
atgttctttc aaactatttg aaatcgggct gtcggagttc cagatcacgg gcggcaggat    3420
aggtgatgtg acctagataa atgtacgaga cacatgacaa atctatacta cttattaaaa    3480
gtgtaatagc agtctgccgt tctgccatcc tgcaacctca accgtccatt ccattgttct    3540
gcaatttcaa ccgttcgatc ccacccacca g                                   3571

<210> SEQ ID NO 51
<211> LENGTH: 1896
<212> TYPE: DNA
<213> ORGANISM: Zea mays

<400> SEQUENCE: 51
ccaaggcgga ggacaaaccg gccgccgctg cagaagattg gtgctaccaa tttggaaaca      60
aggttcgatt tcttcaccat ttgcactcct ctgcaagact gggacacgtt tccgggtttc     120
gttctgcctg ggcggcgaca atctcatgg caaattgcct ttgggggggct cattccctgg     180 gttcacactc caaatccttc cttgcgacct tctctcagcc gtcgcgcttt ccgtggcaag     240
ccttttggaa ccctgatctg aagtgtcact cagatcaatg cagtcgcatt gattctattc     300
gtttcctgtt tccgtttccc ccttttaacg tgtctgctag ttccaagtcc cgagcgtttt     360
ccgttctctg tttcagaatt gaagcttgtt aagttctgtt ttttttttaca atccttcgtt     420 tttgtcccag tcctttctat tcctggagaa gttaggaatc tgttgttctc ctgttccatt     480
tctcggtgca gtattagttg cagaacagga atccacttga tttgtcagtt taattatgct     540
tgtgtcacct cagatgtgtc atattgatga tgactgcatt ttttttttcag ctgtaatatg     600 cgtgttggct tgcatttgtt tctctcttta ttagtactac cagcattttc ggtcagtatt     660
ttttgtcttc cttgctgaag aatgagaagg aaagctgtca tactcctcgt cgggatagct     720
tcatttatta tggcagctgg gcgacagaat atatgggaat gtacttgaac ttcacaaaaa     780
agggcctttt catcccttgc cgtgtcttcc atgttggtaa aaaggctagt agctgaattg     840
aatagtacgt gctcatttta actaccctga ggactagata gatcttgaag ttttatttgt     900
ttatttcttt ttacttctgc ttatatagat gtagccaaat atatgcttct tcagctcacg     960
ttgaacatta atgtttgtgt tgtttgctga aaggtttttt actgtagcag aaggttacaa    1020
aataacagat cttacctcaa aaagggctg caatgcatat atactggcac tgaaccgcgt    1080
atgcgcagtg caacctgctg attggttttg tactggtcgg atctgtttgc aggatgcatt    1140
tgacttgaag cccccgaaaa aatcaccgat cgcgttgaga acggttgtct ttgctatgac    1200
tatgttatgc gggatatcta tttgctcaat gtgcatgaag caactaggga gtgatggctg    1260
gtcaagagtt gtcaagattg aagttgtgga acaaccatgt aataagtcca ttgctcctct    1320
ttcggaggct caatttgtgc gctatcctca accgataact tacagcaggt gagatttgca    1380
ctgtggtaag attgagcaat ctcgtttgtt taatgcctaa tatataattt ttaatttcta    1440
gggaggaatg caagtgcaat gctgtccggt cctttgcaat tatatcatcg cagcgatctg    1500
gaagtggctg gtttgaaaca cttcttaaca gccacatgaa tgttagctcc aatggtgaaa    1560
ttttctctag aaaagaaagg aggagtaaca tttcctctat agtagatacc ctggataaag    1620
```

```
tgtacaattt ggactggaat agtagtgctt ccaagaatga gtgcactgca gctattggct    1680
tcaagtggat gctgaatcag gtgcggacta aaacatgcag tatagataat ttatttggat    1740
gatccttttt catttattgt tccatttagt tccagtatgt ttcaattatt actatctgta    1800
gtctcctaaa cggcctacat gttctcaact gtagatgcta gatgttattg catattgcgc    1860
caaactttcc tcaagaccat ggaactttt tttttt                               1896
```

<210> SEQ ID NO 52
<211> LENGTH: 1371
<212> TYPE: DNA
<213> ORGANISM: Zea mays

<400> SEQUENCE: 52

```
agttcatcac taatcacact tattgtgccc tcgacgagta tctatagcta gctcattaat     60
cgattcgggg gtgtgttgtc gaaggcggca atggcgagct actcgtcgcg gcgtccatgc    120
aatacctgta gcacgaaggc gatggccggg agcgtggtcg gcgagcccgt cgtgctgggg    180
cagagggtga cggtgctgac ggtggacggc ggcggcgtcc ggggtctcat cccgggaacc    240
atcctcgcct tcctggaggc caggctgcag gagctggacg gaccggaggc gaggctggcg    300
gactacttcg actacatcgc cggaaccagc accggcggtc tcatcaccgc catgctcacc    360
gcgcccggca aggacaagcg gcctctctac gctgccaagg acatcaacca cttttacatg    420
cagaactgcc cgcgcatctt tcctcagaag gcaggcttg cggccgccat gtccgcgctg    480
aggaagccaa agtacaacgg caagtgcatg cgcagcctga ttaggagcat cctcggcgag    540
acgagggcca agagcacgcc tctgaagaac gctctgctct cggacgtgtg cattggcacg    600
tccgccgcgc cgacctacct cccggcgcac tacttccaga ctgaagacgc caacggcaag    660
gagcgcgaat acaacctcat cgacggcggt gtggcggcca acaacccgac gatggttgcg    720
atgacgcaga tcaccaaaaa gatgcttgcc agcaaggaca aggccgagga gctgtaccca    780
gtgaagccgt cgaactgccg caggttcctg gtgctgtcca tcgggacggg gtcgacgtcc    840
gagcagggcc tctacacggc gcggcagtgc tcccgtgggg gtatctgccg gtggctccgc    900
aacaacggca tggcccccat catcgacatc ttcatggcgg ccagctcgga cctggtggac    960
atccacgtcg ccgcgatgtt ccagtcgctc cacagcgacg gcgactacct gcgcatccag   1020
gacaactcgc tccgtggcgc cgcggccacc gtggacgcgg cgacgccgga gaacatgcgg   1080
acgctcgtcg ggatcgggga gcggatgctg gcacagaggg tgtccagggt caacgtggag   1140
acagggaggt acgaaccggt gactggcgaa ggaagcaatg ccgatgccct cggtgggctc   1200
gctaggcagc tctccgagga gaggagaaca aggctcgcgc gccgcgtctc tgccatcaac   1260
ccaagaggct ctagatgtgc gtcgtacgat atctaagaca agtggcttta ctgtcagtca   1320
catgcttgta aataagtaga ctttatttta ataaaacata aaaatatata t            1371
```

<210> SEQ ID NO 53
<211> LENGTH: 1458
<212> TYPE: DNA
<213> ORGANISM: Zea mays

<400> SEQUENCE: 53

```
agttcatcac taatcacact tattgtgccc tcgacgagta tctagctagc tcattaatcg     60
atcaatcggg gtgtgcggtc gaaggcggca atggcgagct actcgtcgcg gcgtccatgc    120
aatacctgta gcacgaaggc gatggccggg agcgtggtcg gcgagcccgt cgtgctgggg    180
cagagggtga cggtgctgac ggtggacggc ggcggcgtcc ggggtctcat cccgggaacc    240
```

```
atcctcgcct tcctggaggc caggctgcag gagctggacg gaccggaggc gaggctggcg       300
gactacttcg actacatcgc cggaaccagc accggcggtc tcatcaccgc catgctcacc       360
gcgcccggca aggacaagcg gcctctctac gctgccaagg acatcaacta cttttacatg       420
gagaactgcc cgcgcatctt ccctcagaag agcaggcttg cggccgccat gtccgcgctg       480
aggaagccaa agtacaacgg caagtgcatg cgcagcctga ttaggagcat cctcggcgag       540
acgagggtaa gcgagacgct gaccaacgtc atcatccctg ccttcgacat caggctgctg       600
cagcctatca tcttctctac ctacgacgcc aagagcacgc tctgaagaa cgcgctgctc        660 tcggacgtgt gcattggcac gtccgccgcg ccgacctacc tcccggcgca ctacttccag       720
actgaagacg ccaacggcaa ggagcgcgaa tacaacctca tcgacggcgg tgtggcggcc       780
aacaacccga cgatggttgc gatgacgcag atcaccaaaa agatgcttgc cagcaaggac       840
aaggccgagg agctgtaccc agtgaacccg tcgaactgcc gcaggttcct ggtgctgtcc       900
atcgggacgg ggtcgacgtc cgagcagggc ctctacacgg cgcggcagtg ctcccggtgg       960
ggcatctgcc ggtggctccg caacaacggc atggcccca tcatcgacat cttcatggcg      1020
gccagctcgg acctggtgga catccacgtc gccgcgatgt ccagtcgct ccacagcgac       1080 ggcgactacc tacgcatcca ggacaactcg ctccgtggcg ccgcggcaac cgtggacgcg      1140
gcgacgccgg agaacatgcg gacgctcgtc gggatcgggg agcggatgct ggcacagcgg      1200
gtgtccaggg tcaacgtgga cagggagc gaggtacgaa ccggtgaccg gagaaggaag        1260
caatgccgat gccctcggtg ggctcgctag gcagctctcc gaggagagga gaacaaggct      1320
cgcgcgccgc gtctctgcca tcaaccccag aagctctaga tgtgcgccct acgatatcta      1380
agacaagtgg ctttactgtc aatcacatgc ttgtaaataa gtagacttta ttttaataaa      1440
atataaatat atatatat                                                     1458
```

<210> SEQ ID NO 54
<211> LENGTH: 401
<212> TYPE: PRT
<213> ORGANISM: Zea mays

<400> SEQUENCE: 54

```
Met Ala Ser Tyr Ser Arg Arg Pro Cys Asn Thr Cys Ser Thr Lys
1               5                   10                  15

Ala Met Ala Gly Ser Val Val Gly Glu Pro Val Leu Gly Gln Arg
                20                  25                  30

Val Thr Val Leu Thr Val Asp Gly Gly Val Arg Gly Leu Ile Pro
            35                  40                  45

Gly Thr Ile Leu Ala Phe Leu Glu Ala Arg Leu Gln Glu Leu Asp Gly
        50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Ala Lys Ser Thr Pro Leu Lys Asn
```

```
                145                 150                 155                 160
Ala Leu Leu Ser Asp Val Cys Ile Gly Thr Ser Ala Ala Pro Thr Tyr
                    165                 170                 175

Leu Pro Ala His Tyr Phe Gln Thr Glu Asp Ala Asn Gly Lys Glu Arg
            180                 185                 190

Glu Tyr Asn Leu Ile Asp Gly Val Ala Ala Asn Pro Thr Met
                195                 200                 205

Val Ala Met Thr Gln Ile Thr Lys Lys Met Leu Ala Ser Lys Asp Lys
    210                 215                 220

Ala Glu Glu Leu Tyr Pro Val Lys Pro Ser Asn Cys Arg Arg Phe Leu
225                 230                 235                 240

Val Leu Ser Ile Gly Thr Gly Ser Thr Ser Glu Gln Gly Leu Tyr Thr
                245                 250                 255

Ala Arg Gln Cys Ser Arg Trp Gly Ile Cys Arg Trp Leu Arg Asn Asn
                260                 265                 270

Gly Met Ala Pro Ile Ile Asp Ile Phe Met Ala Ala Ser Ser Asp Leu
                275                 280                 285

Val Asp Ile His Val Ala Ala Met Phe Gln Ser Leu His Ser Asp Gly
    290                 295                 300

Asp Tyr Leu Arg Ile Gln Asp Asn Ser Leu Arg Gly Ala Ala Ala Thr
305                 310                 315                 320

Val Asp Ala Ala Thr Pro Glu Asn Met Arg Thr Leu Val Gly Ile Gly
                325                 330                 335

Glu Arg Met Leu Ala Gln Arg Val Ser Arg Val Asn Val Glu Thr Gly
                340                 345                 350

Arg Tyr Glu Pro Val Thr Gly Glu Gly Ser Asn Ala Asp Ala Leu Gly
                355                 360                 365

Gly Leu Ala Arg Gln Leu Ser Glu Glu Arg Arg Thr Arg Leu Ala Arg
                370                 375                 380

Arg Val Ser Ala Ile Asn Pro Arg Gly Ser Arg Cys Ala Ser Tyr Asp
385                 390                 395                 400

Ile

<210> SEQ ID NO 55
<211> LENGTH: 428
<212> TYPE: PRT
<213> ORGANISM: Zea mays

<400> SEQUENCE: 55

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
                20                  25                  30

Val Thr Val Leu Thr Val Asp Gly Gly Val Arg Gly Leu Ile Pro
            35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
                100                 105                 110

Cys Pro Arg Ile Phe Pro Gln Lys Ser Arg Leu Ala Ala Ala Met Ser
```

```
            115                 120                 125
Ala Leu Arg Lys Pro Lys Tyr Asn Gly Lys Cys Met Arg Ser Leu Ile
130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Asn Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Thr Val Asp Ala Ala Thr
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Arg Tyr Glu Pro Val
    370                 375                 380

Thr Gly Glu Gly Ser Asn Ala Asp Ala Leu Gly Gly Leu Ala Arg Gln
385                 390                 395                 400

Leu Ser Glu Glu Arg Arg Thr Arg Leu Ala Arg Arg Val Ser Ala Ile
                405                 410                 415

Asn Pro Arg Gly Ser Arg Cys Ala Ser Tyr Asp Ile
            420                 425

<210> SEQ ID NO 56
<211> LENGTH: 372
<212> TYPE: PRT
<213> ORGANISM: Zea mays

<400> SEQUENCE: 56

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60
```

Pro Glu Ala Arg Leu Ala Asp Tyr Phe Asp Tyr Ile Ala Gly Thr Ser
 65                  70                  75                  80

Thr Gly Gly Leu Ile Thr Ala Met Leu Thr Ala Pro Gly Lys Asp Lys
             85                  90                  95

Arg Pro Leu Tyr Ala Ala Lys Asp Ile Asn Tyr Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
130                 135                 140

Arg Ser Ile Leu Gly Glu Thr Arg Ala Lys Ser Thr Pro Leu Lys Asn
145                 150                 155                 160

Ala Leu Leu Ser Asp Val Cys Ile Gly Thr Ser Ala Ala Pro Thr Tyr
                165                 170                 175

Leu Pro Ala His Tyr Phe Gln Thr Glu Asp Ala Asn Gly Lys Glu Arg
            180                 185                 190

Glu Tyr Asn Leu Ile Asp Gly Val Ala Ala Asn Pro Thr Met
        195                 200                 205

Val Ala Met Thr Gln Ile Thr Lys Lys Met Leu Ala Ser Lys Asp Lys
210                 215                 220

Ala Glu Glu Leu Tyr Pro Val Asn Pro Ser Asn Cys Arg Arg Phe Leu
225                 230                 235                 240

Val Leu Ser Ile Gly Thr Gly Ser Thr Ser Glu Gln Gly Leu Tyr Thr
                245                 250                 255

Ala Arg Gln Cys Ser Arg Trp Gly Ile Cys Arg Trp Leu Arg Asn Asn
            260                 265                 270

Gly Met Ala Pro Ile Ile Asp Ile Phe Met Ala Ala Ser Ser Asp Leu
        275                 280                 285

Val Asp Ile His Val Ala Ala Met Phe Gln Ser Leu His Ser Asp Gly
        290                 295                 300

Asp Tyr Leu Arg Ile Gln Asp Asn Ser Leu Arg Gly Ala Ala Ala Thr
305                 310                 315                 320

Val Asp Ala Ala Thr Pro Glu Asn Met Arg Thr Leu Val Gly Ile Gly
                325                 330                 335

Glu Arg Met Leu Ala Gln Arg Val Ser Arg Val Asn Val Glu Thr Gly
            340                 345                 350

Ser Glu Val Arg Thr Gly Asp Arg Arg Lys Gln Cys Arg Cys Pro
        355                 360                 365

Arg Trp Ala Arg
    370

<210> SEQ ID NO 57
<211> LENGTH: 399
<212> TYPE: PRT
<213> ORGANISM: Zea mays

<400> SEQUENCE: 57

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

```
Pro Glu Ala Arg Leu Ala Asp Tyr Phe Asp Tyr Ile Ala Gly Thr Ser
 65                  70                  75                  80

Thr Gly Gly Leu Ile Thr Ala Met Leu Thr Ala Pro Gly Lys Asp Lys
                 85                  90                  95

Arg Pro Leu Tyr Ala Ala Lys Asp Ile Asn Tyr Phe Tyr Met Gln Asn
            100                 105                 110

Cys Pro Arg Ile Phe Pro Gln Lys Ser Arg Leu Ala Ala Ala Met Ser
            115                 120                 125

Ala Leu Arg Lys Pro Lys Tyr Asn Gly Lys Cys Met Arg Ser Leu Ile
130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
            195                 200                 205

Phe Gln Thr Glu Asp Ala Asn Gly Lys Glu Arg Glu Tyr Asn Leu Ile
210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Asn Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
            275                 280                 285

Arg Trp Gly Ile Cys Arg Trp Leu Arg Asn Asn Gly Met Ala Pro Ile
290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
            355                 360                 365

Gln Arg Val Ser Arg Val Asn Val Glu Thr Gly Ser Glu Val Arg Thr
370                 375                 380

Gly Asp Arg Arg Lys Gln Cys Arg Cys Pro Arg Trp Ala Arg
385                 390                 395
```

<210> SEQ ID NO 58
<211> LENGTH: 2088
<212> TYPE: DNA
<213> ORGANISM: Zea mays

<400> SEQUENCE: 58

| | | | | | |
|---|---|---|---|---|---|
| tatttgtact | cattccatgt | ctcataaact | ttgggcacca | tccatccaac | acatccaatc | 60 |
| taaacacacc | aaacgatggg | gaatggaaag | agcagtattc | gattcaacaa | tggcaaacaa | 120 |
| atatcactga | attagaccaa | gaataaacct | aattagacaa | cgacctccca | accatcattc | 180 |
| gtcaggctgt | aaagaagata | aagctgcctt | ggggcatgga | tcaagcagaa | caccagagat | 240 |

```
gaatccaaac acacagaaaa tcacgcgcgc tgtctacaat gacaacaagc cccacatttc    300
attgcagtac actgggctac aaaggcacgt acaacaaaga gctagggaaa cattgcggag    360
ggcacgagag agcagctaac ttgacaatat agcagactga gcttgcactg ttagcaggcg    420
aggaagggaa tcatggggac ggagaatggg gtccatgccc gcgaaggaga aggcggacgc    480
cgccacggtg gcaccggcgc acgcgcacac agggaacccg cacaggcagc caaggatgct    540
gcctcgccat tgcgccggtc gtctctgcca cgctcctctc tctctcccgc tgcatcgccg    600
tggatggggc aagcagagag cagggactgc gacgatctgg gcggaggact cgccttggag    660
agcgcggacg cagacgggat tctagggaga gagcgaagac ggggcgcgcg cggcgctcgc    720
gcggcgtggt ggcggcgaga ttagcggggg tgggggagg gcggagccgt ggtgagggtg    780
tggacgccct ccttaccctc ttaagtagta gtagagatat aatccgttcc aaaatatcca    840
tccgttcaat ttatatttcg tttgatcttt ttaccctaaa tttgattgac tcatcttatt    900
aaaaaagttc ataactatta ttaatcttta ttgagatatc atttagcata taatatactt    960
taagtgtggt tttagatttt ttttaaaaaa aaaaattcgc aaaaattaaa tgaaacgacc   1020
caatcaaact tgaaaagtaa aactaattat aaatttgaac ggaaggagta agaggatgtt   1080
tgaatgtact agagctaata gttggttgct ttaaaatttg ctagtagaat tagctagcta   1140
ataaatatct agataactat tagctaattt gctaaaacag ctaatagttg aactattagc   1200
tagattgttt ggatgtattc ggctaatttt aatggctaac tattagctat agtacaatat   1260
tcaaacacct cctaattaaa atggacaaat atctcttctt ttggtccctt gcgttagatt   1320
tttcatatct ccttatttag tataaaagaa tcatcaaaaa gtggacaacc cctagtggaa   1380
caccatttta gtagtggttg catgaaacct ttcgcgcacc agtttctatg tgtcactcta   1440
aaaatgggac agcatgtacg tagtgcctat atatatacaa gtcatctatc gttgcctcct   1500
cagttcatca ctaatcacac ttattgtgcc ctcgacgagt atctatagct agctcattaa   1560
tcgattcggg ggtgtgttgt cgaaggcggc attggcgagc tactcgtcgc ggcgtccaag   1620
caatacctgt agcacgaagg cgatcgccgg gagcgtggtc ggcgagcccg tcgtgctggg   1680
gcagagggtg acggtgctga cggtggacgg cggcggcgtc cggggtctca tcccgggaac   1740
catcctcgcc ttcctggagg ccaggctgca ggagctggac gcaccggagg cgaggctggc   1800
ggactacttc gactacatcg ccggaaccag caccggcggt ctcatcaccg ccttgctgac   1860
cgcgcccggc aaggacaagc ggcctctcta ggctgccaag gacatcaacc acttttacat   1920
ccataactgc ccgcgcatct ttcctcagaa gtgagtccga tgctgccgcc attgttcttg   1980
catccatcca gcatcgtacg tacgtcctct atacatctgc ggatcatcat gtgcgcatgt   2040
ttgtggcatg catgcatgca tgtgagcagg agcaggcttg cgaaaacc               2088
```

<210> SEQ ID NO 59
<211> LENGTH: 996
<212> TYPE: DNA
<213> ORGANISM: Zea mays

<400> SEQUENCE: 59

```
gacaagtggc tttactgtca gtcacatgct tgtaaataag tagactttat tttaataaaa     60
cataaaaata tatatatgtt cttgaatata aaattgataa ccaaattaaa attcgaacca    120
tcacttatac ataattttac tttattttt ataaaacgtg aacgggaagg actaccgtga    180
atgactatag aaccaatcat actagtataa aatatatgat gacactacgg gagagacaaa    240
```

```
ctttgtctgg cgctaaatat tttgccgagt gtgaattcac gggcactagg caaagatctt      300
ctttgccgag tgttacgctg ggcaaagtaa gacactaggt aaatcagtca tttgccgagt      360
gtccgccact aggcaaagca aaacactggc aaatcaaaag tttacctagt gccagacact      420
aggcaaaaaa aaaacgctcg gcaaatcgga agtttcccta gtgccagaca ctagacaaag      480
aaaaacactt gataaactag cgtcgtcagc taacaccatc caccaaccgt taacgttgcc      540
gagtatctga cttcgacact cggcaaagaa ggtctctttg cctagtgtcg gtctggaaca      600
ctaggcaaag aggcactttta cctagtgtcg tattttgaca ctcagtaaaa taatttttt       660 tctttctgct tccaaacttt ttatgatgtg ttcctatagc acctagaact acatgtcaag      720
ttttggtaaa attttgaag tttttgctat atttacttaa tttattttat ttaattgaat       780
ttcttttgat aattcaaatt tgaactcggc aaggtaagaa gcgagggtag cctggaaaca      840
cactttgcct agtgttacac tcggtacagg agcctcccct gcctagtgct gcactcgaca      900
aaagattcgc ctttgcctag cgctgcactc ggcacaggag tcgcctttgc ctagtgctgc      960
actaggcaaa gcctccgtta ccgtgccttc catcgt                                996
```

<210> SEQ ID NO 60
<211> LENGTH: 1089
<212> TYPE: DNA
<213> ORGANISM: Artificial Sequence
<220> FEATURE:
<223> OTHER INFORMATION: Synthetic

<400> SEQUENCE: 60

```
ttgcgatggc gcagatcacc aaaaagatgc ttgccaacaa ggacaaggcc gaggagctgt       60
acccagtgaa gccgtcgaac tgccgcaggt tcctggtgct gtccatcggg acggggtcga      120
cgtccgagca gggcctctac acggcgcggc agtgctcccg gtggggtatc tgccggtggc      180
tccgcgtcga ctcgggagca tgccctttgt gcttatgcct ccgttctgcc ttctgacgaa      240
tttggtactg gaagcagatg agttttggtt cactatcatt ctgaatttac acctgcgctt      300
gctgtcagac taggcaacca agtgactttt gtgactttga tcatgttcag tgtgtttcca      360
agtcctaatc aatcaaaaag aaaaacagtt tgttaacgat gtttgccat gtctatataa       420 taaagttgct tttatagtag cttagaattc aatcggccaa cttatctcg tacgctgaca       480 gtaaaggtac atttaaaagg tgacaatgga tagtctaata cttgaactga caatagagac      540
acattacatg tcagttgatt aagtttgtaa cagaaaaata aacaatacta cataattgca      600
aagtttcttt gatgtctttc tttcaagaaa cacaaatata tcaatgctac agtattgctg      660
atgaatttat ccatgttgag atgttttct ggtttctgat ctgatcagtc tcaattggtg       720
tgctgtttca ttttcatttg ctgatgatcg tccgagtagt taattcttac taatatttag      780
ataatttggc atacaagcga atcacgtaga acatgatact tttgaatgaa tttatcaaag      840
ttttatcact tggtgagttg tttcatggtt ttcctactga tgtctcttct tcagatttct      900
cgaggcggag ccaccggcag ataccccacc gggagcactg ccgcgccgtg tagaggccct      960
gctcggacgt cgaccccgtc ccgatggaca gcaccaggaa cctgcggcag ttcgacggct     1020
tcactgggta cagctcctcg gccttgtcct tgctggcaag catctttttg gtgatctgcg     1080
tcatcgcaa                                                              1089
```

<210> SEQ ID NO 61
<211> LENGTH: 915
<212> TYPE: DNA
<213> ORGANISM: Artificial Sequence
<220> FEATURE:
<223> OTHER INFORMATION: Synthetic

<400> SEQUENCE: 61

| | | | | | |
|---|---|---|---|---|---|
| gaacaggctt | gcggccgccg | tgtccgcgct | gaggaagcca | aagtacaacg gcaagtgcat | 60 |
| gcgcagcctg | attaggagca | tcctcggcga | gacgaggggt | cgactcggga gcatgccctt | 120 |
| tgtgcttatg | cctccgttct | gccttctgac | gaatttggta | ctggaagcag atgagttttg | 180 |
| gttcactatc | attctgaatt | tacacctgcg | cttgctgtca | gactaggcaa ccaagtgact | 240 |
| tttgtgactt | tgatcatgtt | cagtgtgttt | ccaagtccta | atcaatcaaa agaaaaaaca | 300 |
| gtttgttaac | gattgtttgc | catgtctata | taataaagtt | gcttttatag tagcttagaa | 360 |
| ttcaatcggc | caactttatc | tcgtacgctg | acagtaaagg | tacatttaaa aggtgacaat | 420 |
| ggatagtcta | atacttgaac | tgacaataga | gacacattac | atgtcagttg attaagtttg | 480 |
| taacagaaaa | ataaacaata | ctacataatt | gcaaagtttc | tttgatgtct ttctttcaag | 540 |
| aaacacaaat | atatcaatgc | tacagtattg | ctgatgaatt | tatccatgtt gagatgtttt | 600 |
| tctggtttct | gatctgatca | gtctcaattg | gtgtgctgtt | tcattttcat ttgctgatga | 660 |
| tcgtccgagt | agttaattct | tactaatatt | tagataattt | ggcatacaag cgaatcacgt | 720 |
| agaacatgat | acttttgaat | gaatttatca | aagttttatc | acttggtgag ttgtttcatg | 780 |
| gttttcctac | tgatgtctct | tcttcagatt | tctcgagccc | tcgtctcgcc gaggatgctc | 840 |
| ctaatcaggc | tgcgcatgca | cttgccgttg | tactttggct | tcctcagcgc ggacatggcg | 900 |
| gccgcaagcc | tgctc | | | | 915 |

<210> SEQ ID NO 62
<211> LENGTH: 1452
<212> TYPE: DNA
<213> ORGANISM: Zea mays

<400> SEQUENCE: 62

| | | | | | |
|---|---|---|---|---|---|
| atatatattt | ttatgtttta | ttaaaataaa | gtctacttat | ttacaagcat gtgactgaca | 60 |
| gtaaagccac | ttgtcttaga | tatcgtacga | cgcacatcta | gagcctcttg ggttgatggc | 120 |
| agagacgcgg | cgcgcgagcc | ttgttctcct | ctcctcggag | agctgcctag cgagcccacc | 180 |
| gagggcatcg | gcattgcttc | cttcgccagt | caccggttcg | tacctccctg tctccacgtt | 240 |
| gaccctggac | accctctgtg | ccagcatccg | ctccccgatc | ccgacgagcg tccgcatgtt | 300 |
| ctccggcgtc | gccgcgtcca | cggtggccgc | ggcgccacgg | agcgagttgt cctggatgcg | 360 |
| caggtagtcg | ccgtcgctgt | ggagcgactg | gaacatcgcg | gcgacgtgga tgtccaccag | 420 |
| gtccgagctg | gccgccatga | agatgtcgat | gatggggggcc | atgccgttgt tgcggagcca | 480 |
| ccggcagata | ccccaccggg | agcactgccg | cgccgtgtag | aggccctgct cggacgtcga | 540 |
| ccccgtcccg | atggacagca | ccaggaacct | gcggcagttc | gacggcttca ctgggtacag | 600 |
| ctcctcggcc | ttgtccttgc | tggcaagcat | ctttttggtg | atctgcgtca tcgcaaccat | 660 |
| cgtcgggttg | ttggccgcca | caccgccgtc | gatgaggttg | tattcgcgct ccttgccgtt | 720 |
| ggcgtcttca | gtctggaagt | agtgcgccgg | gaggtaggtc | ggcgcggcgg acgtgccaat | 780 |
| gcacacgtcc | gagagcagag | cgttcttcag | aggcgtgctc | ttggcgtcgt aggtagagaa | 840 |
| gatgataggc | tgcagcagcc | tgatgtcgaa | ggcagggatg | atgacgttgg tcagcgtctc | 900 |
| gcttaccctc | gtctcgccga | ggatgctcct | aatcaggctg | cgcatgcact tgccgttgta | 960 |
| ctttggcttc | ctcagcgcgg | acatggcggc | cgcaagcctg | ctcttctgag gaaagatgcg | 1020 |

| | |
|---|---|
| cgggcagttc tgcatgtaaa agtggttgat gtccttggca gcgtagagag gccgcttgtc | 1080 |
| cttgccgggc gcggtgagca tggcggtgat gagaccgccg gtgctggttc cggcgatgta | 1140 |
| gtcgaagtag tccgccagcc tcgcctccgg tccgtccagc tcctgcagcc tggcctccag | 1200 |
| gaaggcgagg atggttcccg ggatgagacc ccggacgccg ccgccgtcca ccgtcagcac | 1260 |
| cgtcaccctc tgccccagca cgacgggctc gccgaccacg ctcccggcca tcgccttcgt | 1320 |
| gctacaggta ttgcatggac gccgcgacga gtagctcgcc attgccgcct tcgacaacac | 1380 |
| accccgaat cgattaatga gctagctata gatactcgtc gagggcacaa taagtgtgat | 1440 |
| tagtgatgaa ct | 1452 |

<210> SEQ ID NO 63
<211> LENGTH: 1382
<212> TYPE: DNA
<213> ORGANISM: Zea mays

<400> SEQUENCE: 63

| | |
|---|---|
| tcagaatata tatatattta tattttatta aaataaagtc tacttattta caagcatgtg | 60 |
| attgacagta aagccacttg tcttagatat cgtagggcgc acatctagag cttctggggt | 120 |
| tgatggcaga gacgcggcgc gcgagccttg ttctcctctc ctcggagagc tgcctagcga | 180 |
| gcccaccgag ggcatcggca ttgcttcctt ctccggtcac cggttcgtac ctcgctccct | 240 |
| gtctccacgt tgaccctgga cacccgctgt gccagcatcc gctccccgat ccgacgagc | 300 |
| gtccgcatgt tctccggcgt cgccgcgtcc acggttgccg cggcgccacg gagcgagttg | 360 |
| tcctggatgc gtaggtagtc gccgtcgctg tggagcgact ggaacatcgc ggcgacgtgg | 420 |
| atgtccacca ggtccgagct ggccgccatg aagatgtcga tgatggggggc catgccgttg | 480 |
| ttgcggagcc accggcagat gccccaccgg gagcactgcc gcgccgtgta gaggccctgc | 540 |
| tcggacgtcg accccgtccc gatggacagc accaggaacc tgcggcagtt cgacgggttc | 600 |
| actgggtaca gctcctcggc cttgtccttg ctggcaagca tctttttggt gatctgcgtc | 660 |
| atcgcaacca tcgtcgggtt gttggccgcc acaccgccgt cgatgaggtt gtattcgcgc | 720 |
| tccttgccgt tggcgtcttc agtctggaag tagtgcgccg ggaggtaggt cggcgcggcg | 780 |
| gacgtgccaa tgcacacgtc cgagagcagc gcgttcttca gaggcgtgct cttggccctc | 840 |
| gtctcgccga ggatgctcct aatcaggctg cgcatgcact tgccgttgta ctttggcttc | 900 |
| ctcagcgcgg acatggcggc cgcaagcctg ctcttctgag ggaagatgcg cgggcagttc | 960 |
| tccatgtaaa agtagttgat gtccttggca gcgtagagag gccgcttgtc cttgccgggc | 1020 |
| gcggtgagca tggcggtgat gagaccgccg gtgctggttc cggcgatgta gtcgaagtag | 1080 |
| tccgccagcc tcgcctccgg tccgtccagc tcctgcagcc tggcctccag gaaggcgagg | 1140 |
| atggttcccg ggatgagacc ccggacgccg ccgccgtcca ccgtcagcac cgtcaccctc | 1200 |
| tgccccagca cgacgggctc gccgaccacg ctcccggcca tcgccttcgt gctacaggta | 1260 |
| ttgcatggac gccgcgacga gtagctcgcc attgccgcct tcgaccgcac accccgattg | 1320 |
| atcgattaat gagctagcta gatactcgtc gagggcacaa taagtgtgat tagtgatgaa | 1380 |
| ct | 1382 |

<210> SEQ ID NO 64
<211> LENGTH: 19
<212> TYPE: DNA
<213> ORGANISM: Zea mays

<400> SEQUENCE: 64

```
tacgccgtgc gctaacata                                        19

<210> SEQ ID NO 65
<211> LENGTH: 20
<212> TYPE: DNA
<213> ORGANISM: Zea mays

<400> SEQUENCE: 65
gtacctcgct ccctgtctcc                                       20

<210> SEQ ID NO 66
<211> LENGTH: 18
<212> TYPE: DNA
<213> ORGANISM: Zea mays

<400> SEQUENCE: 66
gtacgccgtg cgctaaca                                         18

<210> SEQ ID NO 67
<211> LENGTH: 20
<212> TYPE: DNA
<213> ORGANISM: Zea mays

<400> SEQUENCE: 67
tcgtacctcc ctgtctccac                                       20
```

HAPLOID INDUCTION COMPOSITIONS AND METHODS FOR USE THEREFOR

STATEMENT OF PRIORITY

This application is a divisional of, and claims the benefit under 35 U.S.C. § 120, of pending U.S. patent application Ser. No. 14/212,504, filed on Mar. 14, 2014, incorporated herein by reference in its entirety, which claims the benefit, under 35 U.S.C. § 119 (e), of U.S. Provisional Application No. 61/852,428, filed on Mar. 15, 2013, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 80225_USDIV1_ST25.txt, 287 kilobytes in size, generated on May 2, 2017 and filed via EFS-Web, is provided in lieu of a paper copy. This Sequence Listing is hereby incorporated herein by reference into the specification for its disclosures.

TECHNICAL FIELD

The presently disclosed subject matter relates to the diagnostic detection of haploid induction (HI) or its absence and/or presence in plants which are, or are not haploid inducers. More particularly, the presently disclosed subject matter relates to nucleic acids that can be employed for inducing HI in plants and/or the biological activities which can be modified in order to produce or prevent HI in either a plant that would otherwise exhibit HI or in a plant that would otherwise not exhibit HI. Even more particularly, the presently disclosed subject matter relates to a nucleic acid molecule that encodes a biologically active molecule as well as methods for using the same to regulate HI in plants.

BACKGROUND

Maize breeders have been crossing inbred parent lines, one acting as a male and one as a female to form hybrid seed. The process of developing inbred parent lines which are substantially homozygous usually required a hybrid cross to be selected and self-pollinated (selfed) for numerous generations to become nearly homozygous. This was a time consuming and expensive process. To shorten the time to develop homozygous inbreds in maize, maize breeders have been using a process of using a haploid inducer line to induce haploid seed on a hybrid parent. The chromosomes of the haploid plants are doubled to form double haploid homozygous inbred lines.

A high haploid induction rate allows a higher frequency of haploid seeds to be formed on the parent plant of interest. The parent plants can be pre-screened with genetic markers associated with desired traits or phenotypic observed traits to enrich the genetic potential of the parent plants. When these desired parent plants are pollinated by a haploid inducer that has a higher haploid induction rate, a higher potential of desired doubled haploids can be obtained with the desired genotype and phenotype.

Although the doubled haploid process resulted in faster production of homozygous inbreds, the volume of doubled haploid inbreds that could be produced was limited. The inducer lines had a low frequency of induction of haploids. A number of known haploid-inducing maize lines exist including but not limited to: stock 6, MHI (Moldovian Haploid Inducer), indeterminate gametophyte (ig) mutation, KEMS, RWK, ZEM, ZMS, KMS. The standard inducer lines such as Stock 6 were inducing only 1-3% haploid seeds. Induction of haploids was a rate limiting step in the process of producing doubled haploid lines.

Haploid induction (HI) is a class of plant phenomena characterized by loss of the male inducer chromosomes during embryo development. WO2012/030893 describes a slightly different region of chromosome (1) that is found responsible for haploid induction. The identified markers in the region responsible for haploid induction and increased haploid induction was described as being between 48,249, 509-51,199,249 which is associated with a public marker umc1169 that has the physical position of (60/213,661). This region apparently aligns with the Haploid Induction region in Stock 6. Dong et al. (2013) Theor. Appl. Genet. 126: 1713-1720 describe a QTL located in bin 1.04 which explains up to 66% of the genotypic variance for haploid induction rate.

Haploid induction has been observed in numerous plant species, such as sorghum, rice, and other grasses. The HI appears to be a result of rearrangements of, mutations in, and/or recombinations, insertion, or deletions within a region of chromosome 1. Purported HI-lines have been studied and roughly identified. However, experimental evidence demonstrating a causative genetic agent of HI in maize has not been presented. Nor have the markers listed herein that associate with this trait been previously identified.

The presently disclosed subject matter provides isolated cDNA. In some embodiments, the isolated cDNA are selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 91-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, or SEQ ID NO: 55, or SEQ ID NO: 56, or SEQ ID NO: 57 optionally wherein the percent identity is calculated over the entire length of SEQ ID NO: 54, or SEQ ID NO: 55, or SEQ ID NO: 56, or SEQ ID NO: 57.

In other embodiments, a synthetic hairpin nucleic acid construct comprising between 15 and 1000 nucleotides from SEQ ID NO. 33, 37, 52 or 53 and the antisense-complement thereof, such that the first and the second polynucleotide sequences hybridize when transcribed into a ribonucleic acid to form the hairpin-like double stranded ribonucleotide molecule. In further embodiments, the synthetic hairpin nucleic acid construct is selected from the group consisting of SEQ ID NO: 60 and SEQ ID NO: 61.

In other embodiments, an expression cassette for RNAi comprises a promoter operably linked to the synthetic hairpin. In further embodiments, the promoter is a constitutive promoter, optionally a maize ubiquitin-1 promoter, a rice actin-1 promoter, a rice ubiquitin-3 promoter, a rice alpha tubulin (tubA1) promoter, a cauliflower mosaic virus (CaMV) 35S promoter, a cestrum yellow leaf curling virus (CmYLCV) CMP promoter, a super MAS promoter, a sorghum ubiquitin-3 promoter, or a sugarcane ubiquitin-4 promoter. In other embodiments, the promoter is a stamen-, anther-, and/or pollen-specific promoter, optionally selected from the group consisting of SEQ ID NO: 58, a *Triticum aestivum* P19 promoter, a maize B200 promoter, a maize prCDPK-01 promoter, a maize prCDPK-02 promoter, a rice alpha-N-acetylglucosaminidase (prOsANG) promoter, a rice MADS box gene promoter (optionally a prOsMADS1 promoter, a prOsMADS2 promoter, a prOsMADS6 promoter, a prOsMADS14 promoter, or a prOsMADS16 promoter), a rice anther specific-promoter (optionally a prRA8 promoter or a prOsG6 promoter). In other embodiments, the expression vector may optionally comprise a terminator. In further embodiments, the terminator may be SEQ ID NO: 59. In some embodiments consist of a plant comprising hairpin nucleic acid construct of the previous embodiments. This plant could be a monocot such as a maize plant.

Some embodiments consist of a method of creating a new haploid inducer plant with a silenced patatin-like phospholipase 2A, comprising transcribing a polynucleotide sequence capable of silencing the patatin-like phospholipase 2A, wherein said polynucleotide sequence is selected from the group consisting of: a polynucleotide sequence comprising the nucleic acid sequence set forth in SEQ ID NOs 33, 37, 52, 53 or the complement thereof, a functional fragment comprising at least 15 contiguous bases of any one of SEQ ID NOs 33, 37, 52, 53 or the complement thereof, a polynucleotide sequence having at least 95% sequence identity as determined using the BLASTN alignment tool to the nucleic acid sequence set forth in any one of SEQ ID NOs 33, 37, 52, 53 or the complement thereof, and a double-stranded ribonucleotide sequence produced from the expression of a polynucleotide sequence of any one of the above polynucleotide sequences, wherein silencing of the patatin-like phospholipase 2A creates a new haploid inducer plant.

Other embodiments are a plant made by the above method. The plant may be a maize plant or other monocot. Other embodiments are a method of inducing haploid embryos by using the pollen of the plant made by the above method to fertilize another plant, wherein the fertilization induces haploid embryos. Other embodiments are a method of identifying a maize plant that comprises a genotype associated with an increased haploid induction phenotype, comprising: isolating DNA from a maize plant, providing a reaction mixture comprising the DNA from a maize plant, the pair of primers comprising SEQ ID NO: 64 and SEQ ID NO 65 wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; heating the reaction mixture to a first predetermined temperature for a first predetermined time to separate the strands of the target DNA from each other; cooling the reaction mixture to a second predetermined temperature for a second predetermined time under conditions to allow the first and second primers to hybridize with their complementary sequences on the first and second strands of the target DNA, and to allow the Taq polymerase to extend the primers; and repeating steps (b) and (c) at least 20 times, wherein an amplification product of about 822 nucleotides indicates a maize plant that comprises a genotype associated with an increased haploid induction phenotype.

Some embodiments consist of an expression cassette for expression of a fertility restoring polypeptide in a plant, the expression cassette comprising an isolated nucleic acid of SEQ ID NO. 33 or 52 operably linked to a promoter that regulates transcription of the isolated nucleic acid of SEQ ID NO. 33 or 52 in a plant cell and/or tissue of interest, wherein the isolated cDNA of claim 1 encodes an amino acid sequence that is at least 95% identical to SEQ ID NO: 54 or 55, optionally wherein the percent identity is calculated over the entire length of SEQ ID NO: 54 or 55.

Other embodiments consist of a kit for detecting the presence of absence of a HI-inducing allele in a plant, the kit comprising one or more nucleic acid- and/or amino acid-based reagents derived from the maize HI locus or from a locus linked thereto wherein the one or more nucleic acid- and/or amino acid-based reagents are designed to be employed in a nucleic acid- and/or amino acid-based assay for the presence or absence in the plant of: a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33; a nucleic acid having at least 95% identity over nucleotides 91-1452 of SEQ ID NO: 33; a nucleic acid that is the reverse complement of either of (a) or (b); and/or a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57, or nucleic acid comprising nucleotides 1230-1233 of SEQ ID NO: 53.

In some embodiments, the isolated nucleic acids are selected from the group consisting of: a sequence having at least 90% identity to the listed SEQ ID NOs which comprise at least one sequence evidencing an association with a haploid inducing trait by its presence or absence selected from the group consisting of genes identified as GRMZM2G305400, GRMZM2G082836, GRMZM2G382717, GRMZM2G120587, GRMZM2G471240, GRMZM2G866758, and GRMZM2G003530.

The presently disclosed subject matter also provides expression cassettes for expression of the gene products made by the gene which is absent in HI plants. In some embodiments, an expression cassette of the presently disclosed subject matter comprises a nucleic acid sequence as described herein as a synthetic hairpin nucleic acid construct comprising between 15 and 1000 nucleotides from SEQ ID NO: 33, SEQ ID NO: 37, SEQ ID NO: 52 or SEQ ID NO: 53 (such as, but not limited to SEQ ID NO: 60 or 61) operably linked to a promoter that regulates transcription of the isolated nucleic acid in a plant cell and/or tissue of interest, and/or an organelle or subcellular structure thereof. In some embodiments, the isolated nucleic acid present in the expression cassette encodes an amino acid sequence that is at least 95% identical to SEQ ID NO: 54, SEQ ID NO: 55, SEQ ID NO: 56 or SEQ ID NO: 57, optionally wherein the percent identity is calculated over the entire length of SEQ ID NO: 54, SEQ ID NO: 55, SEQ ID NO: 56 or SEQ ID NO: 57. In some embodiments, the promoter is a native promoters associated with the genes within this haploid induction region (such as, but not limited to SEQ ID NO: 58). In some embodiments, constitutive promoter, which can optionally be selected from the group consisting of the native promoter, a constitutive promoter such as ZmUbi1, ZmUbi158, ZmUbi361, SbUBiCh3, SbUbiCh4, a maize ubiquitin-1 promoter, a rice actin-1 promoter, a rice ubiquitin-3 promoter, a cauliflower mosaic virus (CaMV) 35S promoter, a sorghum ubiquitin-3 promoter, or a sugarcane ubiquitin-4 promoter, or a promoter that is pollen specific. Examples of pollen promoters are shown in the art in pollen-specific expression cassettes. Pollen-specific genes have been described for maize (Lopez I, Anthony, R. G., Maciver, S. K., Jaing, C.-J., Khan, S., Weeds, A. G., Hussey, P. J. (1996). Pollen specific expression of maize genes encoding actin depolymerizing factor-like proteins. Proc Natl Acad Sci USA 93:7415-7420.) Such information can be used to identify other maize pollen-specific genes, and promoters and produce pollen-specific expression cassettes. In some embodiments, the expression cassette further comprises a transcription terminator operably linked to the promoter and/or coding sequence. Some embodiments are a promoter for anther, stamen or pollen specific expression comprising SEQ ID NO:58.

In some embodiments, the plant cell and/or tissue of interest is selected from the group consisting of a stamen cell, a microspore, a meiotic cell, a cell that differentiates into a stamen cell or a progeny cell thereof, an anther cell, a cell that differentiates into an anther cell or a progeny cell thereof. In some embodiments, the organelle or subcellular structure of the plant cell and/or tissue of interest is a microspore. Thus, in some embodiments, the promoter is a stamen-, anther-, and/or pollen-specific promoter, which in some embodiments is selected from the group consisting of a *Triticum aestivum* P19 promoter, a maize B200 promoter, a maize prCDPK-01 and prCDPK-02 promoter, a rice α-N-acetylglucosaminidase (prOsANG) promoter, a rice MADS box gene promoter (including, but not limited to a prOsMADS1 promoter, a prOsMADS2 promoter, a prOsMADS6 promoter, a prOsMADS7 promoter a prOsMADS14 promoter, or a prOsMADS16 promoter), a rice anther-specific promoter (such as, but not limited to a prRA8 promoter or a prOsG6 promoter), a rice stamen-specific promoter (such as, but not limited to the promoters disclosed in U.S. Pat. No. 5,639,948); and a corn stamen-specific promoter (such as, but not limited to the promoters disclosed in U.S. Pat. No. 5,589,610). In some embodiments, the promoter is a promoter that is transcriptionally active in a plant mitochondrion. Exemplary such promoters include, but are not limited to those disclosed in Fey & Maréchal-Drouard, 1999 and Binder et al., 1996.

In some embodiments, the expression cassette further comprises a transcription terminator, optionally a Nos or ags terminator.

In some embodiments, the expression cassette further comprises a targeting peptide (TP) coding sequence that is operably linked to and in frame with a sequence that encodes an amino acid sequence that is at least 95% identical to SEQ ID NO: 54, SEQ ID NO: 55, SEQ ID NO: 56 or SEQ ID NO: 57.

The presently disclosed subject matter also provides vectors comprising an expression cassette as disclosed herein.

The presently disclosed subject matter also provides transgenic plant cells comprising the presently disclosed expression cassettes, as well as plants, plant parts, and seeds comprising or derived from the presently disclosed transgenic plant cells.

The presently disclosed subject matter also provides isolated polypeptides comprising amino acid sequences that are at least 95% identical to SEQ ID NO: 54, SEQ ID NO: 55, SEQ ID NO: 56 or SEQ ID NO: 57. In some embodiments, wherein the percent identity is calculated over the entire length of SEQ ID NO: 54, SEQ ID NO: 55, SEQ ID NO: 56 or SEQ ID NO: 57. In some embodiments, the isolated polypeptides comprise amino acid sequences that comprise all or substantially all of amino acids 1-429 of SEQ ID NO: 54 locus.

The presently disclosed subject matter also provides subsequences, amplicons, and informative fragments of SEQ ID NO: 33, SEQ ID NO: 37, SEQ ID NO: 52 or SEQ ID NO: 53, as well as allelic variations thereof, wherein the subsequences, amplicons, informative fragments, and/or allelic variations can be used to identify the presence or absence of an allele associated with HI in a plant, or plant tissue, or plant cell.

The presently disclosed subject matter also provides compositions comprising amplification primer pairs capable of amplifying plant nucleic acid templates to generate marker amplicons, wherein the marker amplicons correspond to markers comprising informative subsequences of any of SEQ ID NO: 33, SEQ ID NO: 37, SEQ ID NO: 52 or SEQ ID NO: 53, or of the listed SEQ ID NOs. from this 0.6 MB region which comprise at least one sequence evidencing an association with a haploid inducing trait in this by its presence or absence selected from the group consisting of genes identified as GRMZM2G305400, GRMZM2G082836, GRMZM2G382717, GRMZM2G120587, GRMZM2G471240 (two), GRMZM2G003530, and GRMZM2G866758 (two) wherein the informative subsequences permit identification of the presence or absence of an allele associated with HI in plants. In some embodiments, the amplification primers are designed to amplify a subsequence of SEQ ID NO: 33, SEQ ID NO: 37, SEQ ID NO: 52 or SEQ ID NO: 53 (exemplary primers, but not limited to SEQ ID NO: 64, SEQ ID NO: 65, SEQ ID NO: 66 or SEQ ID NO: 67). The presently disclosed subject matter also provides methods for producing plants that exhibit a new or increased HI trait. In some embodiments, the methods comprise (a) transforming a plant cell with an expression cassette comprising a nucleic acid as disclosed herein to produce a transformed plant cell; and (b) generating a plant from the transformed plant cell.

The presently disclosed subject matter also provides methods for identifying the presence or absence of allele associated with HI in plants. In some embodiments, the methods comprise (a) obtaining a sample from the plant comprising genomic and/or nuclear DNA and/or an RNA product derived therefrom; (b) contacting the sample with a pair of primers that, when used in a nucleic acid amplification reaction with a nucleic acid sample from the plant, produces an amplicon that can be used to identify the presence or absence of an allele associated with HI; (c) amplifying a fragment from said sample using the primer pair of (b), wherein the primer pair is complementary and binds to the nucleotide sequence of (b); and (d) detecting an amplicon that can be used to identify the presence or absence of an allele associated with HI in the plant.

The presently disclosed subject matter also provides methods for introgressing HI-inducing nucleotide sequences or haplotypes into plants. In some embodiments, the methods comprise crossing a first plant with a second plant to produce a third plant, wherein the genome of the first plant or the second plant comprises a nucleic acid sequence (in some embodiments a recombinant nucleic acid sequence) encoding a HI-associated gene product of the presently disclosed subject matter and selecting those plants that do not exhibit production of the gene product, or a gene product at substantially reduced levels. In some embodiments, the methods further comprise assaying the genome of the third plant for the presence or absence of the nucleic acid sequence (in some embodiments, the recombinant nucleic acid sequence) encoding the HI-associated gene product. A HI-associated gene product, can be a negative or positive association. In this instance the association is a negative association, i.e. the presence of the gene product is associated with the absence of the haploid induction trait. In some embodiments, the recombinant nucleic acid comprises SEQ ID NO: 33, SEQ ID NO: 37, SEQ ID NO: 52 or SEQ ID NO: 53, and/or encodes a polypeptide that is at least 95% identical to SEQ ID NO: 54, SEQ ID NO: 55, SEQ ID NO: 56 or SEQ ID NO: 57. In some embodiments, the genome of the third plant that is assayed is the third plant's genome.

The presently disclosed subject matter also provides methods for selecting $F_0$ parental plants predicted to produce haploid inducing plants that exhibit inducible HI traits. In some embodiments, the methods comprise identifying in the genome of an $F_0$ plant the present or absence of a nucleic acid comprising a nucleotide sequence selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 1-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, SEQ ID NO: 55, SEQ ID NO: 56 or SEQ ID NO: 57, optionally wherein the percent identity is calculated over the entire length of SEQ ID NO: 54, SEQ ID NO: 55, SEQ ID NO: 56 or SEQ ID NO: 57.

In some embodiments, the methods comprise identifying in the genome of an $F_0$ plant the present or absence of a nucleic acid comprising a nucleotide sequence selected from the group consisting of the listed SEQ ID NOs. 3, 9-46 from this 0.6 MB region which comprise at least one sequence evidencing an association with a haploid inducing trait in this by its presence or absence selected from the group consisting of genes identified as GRMZM2G305400, GRMZM2G082836, GRMZM2G382717, GRMZM2G120587, GRMZM2G471240 (two), and GRMZM2G866758 (two) wherein the nucleic acid has at least 90% identity to the selected SEQ ID NO. optionally wherein the percent identity is calculated over the entire length of the selected SEQ ID NO.

Thus, it is an object of the presently disclosed subject matter to identify and/or introgress and/or provide nucleic acids for inducing and/or inhibiting the HI trait in a plant.

BRIEF DESCRIPTION OF THE SEQUENCE LISTING

SEQ ID NO: 1 is a cDNA nucleotide sequence from the maize NIL-genome of SEQ ID NO:3

SEQ ID NO: 2 is an amino acid sequence of a polypeptide encoded by SEQ ID NO: 1 which is a cDNA from the NIL-genome designated GRMZM2G062320-B SEQ ID NO: 3 is the NIL-genome genomic nucleotide sequence SEQ ID NO: 4 is the sequence of ZmABP2-GRMZM2G062320.

SEQ ID NOs: 5-8 are amino acid sequences for maize GRMZM2G062320-A, GRMZM2G062320-C, GRMZM2G062320-D, GRMZM2G062320-E SEQ ID NO: 9 GRMZM2G305400 gDNA (from B73 genome)

SEQ ID NO: 10 GRMZM2G305400 cDNA (from B73 genome)

SEQ ID NO: 11 GRMZM2G082836 gDNA (from the B73 genome)

SEQ ID NO: 12 GRMZM2G082836 cDNA1 (from the B73 genome)

SEQ ID NO: 13 GRMZM2G082836 cDNA2 (from the B73 genome)

SEQ ID NO: 14 GRMZM2G082836 cDNA3 (from the B73 genome)

SEQ ID NO: 15 GRMZM2G082836 gDNA (from the NIL genome)

SEQ ID NO: 16 GRMZM2G082836 gDNA (from the Stock 6 genome)

SEQ ID NO: 17 GRMZM2G082836 gDNA (from the RWK genome)

SEQ ID NO: 18 GRMZM2G382717 gDNA (from B73 genome)

SEQ ID NO: 19 GRMZM2G382717 cDNA2 (from B73 genome)

SEQ ID NO: 20 GRMZM2G382717 gDNA (from NIL genome)

SEQ ID NO: 21 GRMZM2G382717 gDNA (from RWK genome)

SEQ ID NO: 22 GRMZM2G382717 gDNA (991832 from Stock 6 genome)

SEQ ID NO: 23 GRMZM2G382717 gDNA (989131 from Stock 6 genome)

SEQ ID NO: 24 GRMZM2G382717 protein coding sequence (from RWK genome)

SEQ ID NO: 25 GRMZM2G120587 gDNA (from the B73 genome)

SEQ ID NO: 26 GRMZM2G120587 cDNA1 (from the B73 genome)

SEQ ID NO: 27 GRMZM2G120587 cDNA2 (from the B73 genome)

SEQ ID NO: 28 GRMZM2G120587 cDNA3 (from the B73 genome)

SEQ ID NO: 29 GRMZM2G120587 GDNA (from the Stock 6 genome)

SEQ ID NO: 30 GRMZM2G120587 GDNA (from the RWK genome)

SEQ ID NO: 31 GRMZM2G120587 GDNA (from the Stock 6/RWK genome)

SEQ ID NO: 32 GRMZM2G471240 gDNA (from the B73 genome)

SEQ ID NO: 33 GRMZM2G471240 cDNA long splice variant (from the B73 genome)

SEQ ID NO: 34 GRMZM2G471240 gDNA (from the NIL genome)

SEQ ID NO: 35 GRMZM2G471240 gDNA (from the maize Stock 6 genome)

SEQ ID NO: 36 GRMZM2G471240 gDNA (from the maize RWK genome)

SEQ ID NO: 37 GRMZM2G471240 cDNA short splice variant (from the Stock6/RWK genome)

SEQ ID NO: 38 GRMZM5G866758 gDNA (from the B73 genome)

SEQ ID NO: 39 GRMZM5G866758 cDNA1 (from the B73 genome)

SEQ ID NO: 40 GRMZM5G866758 cDNA2 (from the B73 genome)

SEQ ID NO: 41 GRMZM5G866758 cDNA-1780 (from the B73 maize genome)

SEQ ID NO: 42 GRMZM5G866758 gDNA (from the NIL maize genome)

SEQ ID NO: 43 GRMZM5G866758 cDNA (from the NIL genome)

SEQ ID NO: 44 GRMZM5G866758 gDNA (from the Stock 6 genome)

SEQ ID NO: 45 GRMZM5G866758 gDNA (from the RWK genome)

SEQ ID NO: 46 GRMZM5G866758 gDNA (from the Stock 6/RWK genome)

SEQ ID NO: 47 GRMZM2G382717 cDNA1 (from B73 genome).

SEQ ID NO: 48 GRMZM2G003530 gDNA (from B73 genome).

SEQ ID NO: 49 GRMZM2G003530 gDNA (from NIL genome).

SEQ ID NO: 50 GRMZM2G003530 gDNA (from RWK genome).

SEQ ID NO: 51 GRMZM2G003530 gDNA (from Stock 6 genome).

SEQ ID NO: 52 GRMZM2G471240 cDNA short splice variant (from the B73 genome)

SEQ ID NO: 53 GRMZM2G471240 cDNA long splice variant (from the RWK genome)

SEQ ID NO: 54 is an amino acid sequence of a polypeptide encoded by SEQ ID NO: 33

SEQ ID NO: 55 is an amino acid sequence of a polypeptide encoded by SEQ ID NO: 52

SEQ ID NO: 56 is an amino acid sequence of a polypeptide encoded by SEQ ID NO: 37

SEQ ID NO: 57 is an amino acid sequence of a polypeptide encoded by SEQ ID NO: 53

SEQ ID NO: 58 is the promoter of the GRMZM2G471240 gene

SEQ ID NO: 59 is the terminator of the GRMZM2G471240 gene

SEQ ID NO: 60 is a synthetic hairpin designed to SEQ ID NO 33 nt 450-547 with 2 mismatches, a spacer sequence and the reverse compliment of SEQ ID NO 33 nt 450-547

SEQ ID NO: 61 is a synthetic hairpin designed to SEQ ID NO 33 nt 797-987 with 2 mismatches, a spacer sequence and the reverse compliment of SEQ ID NO 33 nt 797-987

SEQ ID NO: 62 is the reverse compliment of SEQ ID NO 33

SEQ ID NO: 63 is the reverse compliment of SEQ ID NO 52

SEQ ID NO: 64 is primer rwk.F1
SEQ ID NO: 65 is primer rwk.R1
SEQ ID NO: 66 is primer nil.F1
SEQ ID NO: 67 is primer nil.R1

DETAILED DESCRIPTION

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, the phrase "associated with HI" refers to a trait, locus, gene, allele, marker, phenotype, etc., or the expression thereof, the presence or absence of which can influence an extent and/or degree at which a plant or its progeny exhibits HI. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with HI" refers to a marker whose presence or absence can be used to predict whether and/or to what extent a plant will display haploid induction.

The term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include in some embodiments the use of either of the other two terms. For example, if a subject matter relates in some embodiments to nucleic acids that encode polypeptides comprising amino acid sequences that are at least 95% identical to a SEQ ID NO: 55. It is understood that the disclosed subject matter thus also encompasses nucleic acids that encode polypeptides that in some embodiments consist essentially of amino acid sequences that are at least 95% identical to that SEQ ID NO: 55 as well as nucleic acids that encode polypeptides that in some embodiments consist of amino acid sequences that are at least 95% identical to that SEQ ID NO: 55. Similarly, it is also understood that in some embodiments the methods for the disclosed subject matter comprise the steps that are disclosed herein, in some embodiments the methods for the presently disclosed subject matter consist essentially of the steps that are disclosed, and in some embodiments the methods for the presently disclosed subject matter consist of the steps that are disclosed herein.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form. For each genetic map, distances between loci are measured by the recombination frequencies between them. Recombination events between loci can be detected using a variety of markers. A genetic map is a product of the mapping population, types of markers used, and the polymorphic potential of each marker between different populations. The order and genetic distances between loci can differ from one genetic map to another.

As used herein, the phrase "genetic marker" refers to a nucleic acid sequence (e.g., a polymorphic nucleic acid sequence) that has been identified as associated with a locus or allele of interest and that is indicative of the presence or absence of the locus or allele of interest in a cell or organism. Examples of genetic markers include, but are not limited to genes, DNA or RNA-derived sequences, promoters, any untranslated regions of a gene, microRNAs, siRNAs, QTLs, SNPs, transgenes, mRNAs, ds RNAs, transcriptional profiles, and methylation patterns.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) and/or haplotype(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome (in some embodiments, including the nuclear genome, the mitochondrial genome, plastid genome or all three). Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety, or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants can be grown, as well as plant parts, such as leafs, stems, pollen, or cells that can be cultured into a whole plant.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the terms "informative fragment" and "informative subsequence" refer to nucleotide sequences comprising a fragment of a larger nucleotide sequence, wherein detecting of the presence of absence of the fragment allows for the detecting of the presence of absence of the larger nucleotide sequence. For example, an informative fragment of the nucleotide sequence of SEQ ID NO: 33 comprises a fragment of the nucleotide sequence of SEQ ID NO: 33 that permits the accurate identification of whether or not SEQ ID NO: 33 is present in a sample. This non HI locus lacks the 4 nucleotide insertion that is present in the HI germplasm as found in SEQ ID NO: 53 nucleotides 1230-1233. In some embodiments, an informative fragment of SEQ ID NO: 53 allows identification of the presence or absence of the HI locus. In some embodiments, informative fragments of SEQ ID NO: 53 containing nucleotides 1230-1233 allow identification of the presence or absence of the HI locus.

As used herein, the term "isolated" refers to a nucleotide sequence that is free of sequences that normally flank one or both sides of the nucleotide sequence in a plant genome. Thus, isolated nucleic acids include, without limitation, a recombinant DNA that exists as a separate molecule with no flanking sequences present, as well as a recombinant DNA that is incorporated into a vector, an autonomously replicating plasmid, or into the genomic DNA of a plant as part of a hybrid or fusion nucleic acid molecule.

As used herein, the term "linkage" refers to a phenomenon wherein alleles on the same chromosome tend to be transmitted together more often than expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

As such, "linkage" typically implies and can also refer to physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a HI locus of the presently disclosed subject matter is linked to a marker (e.g., a genetic marker) if it is in some embodiments within 20, 15, 12, 10, 9, 8, 7, 6, 5, 4, 3, 2, or 1 cM of the marker.

Thus, the term "linkage" refers to the degree with which one marker locus is associated with another marker locus or some other locus (for example, a locus associated with HI). The linkage relationship between a molecular marker and a phenotype can be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., HI. The degree of linkage of a molecular marker to a phenotypic trait is measured, e.g., as a statistical probability of co-segregation of that molecular marker with the phenotype.

As used herein, the term "linkage equilibrium" describes a situation where two markers independently segregate, i.e., sort among progeny randomly. Markers that show linkage equilibrium are considered unlinked (whether or not they lie on the same chromosome). As such, the phrase "linkage disequilibrium" is defined as change from the expected relative frequency of gamete types in a population of many individuals in a single generation such that two or more loci act as genetically linked loci. If the frequency in a population of allele S is x, s is x', B is y, and b is y', then the expected frequency of genotype SB is xy, that of Sb is xy', that of sB is x'y, and that of sb is x'y', and any deviation from these frequencies is an example of disequilibrium. Linkage disequilibrium is most commonly assessed using the measure $r^2$, which is calculated using the formula described by Hill & Robertson, 1968. When $r^2=1$, complete linkage disequilibrium exists between the two marker loci, meaning that the markers have not been separated by recombination and have the same allele frequency. In some embodiments, values for $r^2$ above 0.33 indicate sufficiently strong linkage disequilibrium to be useful for mapping. See Ardlie et al., 2002. Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the terms "marker", "genetic marker", and 'molecular marker" are used interchangeably to refer to an identifiable position on a DNA molecule (e.g., a chromosome or a nuclear genome) the inheritance of which can be monitored and/or a reagent that is used in methods for visualizing differences in nucleic acid sequences present at such identifiable positions on a DNA molecule. Thus, in some embodiments a marker comprises a known or detectable nucleic acid sequence. As such, a marker can comprise a nucleotide sequence that has been associated with an allele or alleles of interest and that is indicative of the presence or absence of the allele or alleles of interest in a cell or organism and/or to a reagent that is used to visualize differences in the nucleotide sequence at such an identifiable position or positions. A marker can be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS; Rafalski & Tingey, 1993), an amplified fragment length polymorphism (AFLP; Vos et al., 1995), a single nucleotide polymorphism (SNP) (Brookes, 1993), a sequence-characterized amplified region (SCAR; Paran & Michelmore, 1993), a sequence-tagged site (STS; Onozaki et al., 2004), a single-stranded conformation polymorphism (SSCP; Orita et al., 1989), an inter-simple sequence repeat (ISSR; Blair et al., 1999), an inter-retrotransposon amplified polymorphism (IRAP), a retrotransposon-microsatellite amplified polymorphism (REMAP; Kalendar et al., 1999) or an RNA cleavage product (such as a Lynx tag). A marker can be present in genomic (including but not limited to nuclear genomic and/or 1 genomic) or expressed nucleic acids (e.g., ESTs). In some embodiments, a marker is an informative fragment of SEQ ID NO: 33, SEQ ID NO: 37, SEQ ID NO: 52 or SEQ ID NO: 53 that permits the specific identification of nucleic acids comprising or lacking SEQ ID NO: 33, SEQ ID NO: 37, SEQ ID NO: 52 or SEQ ID NO: 53 in samples.

The term marker can also refer to nucleic acids used as probes or primers (e.g., primer pairs) for use in amplifying, hybridizing to, and/or detecting nucleic acid molecules according to methods well known in the art. In some embodiments, a nucleic acid marker that can be employed to detect the presence or absence of SEQ ID NO: 33, SEQ ID NO: 37, SEQ ID NO: 52 or SEQ ID NO: 53 is a primer pair that comprises a forward primer that comprises a subsequence of nucleotides of SEQ ID NO: 33, SEQ ID NO: 37, SEQ ID NO: 52 or SEQ ID NO: 53 and a reverse primer that is the reverse complement of a subsequence of nucleotides of SEQ ID NO: 33, SEQ ID NO: 37, SEQ ID NO: 52 or SEQ ID NO: 53 and/or is an amplicon that is generated by using such a primer pair to amplify a subsequence of SEQ ID NO: 33, SEQ ID NO: 37, SEQ ID NO: 52 or SEQ ID NO: 53 (i.e., the subsequence of SEQ ID NO: 33, SEQ ID NO: 37, SEQ ID NO: 52 or SEQ ID NO: 53 that comprises nucleotides, optionally including 1, 2, 3, 4, 5, 6, 7, 8, 9, 10, or more nucleotides of SEQ ID NO: 33, SEQ ID NO: 37, SEQ ID NO: 52 or SEQ ID NO: 53 that are 5' to and/or 3' to nucleotides selected nucleotides from the positions listed in the Table on Fine Mapping in Example 3 and a part of SEQ ID NO: 1-47).

As used herein, the terms "marker probe" and "probe" refer to a nucleotide sequence or nucleic acid molecule that can be used to detect the presence or absence of sequence within SEQ ID NO: 33, SEQ ID NO: 37, SEQ ID NO: 52 or SEQ ID NO: 53 (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides can be used for nucleic acid hybridization.

As used herein, the term "molecular marker" can be used to refer to a genetic marker, as defined above, or an encoded product thereof (e.g., a protein) used as a point of reference when identifying the presence/absence of a HI-associated locus. A molecular marker can be derived from genomic nucleotide sequences or from expressed nucleotide sequences (e.g., from an RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution (e.g., according to Watson-Crick base pairing rules). This term also refers to the genetic markers that indicate a trait by the absence of the nucleotide sequences complementary to or flanking the marker sequences, such as nucleotide sequences used as probes and/or primers capable of amplifying the marker sequence.

As used herein, the terms "nucleotide sequence", "polynucleotide", "nucleic acid sequence", "nucleic acid molecule", and "nucleic acid fragment" refer to a polymer of RNA or DNA that is single- or double-stranded, optionally containing synthetic, non-natural, and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. In some embodiments, the percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, Calif., United States of America. See also Smith & Waterman, 1981; Needleman & Wunsch, 1970; Pearson & Lipman, 1988; Ausubel et al., 1988; and Sambrook & Russell, 2001.

One example of an algorithm that is suitable for determining percent sequence identity and sequence similarity is the BLAST algorithm, which is described in Altschul et al., 1990. In some embodiments, a percentage of sequence identity refers to sequence identity over the full length of one of the gDNA, cDNA, or the predicted protein sequences in the largest ORF of SEQ ID No: 33 being compared (e.g., the full length of any of SEQ ID NOs. 1-47 respectively). In some embodiments, a calculation to determine a percentage of nucleic acid sequence identity does not include in the calculation any nucleotide positions in which either of the compared nucleic acids includes an "N" (i.e., where any nucleotide could be present at that position).

The term "open reading frame" (ORF) refers to a nucleic acid sequence that encodes a polypeptide. In some embodiments, an ORF comprises a translation initiation codon, a translation termination (i.e., stop) codon, and the nucleic acid sequence there between that encodes the amino acids present in the polypeptide. The terms "initiation codon" and "termination codon" refer to a unit of three adjacent nucleotides ('codon') in a coding sequence that specifies initiation and chain termination, respectively, of protein synthesis (mRNA translation).

As used herein, the terms "phenotype," "phenotypic trait" or "trait" refer to one or more traits of a plant or plant cell. The phenotype can be observable to the naked eye, or by any other means of evaluation known in the art, e.g., microscopy, biochemical analysis, or an electromechanical assay. In some cases, a phenotype is directly controlled by a single gene or genetic locus (i.e., corresponds to a "single gene trait"). In the case of haploid induction use of color markers, such as R Navajo, and other markers including transgenes visualized by the presences and/or absences of color within the seed evidence if the seed is an induced haploid seed. The use of R Navajo as a color marker and the use of transgenes is well known in the art as means to detect induction of haploid seed on the female plant. In other cases, a phenotype is the result of interactions among several genes, which in some embodiments also results from an interaction of the plant and/or plant cell with its environment.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "primer" refers to an oligonucleotide which is capable of annealing to a nucleic acid target (in some embodiments, annealing specifically to a nucleic acid target) allowing a DNA polymerase and/or reverse transcriptase to attach thereto, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, one or more pluralities of primers are employed to amplify plant nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from a vegetative or sexual reproduction from one or more parent plants. In haploid induction the seed on the female parent is haploid, thus not a progeny of the inducing haploid line. The progeny of the haploid seed is what is the desired progeny. There is also the HI seed and subsequent plant and seed progeny of the haploid inducing plant. Both the haploid seed and the HI seed can be progeny. A progeny plant can be obtained by cloning or selfing a single parent plant, or by crossing two or more parental plants. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are specimens produced from selfings, intercrosses, backcrosses, and/or other crosses of $F_1$s, $F_2$s, and the like. An $F_1$ can thus be (and in some embodiments is) a hybrid resulting from a cross between two true breeding parents (i.e., parents that are true-breeding are each homozygous for a trait of interest or an allele thereof), while an $F_2$ can be (and in some embodiments is) a progeny resulting from self-pollination of the $F_1$ hybrids.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer in some embodiments to a meiotic crossover.

As used herein, the term "reference sequence" refers to a defined nucleotide sequence used as a basis for nucleotide sequence comparison. In some embodiments, any of SEQ ID NOs: 1 and 3 can serve as a reference sequence for comparing to other sequences obtained from plants.

As used herein, the term "regenerate", and grammatical variants thereof, refers to the production of a plant from tissue culture.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Sambrook & Russell, 2001. Generally, stringent conditions are selected to be about 5-10° C. lower than the thermal melting point ($T_m$) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "trait" refers to a phenotype of interest, a gene that contributes to a phenotype of interest, as well as a nucleic acid sequence associated with a gene that contributes to a phenotype of interest. For example, a "HI trait" refers to a haploid induction phenotype as well as a gene that contributes to a haploid induction and a nucleic acid sequence (e.g., a HI-associated gene product) that is associated with the presence or absence of the haploid induction phenotype.

As used herein, the term "transgene" refers to a nucleic acid molecule introduced into an organism or one or more of its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

Maize haploid inducer plants produce pollen which when crossed onto non-inducer germplasm results in the gynogenic development of haploid seeds. Unfortunately, this process often yields a low frequency of haploid kernels. Inefficient haploid induction frequency is a limiting factor in maize doubled haploid breeding programs. The present invention identifies a locus that identifies haploid induction in a plant; and a four nucleotide insertion at positions 1230-1233 of SEQ ID NO: 53 the presence or absence of which distinguishes haploid inducer germplasm from non-inducer germplasm. This locus or the presence or absence of the four nucleotide insertion at positions 1230-1233 of SEQ ID NO: 53 can be employed for selecting, and/or introgressing, and/or transforming the haploid inducing trait into plants.

More specifically, the present invention produces new maize haploid-inducing lines. A number of known haploid-inducing maize lines exist including but not limited to: stock 6, MHI (Moldovian Haploid Inducer), indeterminate gametophyte (ig) mutation, KEMS, ZEM, ZMS, KMS, RWS and RWK. The present invention relates to a method of identifying, and/or selecting germplasm which can or cannot induce haploids. The present invention also relates to increasing and further development of the selected haploid inducing germplasm. The invention further relates to a method of improving haploid inducing germplasm to increase the induction of haploids on the seed producing parent.

The initial step in the production of haploid seeds from a hybrid or segregating maternal parent plant derives from the pollination with pollen from a haploid inducer on to the ear from a seed producing plant. A result of this hybridization process is the production of diploid and maternal haploid (1n) kernels. The induced haploid (1n) kernels are often distinguished from the diploid seed by the use of color markers which indicate embryo ploidy. The diploid seeds are generally discarded, while haploid kernels or embryos are often subjected to chromosome doubling processes to produce doubled haploid plants.

More specifically, the haploid genetic material is treated with one or more mitotic arrest agents to allow the haploid (1n) chromosome complement in one or more cells to produce homolog pairs. After the chemical treatment procedure, the chromosome doubling chemical(s) are removed. The now-doubled haploid maize is allowed to mature and the resulting doubled haploid seeds when planted will produce homozygous plants (also called inbred plant or lines). These inbred lines are the materials that breeders utilize to pursue their hybrid development programs.

The locus for the haploid induction trait was fine mapped. Although a major QTL on chromosome 1 responsible for haploid induction has been mapped and published, Dong et al. Theor. Appl. Genet (2013) 126: 1713-1720, the exact gene/genetic element responsible for the induction process has not been identified until now. The haploid induction locus is fine-mapped to be within a small region of 0.60 Mb (between the markers SM2363 (Chromosome 1, 67851018 nt Maize genome assembly version 3) and SM2712 (Chromosome 1, 68453157 nt Maize genome assembly version 3)). By comparing inducer and non-inducer germplasm, it was determined that a four nucleotide insertion present in haploid inducers which shifts the frame for amino acid coding of GRMZM2G471240 is not present in non-inducer germplasm. Therefore, the present invention has identified a gene with a frameshift mutation in inducer germplasm as being responsible for maize haploid induction. The candidate gene corresponding to gene model GRMZM2G471240 encodes a patatin-like phospholipase 2A.

Also notable are several secondary candidate genes identified as GRMZM2G305400, GRMZM2G082836, GRMZM2G382717, GRMZM2G120587, GRMZM2G062320, and GRMZM2G866758 that also may show differences between inducer and non-inducer lines. The secondary candidate genes may themselves be responsible for improved efficiency in HI. Crossing different HI inducers with these secondary candidate genes such as Stock 6 and RWK lines (each of which lack the candidate gene) can unexpectedly increase haploid induction, which may imply other genetic factors are also contributing to the HI trait. However, improved haploid induction germplasm can be difficult to maintain because it also results in significant seed abortion upon self-pollination and thus, makes HI line maintenance difficult.

DNA sequence was generated for each candidate gene from the two inducer lines and one non-inducer line. In addition, the public B73 genome data was used as a second non-inducer line. Gene model information was compared to EST/cDNA data to confirm the structure of each gene. The annotated sequence data were compared to catalog differences between the four alleles of each gene. The notable exceptions included GRMZM2G305400 which is only identified in the B73 genome and GRMZM2G062320 which is only detected in this study in the NIL and B73 genomes. PCR experiments show that it is present in RWK and Stock 6.

The sequence comparisons revealed that B73 and NIL alleles were similar to each other, and RWK and Stock 6 alleles were similar to each other. Most sequence differences were single nucleotide polymorphisms that do not alter protein coding sequence. There were some insertions and some deletions, most of which are in non-protein coding sequence.

The exceptional sequence difference identified by the method used to generate the sequence data is in GRMZM2G471240, which contains a four nucleotide insertion in RWK and Stock 6. GRMZM2G471240 (annotated as a patatin-like phospholipase 2A protein) has a frame-shift mutation in the RWK and Stock6 lines resulting from a four base pair insertion in the fourth (and last) exon. When the nucleotide sequence is translated, the mutation shifts the coding frame by one base pair, changing the amino acid (AA) identity for each codon after the mutation. This results in 20 incorrect AA followed by a new, premature stop codon. The entire protein lesion thus constitutes a 30 AA truncation of the protein from the C-terminus, in addition to 20 AA of incorrect sequence between the mutation and the premature stop codon.

The presently disclosed subject matter provides the isolated nucleic acids, the genomic sequence and the protein sequence, the presence or absence, showed an association with HI, as well as any subsequences and informative fragments therefrom, The presently disclosed subject matter provides isolated cDNA selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 91-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, or SEQ ID NO: 55, or SEQ ID NO: 56, or SEQ ID NO: 57 optionally wherein the percent identity is calculated over the entire length of SEQ ID NO: 54, or SEQ ID NO: 55, or SEQ ID NO: 56, or SEQ ID NO: 57.

Comparisons of an amino acid sequence encoded thereby (i.e., SEQ ID NO: 54, SEQ ID NO: 55, SEQ ID NO: 56 and SEQ ID NO: 57) to sequences present in the GENBANK® biosequence database indicated the following this was a patatin-like phospholipase 2A protein. The table below lists gene identities in the interval shown in the tables below. This information is from chromosome 1, and lists a short description of the other encoded proteins from the genes within the haploid inducing locus.

TABLE SHOWING INFORMATION ON CHROMOSOME 1

| gene_id | transcript_start | transcript_end | Query length | Subject length | Score | Identity | Similarity | Align length | Short_description |
|---|---|---|---|---|---|---|---|---|---|
| GRMZM2G305400 | 67991172 | 67994092 | 308 | 362 | 385 | 33.3 | 53.33752 | 314 | Cyclin D2; 1 |
| GRMZM2G082836 | 68107606 | 68110989 | 202 | 205 | 729 | 71.2 | 83.33333 | 198 | GTP-binding protein 1 |
| GRMZM2G382717 | 68113455 | 68115168 | 396 | 464 | 489 | 38.77 | 53.17371 | 314 | Chaperone DnaJ-domain superfamily protein |
| GRMZM2G120587 | 68133178 | 68136953 | 458 | 461 | 1329 | 55 | 71.23894 | 452 | serine carboxypeptidase-like 51 |
| GRMZM2G471240 | 68240862 | 68242656 | 428 | 407 | 1049 | 51.5 | 72.36181 | 398 | phospholipase A 2A |
| GRMZM2G471240 | 68240862 | 68242656 | 401 | 407 | 961 | 50.15 | 70.0938 | 395 | phospholipase A 2A |
| GRMZM2G062320 | 68318898 | 68321409 | 335 | 334 | 1064 | 73.3 | 84.21053 | 285 | Phosphoglycerate mutase family protein |
| GRMZM5G866758 | 68430654 | 68436197 | 401 | 403 | 1678 | 80.4 | 90.45226 | 398 | acetoacetyl-CoA thiolase 2 |
| GRMZM5G866758 | 68430654 | 68436197 | 303 | 403 | 1248 | 78.4 | 89.40397 | 302 | acetoacetyl-CoA thiolase 2 |
| GRMZM2G003530 | 68435670 | 68439997 | 360 | 344 | 1063 | 60.5 | 76.41791 | 335 | P-loop containing nucleoside triphosphate hydrolases superfamily protein |
| GRMZM2G077991 | 68543246 | 68546264 | 94 | 95 | 424 | 79.7 | 91.48936 | 94 | Zinc-binding ribosomal protein family protein |
| GRMZM2G077991 | 68543694 | 68546264 | 94 | 95 | 424 | 79.7 | 91.48936 | 94 | Zinc-binding ribosomal protein family protein |
| GRMZM2G077991 | 68543805 | 68546269 | 147 | 95 | 419 | 79.5 | 91.39785 | 93 | Zinc-binding ribosomal protein family protein |
| GRMZM2G077960 | 68554980 | 68559182 | 438 | 428 | 1422 | 65.3 | 79.80998 | 421 | Protein phosphatase 2C family protein |
| GRMZM2G077897 | 68561209 | 68565155 | 784 | 807 | 1561 | 48.1 | 65.69848 | 723 | Plant protein of unknown function (DUF827) |
| GRMZM2G347583 | 68660278 | 68665995 | 1651 | 2156 | 1201 | 41.37 | 55.70954 | 1375 | |
| GRMZM2G173030 | 68668900 | 68671460 | 626 | 2156 | 858 | 35.6 | 48.30299 | 586 | |
| GRMZM2G022061 | 68876150 | 68882226 | 203 | 556 | 618 | 64.9 | 79.89691 | 194 | |
| GRMZM2G022061 | 68876150 | 68882226 | 322 | 556 | 1004 | 66 | 77.47748 | 333 | |
| GRMZM2G022061 | 68876150 | 68882226 | 142 | 556 | 547 | 79.6 | 89.84375 | 128 | |
| GRMZM2G022061 | 68876150 | 68882226 | 322 | 556 | 1004 | 66 | 77.47748 | 333 | |
| GRMZM2G022061 | 68876150 | 68882226 | 534 | 556 | 1802 | 67.7 | 79.81651 | 545 | |
| GRMZM2G340286 | 68928213 | 68929600 | 378 | 403 | 570 | 37.83 | 55.75713 | 407 | |
| GRMZM2G340279 | 68934652 | 68937080 | 746 | 937 | 3095 | 29.34 | 50.31745 | 2517 | Tetratricopeptide repeat (TPR)-like superfamily protein |
| GRMZM2G347808 | 69005208 | 69012612 | 589 | 455 | 1115 | 50.4 | 66.60178 | 423 | S-adenosyl-L-methionine-dependent methyltransferases superfamily protein |

RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant miRNAs show extensive base pairing to, and guide cleavage of their target mRNAs (Jones-Rhoades et al. (2006) Annu. Rev. Plant Biol. 57, 19-53; Llave et al. (2002) Proc. Natl. Acad. Sci. USA 97, 13401-13406). In other instances, interfering RNAs may bind to target RNA molecules having imperfect complementarity, causing translational repression without mRNA degradation. The majority of the animal miRNAs studied so far appear to function in this manner.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand. RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 18 to about 25 base pairs, optionally a sequence of about 18 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to molecule that is double stranded for its full length, corresponding in size to a full length target RNA molecule.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, Cell. 116:281-297 (2004); Zhang et al. Dev. Biol. 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. Genes Dev. 16:1616-1626 (2002), Park et al. Curr. Biol. 12:1484-1495 (2002)) many hundreds have been identified. Furthermore, many plant miRNAs have been shown to be highly conserved across very divergent taxa. (Floyd et al. Nature 428:485-486 (2004); Zhang et al. Plant J. 46:243-259 (2006)). Many microRNA genes (MIR genes) have been identified and made publicly available in a data base (miRBase; microrna.sanger.ac.uk/sequences). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme. Dicer, releasing a miRNA/miRNA* duplex of about 22 nt in size. In contrast to animals, in plants, the processing of pri-miRNAs into mature miRNAs occurs entirely in the nucleus using a single RNaseIII enzyme. DCL1 (Dicer-like 1). (Zhu. Proc. Natl. Acad. Sci. 105:9851-9852 (2008)). Many reviews on microRNA biogenesis and function are available, for example, see. Bartel Cell 116:281-297 (2004). Murchison et al. Curr. Opin. Cell Biol. 16:223-229 (2004), Dugas et al. Curr. Opin. Plant Biol. 7:512-520 (2004) and Kim Nature Rev. Mol. Cell Biol. 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA. The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that or a non-native, heterologous miRNA (amiRNA/amiRNA*; e.g. siRNA/siRNA*) that is then processed into the mature miRNA sequence with the siRNA sequence.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," as used herein, refer to the natural binding of polynucleotides under permissive salt and temperature conditions by basepairing. Complementarity between two single-stranded molecules may be "partial." in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary mean that two nucleic acid sequences are complementary at least a bout 50%. 60%, 70%, 80% or 90% of their nucleotides. In some embodiments, the two nucleic acid sequences can be complementary at least at 85%. 90%, 95%, 96%. 97%, 98%, 99% or more of their nucleotides. The terms "substantially complementary" and "partially complementary" can also mean that two nucleic acid sequences can hybridize under high stringency conditions and such conditions are well known in the art In some embodiments, the dsRNA molecule can comprise, consist essentially of or consist of from at least 18 to a bout 25 consecutive nucleotides (e.g. 18, 19, 20, 21, 22, 23, 24 or 25) to at least about 400 consecutive nucleotides. In some embodiments the dsRNA molecule can comprise, consist essentially of or consist of about 500, or about 50 or about 543 consecutive nucleotides. Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the portion of the mRNA polynucleotide transcribable from a GRMZM2G471240 gene that the antisense strand is complementary to comprises at least 18 consecutive nucleotides of SEQ ID NO:33, SEQ ID NO:37. SEQ ID NO:52 or SEQ ID NO:53. In other embodiments, the portion of mRNA comprises, consists essentially of or consists of at least from 19, 20 or 21 consecutive nucleotides to at least 400 consecutive nucleotides of SEQ ID NO:33, SEQ ID NO:37. SEQ ID NO:52 or SEQ ID NO:53. In other embodiments, the portion of mRNA comprises, consists essentially of or consists of at least about 500, or at least about 98 or at least about 185 consecutive nucleotides of SEQ ID NO:33.

In other embodiments, the portion of the mRNA polynucleotide that is complementary to the antisense strand of a dsRNA of the invention comprises any 19-mer subsequence of SEQ ID NO:33 (GRMZM2G471240) consisting of N to N+18 nucleotides, wherein N is nucleotide 1 to 1452 of SEQ ID NO:33. In other words, the portion of the mRNA that is targeted comprises any of the 1452 19 consecutive nucleotide subsequences (i.e. 19-mer) of SEQ ID NO:33, for example, bases 1-19 (5'-AGTCATCACTAATCACAC-3'), bases 2-20 (5'-GTCATCACTAATCACACT-3'), bases 3-21 (5'-TTCATCACTAATCACACTT-3') and so forth to bases 1434-1452 (5'-AAAACATAAAAATATATAT-3').

In other embodiments, the nucleotide sequence of the antisense strand can consist essentially of the nucleotide sequence of any 19-mer subsequence of SEQ ID NO:62 consisting of N to N+18 nucleotides, wherein N is nucleotide 1 to nucleotide 1452 of SEQ ID NO:62. In other words, the antisense strand consists essentially of the nucleotide sequence of any of the 1452 19 consecutive nucleotide subsequences (i.e. 19-mer) of SEQ ID NO:62, for example, bases 1-19 (5'-ATATATATTTTTATGTTT-3'), bases 2-20 (5'-TATATATTTTTATGTTTTA-3'), bases 3-21 (5'-ATAT-ATTTTTATGTTTTAT-3') and so forth to bases 1434-1452 (5'-GTGTGATAGTGATGAACT-3').

It would be understood that the deletion of the one nucleotide or the addition of up to six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3; end may be present, which is used to stabilize the siRNA duplex and does not affect the specificity of the siRNA.

In some embodiments of this invention, the antisense strand of the double stranded RNA molecule can be fully complementary to the target RNA polynucleotide or the antisense strand can be substantially complementary or partially complementary to the target RNA polynucleotide. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allelel" Acta Pharmacol. Sin. 29:211-216 (2008): Schwarz et al. "Asymmetry in the assembly of the RNAi enzyme complex" Cell 115:199-208 (2003)). Other such mismatches can be introduced into the antisense strand due to eliminating fortuitous open reading frames created in making dsRNA encoding expression cassettes. Such open reading frames are eliminated by making point mutations in the dsRNA encoding nucleotide sequence thus creating some mismatches in the dsRNA compared to the target gene. In some embodiments of this invention, the dsRNA molecule of the invention is a short hairpin RNA (shRNA) molecule. Expression of shRNA in cells is typically accomplished by delivery of plasmids or recombinant vectors, for example in transgenic plants such as transgenic corn.

The invention encompasses a nucleic acid molecule encoding at least one strand of a dsRNA molecule of the invention. The invention further encompasses a nucleic acid construct comprising at least one strand of a dsRNA molecule of the invention or comprising the nucleic acid molecule encoding the at least one strand of a dsRNA molecule of the invention. In one embodiment of the invention, the nucleic acid molecule encodes a short hairpin RNA. In another embodiment, the nucleic acid molecule that encodes the short hairpin RNA comprises SEQ ID NO:62 or SEQ ID NO:63

The invention further encompasses chimeric nucleic acid molecules comprising an antisense strand of a dsRNA of the invention operably linked with a plant microRNA precursor molecule. In some embodiments, the chimeric nucleic acid molecule comprises an antisense strand having the nucleotide sequence of any of the 19-mer subsequences of SEQ ID NO:33. SEQ ID NO:37. SEQ ID NO:52 or SEQ ID NO:53 operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA molecule of the invention. In other embodiments, the artificial plant microRNA precursor molecule comprises an antisense strand having the nucleotide sequence of any of the 19-mer subsequences of SEQ ID NO:62, or SEQ ID NO:63. The use of artificial plant microRNAs to deliver a nucleotide sequence of interest (e.g an artificial miRNA; siRNA/siRNA*) into a plant is known in the art (see, e.g., Schwab et al. 2006. The Plant Cell 18:1121-1133 and Examples section herein). In the invention, the artificial microRNAs are chimeric or hybrid molecules, having a plant microRNA precursor backbone and an insect (i.e. animal) siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Nonlimiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses nucleic acid constructs, nucleic acid molecules or recombinant vectors comprising at least one strand of a dsRNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

In some embodiments, the invention encompasses compositions comprising two or more dsRNA molecules of the invention wherein the two or more RNA molecules each comprise a different antisense strand. In some embodiments the two or more dsRNA molecules are present on the same nucleic acid construct, on different nucleic acid constructs or any combination thereof. In other embodiments, the composition comprises an RNA molecule comprising an antisense strand consisting essentially of the nucleotide sequence of SEQ ID NO:62 and an RNA molecule comprising an antisense strand consisting essentially of the nucleotide sequence of SEQ ID NO:63. In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

RNA interference (RNAi) can be used to produce genetically modified plants that are tolerant or resistant to abiotic and biotic stresses. In the past decade, RNAi has been described and characterized in organisms as diverse as plants, fungi, nematodes, hydra, and humans. Zamore and Haley (2005) Science 309, 1519-24. RNA interference in plants is commonly referred to as post-transcriptional gene silencing or RNA silencing and is referred to as quelling in fungi. The process of post-transcriptional gene silencing is thought to be an evolutionarily conserved cellular defense mechanism used to prevent the expression of foreign genes and is commonly shared by diverse flora and phyla. Fire (1999) Trends Genet. 15, 358-363.

RNA interference occurs when an organism recognizes double-stranded RNA molecules and hydrolyzes them. The resulting hydrolysis products are small RNA fragments of 19-24 nucleotides in length, called small interfering RNAs (siRNAs) or microRNAs (miRNAs). The siRNAs then diffuse or are carried throughout the organism, including across cellular membranes, where they hybridize to mRNAs (or other RNAs) and cause hydrolysis of the RNA. Most plant miRNAs show extensive base pairing to, and guide cleavage of their target mRNAs. Jones-Rhoades et al. (2006) Annu. Rev. Plant Biol 57, 19-53; Llave et al. (2002) Proc. Natl. Acad. Sci. USA 97, 13401-10406. In other instances, interfering RNAs may bind to target RNA molecules having imperfect complementarity, causing translational repression without mRNA degradation.

The mode of action for silencing a plant gene generally includes a double stranded RNA (dsRNA) that associates with a dicer enzyme that cuts the dsRNA into ds fragments 19-24 bps in length (siRNA). There may be more than one dicer enzyme, depending on the organism. Meister and Tuschl, 2004). The siRNA is typically degraded into two single stranded RNAs (ssRNAs), referred to as the passenger strand and the guide strand. A RNA-interference silencing complex (RISC complex) loads the guide strand. The RISC complex associates with a target mRNA that has partial or complete homology to the guide strand. The catalytic RISC component agronaute causes cleavage of the target mRNA preventing it from being used as a translation template. Ahlquist P (2002) RNA-dependent RNA polymerases, viruses, and RNA silencing, Science 296 (5571): 1270-3. The RNAi pathway is exploited in plants by using recombinant technology, which entails transforming a plant with a vector comprising DNA that when expressed produces a dsRNA homologous or nearly homologous to a gene target. The gene target can be homologous to a endogenous plant gene or an insect gene. If the target is an insect gene, the insect eats the plant thereby ingesting the dsRNA, at which the RNAi RISC complex of the insect causes cleavage and targeting of the homologous mRNA, causing disruption of a vital insect process.

To date, plant recombinant technology is the vehicle for delivering gene silencing of target genes, either endogenous plant target genes or target genes of a plant pest organism. In general, a plant is transformed with DNA that is incorporated into the plant genome, and when expressed produces a dsRNA that is complementary to a gene of interest, which can be an endogenous plant gene or an essential gene of a plant pest. Plant recombination techniques to generate transgene and beneficial plant traits require significant investments in research and development, and pose significant regulatory hurdles. Methods and formulations for delivering dsRNA into plant cells by exogenous application to exterior portions of the plant, such as leaf, stem, and/or root surfaces for regulation of endogenous gene expression are not known in the art. Such methods and formulations represent a significant development for gene silencing technology. Known methods for delivering exogenous dsRNA into plant cells are via particle bombardment or viral RNA infection through wounding the plant tissue (e.g. tobacco and rice leaf tissues). Application by spray or brush of RNA molecules, or other non-tissue evasive techniques, resulting in assimilation of the exogenous RNA molecules into plant tissue, thereby causing endogenous and/or pest gene silencing, has not been reported.

The present invention is directed to methods and formulations to incorporate exogenous RNA, by application to external tissue surface(s) of plants, into the plant cells causing silencing of plant endogenous target gene(s) or of the target genes of plant pests.

The present invention is not directed to any particular RNAi mechanism or mode of action of gene silencing, and should not be construed as limited to any such mechanisms, known or unknown.

The terms "silencing" and "suppression" are used interchangeably to generally describe substantial and measurable reductions of the amount of the target mRNA available in the cell for binding and decoding by ribosomes. The transcribed RNA can be in the sense orientation to effect what is referred to as co-suppression, in the anti-sense orientation to effect what is referred to as anti-sense suppression, or in both orientations producing a double-stranded RNA to effect what is referred to as RNA interference. A "silenced" gene includes within its definition a gene that is subject to silencing or suppression of the mRNA encoded by the gene.

MicroRNAs are encoded by genes that are transcribed but not translated into protein (non-coding DNA), although some miRNAs are encoded by sequences that overlap protein-coding genes. By way of background, miRNAs are processed from primary transcripts known as pri-miRNAs to short stem loop structures called pre-miRNAs that are further processed by action of dicer enzyme(s) creating functional siRNAs/miRNAs. Typically, a portion of the precursor miRNA is cleaved to produce the final miRNA molecule. The stem-loop structures may range from, for example, about 50 to about 80 nucleotides, or about 60 nucleotides to about 70 nucleotides (including the miRNA residues, those pairing to the miRNA, and any intervening segments). The secondary structure of the stem-loop structure is not fully base-paired; mismatches, bulges, internal loops, non-WatsonCrick base pairs (i.e., G-U wobble base pairs), and other features are frequently observed in pre-miRNAs and such characteristics are thought to be important for processing. Mature miRNA molecules are partially complementary to one or more mRNA molecules, and they function to regulate gene expression, siRNAs of the present invention have structural and functional properties of endogenous miRNAs (e.g., gene silencing and suppressive functions). Thus, in various aspects of the invention, siRNAs of the invention can derived from miRNAs, from target gene sequence information, or can be produced synthetically based on predictive models known in the art. The phrases "target-specific small interfering RNAs," "target-specific siRNAs," "target-specific microRNAs," "target-specific miRNAs," "target-specific amiRNAs," and "target-specific nucleotide sequence" refer to interfering RNAs that have been designed to selectively hybridize with nucleic acids in a target organism, but not in a non-target organism, such as a host organism (the organism expressing or producing the miRNA) or a consumer of the host organism. Consequently, "target-specific siRNAs" only produce phenotypes in target organisms and do not produce phenotypes in non-target organisms. In the present invention, the target-specific siRNAs selectively hybridize to nucleic acids that are endogenous to the host organism, which are plants. MicroRNAs (miRNAs) are non-protein coding RNAs, generally of between about 19 to about 25 nucleotides (commonly about 20-24 nucleotides in plants). miRNAs direct cleavage in trans of target transcripts, regulating the expression of genes involved in various regulation and development pathways (Bartel. Cell. 116:281-297 (2004); Zhang et al. Dev. Biol. 289:3-16 (2006)). miRNAs have been shown to be involved in different aspects of plant growth and development as well as in signal transduction and protein degradation. In addition, growing evidence indicates that small endogenous mRNAs including miRNAs may also be involved in biotic stress responses such as parasite attack. Since the first miRNAs were discovered in plants (Reinhart et al. Genes Dev. 16:1616-1626 (2002), Park et al. Curr. Biol. 12:1484-1495 (2002)), many hundreds have been identified. Further, many plant miRNAs have been shown to be highly conserved across very divergent taxa. (Floyd et al. Nature 428:485-486 (2004); Zhang et al. Plant J. 46:243-259 (2006)). Many microRNA genes (MIR genes) have been identified and made publicly available in a database ("miRBase," available on line at microrna.sanger.ac.uk/sequences). miRNAs are also described in U.S. Patent Publications 2005/0120415 and 2005/144669A1, the entire contents of which are incorporated by reference herein.

Further encompassed within the presently disclosed subject matter are expression cassettes according to the embodiments of the presently disclosed subject matter as well as expression vectors comprising the same. Also encompassed are plant cells comprising expression cassettes according to the present disclosure, and plants comprising these plant cells. In some embodiments, the plant is a dicot. In some embodiments, the plant is a monocot. In some embodiments, the monocot is a cereal. The plant can be, for example, rice, maize, grass, wheat, maize, barley, brome, oats, rye, millet, sorghum, triticale, secale, einkorn, spelt, emmer, teff, milo, flax, gramma grass, Tripsacum, or teosinte.

Thus, the compositions of the presently disclosed subject matter can comprise nucleic acid sequences for transformation and expression in a plant of interest. The expression is of the primary candidate gene and HI trait is desired the expression may also be for down regulated expression or induced expression in some or all of the female portion of the plant and no expression in the male flowering plant parts. The nucleic acid sequences can be present in DNA constructs or expression cassettes. "Expression cassette" as used herein means a nucleic acid molecule capable of directing expression of a particular nucleotide sequence, or iRNA in an appropriate host cell, comprising a promoter operatively linked to the sequence of interest (e.g., a sequence encoding a gene product or iRNA associated with HI) which is optionally also operatively linked to termination signals. It also typically comprises sequences required for proper translation of the nucleotide sequence. The coding region usually codes for a protein of interest but can also code for a functional RNA of interest, for example antisense RNA or a nontranslated RNA such as, but not limited to a siRNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, the expression cassette is heterologous with respect to the host (i.e., the particular DNA sequence of the expression cassette, or a subsequence thereof, does not occur naturally in the host cell and must have been introduced into the host cell or an ancestor of the host cell by a transformation event). The expression of the nucleotide sequence in the expression cassette can be under the control of a constitutive promoter, a tissue specific promoter, and/or an inducible promoter that initiates transcription only when the host cell is exposed to some particular external stimulus, a minimal promoter, etc. Additionally, the promoter can also be specific to a particular cell type, tissue, organ, and/or stage of development. In some embodiments, an expression cassette is present in a vector that permits replication of the expression cassette in a host cell.

The present presently disclosed subject matter encompasses the transformation of plants with expression cassettes capable of expressing a polynucleotide of interest (e.g., a polynucleotide encoding a gene product or iRNA associated with HI) alone or in combination with one or more additional nucleic acid molecules encoding polypeptides that confer desirable traits. However, if the polynucleotide is the primary gene, GRMZM2G062320, it maybe preferred that the cassette is adapted to down regulate or knock out the gene in nonhaploid inducing material. Or expressed in an inducible matter so that the pollen used to self the HI plant is expressing the gene product that occurs in B73 and other non haploid inducing material. In some embodiments, the expression cassette includes at least the following basic elements oriented in the 5'-3' direction of transcription: a transcriptional and translational initiation region (i.e., a promoter) and a polynucleotide of interest. The expression cassette can optionally comprise a transcriptional and translational termination region (e.g., termination region) functional in plants. In some embodiments, the expression cassette comprises a selectable marker gene to allow for selection for stable transformants.

In some embodiments, the regulatory sequences of the expression construct are operably linked to the polynucleotide of interest. By "operably linked" is intended a functional linkage between a first sequence (e.g., a promoter) and a second sequence (e.g., a coding sequence), wherein the first sequence influences a biological event (e.g., transcription, transcription, replication, etc.) that occurs with respect to the second sequence. Generally, operably linked means that the nucleotide sequences being linked are contiguous in a single molecule.

Any promoter capable of driving expression in the plant of interest can be used in the practice of the presently disclosed subject matter. In some embodiments, the expression cassette is expressed throughout the plant. In some embodiments, the expression cassette is expressed in a specific location and/or tissue of a plant, or at a certain time during the development of the plant. In some embodiments, the location and/or tissue includes, but is not limited to, anther, ovule, plastid, pollen, mitochondrion, chloroplast, epidermis, root, vascular tissue, meristem, cambium, cortex, pith, leaf, flower, and combinations thereof. In another embodiment, the location and/or tissue is a seed.

The promoter can be native or analogous, or can be heterologous or exogenous, to the plant or plant cell in which it is intended to be active. The terms "heterologous" and "exogenous" when used herein to refer to a nucleic acid sequence (e.g., a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, in some embodiments the terms refer to a DNA segment that is foreign or heterologous to the cell, or homologous to the cell but in a position within the host cell nucleic acid in which the element is not ordinarily found. In some embodiments, an exogenous DNA segment is expressed to yield an exogenous polypeptide in a cell or tissue type of interest. In some embodiments, a heterologous or exogenous nucleic acid is referred to herein as a transgene.

A "homologous" nucleic acid (e.g., DNA) sequence is a nucleic acid (e.g., DNA or RNA) sequence that is naturally associated with a host cell into which it is introduced. As such, and by way of example and not limitation, a nucleic acid that is derived from (i.e., isolated from with or without subsequent modification) a plant cell or tissue could be considered a homologous nucleic acid when reintroduced into a plant cell or tissue of the same species, but could be considered heterologous or exogenous when introduced into a cell or tissue of a plant other than the plant species from which it was derived. In some embodiments, a homologous nucleic acid can also be referred to herein as a heterologous or a transgene when the homologous nucleic acid is operatively linked to a nucleotide sequence to which it is not naturally operatively linked.

The choice of promoters to be included depends in some embodiments upon several factors, including, but not limited to, efficiency, selectability, inducibility, desired expression level, and/or cell- or tissue-preferential and/or -specific expression. It is a routine matter for one of skill in the art to modulate the expression of a sequence by appropriately selecting and positioning promoters and other regulatory regions relative to that sequence. The promoters that are used for expression of the transgene(s) can be in some embodiments a strong plant promoter, in some embodiments a viral promoter, and in some embodiments a chimeric promoter comprising such basic transcriptional regulatory elements such as but not limited to a TATA box from any gene (or synthetic, based on analysis of plant gene TATA boxes), optionally fused to the region 5' to the TATA box of plant promoters (which direct tissue and temporally appropriate gene expression), optionally fused to one or more enhancers (such as the 35S enhancer, FMV enhancer, CMP enhancer, etc.).

For example, the selection of the promoter used in expression cassettes can determine the spatial and temporal expression pattern of the transgene in the transgenic plant. Selected promoters can express transgenes in specific cell types and/or in specific tissues or organs, and the selection can reflect the desired location for accumulation of the gene product. Alternatively, the selected promoter can drive expression of the gene under various inducing conditions. Promoters vary in their strength; i.e., their abilities to promote transcription. Depending upon the host cell system utilized, any one of a number of suitable promoters can be used, including the gene's native promoter. The following are non-limiting examples of promoters that can be used in expression cassettes.

Promoters which are directing expression of the gene are referred to herein as "constitutive" promoters and are active under most environmental conditions and states of development or cell differentiation. Examples of constitutive promoters include the 1'- or 2'-promoter derived from T-DNA of *Agrobacterium tumefaciens*, and other transcription initiation regions from various plant genes known to those of ordinary skill in the art. Such genes include, but are not limited to, the inducible promoters of AP2 gene; ACTII from *Arabidopsis* (Huang et al., 1996); Cat3 from *Arabidopsis* (GENBANK® Accession No. U43147; Zhong et al., 1996); the gene encoding stearoyl-acyl carrier protein desaturase from *Brassica napus* (GENBANK® Accession No. X74782; Solocombe et al., 1994); GPc1 from maize (GENBANK® Accession No. X15596; Martinez et al., 1989); and Gpc2 from maize (GENBANK® Accession No. U45855; Manjunath et al., 1997). Additional non-limiting examples of constitutive promoters include, for example, the core promoter of the Rsyn7 promoter and other constitutive promoters disclosed in PCT International Patent Application Publication No. WO 1999/43838 and U.S. Pat. No. 6,072, 050; various ubiquitin promoters (see e.g., U.S. Pat. Nos. 5,641,876 and 8,168,859; Christensen et al., 1989; Christensen et al., 1992; Wei et al., 2003; Lu et al., 2008); the core CaMV 35S promoter (Odell et al., 1985; Benfey & Chua, 1990); the CaMV 19S promoter; the figwort mosaic virus (FMV) promoter; the rice actin-1 promoter (McElroy et al., 1990); the rice alpha tubulin (tubA1) promoter (Fiume et al., 2004); pEMU (Last et al., 1991); the Cestrum yellow leaf curling virus (CmYLCV) CMP promoter (Hohn et al., 2007; U.S. Pat. No. 7,166,770); the MAS promoter (Velten et al., 1984); the Super MAS promoter (Ni et al., 1995; Lee et al., 2007); the ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

The present invention shows a frame shift mutation in GRMZM2G471240 in the Haploid inducing material, thus RNAi silencing of GRMZM2G471240 will create a HI line. The silencing can be accomplished in numerous ways including expression of a hairpin or artificial mircoRNA to target GRMZM2G471240. The down regulated expression transformants will allow various types of germplasm to act as HI lines.

It should also be possible to compensate the defect in a HI line. Transgenic material with the non-haploid inducing sequence when expressed (SEQ ID NO: 33) should if joined with an inducible promoter make the HI line switchable between being a HI line and a non-HI line. Therefore, transformation methods, cassettes, vectors and transgenic plant with the non-HI sequence are described herein.

Appropriate plant or chimeric promoters are useful for applications such as expression of transgenes and/or other heterologous or homologous nucleic acids in certain tissues, while minimizing expression (including but not limited to a level of expression that is below detection using routine techniques) in other tissues, in some embodiments such as but not limited to seeds and/or female reproductive tissues. In some embodiments, expression of a nucleic acid designed to silence a gene product associated with HI of the current presently disclosed subject matter can optionally be localized to seed, or fruit tissues and preferably no expression in the anther or pollen or very downregulated expression if this gene product is present at all in the anther or pollen. The data suggests that expression of the expression is most likely important in early reproductive structures, particularly female structures. Exemplary cell type- or tissue-preferential (in some embodiments, tissue-specific) promoters drive expression preferentially (or in some embodiments essentially specifically) in the target tissue, but can also lead to some expression in other cell types or tissues as well. Methods for identifying and characterizing promoter regions in plant genomic DNA include, for example, those described in the following references: Green et al., 1988; Bustos et al., 1989; Jordano et al., 1989; Meier et al., 1991; and Zhang et al., 1996.

Alternatively, the plant promoter can direct expression of the nucleic acid molecules of the presently disclosed subject matter in a specific tissue or can be otherwise under more precise environmental or developmental control. Examples of environmental conditions that can effect transcription by inducible promoters include anaerobic conditions, elevated temperature, or the presence of light. Such promoters are referred to herein as "inducible", "cell type-specific", or "tissue-specific" promoters. Those of ordinary skill in the art will recognize that a tissue-specific promoter can drive expression of operatively linked sequences in tissues other than the target tissue. Thus, as used herein a "tissue-specific" promoter is one that drives expression preferentially in the target tissue, but can also lead to some expression in other tissues as well.

Examples of promoters under developmental control include promoters that initiate transcription preferentially or exclusively in certain tissues, such as pollen, anthers, fruit, seeds, or flowers. Promoters that direct expression of nucleic acids in pollen, anthers, and the like and possibly in ovules, flowers, or seeds are particularly useful in the presently disclosed subject matter. As used herein a seed-specific promoters are active in cells destined to produce the ovule and tend to direct expression specifically or preferentially in the seed tissues. And reproduction specific promoters are promoters that are active in cells destined to produce the male parts such as the anther, pollen and microspores and the female parts such as the ovule, silks, embryo, and seed. And male Reproductive specific promoters are promoters that are active in cells destined to produce the male parts like pollen.

Seed specific promoters can be, for example, ovule-specific, embryo-specific, endosperm-specific, integument-specific, seed coat-specific, or some combination thereof. Examples include a promoter from the ovule-specific BEL1 gene described in Reiser et al., 1995 (GENBANK® Accession No. U39944). Non-limiting examples of seed specific promoters are derived from the following genes: MAC1 from maize (Sheridan et al., 1996); Cat3 from maize (GENBANK® Accession No. L05934; Abler et al., 1993); the gene encoding oleosin 18 kD from maize (GENBANK® Accession No. J05212; Lee & Huang, 1994); vivparous-1 from *Arabidopsis* (GENBANK® Accession No. U93215); the gene encoding oleosin from *Arabidopsis* (GENBANK® Accession No. Z17657); Atmycl from *Arabidopsis* (Urao et al., 1996); the 2s seed storage protein gene family from *Arabidopsis* (Conceicao et al., 1994); the gene encoding oleosin 20 kD from *Brassica napus* (GENBANK® Accession No. M63985); napA from *Brassica napus* (GENBANK® Accession No. J02798; Josefsson et al., 1987); the napin gene family from *Brassica napus* (Sjodahl et al., 1995); the gene encoding the 2S storage protein from *Brassica napus* (Dasgupta et al., 1993); the genes encoding oleosin A (GENBANK® Accession No. U09118) and oleosin B (GENBANK® Accession No. U09119) from soybean; and the gene encoding low molecular weight sulfur rich protein from soybean (Choi et al., 1995). Additional cell type- and/or tissue-specific promoters include, but are not limited to the *Triticum aestivum* pistil specific P19 promoter (see Japanese Patent Application JP 2001512988-A/13); the maize silk promoter prB200 (see Japanese Patent Application JP 001512988-A/13), the maize prCDPK-01 and prCDPK-02 promoters (Estruch et al., 1994); the rice α-N-acetylglucosaminidase (prOsANG) promoter (U.S. Pat. No. 7,550,578); the rice MADS box gene promoters prOsMADS1, prOsMADS2, prOsMADS6, prOsMADS7, prOsMADS14; and prOsMADS16 (U.S. Patent Application Publication Nos. 2007/0006344, 2010/0205692 A1, and 2012/0021506 A1); the rice anther-specific promoter prRA8 (see Japanese Patent Application JP 2001512988-A/13); the rice prOsG6 promoter (Tsuchiya et al., 1994); the whole seed-specific promoter disclosed in U.S. Patent Application Publication No. 2012/0036595; and the endosperm promoter disclosed in U.S. Patent Application Publication No. 2012/0036593.

Additional promoters that can be employed with the presently disclosed subject matter include, but are not limited to those described in U.S. Pat. No. 7,151,201; the PsEND1 promoter described in Roque et al., 2007; the corn stamen-specific promoters described in PCT International Patent Application Publication No. WO 1992/013957; and the APETALA3 promoter described in U.S. Pat. No. 7,253,340.

In some embodiments, an inducible promoter might be desired. Inducible promoters drive transcription in response to external stimuli such as chemical agents or environmental stimuli. For example, inducible promoters can confer transcription in response to hormones such as gibberellic acid or ethylene, or in response to light, heat or drought.

In some embodiments, an expression construct further comprises a transcription terminator operably linked to the nucleic acid of interest. These are responsible for the termination of transcription beyond the transgene and/or correct mRNA polyadenylation. A variety of transcriptional terminators are available for use in expression cassettes. The termination region can be native with respect to the transcriptional initiation region/promoter (i.e., the promoter and transcription terminator can be derived from the same genetic locus), can be native with the operably linked DNA sequence of interest, can be native with the plant host, and/or can be derived from another source (e.g., can be foreign or heterologous to the promoter, the DNA sequence of interest, the plant host, or any combination thereof). Exemplary transcriptional terminators are those that are known to function in plants and include the CAMV 35S terminator, the tml terminator, the nopaline synthase (Nos) terminator, and the pea rbcs E9 terminator. These can be used in both monocotyledons and dicotyledons. In addition, a gene's native transcription terminator can be used.

In some embodiments, an expression cassette comprises a selectable marker gene for the selection of transformed cells.

Additionally, various sequences have been found to enhance gene expression from within the transcriptional unit, and in some embodiments these sequences are used in conjunction with the nucleic acids of the presently disclosed subject matter to increase their expression in transgenic plants. For example, certain intron sequences have been shown to enhance expression, particularly in monocotyledonous cells. For example, the introns of the maize Adh1 gene have been found to significantly enhance the expression of the wild type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronze 1 gene had a similar effect in enhancing expression of an operably linked nucleic acid sequence. Intron sequences have been routinely incorporated into plant transformation vectors, typically within the non-translated leader.

Expression constructs of the presently disclosed subject matter can also comprise a leader sequence and/or a sequence allowing for inducible expression of the polynucleotide of interest. See e.g., Guo et al., 2003; Chen et al., 2003 for examples of sequences allowing for inducible expression.

A number of non-translated leader sequences derived from viruses are also known to enhance expression of operably linked nucleic acid sequences, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (see e.g., Gallie et al., 1987; Skuzeski et al., 1990). Other leader sequences known in the art include, but are not limited to, picornavirus leaders (e.g., the EMCV leader (the encephalomyocarditis 5'-noncoding region); Elroy-Stein et al., 1989); potyvirus leaders (e.g., the Tobacco Etch Virus (TEV) leader; Allison et al., 1986); the Maize Dwarf Mosaic Virus (MDMV) leader (see GENBANK® Accession No. NC_003377); the human immunoglobulin heavy-chain binding protein (BiP) leader (Macejak & Samow, 1991); the untranslated leader from the coat protein mRNA of alfalfa mosaic virus (AMV RNA 4; Jobling & Gehrke, 1987); the tobacco mosaic virus leader (TMV) leader (Gallie et al., 1989); and the Maize Chlorotic Mottle Virus (MCMV) leader (Lommel et al., 1991). See also, Della-Cioppa et al., 1987.

Alternatively or in addition, an expression construct of the present invention can include a presequence that directs the localization polypeptide encoded by the expression construct to an organelle within a plant cell. A nucleotide sequence encoding a presequence can be introduced in frame at the 5' end of a coding sequence in order to target the polypeptide encoded by the presequence/coding sequence hybrid to the target area. In some embodiments, the coding sequence encodes a subsequence or the entire sequence set forth in SEQ ID NO: 54. In some embodiments 454 amino acids of SEQ ID NO: 54 or a subsequence thereof that comprised amino acids non HI trait or less consecutive amino acids or more consecutive amino acids or an amino acid sequence that is 95% identical thereto can be fused to any presequence using standard molecular cloning techniques.

The transformation of non HI; or HI germplasm can include transformants in monocots and dicots which may be for example orthologs. Species that have orthologues to this sequence can readily be employed in the transformation process these include but are not limited to the species: sorghum bicolor, maize, wheat, millet, *Setaria Italica*, *Oryza brachyantha*, *Oryza indica*, *Oryza glaberrima*, *Hordeum vulgare*, *Oryza sativa*, *Solanum lycopersicum* (tomato), and brachypodium distachyon.

In some embodiments, the presently disclosed subject matter provides markers for detecting and/or assaying for the presence or absence of gene products associated with HI in a plant cell or other source of biomolecules. In some embodiments, a marker is intended to detect the presence of a nucleic acid molecule that includes the deletion junction where the maize HI sequences show an insertion in the sequence in SEQ ID NO. 53 to allow for the specific detection of the presence or absence of a chimeric nucleic acid comprising SEQ ID NO: 33, SEQ ID NO: 37, SEQ ID NO: 52 or SEQ ID NO: 53 in a sample. The number of nucleotides 5' and/or 3' of the deletion junction that allow for specific detection of the presence of absence of a chimeric nucleic acid comprising SEQ ID NO: 53 in a sample can vary based on the identification method employed, but can be in some embodiments at least about 5 nucleotides, in some embodiments at least about 10 nucleotides, in some embodiments at least about 15 nucleotides, in some embodiments at least about 20 nucleotides, in some embodiments at least about 25 nucleotides, and in some embodiments at least about 50 nucleotides 5' and/or 3' to the insertion junction on either side of nucleotides 1230-1233 in SEQ ID NO: 53 should have fit within the HI Locus and does appear in the nonHI locus at this position. In some embodiments, an informative fragment of SEQ ID NO: 33, SEQ ID NO: 37, SEQ ID NO: 52 or SEQ ID NO: 53 can be a marker as defined herein below. A marker which tracks the lesion which causes the phenotype will be superior to any marker which is merely linked because the marker to the causative lesion will never disassociate from the phenotype. Linked markers can and become disassociated by a recombination event.

The presently disclosed subject matter also provides reagents for use in detecting and/or assaying for the presence of gene products associated with HI in a plant cell or other source of biomolecules. Such reagents can include in some embodiments an amplification primer pair capable of amplifying a plant nucleic acid template to generate a marker amplicon, wherein the marker amplicon corresponds to a marker comprising an informative subsequence of SEQ ID NO: 33, SEQ ID NO: 37, SEQ ID NO: 52 or SEQ ID NO: 53, wherein the informative subsequence permits identification of the presence or absence of an allele associated with HI in a plant. By way of example and not limitation, such a amplification primer pair can be designed with a forward primer that is located 5' to the fusion junction and a reverse primer that is located 3' to the fusion junction present in SEQ ID NO: 53. Such an amplification primer pair would not be expected to amplify a gene product derived from a wildtype maize non HI locus.

In some embodiments, one or more amplification primer pairs of the presently disclosed subject matter are provided in the form of a kit, wherein the kit further comprises one or more positive and/or negative amplification primer pairs (such as but not limited to an amplification primer pair designed to amplify a wild type (HI) gene product), instructions for employing the amplification primer pairs, and/or one or more additional reagents necessary for performing an amplification reaction (e.g., a DNA polymerase, a reverse transcriptase, a buffer solution, etc.).

Thus, in some embodiments, a method for detecting and/or assaying for the presence of gene products associated with HI in a plant cell or other source of biomolecules can employ the polymerase chain reaction (PCR) using appropriately designed primers to detect the presence in a plant cell or other source of biomolecules of a gene product associated with HI (including, but not limited to a gene product comprising SEQ ID NO: 33, SEQ ID NO: 37, SEQ ID NO: 52 or SEQ ID NO: 53 or an informative fragment thereof. It is understood that other molecular biological techniques can also be employed for this purpose including, but not limited to TAQMAN® assays, KASPAR™ assays, ILLUMINA® GOLDENGATE® assays, etc.

In some embodiments, the presently disclosed subject matter provides methods for diagnostic determination of whether a plant having such DNA will or will not exhibit HI and/or producing plants that exhibit HI. In some embodiments, the methods comprise (a) transforming a plant cell with an expression cassette as disclosed herein to produce a transformed plant cell; and (b) generating a plant from the transformed plant cell.

In some embodiments, a plant cell is stably transformed with an expression cassette of the presently disclosed subject matter. "Stable transformation" or "stably transformed" is intended to mean that a polynucleotide, for example, an expression cassette as described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the nucleic acids pertinent to the presently disclosed subject matter can be used in conjunction with any such vectors. The selection of a vector will depend upon the transformation technique to be employed and the target species for transformation. For certain target species, different antibiotic or herbicide selection markers might be preferred. Selection markers used routinely in transformation include the nptII gene, which confers resistance to kanamycin and related antibiotics (Viera & Messing, 1982; Bevan et al., 1983); the pat and bar genes, which confer resistance to the herbicide glufosinate (also called phosphinothricin; see White et al., 1990; Spencer et al., 1990; and U.S. Pat. Nos. 5,561,236 and 5,276,268); the hph gene, which confers resistance to the antibiotic hygromycin (Blochinger & Diggelmann, 1984), and the dhfr gene, which confers resistance to methatrexate (Bourouis & Jarry, 1983); the EPSPS gene, which confers resistance to glyphosate (U.S. Pat. Nos. 4,940,935 and 5,188,642); the glyphosate N-acetyltransferase (GAT) gene, which also confers resistance to glyphosate (Castle et al., 2004; U.S. Patent Application Publication Nos. 2005/0060767, 2005/0246798, and 2007/0004912); and the mannose-6-phosphate isomerase gene, which provides the ability to metabolize mannose (U.S. Pat. Nos. 5,767,378 and 5,994,629), the gene encoding a mutant D-amino acid oxidase which can be derived from *Rhodotorula gracilis*, with a lysine at position 58 rather than a phenylalanine which interacts with D-phosphinothricin to produce a toxin (U.S. Pat. No. 7,939,709).

Thus, in some embodiments the presently disclosed subject matter relates to inducing HI in a plant. In some embodiments, a general technique for producing plants that exhibit HI comprises transforming a plant cell with an expression cassette to produce a transformed plant cell, wherein the expression cassette encodes an RNAi construct targeted to a gene associated with HI; and (b) generating a plant from the transformed plant cell. After a plant cell is transformed with an expression vector or expression cassette encodes an RNAi construct targeted to a gene associated with HI, a whole plant or plant tissue can be regenerated, if desired. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19

(Bevan, 1984). For the construction of vectors useful in *Agrobacterium* transformation, see e.g., U.S. Patent Application Publication No. 2006/0260011. See also Lee & Glevin, 2008.

Transformation without the use of *Agrobacterium tumefaciens* circumvents the requirement for T-DNA sequences in the chosen transformation vector and consequently vectors lacking these sequences can be utilized in addition to vectors such as the ones described above which contain one or more T-DNA sequences. Transformation techniques that do not rely on 15 *Agrobacterium* include transformation via particle bombardment, protoplast uptake (e.g., PEG and electroporation), whiskering, and microinjection. The choice of vector depends largely on the chosen selection for the species being transformed. For the construction of such vectors, see e.g., U.S. Patent Application Publication No. 2006/0260011.

For expression of a nucleotide sequence of the presently disclosed subject matter in plant plastids, plastid transformation vector pPH143 (PCT International Patent Application Publication No. WO 1997/32011, example 36) can be used. The nucleotide sequence is inserted into pPH143 thereby replacing the PROTOX coding sequence.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, and/or microinjection. Examples of these techniques are described by Paszkowski et al., 1984; Potrykus et al., 1985; Reich et al., 1986; and Klein et al., 1987. In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g., pCIB200 or pCIB2001) to an appropriate *Agrobacterium* strain which may depend of the complement of vir genes carried by the host *Agrobacterium* strain either on a co-resident Ti plasmid or chromosomally (e.g., strain CIB542 for pCIB200 and pCIB2001 (Uknes et al., 1993). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, 1988).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. Variations of this technique are disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

Transformation of most monocotyledon species has now also become routine. Exemplary techniques include direct gene transfer into protoplasts using PEG or electroporation techniques, and particle bombardment into callus tissue. Transformations can be undertaken with a single DNA species or multiple DNA species (i.e., co-transformation), and both of these techniques are suitable for use with the presently disclosed subject matter. Co-transformation can have the advantage of avoiding complete vector construction and of generating transgenic plants with unlinked loci for the gene of interest and the selectable marker, thereby permitting the removal of the selectable marker in subsequent generations, should this be regarded desirable. However, a disadvantage of the use of co-transformation can be the less than 100% frequency with which separate DNA species are integrated into the genome (Schocher et al. Biotechnology 4: 1093-1096 (1986)).

European Patent Applications EP 0 292 435 and EP 0 392 225, and PCT International Patent Application Publication No. WO 1993/07278 describe techniques for the preparation of callus and protoplasts from an elite inbred line of maize, transformation of protoplasts using PEG or electroporation, and the regeneration of maize plants from transformed protoplasts. Gordon-Kamm et al., 1990) and Fromm et al., 1990 have published techniques for transformation of A188-derived maize line using particle bombardment. Furthermore, PCT International Patent Application Publication No. WO 1993/07278 and Koziel et al., 1993 describe techniques for the transformation of elite inbred lines of maize by particle bombardment. This technique utilizes immature maize embryos of 1.5-2.5 mm length excised from a maize ear 14-15 days after pollination and a BIOLISTIC® PDS-1000/He (Bio-Rad Laboratories, Hercules, Calif., United States of America) device for bombardment.

Transformation of rice can also be undertaken by direct gene transfer techniques utilizing protoplasts or particle bombardment. Protoplast-mediated transformation has been described for Japonica-types and Indica-types (Zhang et al., 1988; Shimamoto et al., 1989; Datta et al., 1990). Both types are also routinely transformable using particle bombardment (Christou et al., 1991). Furthermore, PCT International Patent Application Publication No. WO 1993/21335 describes techniques for the transformation of rice via electroporation.

European Patent Application EP 0 332 581 describes techniques for the generation, transformation and regeneration of Pooideae protoplasts. These techniques allow the transformation of Dactylis and wheat. Furthermore, wheat transformation has been described by Vasil et al., 1992 using particle bombardment into cells of type C long-term regenerable callus, and also by Vasil et al., 1993 and Weeks et al., 1993 using particle bombardment of immature embryos and immature embryo-derived callus. An exemplary technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige & Skoog, 1962) and 3 mg/l 2,4-D for induction of somatic embryos, which is allowed to proceed in the dark. On the chosen day of bombardment, embryos are removed from the induction medium and placed onto the osmoticum (i.e., induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hours, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See e.g., PCT International Patent Application Publication No. WO 1994/00977 and U.S. Pat. No. 5,591,616. See also Negrotto et al., Plant Cell Reports 19: 798-803 (2000), incorporated herein by reference.

For example, rice (*Oryza sativa*) can be used for generating transgenic plants. Various rice cultivars can be used (Hiei et al., 1994; Dong et al., 1996; Hiei et al., 1997). Also, the various media constituents described below can be either varied in quantity or substituted. Embryogenic responses are initiated and/or cultures are established from mature embryos by culturing on MS-CIM medium (MS basal salts, 4.3 g/liter; B5 vitamins (200x), 5 ml/liter; Sucrose, 30 g/liter; proline, 500 mg/liter; glutamine, 500 mg/liter; casein hydrolysate, 300 mg/liter 2,4-D (1 mg/ml), 2 ml/liter; adjust pH to 5.8 with 1 N KOH; PHYTAGEL™ plant tissue culture reagent, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is resuspended in liquid MS-CIM medium. The *Agrobacterium* culture is diluted to an $OD_{600}$ of 0.2-0.3 and acetosyringone is added to a final concentration of 200 µM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., 2001), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin, 2% Mannose, and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the Ti seed is harvested.

The plants obtained via transformation with a nucleic acid sequence of interest in the presently disclosed subject matter can be any of a wide variety of plant species, including those of monocots and dicots. The plants used in the methods of the presently disclosed subject matter are in some embodiments selected from the list of agronomically important target crops set forth elsewhere herein. The expression of a nucleic acid of the presently disclosed subject matter in combination with other characteristics important for production and quality can be incorporated into plant lines through breeding. Breeding approaches and techniques are known in the art. See e.g., Welsh, 1981; Wood, 1983; Mayo, 1987; Singh, 1986; and Wricke & Weber, 1986.

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad Laboratories, Hercules, Calif., United States of America) coated with DNA from plasmids pPH143 and pPH145 essentially as described in Svab & Maliga, 1993. Bombarded seedlings are incubated on T medium for two days after which leaves are excised and placed abaxial side up in bright light (350-500 µmol photons/$m^2$/s) on plates of RMOP medium (see Svab et al., 1990) containing 500 µg/ml spectinomycin dihydrochloride (Sigma, St. Louis, Mo., United States of America). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (see Sambrook & Russell, 2001). BamHI/EcoRI-digested total cellular DNA (Mettler, 1987) is separated on 1% Tris-borate (TBE) agarose gels, transferred to nylon or nitrocellulose membranes, and probed with $^{32}$P-labeled random-primed DNA sequences corresponding to a 0.7 kb BamHIIHindIII DNA fragment from pC8 containing a portion of the rps 7/12 plastid targeting sequence. Homoplasmic shoots are rooted aseptically on spectinomycin-containing MS/IBA medium (McBride et al., 1994) and transferred to the greenhouse.

To test the haploid induction capacity of newly created lines, the pollen from each line is to be crossed onto an ear to induce fertilization, and the resulting progeny of the cross subjected to ploidy analysis. Ploidy analysis can be defined in this case as any experimental test where the ploidy level of an individual plant is determined. In crosses between two non-inducing lines, the resulting progeny should be almost exclusively diploid, or 2N. However, if a haploid induction line is the male parent, the resulting progeny will be a mixed population of haploids (1N), diploids (2N), aneuploids (somewhere between 1N and 2N), and chimeras (containing tissues with mixed ploidy). The determination of haploid induction capacity can be made binary by setting a cutoff value for the haploid induction rate, which is defined as the number of haploid embryos over the total number of viable embryos. The rate should be at least greater than 0.5%, and for high stringency, a good cutoff off is greater than 1% haploids. This is because a natural 'background' haploid induction rate of around 0.1% exists in maize. Because haploidy is only induced through the male parent during in vivo maize haploid induction, the female simply serves as a "tester" and thus, the female germplasm could be any number of lines. The female tester could be the inducer line itself (and the cross would thus be a self hybridization), or the tester could be any inbred, hybrid, or backcrossed maize line. The ploidy analysis can involve different methods, as described below.

One method of plant ploidy analysis is to evaluate the phenotypic characteristics of the plant, paying attention to those characteristics associated with haploidy, including but not limited to short plant stature, altered phylotaxy, smaller leaf width, low overall body mass, and male sterility. Plants could be given a score on each characteristic and then the scores could be added together and compared to known haploid and diploid controls. In another embodiment, the embryos resulting from a haploid induction cross may be extracted mechanically from immature kernels anytime between day 9 and day 20 after pollination, and then subjected to ploidy analysis by a ploidy analyzer (Partec) which uses DAPI stain combined with flow cytometry to quantify the total DNA amount per cell. In one embodiment, embryonic and/or scutellar tissue is used for processing; in another embodiment, adult plant tissues including roots, leaves, stems, or flowers are used. In one embodiment, the selected tissues are chopped up with a razor blade, incubated in an extraction buffer, filtered through a nylon mesh filter and then incubated in a DAPI stain before loading into the ploidy analyzer. In another embodiment, embryonic or adult tissue including those described above is first digested into protoplasts using a combination of cellulose and maceroenzyme in a buffer solution, then filtered and incubated in DAPI.

In yet another method of ploidy analysis, microscopic imaging of mature, juvenile, or embryonic plant tissues can be used to identify the ploidy by counting the number of chromosomes in certain cells that are undergoing mitosis. The DNA in this case may be stained with DAPI or any other common DNA stain such as propidium iodide. In maize a diploid plant will have 20 chromosomes per cell while a haploid plant will have 10 per cell. In such an approach, the embryos can be incubated on media for anywhere from zero to fourteen days, during which many embryos may germinate and grow small rootlets.

Alone or in combination with any of the ploidy analysis methods described above, the putative novel haploid induction line may be first crossed to a marker line, including but not limited to lines that contain the R1-navajo (R1-nj) or R1-scutellum2 (R1-Scm2) markers, or any line having DNA that encode for protein products that confer a visual identifier, such as a color visible to the human eye (e.g. anthocyanin) or a fluorescence-based marker visible only via fluorescent microscopy. Such markers, having been introgressed into the putative haploid inducer line, can serve as evidence of the existence of the paternal genome in progeny indicating a diploid state, with absence indicating a haploid state. The presence or absence of the marker may be detected using a visual test or microscopy.

The presently disclosed subject matter also provides methods for identifying the presence or absence of an allele associated with HI in a plant. In some embodiments, the methods comprise (a) obtaining a sample from the plant comprising genomic and/or nuclear DNA and/or an RNA product derived therefrom; (b) contacting the sample with a pair of primers that, when used in a nucleic-acid amplification reaction with a nucleic acid sample from the plant, produces an amplicon that can be used to identify the presence or absence of an allele associated with HI; (c) amplifying a fragment from said sample using the primer pair of (b), wherein the primer pair is complementary and binds to the nucleotide sequence of (b); and (d) detecting an amplicon that can be used to identify the presence or absence of an allele associated with HI in the plant.

The presently disclosed subject matter also provides methods for introgressing HI-inducing nucleotide sequences into plants. In some embodiments, the methods comprise crossing a first plant with a second plant to produce a third plant, wherein the genome of the first plant or the second plant comprises a recombinant nucleic acid sequence encoding a HI-associated gene product of the presently disclosed subject matter. In some embodiments, the methods further comprise assaying the genome of the third plant for the presence of the recombinant nucleic acid sequence encoding the HI-associated gene product. In some embodiments, the recombinant nucleic acid comprises (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

The presently disclosed subject matter also provides methods for selecting $F_0$ parental plants that are predicted to produce subsequent (e.g., $F_1$, $F_2$, $F_3$, etc.) generations with plants that exhibit HI. In some embodiments, the methods comprise identifying in the absence of sequence in the genome of an $F_0$ plant a nucleic acid comprising a sequence selected from the group consisting of The presently disclosed subject matter also provides kits for detecting the presence or absence of a HI-inducing allele in a plant. In some embodiments, the kits comprise one or more nucleic acid- and/or amino acid-based reagents derived from the maize HI locus or from a locus linked thereto, wherein the one or more nucleic acid- and/or amino acid-based reagents are designed to be employed in a nucleic acid- and/or amino acid-based assay for the presence or absence in the plant (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f).In some embodiments, the recombinant nucleic acid encodes an amino acid sequence that comprises all or substantially all of amino acids 1-454 of SEQ ID NO: 54.

In some embodiments, the one or more nucleic acid- and/or amino acid-based reagents derived from the maize HI locus or from a locus linked thereto comprise one or more oligonucleotide primers that are diagnostic of the presence in the plant of in the plant of the nucleic acid having at (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f).In some embodiments, the recombinant nucleic acid encodes an amino acid sequence that comprises all or substantially all of amino acids 1-454 of SEQ ID NO: 54.

As used herein, a "nucleic acid- or amino acid-based reagent" of the presently disclosed subject matter refers to any nucleic acid, peptide, or polypeptide that can be used to detect the presence or absence of SEQ ID NO: 33, SEQ ID NO: 37, SEQ ID NO: 52 or SEQ ID NO: 53 or an informative fragment thereof in a plant in any type of assay. By way of example and not limitation, a nucleic acid-based reagent of the presently disclosed subject matter can be an oligonucleotide primer pair that is designed to flank the deletion junction such that an amplification product will occur only if (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f).In some embodiments, the recombinant nucleic acid encodes an amino acid sequence that comprises all or substantially all of amino acids 1-454 of SEQ ID NO: 54.

Similarly, an amino acid-based reagent of the presently disclosed subject matter can be, but is not limited to, an antibody that binds to a polypeptide having SEQ ID NO: 54, SEQ ID NO: 55, SEQ ID NO: 56 or SEQ ID NO: 57 or an informative fragment thereof. In some embodiments, an antibody that binds to both a polypeptide of SEQ ID NO: 54, SEQ ID NO: 55, SEQ ID NO: 56 or SEQ ID NO: 57 and a maize HI gene product can be employed, wherein in an appropriate assay (e.g., a Western blot or an SDS-PAGE gel), the polypeptide of SEQ ID NO: 54, SEQ ID NO: 55, SEQ ID NO: 56 or SEQ ID NO: 57 and its absence or presence shows the maize HI gene product can be distinguished. In some embodiments, the kit further comprises a set of instructions for performing an assay with the nucleic acid- or amino acid-based reagent. In some embodiments, the kit further comprises one or more additional reagents that can be employed in the performance of the assay with the nucleic acid- or amino acid-based reagent.

EXAMPLES

The following Examples provide illustrative embodiments of the presently disclosed subject matter. In light of the present disclosure and the general level of skill in the art, those of skill will appreciate that the following examples are intended to be exemplary only and that numerous changes, modifications, and alterations can be employed without departing from the scope of the presently disclosed subject matter.

Example 1

QTL Mapping Material Choices

Two mapping populations involving a haploid inducer inbred (RWK) and two non-inducer inbreds (NP2391, NP2460) were generated. RWK was selected because of its high haploid induction ability compared to stock 6. The two non-inducer lines were selected due to existence of extensive data relevant to them. The recombinant inbred populations were backcross populations (BC1) such that the theoretical allele content was 75% RWK and 25% NP2391 for the first population (138 RILs, Recombinant Inbred Lines) and 75% RWK and 25% NP2460 for the second population (123 RILs). The mapping populations were self-pollinated two generations to make the BC1F3. The subsequent BC1F4 plants were testcrossed onto eight plants in two tester rows. The testcrosses were harvested and bulk shelled. Approximately 500 kernels of testcross seed were planted for each entry to observe the number of haploid and diploid plants and thereby determine the haploid induction rate of each recombinant inbred entry within that population.

QTL analysis was performed for both the populations using a version of "QTL Cartographer" software by combining the testcross induction rates with the SNP genotyping data of RILs. QTLs were declared when the LOD score is higher than 2. In total about ~70% variation in haploid induction rate was explained by QTL Bin 1.04. A number of other QTLs were also detected but these accounted for less of the variation. The two important values in QTL studies are the LOD (logarithm of odds) and the $R^2$. A high LOD value represents greater statistical evidence for the present of a QTL, and a higher $R^2$ indicates that the particular QTL has more effect on the trait of interest. The major QTL detected was on Chromosome 1, in a somewhat different region of Chromosome 1 than what was previously indicated by a patent application publication. Additional information about the fine mapping is provided in the subsequent examples.

| Breeding - Mapping Strategy | | |
|---|---|---|
| Season | What | Result |
| Year 0 | F1 | Two non-inducers inbreds (NP2391; P2460) were crossed with RWK |
| Year 0 | F1->BC1 | Both F1 backcrossed to RWK |
| Year 1 | BC1F1->BC1F2 | |
| Year 1 | BC1F2->BC1F3 | |
| Year 1 | BC1F4 testcrosses made × 2 testers | Two mapping Populations × two testers |
| Year 1 | BC1F4 testcrosses phenotyped | QTL Bin 1.04 identified, ~70% variation explained |
| Year 1 | BC2 made | |
| Year 2 | BC3 made | |
| Year 2 | BC3F2 made | |
| Year 2 | BC3F3 testcrosses made × 2 testers | Two fine mapping Populations × two testers |
| Year 3 | BC3F3 testcrosses phenotyped | First fine mapping completed |
| Year 3 | BC3F4 testcrosses made × 2 testers | |
| Year 3 | BC3F4 testcrosses phenotyped | Second fine mapping completed |
| Year 4 | BC3F5 testcrosses made × 2 testers | |
| Year 5 | BC3F5 testcrosses phenotyped | Fine mapping completed |
| Year 5 | RWK, RWK-NIL, Stock 6 gemones sequences | Annotations |

Example 2

Development of Near Isogenic Lines

To accurately position and fine-map the QTL for Haploid induction, near isogenic lines (NIL's) are created by back-crossing to RWK for three generations and followed by selfing for another 3 generations. During this process several NIL's were created in RWK background with regions from NP2391 and NP2460 in the target QTL region. This particular strategy was utilized to create NIL's because, haploid induction efficiency can change with the background and also to keep the rest of the RWK genome mostly uniform while focusing on the small non-inducer chromosome regions that were back-crossed into RWK.

Example 3

Fine Mapping

When the experiment was initiated, the haploid induction locus was localized in a region of 3.3 MB containing approximately 90 putative genes within that interval. The fine mapping process reduced the haploid induction locus to a 0.88 MB region with twenty five annotated genes. Additional fine mapping reduced the haploid induction locus to a 0.60 region.

The BC3F3 plants described in the above examples, which were heterozygous at the region of interest were selfed to create additional recombinations. These BC3F4 recombinants were testcrossed with two different testers and phenotypic information was gathered by measuring their haploid induction (HI) ability. The genotypic information from this localized haploid induction region and the phenotypic information taken concerning these line's haploid induction ability were correlated to fine-map the haploid induction locus to a 0.60 MB region with fewer than 7 annotated genes.

TABLE ON FINE MAPPING

| Old interval | New Confidence interval | Refined interval | Gene_ID | transcript_start | transcript_end | transcript_strand |
|---|---|---|---|---|---|---|
| x | x | x | GRMZM2G305400 | 67991172 | 67994092 | −1 |
| x | x | x | GRMZM2G082836 | 68107606 | 68110989 | 1 |
| x | x | x | GRMZM2G382717 | 68113455 | 68115168 | −1 |
| x | x | x | GRMZM2G120587 | 68133178 | 68136953 | −1 |
| x | x | x | GRMZM2G471240 | 68240862 | 68242656 | 1 |
| x | x | x | GRMZM2G471240 | 68240862 | 68242656 | 1 |
| x | x | x | GRMZM2G062320 | 68318898 | 68321409 | 1 |
| x | x | | GRMZM5G866758 | 68430654 | 68436197 | 1 |
| x | x | | GRMZM5G866758 | 68430654 | 68436197 | 1 |
| x | x | | GRMZM2G003530 | 68435670 | 68439997 | −1 |
| x | | | GRMZM2G077991 | 68543246 | 68546264 | −1 |
| x | | | GRMZM2G077991 | 68543694 | 68546264 | −1 |
| x | | | GRMZM2G077991 | 68543805 | 68546269 | −1 |
| x | | | GRMZM2G077960 | 68554980 | 68559182 | 1 |
| x | | | GRMZM2G077897 | 68561209 | 68565155 | −1 |
| x | | | GRMZM2G347583 | 68660278 | 68665995 | 1 |
| x | | | GRMZM2G173030 | 68668900 | 68671460 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G340286 | 68928213 | 68929600 | 1 |
| x | | | GRMZM2G340279 | 68934652 | 68937080 | −1 |
| x | | | GRMZM2G347808 | 69005208 | 69012612 | 1 |

Example 4

Markers for Refining Fine Mapping

The Table shown in example four shows the marker or locus name on the far left of the table. The limiting factor for further refining the locus was the availability of markers and not the maize line recombinants. Thus additional taqman assays were developed for gathering genotypic information from the haploid induction region. The Table shows the SNPs and their map positions. Each of these markers identifies an allele. The desirable nucleotides for a haploid inducing allele in the RWK (haploid inducing line) are also listed. These markers can be utilized in a marker assisted breeding program to select for or against the haploid induction ability in germplasm.

MARKER TABLE

| Marker or Locus Name | Chromosome | Map Position | RWK Allele |
|---|---|---|---|
| SM0262A | 1 | 45441103 | G/G |
| SM0390D | 1 | 45514003 | G/G |
| SM0657AQ | 1 | 56221199 | A/A |
| SM0103A | 1 | 60144794 | A/A |
| SM2317 | 1 | 60806574 | G/G |
| SM2318 | 1 | 60808690 | A/A |
| SM2315 | 1 | 60834691 | A/A |
| SM2322 | 1 | 61019467 | G/G |
| SM1994CQ | 1 | 61940683 | C/C |
| SM1994AQ | 1 | 61948232 | A/A |
| SM2014DQ | 1 | 62141179 | A/A |
| SM2014CQ | 1 | 62141297 | G/G |
| SM1208A | 1 | 62890212 | C/C |
| SM1208BQ | 1 | 62890343 | C/C |
| SM2332 | 1 | 62890343 | C/C |
| SM2331 | 1 | 62918261 | C/C |
| SM2542 | 1 | 65086371 | A/A |
| SM2543 | 1 | 65086379 | A/A |
| SM2547 | 1 | 65086882 | C/C |
| SM2548 | 1 | 65087687 | G/G |
| SM2359 | 1 | 65222457 | C/C |
| SM2366 | 1 | 65223245 | C/C |
| SM2333 | 1 | 65657736 | G/G |
| SM2338 | 1 | 66955942 | C/C |
| SM2340 | 1 | 67130654 | G/G |
| SM2339 | 1 | 67130683 | A/A |
| SM2356 | 1 | 67645465 | A/A |
| SM2357 | 1 | 67645486 | G/G |
| SM2361 | 1 | 67850657 | G/G |
| SM2363 | 1 | 67851018 | A/A |
| SM2587 | 1 | 68128675 | A/A |
| SM2589 | 1 | 68128928 | G/G |
| SM2593 | 1 | 68129217 | G/G |
| SM2594 | 1 | 68129237 | C/C |
| SM2602 | 1 | 68130522 | A/A |
| SM2607 | 1 | 68424731 | A/A |
| SM2608 | 1 | 68428500 | A/A |
| SM2365 | 1 | 68431623 | G/G |
| SM2362 | 1 | 68431768 | C/C |
| SM2712 | 1 | 68453157 | A/A |
| SM2709 | 1 | 68454360 | G/G |
| SM2706 | 1 | 68455010 | A/A |
| SM2710 | 1 | 68565361 | C/C |
| SM2707 | 1 | 68658060 | G/G |
| SM2550 | 1 | 68670604 | C/C |
| SM2551 | 1 | 68670713 | C/C |
| SM2708 | 1 | 68678452 | A/A |
| SM2610 | 1 | 69012158 | A/A |
| SM2613 | 1 | 69158347 | A/A |
| SM2552 | 1 | 69543214 | A/A |
| SM2553 | 1 | 69587711 | G/G |
| SM2554 | 1 | 69881293 | C/C |
| SM2556 | 1 | 69887955 | A/A |
| SM2557 | 1 | 69889226 | G/G |
| SM2558 | 1 | 70155695 | A/A |
| SM2616 | 1 | 70158847 | A/A |
| SM2617 | 1 | 70159265 | A/A |
| SM2559 | 1 | 70162230 | A/A |
| SM2621 | 1 | 70164485 | A/A |
| SM2624 | 1 | 70213152 | A/A |
| SM2626 | 1 | 70244705 | A/A |
| SM2560 | 1 | 70251144 | A/A |
| SM2628 | 1 | 70347954 | A/A |
| SM2629 | 1 | 70512212 | G/G |
| SM2013BQ | 1 | 71020438 | C/C |
| SM2573 | 1 | 71066077 | C/C |
| SM2575 | 1 | 71541039 | A/A |
| SM2576 | 1 | 71590349 | A/A |
| SM2579 | 1 | 71794881 | G/G |
| SM2580 | 1 | 71794974 | C/C |
| SM2581 | 1 | 72013466 | A/A |
| SM2347 | 1 | 72233113 | G/G |
| SM2349 | 1 | 72233448 | G/G |
| SM2368 | 1 | 73246562 | G/G |
| SM2352 | 1 | 73379493 | A/A |
| SM2369 | 1 | 73380804 | C/C |
| SM2351 | 1 | 73635946 | G/G |
| SM2354 | 1 | 73966550 | G/G |
| SM2353 | 1 | 73966557 | G/G |
| SM2345 | 1 | 73967645 | A/A |
| SM0118A | 1 | 75203350 | G/G |
| SM0251A | 1 | 82575679 | G/G |
| SM0241C | 1 | 147159831 | A/A |
| SM0201B | 1 | 178008426 | A/A |
| SM1990AQ | 1 | 184012848 | G/G |
| SM0376B | 1 | 195332392 | G/G |

Example 5

New Interval Developed with Fine Mapping

As indicated in Example 4, the limiting factor for further refinement of the haploid induction QTL region was resolved with the development of additional markers for the haploid induction region on Chromosome 1. The recombinants were screened with these newly developed markers. The original haploid induction locus was reduced from a starting interval containing ~64 genes, which was then reduced its size to 17-25 genes. Further fine mapping resolved the region to 0.60 MB with 8 genes in the interval. The eight genes include two genes GRMZ2G471240, and GRMZ2G866758 which appear twice because expression data suggests alternative transcripts. Each of the genes are listed in the Table below and are identified by the public Gene ID with the transcript start and end identified. The new refined haploid induction locus is indicated in the new confidence level. With the data from a single recombinant, a subset of approximately 8 genes were identified to be highly likely to have impact on the haploid induction trait. These are indicated by the highlighted section of the third column from the left of the Haploid Interval Table below.

Table Describing Haploid Induction QTL Interval

| New Confidence interval | Refined interval | Sequencing data analysis | gene_id |
|---|---|---|---|
| x | x | Appears to be missing from all three lines | GRMZM2G305400 |
| x | x | NIL and B73 gDNAs align in coding region. RWK/Stock 6 gDNAs are very similar. All protein coding sequences appear similar. | GRMZM2G082836 |
| x | x | NIL/B73 are identical. RWK differs at several bases and three AA residues. It also has a 21 base insert just downstream of the stop codon. Stock 6 data not so good at amino terminus, but suggests it's similar to RWK at the carboxy terminus. | GRMZM2G382717 |
| x | x | Stock 6, RWK and NIL differ from B73 outside protein coding region. RWK and Stock 6 have 2 additional amino acids | GRMZM2G120587 |
| x | x | NIL and B73 are virtually identical. Stock 6 and RWK are identical and a frame shift results in 20 incorrect AA followed by a new, premature stop codon | GRMZM2G471240 |
|  | x |  | GRMZM2G471240 |
| x | x | Not present in Stock 6/RWK. NIL/B73 are virtually identical. Some evidence this is a transcribed gene. | GRMZM2G062320 |
|  | x | NIL and B73 are virtually identical. Stock 6 and RWK are identical. The pairs differ slightly at the protein level and outside the coding region. | GRMZM5G866758 |
| x |  |  | GRMZM5G866758 |
| x |  | NIL is 97-98% identical to B73; RWK/Stock 6 95-99% similar to B73. Adjacent to GRMZM5G866758 but transcribed from opposite strand. All 4 encode the same protein. | GRMZM2G003530 |

Example 6

Sequence Analysis of Inducer and Non-Inducer Genomes

The maize haploid induction locus was understood to be present in a 2.2 Mb QTL located on Chromosome 1. This QTL represents approximately 70% of the variation associated with the haploid induction trait, and is therefore required for haploid induction. To date, no one has identified the genetic element responsible for haploid induction. As indicated in the earlier examples the haploid induction QTL was fine-mapped to reduce its size to 0.60 Mb In order to further identify the genes in this Haploid Induction region, the genomes of two haploid inducer lines, Stock 6 and RWK, and an RWK-NIL line were sequenced. Stock 6 is a maize haploid inducer line which is available from the Maize Genetics Stock Center in Champaign Ill. RWK is a maize line which is a haploid inducer line available from the University of Hohenhiem in Germany. B73 is a stiff stalk maize line produced and is broadly available from many sources including the Iowa State University in Ames, Iowa Genomic DNA from the leaf tissue of RWK, RWK-NIL, and Stock 6, was prepared and fragmented to produce two short-insert paired end (SIPE) libraries and one long-insert paired end (LIPE) library. Sufficient DNA sequence data were generated for 50x coverage of each genome, as indicated in the table below. The raw data were trimmed and compiled into sequence contigs. B73 sequence data for the Haploid Induction QTL on Chromosome 1 was used as a scaffold to enrich and refine contigs corresponding to this region from each genome.

| | Sequence Coverage | | | | | |
|---|---|---|---|---|---|---|
| | SIPE data | | LIPE data | | | | |
| | total Mb | Coverage | total Mb | coverage | total cov | % SIPE | % LIPE |
| Stock6 | 185,117 | 74.0 | 47,301 | 18.9 | 93.0 | 80% | 20% |
| NIL | 117,060 | 46.8 | 17,649 | 7.1 | 53.9 | 87% | 13% |
| RNK | 215,666 | 86.3 | 28,108 | 11.2 | 97.5 | 88% | 12% |

Total = total Mb of sequence data
coverage = average depth of sequence coverage (based on maize genome estimate of 2.5 Gb)
SIPE = short insert paired end library data (average insert size ~330 bp)
LIPE = long insert paired end library data (average insert size ~5000 bp)
Sequencing target was >=50x coverage, >=10% of data from LIPE reads The contigs were assembled and analyzed. The process produced ~300 contigs. These were then BLASTed against the 25 genes found within the HI interval. The candidate sequence from each line was annotated and compared. Expression was verified by cDNA/EST analysis, and the annotation was verified by cDNA/gDNA alignment. The differences between the lines were noted and distinguished. (see Tables in earlier examples)

Example 7

Sequence Analysis of Inducer and Non-Inducer Genomes

The assembled Stock 6, RWK and NIL (RWK-NIL) sequence contigs were compared to corresponding B73 sequence data. Gene models for each candidate gene were confirmed with additional sequence data from public and proprietary databases. The sequence data for each gene in the reduced HI interval were compared.

Structural Variants in Haploid Induction Interval

| Gene | structural variants? | # SNPs altering protein sequence | annotation |
|---|---|---|---|
| GRMZM2G120587 | No | 3 | Serine carboxypeptidase |
| GRMZM2G471240 | No | 4 | Patatin-like phospholipase |
| GRMZM2G062320 | Yes | 1 | Histidine phosphatase superfamily, Phosphoglycerate mutase family |
| AC213048.3 | No | 0 | pseudogene/hypothetical protein |
| GRMZM5G866758 | Yes | 2 | acetyl-CoA acetyltransferase, cytosolic 1 [Zea mays] |
| GRMZM2G003530 | Yes | 2 | Putative uncharacterized protein |
| GRMZM2G077991 | Yes | 2 | Ribosomal protein L37e |
| GRMZM2G077960 | No | 0 | Protein phosphatase 2C family protein |
| GRMZM2G077897 | No | 15 | Plant protein of unknown function, paramyosin, |
| GRMZM2G347583 | No | 2 | uncharacterized protein |
| GRMZM2G173030 | No | 0 | hypothetical protein |
| GRMZM2G031591 | Yes | 0 | hypothetical protein |
| GRMZM2G070462 | Yes | 0 | FHA domain-containing protein |
| GRMZM2G022061 | No | 5 | hypothetical protein LOC100279962 (LOC100279962 |
| GRMZM2G340286 | No | 4 | uncharacterized protein |
| GRMZM2G340279 | Yes | 8 | pentatricopeptide repeat-containing protein |
| GRMZM2G347808 | No | 4 | uncharacterized protein |

The experiment did not find DNA sequence evidence that GRMZM2G305400 is present in the Stock 6, RWK or Nil genomes.

The gene GRMZM2G062320 is encoding a phosphoglycerate mutase and is absent in RWK and Stock 6 but present in NIL and B73. This result will be tested by PCR. This gene product has expression in most plant tissues and stages of development. The gene product can be classified as a phosphoglycerate mutase and has sequence that places it in the histidine phosphatase superfamily.

We noted that other genes in the refined HI interval differ in sequence between the various genomes we examined. GRMZM2G471240 encodes a phospholipase that is exclusively expressed in meiotic anthers, and has a four nucleotide insertion resulting in 20 incorrect AA followed by a new, premature stop codon.

GRMZM2G120587 encodes a serine carboxypeptidase-like 51 (SCPL51) that is expressed in anthers and is a good candidate for a haploid induction because proteolysis has been shown to contribute towards centromere-specific localization of CENH3 proteins. The proteins encoded by RWK and Stock 6 have 2 additional amino acids.

GRMZM2G305400 encodes a cyclin and this gene was not present in the inducers or NIL, but it was present in B73.

GRMZM2G082836 gDNAs in Stock 6 and RWK are more similar to each other, and the GRMZM2G082836 gDNAs in NIL and B73 gene are more similar to each other. However the GRMZM2G082836 protein coding sequences of Stock 6, RWK, NIL and B73 are identical. This gene encodes a GTP-binding protein 1.

GRMZM2G382717 gDNAs in the NIL and B73 lines are identical. Sequence coverage for Stock 6 was not complete, but the available data align precisely to the RWK sequence data. RWK differs from NIL/B73 at several bases and at three amino acids, and there is an additional 21 base pair insertion in RWK downstream of the translation stop codon. This gene encodes a chaperone DnaJ-domain superfamily protein.

GRMZM5G866758 gDNAs from the B73 and NIL lines are virtually identical. GRMZM5G866758 gDNAs from the inducer lines, RWK and Stock 6, are identical. The data indicate some sequence differences between RWK/stock 6 and B73/NIL at the protein level and outside the protein coding sequence. This gene encodes an acetoacetyl-CoA thiolase 2.

Example 8

A Method to Knock Out GRMZM2G062320 Expression in Pollen

Any unique GRMZM2G062320 transcript sequence ranging from 200-500 contiguous bases can be used to make an RNAi molecule targeting this gene. Sequences comprising the double stranded RNA can separate by an intron, or other DNA strand that doesn't constrain formation of the GRMZM2G062320 double-strand RNA. Any number of constitutive promoters could be selected. A short list of some constitutive promoters include ZmUbi1, ZmUbi158, ZmUbi361, SbUbiCh3, SbUbiCh4. Pollen specific: Pollen-specific genes have been described for maize (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.) Such information can be used to identify other maize pollen-specific genes and produce pollen-specific expression cassettes. A general expression cassette design strategy is given in U.S. Pat. No. 8,129,58. Use of the NOS, AGS terminator components in the design is optional. The gene regulatory sequences are derived from the ZmABP2 gene (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.).

Example 9

Example Demonstrating Conservation of GRMZM2G062320 Protein Sequence in Maize

Syngenta's Maize Solexa Association panel is a collection of RNA-seq data derived from 790 lines. Lines in this collection were chosen based on their phenotypic and genotypic diversity from a larger collection of maize germplasm. Seedling leaf tissue was used to generate the data. The largest open reading frame for each cDNA was translated to the encoded protein for each line. The proteins were then compared to establish diversity across all lines. This evidence shows that there are five GRMZM2G062320 variants in this collection. Sequence analysis of these 790 diverse maize lines showed that version A, SEQ ID NO: 5 is present in 784 lines, version B, SEQ ID NO: 2 is present in 3 lines and versions C SEQ ID NO: 6, D SEQ ID NO: 7, and E SEQ ID NO: 8 are present in one line each. The protein sequences are derived from RNA-seq data. The evidence suggests the GRMZM2G062320 protein is highly conserved.

>SEQ ID NO: 5 GRMZM2G062320-A
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTAMLAMMQH

RRKKIPVITHNESEQAHRWSQIYSEETMKQSIPVITAWQLNERMYGELQG

LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

>SEQ ID NO: 2 GRMZM2G062320-B
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

PGCIDVPLTPKGVEEAIEAGKRICNIPIDVIYTSSLICAQMTAMLAMMQH

RRKKILVITHNESEQAHRWSQIYSEETMKQSIPVITAWQLNERMYGELQG

LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

>SEQ ID NO: 6 GRMZM2G062320-C
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

PGCIDVPLTPKGVEEAIEAGKRICNIPIDVIYTSSLICAQMTAMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

>SEQ ID NO: 7 GRMZM2G062320-D
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTSMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

>SEQ ID NO: 8 GRMZM2G062320-E
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTSMLAMMQH

RRKKIPVITHNESEQAHRWSQIYSEETMKQSIPVITAWQLNERMYGELQG

LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

Example 10

PCR Experiments to Determine the Presence or Absence of GRMZM2G062320 in the Haploid Inducer Lines These pairs worked as expected on NIL, RWK, and Stock6 DNA: NIL gDNA only amplified the NIL primer pair. RWK and Stock6 gDNA only amplified the RWK/Stock6 primer pair, which specifically detects the frameshift allele. The PCR products were sequenced and the sequences were identical to that from whole genome sequencing. The primer pairs are "nil.F1/R1" and "rwk.F1/R1".

Three PCR reactions spanning all but the first two exons of the gene model amplified in RWK and Stock6, and the amplicons had the correct size PCR gel band. These bands were excised from the gel, sub-cloned and sequenced, and were found to be nearly identical in sequence to the B73 and NIL amplicons, except for a few single nucleotide polymorphisms (SNPs). These SNPs may represent normal genetic drift because none of them caused non-conservative amino acid substitutions. The 5' end of the gene model could not be detected by PCR in RWK, Stock6, or NIL DNA samples. After multiple rounds of PCR and primer redesign, the 5' end was never amplified or cloned in any of the lines. Overall, this data contradicts the genome assemblies, suggesting that at least part of the gene model exists in RWK and Stock6 inducers.

One primer pair, designed to amplify an approximately 400 bp amplicon spanning exons 6-8, not only amplified in all lines tested, but the DNA sequence also matched B73 with 100% nucleotide identity. This primer pair was used to query a panel of high, low, and non-inducer maize plants. The high inducers all give greater than 7% haploid embryos upon outcrossing through the male (>7% haploid induction rate (HIR)). The low inducers have a HIR between 1 and 3%, and the non-inducers have a HIR of <0.1%. All of the high and low inducer lines were derived from the original Stock6 line, and thus it is assumed that the lesion responsible for haploid induction should be present in all high and low inducers, and absent in non-inducers.

When the exon 6-8 PCR primers were tested on these DNA samples, a band of the correct size and sequence was found in 9/9 non-inducers, 8/12 high inducers, and 6/7 low inducers. No band was present in 4/12 high inducers and 1/7 low inducers (Table 1). This indicates that, contrary to the sequencing data, this gene does exist in RWK and Stock6, but in various other induction lines, there may be presence/absence variation but it does not correlate with induction capacity. This makes it difficult to explain how GRMZM2G062320 is responsible for haploid induction.

| GRMZM2G062320 PCR test for presence of amplicon exon 6-8 | Induction Rate | Band present? |
|---|---|---|
| Controls: | | |
| Stock 6 (low) | 2.50% | + |
| RWK (high) | 12% | + |
| RWK-NIL (non) | <1% | + |
| High Inducers: | | |
| ZMS | 7% | − |
| Z19-PR | 7% | − |
| RWS-Z86 | 10% | + |
| K13 | 9% | + |
| (ID3002/Z22)B>29-5>2-5-1-B- | 7% | − |
| Z-19-//AF4031PR//Z-19-)1-1-2-3-1-3-B- | 9.5% | + |
| ZR86 | 12% | + |
| ZR53 | 12% | − |
| ZR75 | 13% | + |
| (Z21/RWS)B(GS)-75-1-2-3-B- | ~8% | + |
| AX5707 inducer-good | ~9% | + |
| Poor Inducers: | | |
| Stock6 R1-nj | 2.5% | + |
| (Z21/RWS//[RWS]B$)33-5- | <2% | + |
| (K-13-/(ZMS/SEW-PR)B>2>B-9//K-13-)2-4-1- | <2% | + |
| (K-13-/(ZMS/SEW-PR)B>2>B-9//K-13-)6-1-2- | <2% | + |
| (ZMS/SEW-PR)B>2>B-7-2-1-2- | <2% | − |
| AX5707 inducer-low | ~3% | + |
| Non-inducers: | | |
| Stock6 R1-nj B1Pl1 | <0.1% | + |
| (Z-21-/AF4031PR//Z-21-1-B-)1-1-1-1-B- | <0.1% | + |
| FF6096 | <0.1% | + |
| ID5829 | <0.1% | + |
| XO5744 | <0.1% | + |
| ID3002 | <0.1% | + |
| AF4031PR | <0.1% | + |
| AX5707 | <0.1% | + |

Example 11

PCR Experiments to Determine the Presence or Absence of GRMZM2G471240 in the Haploid Inducer Lines In order to develop a PCR test that would distinguish between RWK/Stock6 and NIL haplotypes, two primer pairs were designed: one pair should amplify the RWK/Stock6 frame-shift allele, while the other should amplify the B73/NIL allele.

```
For STOCK6/RWK allele (mutant, frameshift allele):
rwk.F1
TACGCCGTGCGCTAACATA rwk.R1
GTACCTCGCTCCCTGTCTCC SIZE: 822 bp FOR B73/RWK-NIL
nil.F1
GTACGCCGTGCGCTAACA nil.R1
TCGTACCTCCCTGTCTCCAC

SIZE: 821
```

Use: In a PCR reaction, these would be used at 500 nMol final concentration. The reaction may also contain:
1×PCR reaction buffer
200 uM of dNTPs (dATP, dCTP, dGTP, and dTTP)
<250 ng of genomic DNA
deionized water
Taq enzyme (1 unit—many different types available—usually 0.2 uL or 0.5 uL depending on the units/uL
magnesium chloride or magnesium sulfate (1 mM)
Reaction volume: 25 or 50 uL
recommended reaction:
1. 95 degrees C. 3'
2. 95 degrees C. 30" (denature)
3. 62 degrees C. 30" (anneal)
4. 72 degrees C. 1' (extend)
5. Repeat steps 2-4, 35 times
6. 72 degrees C., 10" (final extension)
7. 4 degrees C., forever These pairs worked as expected on NIL, RWK, and Stock6 DNA, NIL gDNA only amplified the NIL primer pair. RWK and Stock6 gDNA only amplified the RWK/Stock6 primer pair, which specifically detects the frame-shift allele. The PCR products were sequenced and the sequences were identical to that from whole genome sequencing. SNPs that were identified in the whole genome sequencing were confirmed in the PCR products (data not shown). The primer pairs are "nil.F1/R1" and "rwk.F1/R1". Detecting the Frame-Shift Mutation in the Panel of Inducer Lines:

The "rwk.F1/R1" and "nil.F1/R1" primer pairs were used to genotype the panel of high, low, and non-inducers. The data indicates that the frame-shift allele correlates with induction capacity. 14/14 high and 7/7 low inducers amplified the RWK/Stock6 allele, but not the NIL allele, while 9/9 non-inducers amplified the NIL allele, but not the RWK/Stock6 allele (Table 2).

| GRMZM2G471240 | Induction Rate | RWK amplicon | NIL amplicon |
|---|---|---|---|
| Controls: | | | |
| Stock 6 (low) | 2.50% | + | − |
| RWK (high) | 12% | + | − |
| RWK-NIL (non) | <1% | − | + |
| Good Inducers: | | | |
| ZMS | 7% | + | − |
| Z19-PR | 7% | + | − |
| Z22 | 7% | | |
| Z21 | 7% | | |
| RWS-Z86 | 10% | + | − |
| K13 | 9% | + | − |
| (ID3002/Z22)B>29-5>2-5-1-B- | 7% | + | − |
| Z-19-//AF4031PR//Z-19-)1-1-2-3-1-3-B- | 9.5% | + | − |
| ZR86 | 12% | + | − |
| ZR53 | 12% | + | − |
| ZR75 | 13% | + | − |
| (Z21/RWS)B(GS)-75-1-2-3-B- | ~8% | + | − |
| AX5707 inducer-good | ~9% | + | − |
| Poor Inducers: | | | |
| Stock6 R1-nj | 2.5% | + | − |
| (Z21/RWS//[RWS]B$)33-5- | <2% | + | − |
| (K-13-/(ZMS/SEW-PR)B>2>B-9//K-13-)2-4-1- | <2% | + | − |
| (K-13-/(ZMS/SEW-PR)B>2>B-9//K-13-)6-1-2- | <2% | + | − |
| (ZMS/SEW-PR)B>2>B-7-2-1-2- | <2% | + | − |
| AX5707 inducer-low | ~3% | + | − |
| Non-inducer Lines and Donors: | | | |
| Stock6 R1-nj B1Pl1 | <0.1% | − | + |
| (Z-21-/AF4031PR//Z-21-1-B-)1-1-1-1-B- | <0.1% | − | + |
| FF6096 | <0.1% | − | + |
| ID5829 | <0.1% | − | + |

-continued

| GRMZM2G471240 | Induction Rate | RWK amplicon | NIL amplicon |
|---|---|---|---|
| XO5744 | <0.1% | − | + |
| ID3002 | <0.1% | − | + |
| AF4031PR | <0.1% | − | + |
| AX5707 | <0.1% | − | + |

Example 12

A Method to Knock Out GRMZM2G471240 Expression

Any unique GRMZM2G471240 transcript sequence ranging from 200-1000 contiguous bases can be used to make an RNAi molecule targeting this gene. Sequences comprising the double stranded RNA can separate by an intron, or other DNA strand that doesn't constrain formation of the GRMZM2G471240 double-strand RNA. Any number of constitutive promoters could be selected. A short list of some constitutive promoters include ZmUbi1, ZmUbi158, ZmUbi361, SbUbiCh3, SbUbiCh4. Pollen specific: Pollen-specific genes have been described for maize (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.) Such information can be used to identify other maize pollen-specific genes and produce pollen-specific expression cassettes. A general expression cassette design strategy is given in U.S. Pat. No. 8,129,58. Use of the NOS, AGS terminator components in the design is optional. The gene regulatory sequences are derived from the ZmABP2 gene (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.). Expression constructs have been built comprising The promoter of GRMZM2G471240 as in SEQ ID NO: 58 operably linked to the hairpin construct in SEQ ID NO: 60 operably linked to the terminator of SEQ ID NO:59. Another construct was made with The promoter of GRMZM2G471240 as in SEQ ID NO: 58 operably linked to the hairpin construct in SEQ ID NO: 61 operably linked to the terminator of SEQ ID NO:59.

Example 13

Generation of Transgenic Maize Plants

Transformation of immature maize embryos is performed essentially as described in Negrotto et al., Plant Cell Reports 19:798-803 (2000). Various media constituents described therein can be substituted.

*Agrobacterium* strain LBA4404 (Invitrogen) containing the plant transformation plasmid is grown on YEP (yeast extract (5 g/L), peptone (10 g/L), NaCl (5 g/L), 15 g/l agar, pH 6.8) solid medium for 2 to 4 days at 28° C. Approximately 0.8×109 Agrobacteria are suspended in LS-inf media supplemented with 100 µM acetosyringone (As) (LSAs medium) (Negrotto et al., Plant Cell Rep 19:798-803 (2000)). Bacteria are pre-induced in this medium for 30-60 minutes.

Immature embryos from maize line, A188, or other suitable maize genotypes are excised from 8-12 day old ears into liquid LS-inf+100 µM As (LSAs). Embryos are vortexed for 5 seconds and rinsed once with fresh infection medium. Infection media is removed and *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) (Negrotto et al., Plant Cell Rep 19:798-803 (2000)) and cultured in the dark for 28° C. for 10 days.

Immature embryos producing embryogenic callus are transferred to LSD1M0.5S medium (LSDc with 0.5 mg/l 2,4-D instead of Dicamba, 10 g/l mannose, 5 g/l sucrose and no silver nitrate). The cultures are selected on this medium for 6 weeks with a subculture step at 3 weeks. Surviving calli are transferred either to LSD1M0.5S medium to be bulked-up or to Reg1 medium (as described in Negrotto et al., Plant Cell Rep 19:798-803 (2000)). Calli transformed with an *agrobacterium* binary vector carrying the RNAi expression cassette comprising or SEQ ID NO: 61 are surviving selection indicating successful transformation. An *agrobacterium* binary vector carrying the RNAi expression cassette comprising or SEQ ID NO: 60 will be transformed into maize. Following culturing in the light (16 hour light/8 hour dark regiment), green tissues will be transferred to Reg2 medium without growth regulators (as described in Negrotto et al., Plant Cell Rep 19:798-803 (2000)) and incubated for 1-2 weeks. Plantlets will be transferred to Magenta GA-7 boxes (Magenta Corp, Chicago Ill.) containing Reg3 medium (as described in Negrotto et al. (2000)) and grown in the light. Plants that are PCR positive for PMI and negative for Spectinomycin will be transferred to soil and grown in the greenhouse.

Example 14

Haploid Induction

T0 transgenic plants expressing an RNAi construct which silences GRMZM2G471240 will be tested for haploid induction capacity. The pollen from each plant is to be crossed onto an ear to induce fertilization, and the resulting progeny of the cross subjected to ploidy analysis. Ploidy analysis can be defined in this case as any experimental test where the ploidy level of an individual plant is determined. In crosses between two non-inducing lines, the resulting progeny should be almost exclusively diploid, or 2N. However, if a haploid induction line is the male parent, the resulting progeny will be a mixed population of haploids (1N), diploids (2N), aneuploids (somewhere between 1N and 2N), and chimeras (containing tissues with mixed ploidy). The determination of haploid induction capacity can be made binary by setting a cutoff value for the haploid induction rate, which is defined as the number of haploid embryos over the total number of viable embryos. The rate should be at least greater than 0.5%.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of creating a new haploid inducer maize plant with a silenced patatin-like phospholipase 2A, comprising transcribing a polynucleotide sequence that silences the patatin-like phospholipase 2A in maize, wherein said polynucleotide sequence comprises a first sequence selected from the group consisting of:
   a) a polynucleotide sequence comprising the nucleic acid sequence set forth in SEQ ID NO: 33 or the complement thereof;
   b) a functional fragment comprising at least 22 contiguous bases of SEQ ID NO: 33 or the complement thereof; and
   c) a polynucleotide sequence having at least 95% sequence identity as determined using the BLASTN alignment tool to the nucleic acid sequence set forth in SEQ ID NO: 33 or the complement thereof, and a second sequence that is the complement of the first sequence, wherein the polynucleotide sequence expresses a double-stranded ribonucleotide sequence which silences the patatin-like phospholipase 2A when contacted with a maize plant and thus creates a new haploid inducer maize plant.

2. The method of claim 1, wherein the contacting is achieved by transforming the plant with a polynucleotide sequence which when expressed produces a double-stranded ribonucleotide sequence that silences the patatin-like phospholipase 2A.

* * * * *